US008722720B2

(12) United States Patent
Mautino et al.

(10) Patent No.: US 8,722,720 B2
(45) Date of Patent: *May 13, 2014

(54) IMIDAZOLE DERIVATIVES AS IDO INHIBITORS

(75) Inventors: Mario R. Mautino, Ankeny, IA (US); Sanjeev Kumar, Ames, IA (US); Firoz Jaipuri, Ames, IA (US); Jesse Waldo, Huxley, IA (US); Tanay Kesharwani, Lake Katrine, NY (US)

(73) Assignee: NewLink Genetics Corporation, Ames, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/501,633

(22) PCT Filed: Oct. 27, 2010

(86) PCT No.: PCT/US2010/054289
§ 371 (c)(1),
(2), (4) Date: Jul. 12, 2012

(87) PCT Pub. No.: WO2011/056652
PCT Pub. Date: May 12, 2011

(65) Prior Publication Data
US 2012/0277217 A1 Nov. 1, 2012

(51) Int. Cl.
*A61K 31/4174* (2006.01)
*C07D 233/64* (2006.01)
(52) U.S. Cl.
USPC .......................... 514/399; 548/341.1
(58) Field of Classification Search
USPC ........................ 548/341.1; 514/399
See application file for complete search history.

(56) References Cited

FOREIGN PATENT DOCUMENTS

WO     2009/073620 A2    6/2009
WO     2009/132238 A2    10/2009
WO     WO-2009/132238    * 10/2009 ........... A61K 31/538

OTHER PUBLICATIONS

Arai et al, SYNLETT (2006), No. 18, pp. 3170-3172.*
Pandit et al, J. Am. Chem. Society (1960), pp. 3386-3390.*
Co-pending U.S. Appl. No. 12/988,391, commonly assigned to NewLink Genetics.*
Muller A J et al: "Indoleamine 2,3-dioxygenase in cancer: Targeting pathological immune tolerance with small-molecule inhibitors", Expert Opinion on Therapeutic Targets, Ashley Publications, London, GB, vol. 9, No. 4, Aug. 1, 2885 (2885-88-81).*
Muller et al., "Indoleamine 2,3-dioxygenase in cancer: Targeting pathological immune tolerance with small-molecule inhibitors", Expert Opinion on Therapeutic Targets, 2005, 9(4), 831-849.
Kumar et al., "Structure based development of phenylimidazole-derived inhibitors of indoleamine 2,3-dioxygenase", Journal of Medicinal Chemistry, 2008, 51(16), 4968-4977.

* cited by examiner

*Primary Examiner* — Kamal Saeed
*Assistant Examiner* — Janet L Coppins
(74) *Attorney, Agent, or Firm* — McDonnell Boehnen Hulbert & Berghoff LLP

(57) ABSTRACT

Presently provided are IDO inhibitors of general formulae (VII), (VIII) as shown below and pharmaceutical compositions thereof, useful for modulating an activity of indoleamine 2,3-dioxygenase; treating indoleamine 2,3-dioxygenase (IDO) mediated immunosuppression; treating a medical conditions that benefit from the inhibition of enzymatic activity of indoleamine-2,3-dioxygenase; enhancing the effectiveness of an anti-cancer treatment comprising administering an anti-cancer agent; treating tumor-specific immunosuppression associated with cancer; and treating immunosupression associated with an infectious disease.

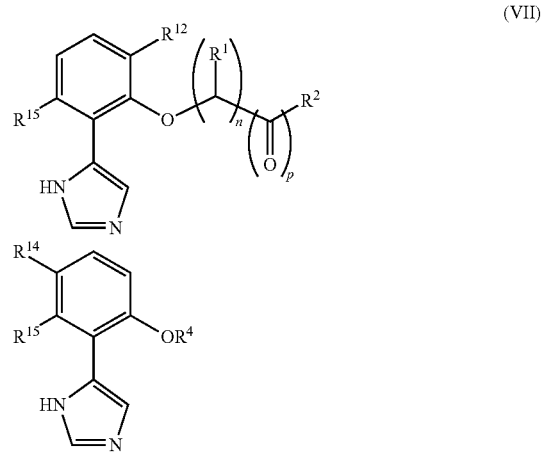

15 Claims, No Drawings

IMIDAZOLE DERIVATIVES AS IDO INHIBITORS

CROSS-REFERENCE TO RELATED APPLICATIONS

This application is a U.S. national phase of International Application No. PCT/US2010/054289, filed Oct. 27, 2010, which claims the benefit of the filing date of U.S. Provisional Application Ser. 61/255,762, filed Oct. 28, 2009, the disclosures of which are hereby incorporated by reference in their entirety.

BACKGROUND OF THE INVENTION

1. Field of the Invention

The present disclosure relates to compounds and methods for inhibition of indoleamine 2,3-dioxygenase; further the disclosure relates to method of treatment of diseases and disorders mediated by indoleamine 2,3-dioxygenase.

2. Summary of the Related Art

Tryptophan (Trp) is an essential amino acid required for the biosynthesis of proteins, niacin and the neurotransmitter 5-hydroxytryptamine (serotonin). The enzyme indoleamine 2,3-dioxygenase (also known as INDO or IDO) catalyzes the first and rate limiting step in the degradation of L-tryptophan to N-formyl-kynurenine. In human cells, IFN-y stimulation induces activation of IDO, which leads to a depletion of Trp, thereby arresting the growth of Trp-dependent intracellular pathogens such as *Toxoplasma gondii* and *Chlamydia trachomatis*. IDO activity also has an antiproliferative effect on many tumor cells, and IDO induction has been observed in vivo during rejection of allogeneic tumors, indicating a possible role for this enzyme in the tumor rejection process.

It has been observed that HeLa cells co-cultured with peripheral blood lymphocytes (PBLs) acquire an immunoinhibitory phenotype through up-regulation of IDO activity. A reduction in PBL proliferation upon treatment with interleukin-2 (IL-2) was believed to result from IDO released by the tumor cells in response to IFN-y secretion by the PBLs. This effect was reversed by treatment with 1-methyl-tryptophan (1MT), a specific IDO inhibitor. It was proposed that IDO activity in tumor cells may serve to impair antitumor responses (Logan, et al., 2002, Immunology, 105: 478-87).

Several lines of evidence suggest that IDO is involved in induction of immune tolerance. Studies of mammalian pregnancy, tumor resistance, chronic infections and autoimmune diseases have shown that cells expressing IDO can suppress T-cell responses and promote tolerance. Accelerated Trp catabolism has been observed in diseases and disorders associated with cellular immune activation, such as infection, malignancy, autoimmune diseases and AIDS, as well as during pregnancy. It was proposed that IDO is induced chronically by HIV infection, and is further increased by opportunistic infections, and that the chronic loss of Trp initiates mechanisms responsible for cachexia, dementia and diarrhea and possibly immunosuppression of AIDS patients (Brown, et al., 1991, Adv. Exp. Med. Biol., 294: 425-35). To this end, it has recently been shown that IDO inhibition can enhance the levels of virus-specific T cells and, concomitantly, reduce the number of virally infected macrophages in a mouse model of HIV (Portula et al., 2005, Blood, 106:2382-90).

IDO is believed to play a role in the immunosuppressive processes that prevent fetal rejection in utero. More than 40 years ago, it was observed that, during pregnancy, the genetically disparate mammalian conceptus survives in spite of what would be predicted by tissue transplantation immunology (Medawar, 1953, Symp. Soc. Exp. Biol. 7: 320-38). Anatomic separation of mother and fetus and antigenic immaturity of the fetus cannot fully explain fetal allograft survival. Recent attention has focused on immunologic tolerance of the mother. Because IDO is expressed by human syncytiotrophoblast cells and systemic tryptophan concentration falls during normal pregnancy, it was hypothesized that IDO expression at the maternal-fetal interface is necessary to prevent immunologic rejection of the fetal allografts. To test this hypothesis, pregnant mice (carrying syngeneic or allogeneic fetuses) were exposed to 1 MT, and a rapid, T cell-induced rejection of all allogeneic concepti was observed. Thus, by catabolizing tryptophan, the mammalian conceptus appears to suppress T-cell activity and defends itself against rejection, and blocking tryptophan catabolism during murine pregnancy allows maternal T cells to provoke fetal allograft rejection (Munn, et al., 1998, Science 281: 1191-3).

Further evidence for a tumoral immune resistance mechanism based on tryptophan degradation by IDO comes from the observation that most human tumors constitutively express IDO, and that expression of IDO by immunogenic mouse tumor cells prevents their rejection by preimmunized mice. This effect is accompanied by a lack of accumulation of specific T cells at the tumor site and can be partly reverted by systemic treatment of mice with an inhibitor of IDO, in the absence of noticeable toxicity. Thus, it was suggested that the efficacy of therapeutic vaccination of cancer patients might be improved by concomitant administration of an IDO inhibitor (Uyttenhove et al., 2003, Nature Med., 9: 1269-74). It has also been shown that the IDO inhibitor, 1-MT, can synergize with chemotherapeutic agents to reduce tumor growth in mice, suggesting that IDO inhibition may also enhance the anti-tumor activity of conventional cytotoxic therapies (Muller et al., 2005, Nature Med., 11:312-9).

One mechanism contributing to immunologic unresponsiveness toward tumors may be presentation of tumor antigens by tolerogenic host APCs. A subset of human IDO-expressing antigen-presenting cells (APCs) that coexpressed CD123 (IL3RA) and CCR6 and inhibited T-cell proliferation have also been described. Both mature and immature CD123-positive dendritic cells suppressed T-cell activity, and this IDO suppressive activity was blocked by 1MT (Munn, et al., 2002, Science 297: 1867-70). It has also been demonstrated that mouse tumor-draining lymph nodes (TDLNs) contain a subset of plasmacytoid dendritic cells (pDCs) that constitutively express immunosuppressive levels of IDO. Despite comprising only 0.5% of lymph node cells, in vitro, these pDCs potently suppressed T cell responses to antigens presented by the pDCs themselves and also, in a dominant fashion, suppressed T cell responses to third-party antigens presented by nonsuppressive APCs. Within the population of pDCs, the majority of the functional IDO-mediated suppressor activity segregated with a novel subset of pDCs coexpressing the B-lineage marker CD19. Thus, it was hypothesized that IDO-mediated suppression by pDCs in TDLNs creates a local microenvironment that is potently suppressive of host antitumor T cell responses (Munn, et al., 2004, J. Clin. Invest., 114(2): 280-90).

IDO degrades the indole moiety of tryptophan, serotonin and melatonin, and initiates the production of neuroactive and immunoregulatory metabolites, collectively known as kynurenines. By locally depleting tryptophan and increasing proapoptotic kynurenines, IDO expressed by dendritic cells (DCs) can greatly affect T-cell proliferation and survival. IDO induction in DCs could be a common mechanism of deletional tolerance driven by regulatory T cells. Because such tolerogenic responses can be expected to operate in a variety of physiopathological conditions, tryptophan metabolism and kynurenine production might represent a crucial interface between the immune and nervous systems (Grohmann, et al., 2003, Trends Immunol., 24: 242-8).

Small molecule inhibitors of IDO are being developed to treat or prevent IDO-related diseases such as those described above. For example, PCT Publication WO 99/29310 reports methods for altering T cell-mediated immunity comprising altering local extracellular concentrations of tryptophan and tryptophan metabolites, using an inhibitor of IDO such as 1-methyl-DL-tryptophan, p-(3-benzofuranyl)-DL-alanine, p-[3-benzo[b]thienyl]-DL-alanine, and 6-nitro-L-tryptophan) (Munn, 1999). Reported in WO 03/087347, also published as European Patent 1501918, are methods of making antigen-presenting cells for enhancing or reducing T cell tolerance (Munn, 2003). Compounds having indoleamine-2,3-dioxygenase (IDO) inhibitory activity are further reported in WO 2004/094409; and U.S. Patent Application Publication No. 2004/0234623 is directed to methods of treating a subject with a cancer or an infection by the administration of an inhibitor of indoleamine-2,3-dioxygenase in combination with other therapeutic modalities.

In light of the experimental data indicating a role for IDO in immunosuppression, tumor resistance and/or rejection, chronic infections, HIV-infection, AIDS (including its manifestations such as cachexia, dementia and diarrhea), autoimmune diseases or disorders (such as rheumatoid arthritis), and immunologic tolerance and prevention of fetal rejection in utero, therapeutic agents aimed at suppression of tryptophan degradation by inhibiting IDO activity are desirable. Inhibitors of IDO can be used to activate T cells and therefore enhance T cell activation when the T cells are suppressed by pregnancy, malignancy or a virus such as HIV. Inhibition of IDO may also be an important treatment strategy for patients with neurological or neuropsychiatric diseases or disorders such as depression. The compounds, compositions and methods herein help meet the current need for IDO modulators.

SUMMARY OF THE INVENTION

In one aspect, the invention comprises compounds according to one of the formulae (I)-(VIII), wherein $R^1$, $R^2$, X, n, p, and $R^{11}$-$R^{18}$ are each defined herein.

In another aspect pharmaceutical compositions are provided comprising a pharmaceutically acceptable excipient, diluent, or carrier, and a compound according to any one of formulae (I)-(VIII).

In another aspect methods are provided for (a) modulating an activity of indoleamine 2,3-dioxygenase comprising contacting an indoleamine 2,3-dioxygenase with a modulation effective amount of a compound according to any one of formulae (I)-(VIII), as described herein, or a pharmaceutical composition comprising a compound according to any one of formulae (I)-(VIII); (b) treating indoleamine 2,3-dioxygenase (IDO) mediated immunosuppression in a subject in need thereof, comprising administering an effective indoleamine 2,3-dioxygenase inhibiting amount of a compound according to any one of formulae (I)-(VIII), as described herein, or a pharmaceutical composition comprising a compound according to any one of formulae (I)-(VIII); (c) treating a medical conditions that benefit from the inhibition of enzymatic activity of indoleamine-2,3-dioxygenase comprising administering an effective indoleamine 2,3-dioxygenase inhibiting amount of a compound according to any one of formulae (I)-(VIII), as described herein, or a pharmaceutical composition comprising a compound according to any one of formulae (I)-(VIII); (d) enhancing the effectiveness of an anti-cancer treatment comprising administering an anti-cancer agent and a compound according to any one of formulae (I)-(VIII), as described herein, or a pharmaceutical composition comprising a compound according to any one of formulae (I)-(VIII); (e) treating tumor-specific immunosuppression associated with cancer comprising administering an effective indoleamine 2,3-dioxygenase inhibiting amount of a compound according to any one of formulae (I)-(VIII), as described herein, or a pharmaceutical composition comprising a compound according to any one of formulae (I)-(VIII); and (f) treating immunosupression associated with an infectious disease, e.g., HIV-1 infection, comprising administering an effective indoleamine 2,3-dioxygenase inhibiting amount of a compound according to any one of formulae (I)-(VIII), as described herein, or a pharmaceutical composition comprising a compound according to any one of formulae (I)-(VIII).

DETAILED DESCRIPTION OF THE INVENTION

In one aspect, the invention provides compounds of formula (I),

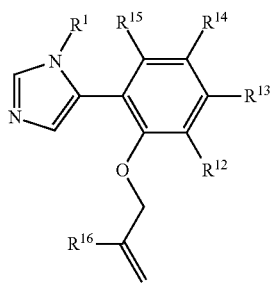

(I)

a tautomer thereof, or a pharmaceutically acceptable salt thereof, wherein $R^1$ is hydrogen, $C_1$-$C_6$ alkyl, $C_1$-$C_6$ haloalkyl, or —($C_1$-$C_6$)alkyl-$R^{B1}$, wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, or —N(R)S(O)$_2$R;

$R^{13}$ is hydrogen, halogen, or —SH;

$R^{12}$, $R^{14}$, and $R^{15}$ are each independently hydrogen or $R^{20}$, or $R^{16}$ is $C_3$-$C_8$cycloalkyl, heterocyclyl, aryl, or heteroaryl, each optionally substituted with 1, 2, or 3 $R^{20}$ groups;

each $R^{20}$ is independently halogen, cyano, —OR, —SR, —$NR_2$, —C(O)OR, —C(O)$NR_2$, —N(R)S(O)$_2$R, —C(O)$R^2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —$OR^{10}$, —$SR^{10}$, —N($R^{10}$)$_2$, —C(O)$OR^{10}$, —C(O)N($R^{10}$)$_2$, —C(O)$R^{10}$, —S(O)$R^{10}$, —S(O)$_2R^{10}$, —S(O)$OR^{10}$, —S(O)$_2OR^{10}$, —S(O)N($R^{10}$)$_2$, —S(O)$_2$N($R^{10}$)$_2$, —OC(O)$R^{10}$, —OC(O)$OR^{10}$, —OC(O)N($R^{10}$)$_2$, —N($R^{10}$)C(O)$R^{10}$, —N($R^{10}$)C(O)$OR^{10}$, —N($R^{10}$)C(O)N($R^{10}$)$_2$, —N($R^{10}$)S(O)$R^{10}$, —N($R^{10}$)S(O)$_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In one embodiment of the first aspect, the compound of formula (I) is according to formula (Ia),

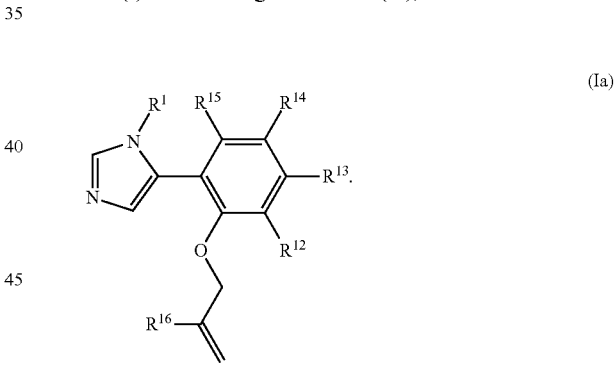

(Ia)

In another embodiment of the first aspect, the compound of formula (I) is according to formula (Ib),

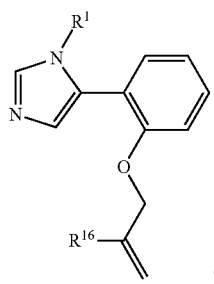

(Ib)

In another embodiment of the first aspect, the compound of formula (I) is according to formula (Ic),

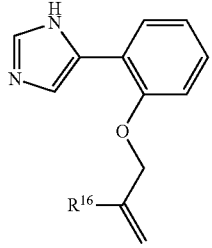

In another embodiment of any of the preceding embodiments of the first aspect, $R^{16}$ is $C_3$-$C_8$cycloalkyl optionally substituted with 1, 2, or 3 $R^{20}$ groups.

In another embodiment of any of the preceding embodiments of the first aspect, $R^{16}$ is heteroaryl optionally substituted with 1, 2, or 3 $R^{20}$ groups.

In another embodiment of any of the preceding embodiments of the first aspect, $R^{16}$ is heterocyclyl optionally substituted with 1, 2, or 3 $R^{20}$ groups.

In another embodiment of any of the preceding embodiments of the first aspect, $R^{16}$ is aryl optionally substituted with 1, 2, or 3 $R^{20}$ groups.

In another embodiment of any of the preceding embodiments of the first aspect, each $R^{20}$ is independently halogen, cyano, —OR, —NR$_2$, —C(O)OR, —C(O)NR$_2$, —N(R)S(O)$_2$R, —C(O)R$^2$, —S(O)$_2$R, —S(O)$_2$OR, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, or $C_1$-$C_6$alkyl.

In another embodiment of any of the preceding embodiments of the first aspect, each $R^{20}$ is independently halogen, cyano, —OR, —NR$_2$, —C(O)OR, —C(O)NR$_2$, or $C_1$-$C_6$alkyl.

In a second aspect, the invention provides compounds of formula (II),

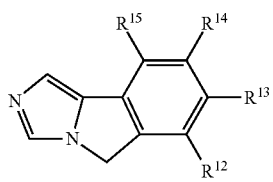

a tautomer thereof, or a pharmaceutically acceptable salt thereof, wherein
$R^{13}$ is hydrogen, halogen, or —SH; and
$R^{12}$, $R^{14}$, and $R^{15}$ are each independently hydrogen or $R^{20}$, or
each $R^{20}$ is independently halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;
each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocycl($C_1$-$C_6$)alkyl, aryl ($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, —C(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$)$_2$, —N(R$^{10}$)C(O)N(R$^{10}$)$_2$, —N(R$^{10}$)S(O)R$^{10}$, —N(R$^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In one embodiment of the second aspect, the compound of formula (II) is according to formula (IIa),

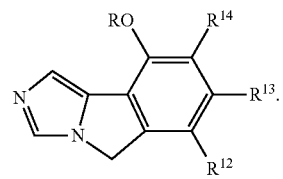

In another embodiment of the second aspect, the compound of formula (II) is according to formula (IIb),

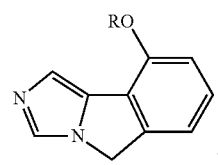

In an embodiment of any of the preceding embodiments of the second aspect, R is hydrogen $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$) alkyl.

In an embodiment of any of the preceding embodiments of the second aspect, R is hydrogen or $C_1$-$C_6$ alkyl.

In a third aspect, the invention provides compounds of formula (III),

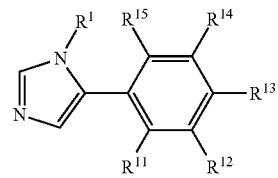

a tautomer thereof, or a pharmaceutically acceptable salt thereof, wherein $R^1$ is $C_3$-$C_8$cycloalkyl, heterocyclyl, aryl, or heteroaryl, each optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, or —N(R)S(O)$_2$R; and $R^{11}$ is hydrogen, $R^{20}$, or $R^{40}$, wherein $R^{40}$ is —OR, —SR, —NR$_2$, $C_1$-$C_6$alkyl-$R^{41}$, -Q-$C_1$-$C_6$alkyl-$R^{41}$, —$C_1$-$C_6$alkyl-Q-$R^{41}$, -Q-$C_1$-$C_6$alkyl -Q-$R^{41}$, —$C_1$-$C_6$alkyl-Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$, wherein each Q is independently —C($R^{42}$)$_2$—, —O—, —N($R^{42}$)—, —S—, —C(O)—, —S(O)—, —S(O)$_2$—, —C(O)N($R^{42}$)—, —N($R^{42}$)C(O)—, —C(O)O—, or —OC(O)—, wherein each $R^{42}$ is independently hydrogen, $C_1$-$C_6$alkyl, or $C_1$-$C_6$haloalkyl;

$R^{41}$ is $R^{43}$, $C_1$-$C_6$ alkyl, —$C_1$-$C_6$ alkyl-$R^{43}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently $R^{30}$ or —$C_1$-$C_6$ alkyl-$R^{30}$, wherein $R^{30}$ is halogen, cyano, nitro, —OR$^{31}$, —SR$^{31}$, —N(R$^{31}$)$_2$, —C(O)OR$^{31}$, —C(O)N(R$^{31}$)$_2$, —C(O)R$^{31}$, —S(O)R$^{31}$, —S(O)$_2$R$^{31}$, —S(O)OR$^{31}$, —S(O)$_2$OR$^{31}$, —S(O)N(R$^{31}$)$_2$, —S(O)$_2$N(R$^{31}$)$_2$, —OC(O)R$^{31}$, —OC(O)OR$^{31}$, —OC(O)N(R$^{31}$)$_2$, —N(R$^{31}$)C(O)R$^{31}$, —N(R$^{31}$)C(O)OR$^{31}$, —N(R$^{31}$)C(O)N(R$^{31}$)$_2$, —N(R$^{31}$)S(O)R$^{31}$, —N(R$^{31}$)S(O)$_2$R$^{31}$, $C_1$-$C_6$ alkyl, or $C_1$-$C_6$ haloalkyl, wherein each $R^{31}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, or $R^{41}$ and $R^{42}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, or $C_1$-$C_6$ haloalkyl;

$R^{13}$ is hydrogen, halogen, or —SH; and $R^{12}$, $R^{14}$, and $R^{15}$ are each independently hydrogen or $R^{20}$;

each $R^{20}$ is independently halogen, cyano, —OR, —SR, —NR$_2$, —C(O)OR, —C(O)NR$_2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl;

$C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, —SR$^{10}$, —N(R$^{10}$)$_2$, —C(O)OR$^{10}$, —C(O)N(R$^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)S(O)R$^{10}$, —N(R$^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In one embodiment of the third aspect, $R^1$ is $C_3$-$C_8$cycloalkyl optionally substituted by 1, or 2 $R^{B2}$ groups.

In another embodiment of the third aspect, $R^1$ is $C_3$-$C_8$cycloalkyl.

In another embodiment of the third aspect, $R^1$ is cyclohexyl.

In another embodiment of the third aspect, $R^1$ is aryl optionally substituted by 1 or 2 $R^{B2}$ groups.

In another embodiment of the third aspect, $R^1$ is phenyl optionally substituted by 1 or 2 $R^{B2}$ groups.

In another embodiment of the third aspect, $R^1$ is phenyl.

In another embodiment of the third aspect, $R^1$ is heteroaryl optionally substituted by 1 or 2 $R^{B2}$ groups.

In another embodiment of the third aspect, $R^1$ is 6-membered heteroaryl each optionally substituted by 1 or 2 $R^{B2}$ groups.

In another embodiment of the third aspect, $R^1$ is pyridyl.

In an embodiment of any of the preceding embodiments of the third aspect, the compound is of the formula (IIIa),

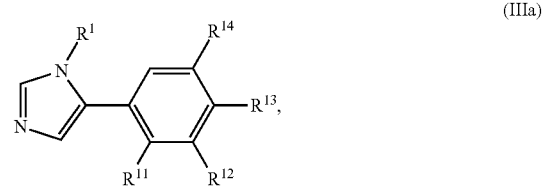

(IIIa)

wherein $R^{11}$ is —OR, —SR, —NR$_2$, -Q-$C_1$-$C_6$alkyl-$R^{41}$, -Q-$C_1$-$C_6$alkyl-Q-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$; and $R^{12}$, $R^{13}$, and $R^{14}$ are each independently hydrogen or halogen.

In an embodiment of any of the preceding embodiments of the third aspect, $R^{11}$ is —OR, —O—$C_1$-$C_6$alkyl-$R^{41}$, —O—$C_1$-$C_6$alkyl-Q-$R^{41}$, —O($C_1$-$C_6$)alkyl-Q-($C_1$-$C_6$)alkyl-$R^{41}$, or —O($C_1$-$C_6$)alkyl-Q-($C_1$-$C_6$)alkyl-Q$R^{41}$.

In an embodiment of any of the preceding embodiments of the third aspect, $R^{11}$ is —OR or —O—$C_1$-$C_6$alkyl-$R^{41}$.

In an embodiment of any of the preceding embodiments of the third aspect, $R^{11}$ is —OH.

In a fourth aspect, the invention provides compounds of formula (IV),

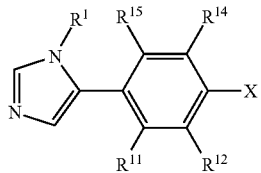

a tautomer thereof, or a pharmaceutically acceptable salt thereof, wherein

X is halogen;

$R^1$ is hydrogen, $C_1$-$C_6$ alkyl, $C_1$-$C_6$ haloalkyl, or —($C_1$-$C_6$)alkyl-$R^{B1}$, wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, or —N(R)S(O)$_2$R; and $R^{11}$ is hydrogen, $R^{20}$, or $R^{40}$, wherein $R^{40}$ is —OR, —SR, —NR$_2$, —$C_1$-$C_6$alkyl-Q-$R^{41}$, -Q-$C_1$-$C_6$alkyl-$R^{41}$, —$C_1$-$C_6$alkyl-$R^{41}$, -Q-$C_1$-$C_6$alkyl-Q-$R^{41}$, —$C_1$-$C_6$alkyl-Q-($C_1$-$C_6$)alkyl-$R^{41}$, -Q($C_1$-$C_6$)alkyl -Q-($C_1$-$C_6$)alkyl-$R^{41}$, or -Q($C_1$-$C_6$)alkyl-Q-($C_1$-$C_6$)alkyl-Q$R^{41}$, wherein each Q is independently —C($R^{42}$)$_2$—, —O—, —N($R^{42}$)—, —S—, —C(O)—, —S(O)—, S(O)—, —S(O)$_2$—, —C(O)N($R^{42}$)—, —N($R^{42}$)C(O)—, —C(O)O—, or —OC(O)—, wherein each $R^{42}$ is independently hydrogen, $C_1$-$C_6$alkyl, or $C_1$-$C_6$haloalkyl;

$R^{41}$ is $R^{43}$, $C_1$-$C_6$ alkyl, —$C_1$-$C_6$ alkyl-$R^{43}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —NR$_2$, —C(O)R, —C(O)OR, —C(O)NR$_2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently $R^{30}$ or —$C_1$-$C_6$ alkyl-$R^{30}$, wherein $R^{30}$ is halogen, cyano, nitro, —OR$^{31}$, —SR$^{31}$, —N(R$^{31}$)$_2$, —C(O)OR$^{31}$, —C(O)N(R$^{31}$)$_2$, —C(O)R$^{31}$, —S(O)R$^{31}$, —S(O)$_2$R$^{31}$, —S(O)OR$^{31}$, —S(O)$_2$OR$^{31}$, —S(O)N(R$^{31}$)$_2$, —S(O)$_2$N(R$^{31}$)$_2$, —OC(O)R$^{31}$, —OC(O)OR$^{31}$, —OC(O)N(R$^{31}$)$_2$, —N(R$^{31}$)C(O)R$^{31}$, —N(R$^{31}$)C(O)OR$^{31}$, —N(R$^{31}$)C(O)N(R$^{31}$)$_2$, —N(R$^{31}$)S(O)R$^{31}$, —N(R$^{31}$)S(O)$_2$R$^{31}$, $C_1$-$C_6$ alkyl, or $C_1$-$C_6$ haloalkyl, wherein each $R^{31}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, or $R^{41}$ and $R^{42}$ taken together, when attached to the same carbon atom, form =$C_3$-$C_8$cycloalkyl, or =heterocyclyl, wherein the cycloalkyl and heterocyclyl are optionally substituted with 1, 2, 3, or 4 groups which are each independently halogen, cyano, nitro, —OR, —SR, —NR$_2$, —C(O)OR, —C(O)NR$_2$, —C(O)R, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, —N(R)S(O)$_2$R, $C_1$-$C_6$ alkyl, or $C_1$-$C_6$ haloalkyl;

$R^{12}$, $R^{14}$, and $R^{15}$ are each independently hydrogen or $R^{20}$, or each $R^{20}$ is independently halogen, cyano, —OR, —SR, —NR$_2$, —C(O)OR, —C(O)NR$^2$, —N(R)S(O)$_2$R, —C(O)R$^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR$^{10}$, SR$^{10}$, —N(R$^{10}$)$_2$, —C(O)OR$^{10}$, —C(O)N(R$^{10}$)$_2$, —C(O)R$^{10}$, —S(O)R$^{10}$, —S(O)$_2$R$^{10}$, —S(O)OR$^{10}$, —S(O)$_2$OR$^{10}$, —S(O)N(R$^{10}$)$_2$, —S(O)$_2$N(R$^{10}$)$_2$, —OC(O)R$^{10}$, —OC(O)OR$^{10}$, —OC(O)N(R$^{10}$)$_2$, —N(R$^{10}$)C(O)R$^{10}$, —N(R$^{10}$)C(O)OR$^{10}$)$_2$, —N(R$^{10}$)C(O)N(R$^{10}$)$_2$, —N(R$^{10}$)S(O)R$^{10}$, —N(R$^{10}$)S(O)$_2$R$^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In one embodiment of the fourth aspect, $R^1$ is hydrogen.

In an embodiment of any of the preceding embodiments of the fourth aspect, $R^{11}$, $R^{12}$, $R^{14}$, and $R^{15}$ are each independently hydrogen, halogen, or —OR.

In an embodiment of any of the preceding embodiments of the fourth aspect, $R^{13}$ is fluorine.

In an embodiment of any of the preceding embodiments of the fourth aspect, $R^{11}$ is —OR.

In an embodiment of any of the preceding embodiments of the fourth aspect, $R^{11}$ is —OH.

In a fifth aspect, the invention provides compounds of formula (V),

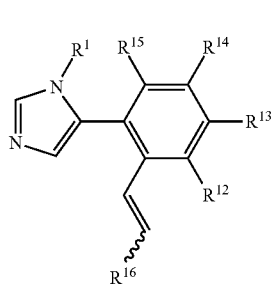

a tautomer thereof, or a pharmaceutically acceptable salt thereof, wherein $R^1$ is hydrogen, $C_1$-$C_6$ alkyl, $C_1$-$C_6$ haloalkyl, or —($C_1$-$C_6$) alkyl-$R^{B1}$, wherein $R^{B1}$ is $R^{B2}$, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{B2}$ groups, wherein each $R^{B2}$ is independently halogen, cyano, nitro, $C_1$-$C_6$ alkyl, $C_1$-$C_6$ haloalkyl, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, or —N(R)S(O)$_2$R;

$R^{13}$ is hydrogen, halogen, or —SH;

$R^{12}$, $R^{14}$, and $R^{15}$ are each independently hydrogen or $R^{20}$, or $R^{16}$ is cyano, —C(O)OR, —C(O)$NR_2$, —C(O)R, —S(O)R, —S(O)$_2$R, —S(O)OR, —S(O)$_2$OR, —S(O)$NR_2$, or —S(O)$_2NR_2$;

each $R^{20}$ is independently halogen, cyano, —OR, —SR, —$NR_2$, —C(O)OR, —C(O)$NR_2$, —N(R)S(O)$_2$R, —C(O)$R^2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —$OR^{10}$—$SR^{10}$, —$N(R^{10})_2$, —$C(O)OR^{10}$—$C(O)N(R^{10})_2$, —$C(O)R^{10}$), —$S(O)R^{10}$—$S(O)_2R^{10}$, —$S(O)OR^{10}$, —$S(O)_2OR^{10}$, —$S(O)N(R^{10})_2$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)R^{10}$, —$N(R^{10})S(O)_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

In one embodiment of the fifth aspect, the compound of formula (V) is according to formula (Va),

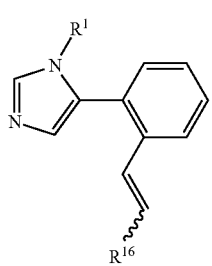

(Va)

In another embodiment of the fifth aspect, the compound of formula (V) is according to formula (Va),

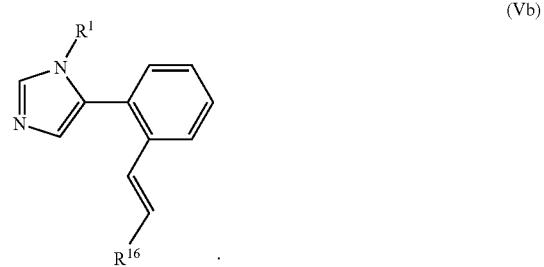

(Vb)

In an embodiment of any of the preceding embodiments of the fifth aspect, $R^{16}$ is —C(O)OR or —C(O)$NR_2$.

In an embodiment of any of the preceding embodiments of the fifth aspect, $R^{16}$ is —C(O)OR.

In an embodiment of any of the preceding embodiments of the fifth aspect, $R^1$ is hydrogen.

In a sixth aspect, the invention provides compounds of formula (VI),

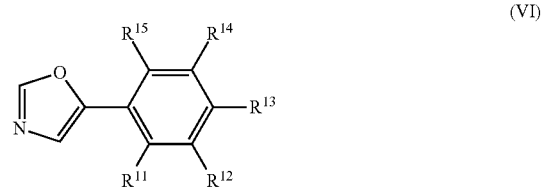

(VI)

a tautomer thereof, or a pharmaceutically acceptable salt thereof, wherein $R^{11}$ is hydrogen, $R^{20}$, or $R^{40}$, wherein $R^{40}$ is —OR, —SR, —$NR_2$, —$C_1$-$C_6$alkyl-$R^{41}$, -Q-$C_1$-$C_6$alkyl-$R^{41}$, —$C_1$-$C_6$alkyl-Q-$R^{41}$, -Q-$C_1$-$C_6$alkyl-Q-$R^{41}$, —$C_1$-$C_6$alkyl -Q-($C_1$-$C_6$)alkyl-$R^{41}$, -Q($C_1$-$C_6$)alkyl-Q-($C_1$-$C_6$)alkyl-$R^{41}$, or -Q($C_1$-$C_6$)alkyl-Q-($C_1$-$C_6$)alkyl-Q$R^{41}$, wherein each Q is independently —$C(R^{42})_2$—, —O—, —$N(R^{42})$—S—, —C(O)—, —S(O)—, —S(O)$_2$—, —C(O)N($R^{42}$)—, —$N(R^{42})C(O)$—, —C(O)O—, or —OC(O)—, wherein each $R^{42}$ is independently hydrogen, $C_1$-$C_6$alkyl, or $C_1$-$C_6$haloalkyl;

$R^{41}$ is $R^{43}$, $C_1$-$C_6$ alkyl, —$C_1$-$C_6$ alkyl-$R^{43}$, $C_1$-$C_6$ haloalkyl, $C_3$-$C_8$cycloalkyl, heterocyclyl, aryl, or heteroaryl, wherein the cycloalkyl, heterocyclyl, aryl, and heteroaryl groups are optionally substituted by 1, 2, 3, or 4 $R^{43}$ groups, wherein each $R^{43}$ is independently halogen, cyano, nitro, —OR, —SR, —$NR_2$, —C(O)R, —C(O)OR, —C(O)$NR_2$, —S(O)R, —S(O)$_2$R, —S(O)OR, —S(O)$_2$OR, —S(O)$NR_2$, —S(O)$_2NR_2$, —OC(O)R, —OC(O)OR, —OC(O)$NR_2$, —N(R)C(O)R, —N(R)C(O)OR, —N(R)C(O)$NR_2$, —N(R)S(O)R, —N(R)S(O)$_2$R, $C_1$-$C_6$ alkyl, $C_1$-$C_6$ haloalkyl, $C_2$-$C_6$ alkenyl, $C_2$-$C_6$ alkynyl, $C_3$-$C_8$cycloalkyl, heterocyclyl, aryl, or heteroaryl, wherein the cycloalkyl, heterocyclyl, aryl, heteroaryl, are each optionally substituted with 1, 2, 3, or 4 groups which are each independently $R^{30}$ or —$C_1$-$C_6$ alkyl-$R^{30}$, wherein $R^{30}$ is halogen, cyano, nitro, —$OR^{31}$, —$SR^{31}$, —$N(R^{31})_2$, —$C(O)OR^{31}$, —$C(O)N(R^{31})_2$, —$C(O)R^{31}$, —$S(O)R^{31}$, —$S(O)_2R^{31}$, —$S(O)OR^{31}$, —$S(O)_2OR^{31}$, —$S(O)N(R^{31})_2$, —$S(O)_2N(R^{31})_2$, —$OC(O)R^{31}$, —OC(O)

OR³¹, —OC(O)N(R³¹)₂, —N(R³¹)C(O)R³¹, —N(R³¹)C(O)OR³¹, —N(R³¹)C(O)N(R³¹)₂, —N(R³¹)S(O)R³¹, —N(R³¹)S(O)₂R³¹, C₁-C₆ alkyl, or C₁-C₆ haloalkyl, wherein each R³¹ is independently hydrogen, C₁-C₆ alkyl, C₂-C₆ alkenyl, C₂-C₆ alkynyl, C₁-C₆ haloalkyl, C₃-C₈cycloalkyl, heterocyclyl, aryl, heteroaryl, C₃-C₈cycloalkyl(C₁-C₆)alkyl, heterocyclyl(C₁-C₆)alkyl, aryl(C₁-C₆)alkyl, or heteroaryl(C₁-C₆)alkyl, or R^{A1} and R^{A2} taken together, when attached to the same carbon atom, form =C₃-C₈cycloalkyl, or =heterocyclyl, wherein the cycloalkyl and heterocyclyl are optionally substituted with 1, 2, 3, or 4 groups which are each independently halogen, cyano, nitro, —OR, —SR, —NR₂, —C(O)OR, —C(O)NR₂, —C(O)R, —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)S(O)₂R, C₁-C₆ alkyl, or C₁-C₆ haloalkyl;

R¹³ is hydrogen, halogen, or —SH; and

R¹², R¹⁴, and R¹⁵ are each independently hydrogen or R²⁰;

each R²⁰ is independently halogen, cyano, —OR, —SR, —NR₂, —C(O)OR, —C(O)NR₂, —N(R)S(O)₂R, —C(O)R², —S(O)R, —S(O)₂R, —S(O)OR, —S(O)₂OR, —S(O)NR₂, —S(O)₂NR₂, —OC(O)R, —OC(O)OR, —OC(O)NR₂, —N(R)C(O)R, —N(R)C(O)OR, —N(R)C(O)NR₂, —N(R)S(O)R, —N(R)C(O)R, C₁-C₆alkyl, C₂-C₆alkenyl, C₂-C₆alkynyl, C₁-C₆haloalkyl, C₃-C₈cycloalkyl, heterocyclyl, aryl, heteroaryl, C₃-C₈cycloalkyl(C₁-C₆)alkyl, heterocyclyl(C₁-C₆)alkyl, aryl(C₁-C₆)alkyl, or heteroaryl(C₁-C₆)alkyl;

each R is independently hydrogen or R², wherein R² is C₁-C₆ alkyl, C₂-C₆ alkenyl, C₂-C₆ alkynyl, C₁-C₆ haloalkyl, C₃-C₈cycloalkyl, heterocyclyl, aryl, heteroaryl, C₃-C₈cycloalkyl(C₁-C₆)alkyl, heterocyclyl(C₁-C₆)alkyl, aryl(C₁-C₆)alkyl, or heteroaryl(C₁-C₆)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —OR¹⁰, —SR¹⁰, —N(R¹⁰)₂, —C(O)OR¹⁰, —C(O)N(R¹⁰)₂, —C(O)R¹⁰, —S(O)R¹⁰, —S(O)₂R¹⁰, —S(O)OR¹⁰, —S(O)₂OR¹⁰, —S(O)N(R¹⁰)₂, —S(O)₂N(R¹⁰)₂, —OC(O)R¹⁰, —OC(O)OR¹⁰, —OC(O)N(R¹⁰)₂, —N(R¹⁰)C(O)R¹⁰, —N(R¹⁰)C(O)OR¹⁰, —N(R¹⁰)C(O)N(R¹⁰)₂, —N(R¹⁰)S(O)R¹⁰, —N(R¹⁰)S(O)₂R¹⁰, C₁-C₆ alkyl, C₂-C₆ alkenyl, C₂-C₆ alkynyl, C₁-C₆ haloalkyl, C₃-C₈cycloalkyl, heterocyclyl, aryl, or heteroaryl, wherein each R¹⁰ is independently hydrogen, C₁-C₆ alkyl, C₂-C₆ alkenyl, C₂-C₆ alkynyl, C₁-C₆ haloalkyl, C₃-C₈cycloalkyl, heterocyclyl, aryl, heteroaryl, C₃-C₈cycloalkyl(C₁-C₆)alkyl, heterocyclyl(C₁-C₆)alkyl, aryl(C₁-C₆)alkyl, or heteroaryl(C₁-C₆)alkyl.

In one embodiment of the sixth aspect, the compound of formula (VI) is according to formula (VIa),

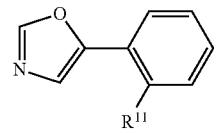

(VIa)

In an embodiment of any of the preceding embodiments of the sixth aspect, R¹¹ is —OR, -Q-C₁-C₆alkyl-R^{A1}, —C₁-C₆alkyl -Q-R^{A1}, -Q-C₁-C₆alkyl-Q-R^{A1}, —C₁-C₆alkyl -Q-(C₁-C₆)alkyl-R^{A1}, -Q(C₁-C₆)alkyl-Q-(C₁-C₆)alkyl-R^{A1}, or -Q(C₁-C₆)alkyl-Q-(C₁-C₆)alkyl-QR^{A1}.

In an embodiment of any of the preceding embodiments of the sixth aspect, R¹¹ is —OR, -Q-C₁-C₆alkyl, -Q-C₁-C₆alkyl-Q-R^{A1}, -Q(C₁-C₆)alkyl-Q-(C₁-C₆)alkyl-R^{A1}, or -Q(C₁-C₆)alkyl-Q-(C₁-C₆)alkyl-QR^{A1}.

In an embodiment of any of the preceding embodiments of the sixth aspect, R¹¹ is —OR or -Q-C₁-C₆alkyl-R^{A1}.

In an embodiment of any of the preceding embodiments of the sixth aspect, R¹¹ is —OR.

In another aspect, the invention provides the compound that is,

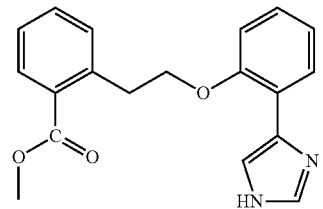

methyl 2-(2-(2-(1H-imidazol-4-yl)phenoxy)ethyl)benzoate;

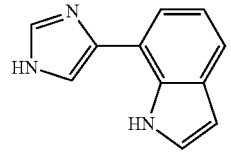

7-(1H-imidazol-4-yl)-1H-indole;

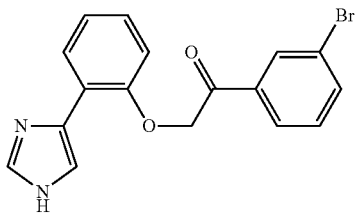 [SMILES: O=C(COc1ccccc1-c1c[nH]cn1)c1cccc(Br)c1]

2-(2-(1H-imidazol-4-yl)phenoxy)-1-(3-bromophenyl)ethanone;

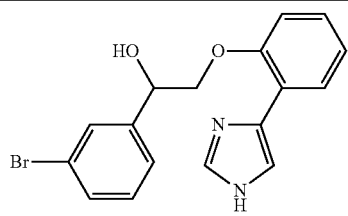 2-(2-(1H-imidazol-4-yl)phenoxy)-1-(3-bromophenyl)ethanol;
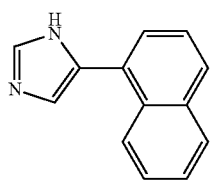 [SMILES: c1ccc2c(-c3cnc[nH]3)cccc2c1] 5-(naphthalen-1-yl)-1H-imidazole;
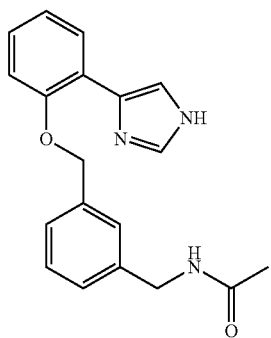 [SMILES: CC(=O)NCc1cccc(COc2ccccc2-c2c[nH]cn2)c1] N-(3-((2-(1H-imidazol-4-yl)phenoxy)methyl)benzyl)acetamide;
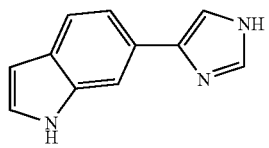 [SMILES: c1nc(-c2ccc3cc[nH]c3c2)c[nH]1] 6-(1H-imidazol-4-yl)-1H-indole;
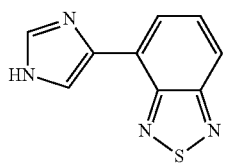 [SMILES: c1cc(-c2c[nH]cn2)c2nsnc2c1] 4-(1H-imidazol-4-yl)benzo[c][1,2,5]thiadiazole;
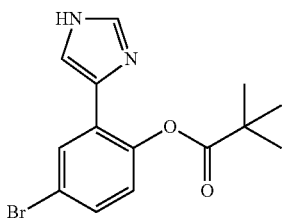 [SMILES: CC(C)(C)C(=O)Oc1ccc(Br)cc1-c1c[nH]cn1] 4-bromo-2-(1H-imidazol-4-yl)phenyl pivalate;
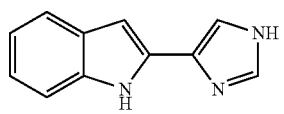 [SMILES: c1ccc2[nH]c(-c3c[nH]cn3)cc2c1] 2-(1H-imidazol-4-yl)-1H-indole;
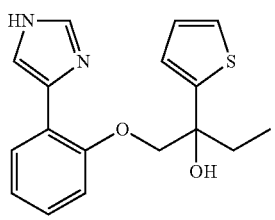 [SMILES: CCC(O)(COc1ccccc1-c1c[nH]cn1)c1cccs1] 1-(2-(1H-imidazol-4-yl)phenoxy)-2-(thiophen-2-yl)butan-2-ol;

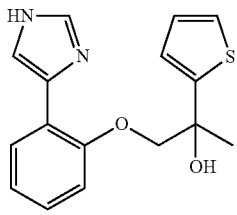 1-(2-(1H-imidazol-4-yl)phenoxy)-2-(thiophen-2-yl)propan-2-ol;
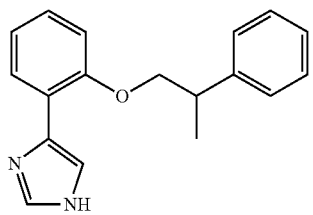 [SMILES: CC(COc1ccccc1-c1c[nH]cn1)c1ccccc1] 4-(2-(2-phenylpropoxy)phenyl)-1H-imidazole;
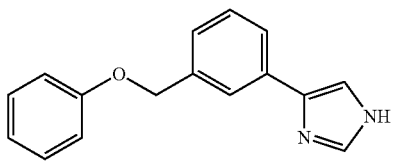 [SMILES: c1ccc(OCc2cccc(-c3c[nH]cn3)c2)cc1] 4-(3-(phenoxymethyl)phenyl)-1H-imidazole;
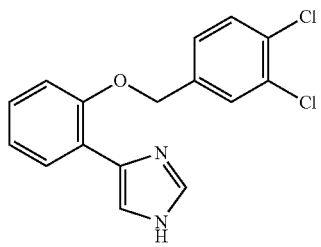 [SMILES: Clc1ccc(COc2ccccc2-c2c[nH]cn2)cc1Cl] 4-(2-(3,4-dichlorobenzyloxy)phenyl)-1H-imidazole;
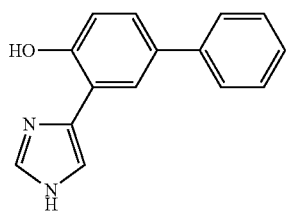 [SMILES: Oc1ccc(-c2ccccc2)cc1-c1c[nH]cn1] 3-(1H-imidazol-4-yl)biphenyl-4-ol;
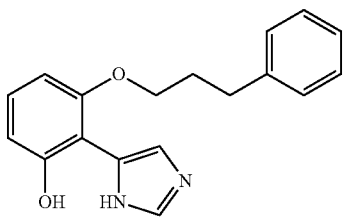 [SMILES: Oc1cccc(OCCCc2ccccc2)c1-c1cnc[nH]1] 2-(1H-imidazol-5-yl)-3-(3-phenylpropoxy)phenol;
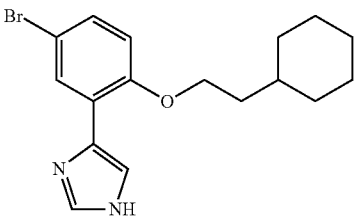 [SMILES: Brc1ccc(OCCC2CCCCC2)c(-c2c[nH]cn2)c1] 4-(5-bromo-2-(2-cyclohexylethoxy)phenyl)-1H-imidazole;

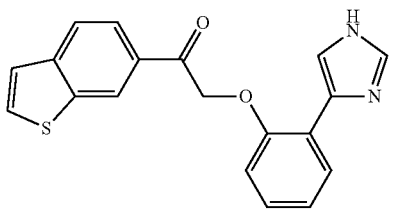 [SMILES: O=C(COc1ccccc1-c1c[nH]cn1)c1ccc2ccsc2c1] 2-(2-(1H-imidazol-4-yl)phenoxy)-1-(benzo[b]thiophen-6-yl)ethanone;
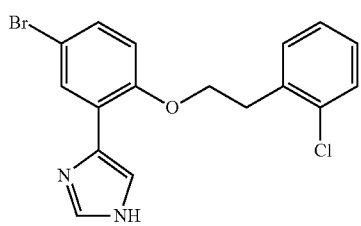 [SMILES: Clc1ccccc1CCOc1ccc(Br)cc1-c1c[nH]cn1] 4-(5-bromo-2-(2-chlorophenethoxy)phenyl)-1H-imidazole;
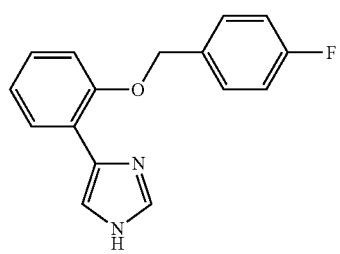 [SMILES: Fc1ccc(COc2ccccc2-c2c[nH]cn2)cc1] 4-(2-(4-fluorobenzyloxy)phenyl)-1H-imidazole;
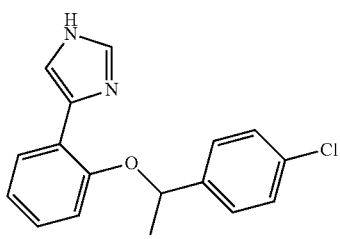 [SMILES: CC(Oc1ccccc1-c1c[nH]cn1)c1ccc(Cl)cc1] 4-(2-(1-(4-chlorophenyl)ethoxy)phenyl)-1H-imidazole;
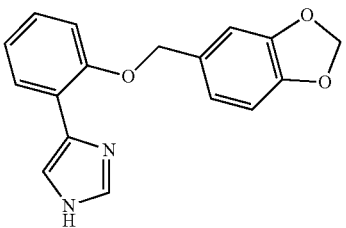 [SMILES: c1ccc(-c2c[nH]cn2)c(OCc2ccc3c(c2)OCO3)c1] 4-(2-(benzo[d][1,3]dioxol-5-ylmethoxy)phenyl)-1H-imidazole;
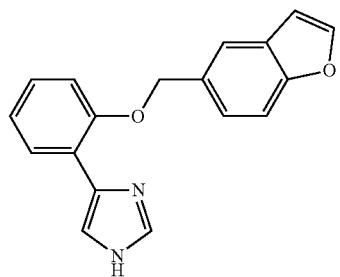 [SMILES: c1ccc(-c2c[nH]cn2)c(OCc2ccc3occc3c2)c1] 4-(2-(benzofuran-5-ylmethoxy)phenyl)-1H-imidazole;

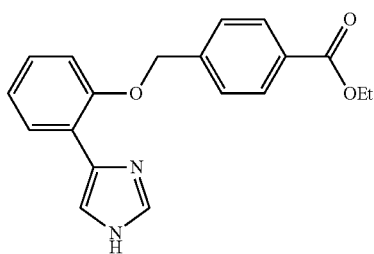 [SMILES: CCOC(=O)c1ccc(COc2ccccc2-c2c[nH]cn2)cc1] ethyl 4-((2-(1H-imidazol-4-yl)phenoxy)methyl)benzoate;
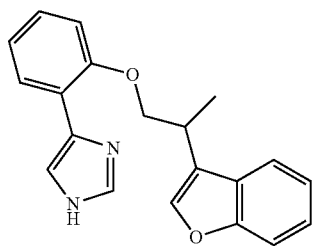 [SMILES: CC(COc1ccccc1-c1c[nH]cn1)c1coc2ccccc12] 4-(2-(2-(benzofuran-3-yl)propoxy)phenyl)-1H-imidazole;
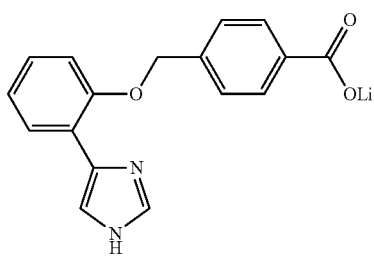 lithium 4-((2-(1H-imidazol-4-yl)phenoxy)methyl)benzoate;
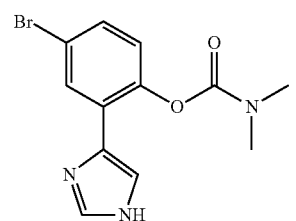 4-bromo-2-(1H-imidazol-4-yl)phenyl dimethylcarbamate;
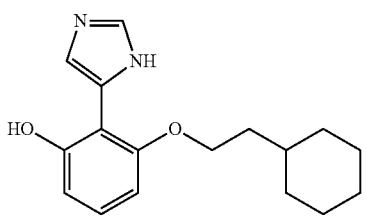 [SMILES: Oc1cccc(OCCC2CCCCC2)c1-c1cnc[nH]1] 3-(2-cyclohexylethoxy)-2-(1H-imidazol-5-yl)phenol;
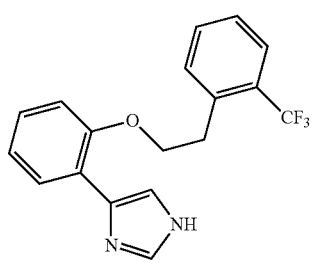 [SMILES: FC(F)(F)c1ccccc1CCOc1ccccc1-c1c[nH]cn1] 4-(2-(2-(trifluoromethyl)phenethoxy)phenyl)-1H-imidazole;

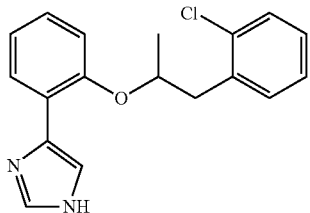 4-(2-(1-(2-chlorophenyl)propan-2-yloxy)phenyl)-1H-imidazole;
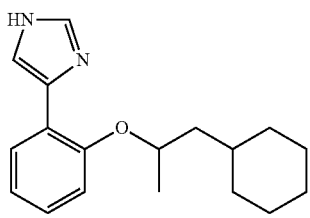 [SMILES: CC(CC1CCCCC1)Oc1ccccc1-c1c[nH]cn1] 4-(2-(1-cyclohexylpropan-2-yloxy)phenyl)-1H-imidazole;
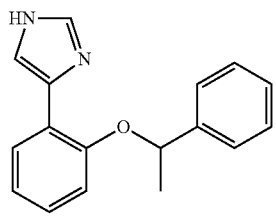 4-(2-(1-phenylethoxy)phenyl)-1H-imidazole;
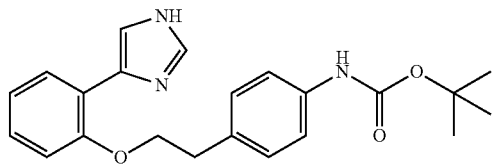 [SMILES: CC(C)(C)OC(=O)Nc1ccc(CCOc2ccccc2-c2c[nH]cn2)cc1] tert-butyl 4-(2-(2-(1H-imidazol-4-yl)phenoxy)ethyl)phenylcarbamate;
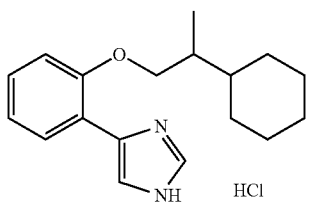 [SMILES: CC(COc1ccccc1-c1c[nH]cn1)C1CCCCC1 ; Cl] 4-(2-(2-cyclohexylpropoxy)phenyl)-1H-imidazole hydrochloride;
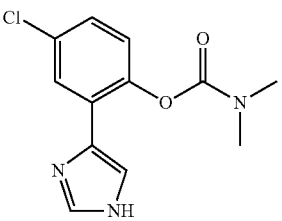 [SMILES: CN(C)C(=O)Oc1ccc(Cl)cc1-c1c[nH]cn1] 4-chloro-2-(1H-imidazol-4-yl)phenyl dimethylcarbamate;
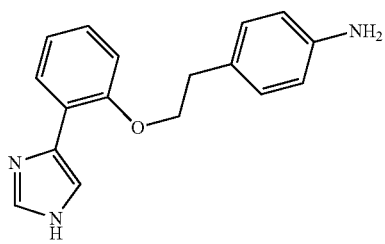 [SMILES: Nc1ccc(CCOc2ccccc2-c2c[nH]cn2)cc1] 4-(2-(2-(1H-imidazol-4-yl)phenoxy)ethyl)aniline;

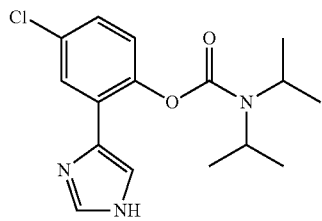 [SMILES: CC(C)N(C(=O)Oc1ccc(Cl)cc1-c1c[nH]cn1)C(C)C]
4-chloro-2-(1H-imidazol-4-yl)phenyl diisopropylcarbamate;

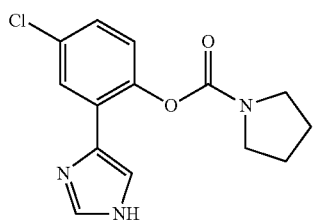 [SMILES: O=C(Oc1ccc(Cl)cc1-c1c[nH]cn1)N1CCCC1]
4-chloro-2-(1H-imidazol-4-yl)phenyl pyrrolidine-1-carboxylate;

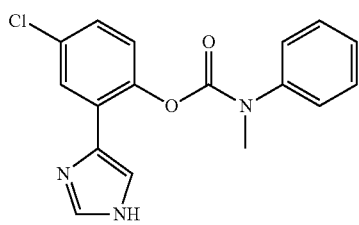 [SMILES: CN(C(=O)Oc1ccc(Cl)cc1-c1c[nH]cn1)c1ccccc1]
4-chloro-2-(1H-imidazol-4-yl)phenyl methyl(phenyl)carbamate;

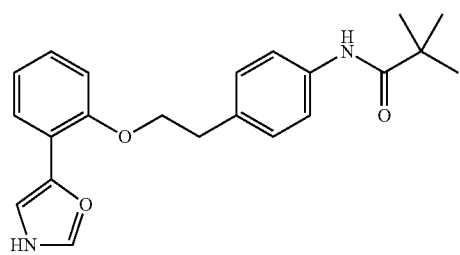
N-(4-(2-(2-(1H-imidazol-4-yl)phenoxy)ethyl)phenyl)pivalamide;

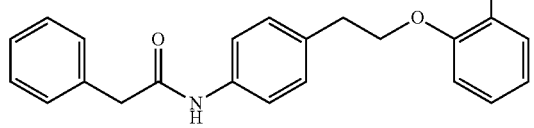
N-(4-(2-(2-(1H-imidazol-4-yl)phenoxy)ethyl)phenyl)-2-phenylacetamide;

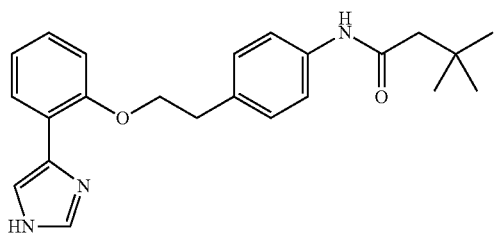 [SMILES: CC(C)(C)CC(=O)Nc1ccc(CCOc2ccccc2-c2c[nH]cn2)cc1]
N-(4-(2-(2-(1H-imidazol-4-yl)phenoxy)ethyl)phenyl)-3,3-dimethylbutanamide;

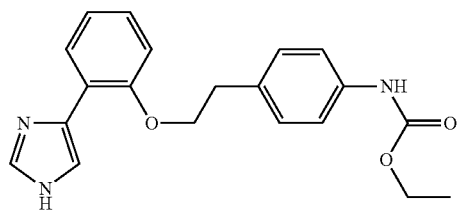 [SMILES: CCOC(=O)Nc1ccc(CCOc2ccccc2-c2c[nH]cn2)cc1]
ethyl 4-(2-(2-(1H-imidazol-4-yl)phenoxy)ethyl)phenylcarbamate;

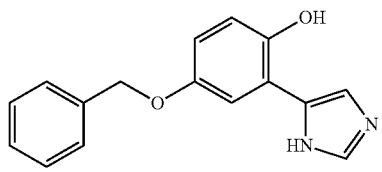 [SMILES: Oc1ccc(OCc2ccccc2)cc1-c1cnc[nH]1] 4-(benzyloxy)-2-(1H-imidazol-5-yl)phenol;
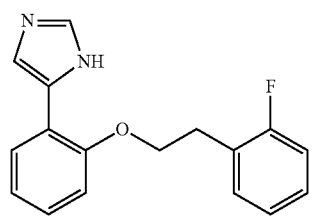 5-(2-(2-fluorophenethoxy)phenyl)-1H-imidazole;
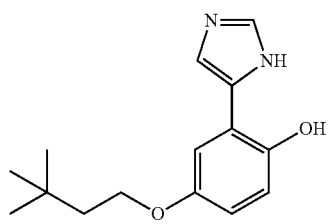 [SMILES: CC(C)(C)CCOc1ccc(O)c(-c2cnc[nH]2)c1] 4-(3,3-dimethylbutoxy)-2-(1H-imidazol-5-yl)phenol;
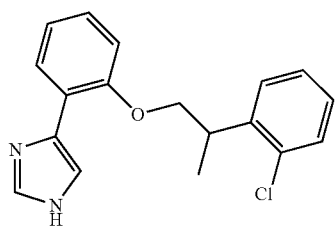 [SMILES: CC(COc1ccccc1-c1c[nH]cn1)c1ccccc1Cl] 4-(2-(2-(2-chlorophenyl)propoxy)phenyl)-1H-imidazole;
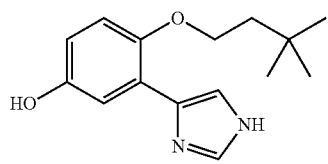 [SMILES: CC(C)(C)CCOc1ccc(O)cc1-c1c[nH]cn1] 4-(3,3-dimethylbutoxy)-3-(1H-imidazol-4-yl)phenol;
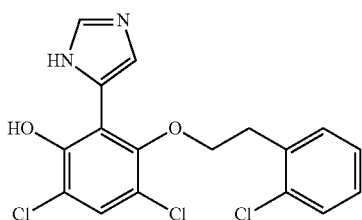 [SMILES: Oc1c(Cl)cc(Cl)c(OCCc2ccccc2Cl)c1-c1cnc[nH]1] 4,6-dichloro-3-(2-chlorophenethoxy)-2-(1H-imidazol-5-yl)phenol;
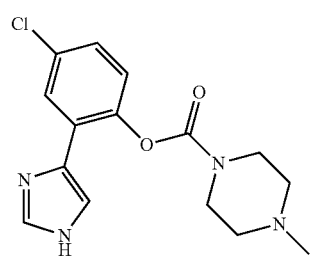 [SMILES: CN1CCN(C(=O)Oc2ccc(Cl)cc2-c2c[nH]cn2)CC1] 4-chloro-2-(1H-imidazol-4-yl)phenyl 4-methylpiperazine-1-carboxylate;

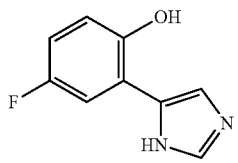 [SMILES: Oc1ccc(F)cc1-c1cnc[nH]1] 4-fluoro-2-(1H-imidazol-5-yl)phenol;
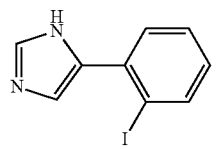 [SMILES: Ic1ccccc1-c1cnc[nH]1] 5-(2-iodophenyl)-1H-imidazole;
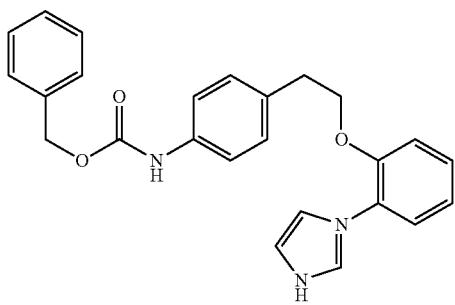 benzyl 4-(2-(2-(1H-imidazol-4-yl)phenoxy)ethyl)phenylcarbamate;
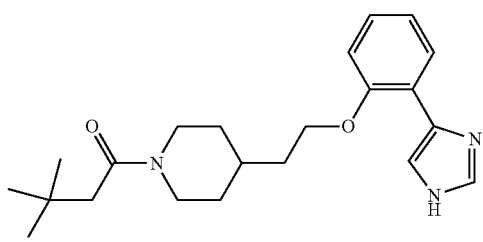 [SMILES: CC(C)(C)CC(=O)N1CCC(CCOc2ccccc2-c2c[nH]cn2)CC1] 1-(4-(2-(2-(1H-imidazol-4-yl)phenoxy)ethyl)piperidin-1-yl)-3,3-dimethylbutan-1-one;
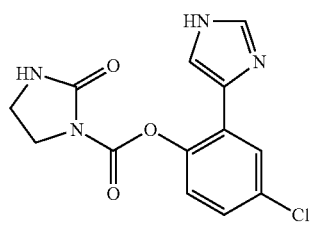 [SMILES: O=C1NCCN1C(=O)Oc1ccc(Cl)cc1-c1c[nH]cn1] 4-chloro-2-(1H-imidazol-4-yl)phenyl 2-oxoimidazolidine-1-carboxylate;
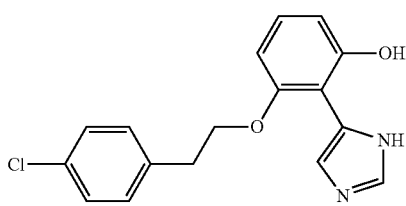 [SMILES: Oc1cccc(OCCc2ccc(Cl)cc2)c1-c1cnc[nH]1] 3-(4-chlorophenethoxy)-2-(1H-imidazol-5-yl)phenol;
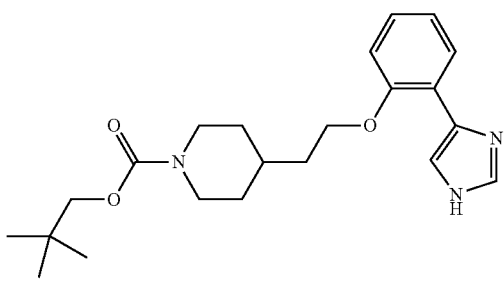 [SMILES: CC(C)(C)COC(=O)N1CCC(CCOc2ccccc2-c2c[nH]cn2)CC1] neopentyl 4-(2-(2-(1H-imidazol-4-yl)phenoxy)ethyl)piperidine-1-carboxylate

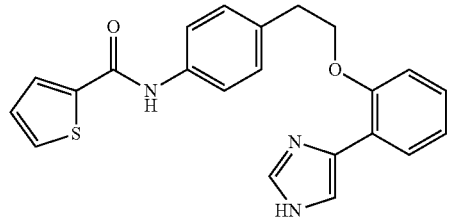 [SMILES: O=C(Nc1ccc(CCOc2ccccc2-c2c[nH]cn2)cc1)c1cccs1]
N-(4-(2-(2-(1H-imidazol-4-yl)phenoxy)ethyl)phenyl)thiophene-2-carboxamide;
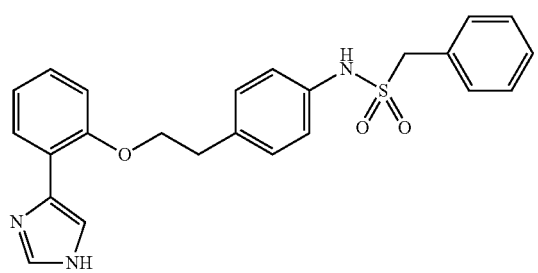 [SMILES: O=S(=O)(Cc1ccccc1)Nc1ccc(CCOc2ccccc2-c2c[nH]cn2)cc1]
N-(4-(2-(2-(1H-imidazol-4-yl)phenoxy)ethyl)phenyl)-1-phenylmethanesulfonamide;
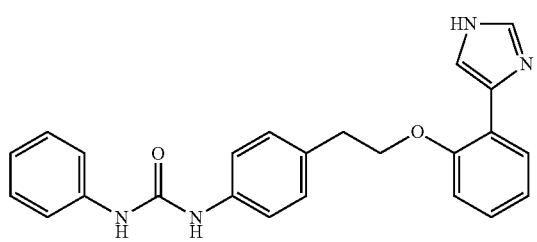 [SMILES: O=C(Nc1ccccc1)Nc1ccc(CCOc2ccccc2-c2c[nH]cn2)cc1]
1-(4-(2-(2-(1H-imidazol-4-yl)phenoxy)ethyl)phenyl)-3-phenylurea;
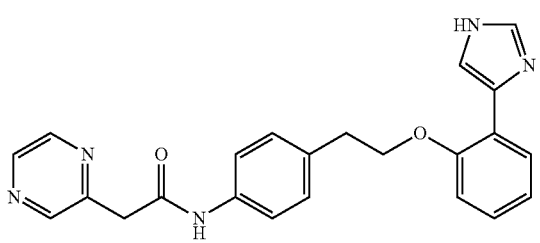 [SMILES: O=C(Cc1cnccn1)Nc1ccc(CCOc2ccccc2-c2c[nH]cn2)cc1]
N-(4-(2-(2-(1H-imidazol-4-yl)phenoxy)ethyl)phenyl)-2-(pyrazin-2-yl)acetamide;
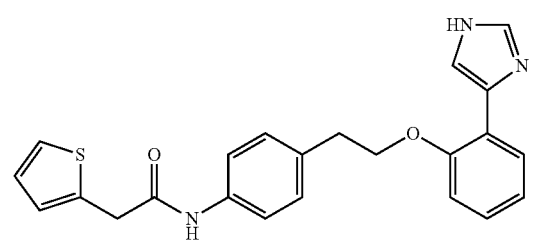 [SMILES: O=C(Cc1cccs1)Nc1ccc(CCOc2ccccc2-c2c[nH]cn2)cc1]
N-(4-(2-(2-(1H-imidazol-4-yl)phenoxy)ethyl)phenyl)-2-(thiophen-2-yl)acetamide;
or a pharmaceutically acceptable salt thereof.

In another aspect, the invention provides the compound, that is,

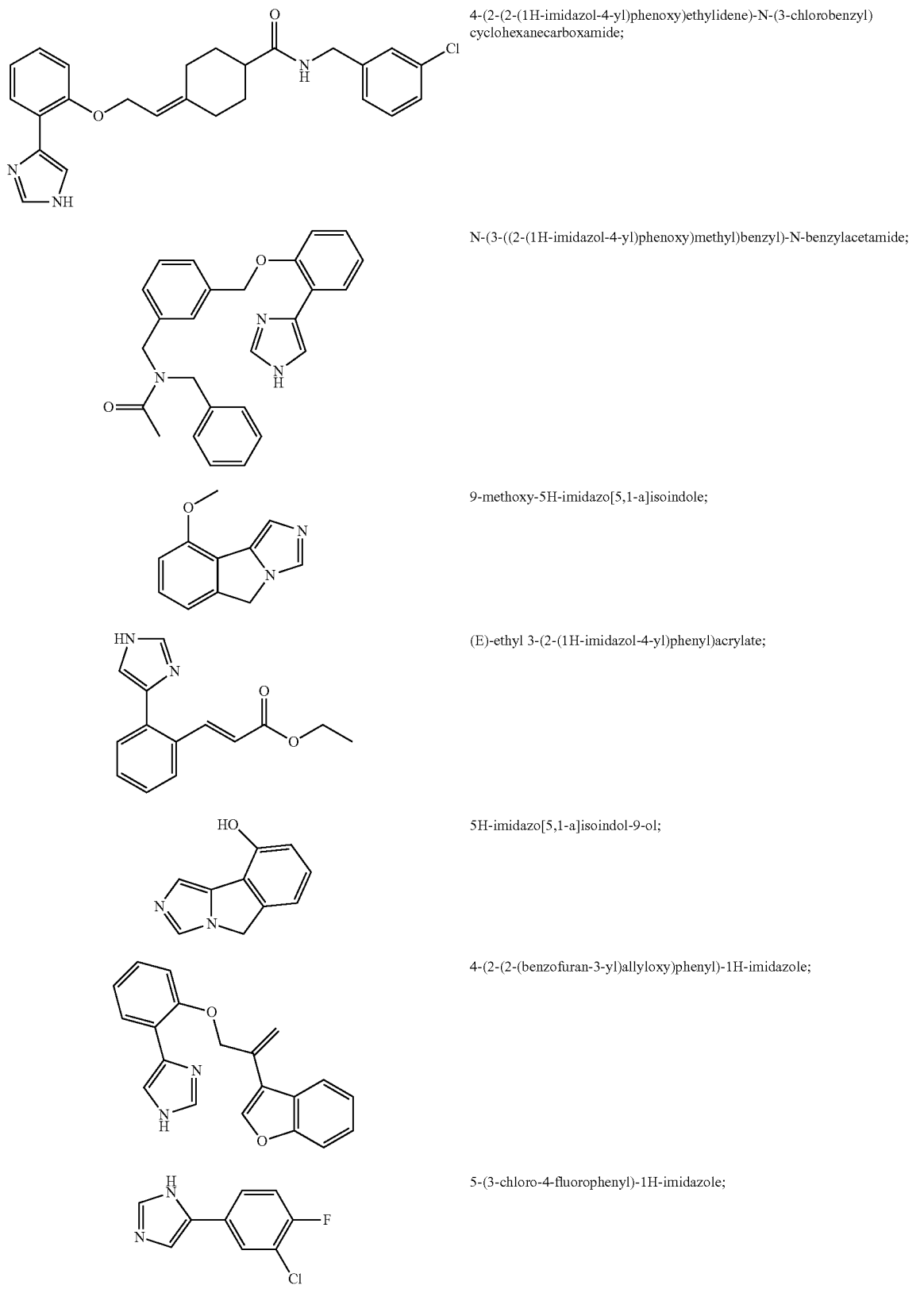

4-(2-(2-(1H-imidazol-4-yl)phenoxy)ethylidene)-N-(3-chlorobenzyl) cyclohexanecarboxamide;

N-(3-((2-(1H-imidazol-4-yl)phenoxy)methyl)benzyl)-N-benzylacetamide;

9-methoxy-5H-imidazo[5,1-a]isoindole;

(E)-ethyl 3-(2-(1H-imidazol-4-yl)phenyl)acrylate;

5H-imidazo[5,1-a]isoindol-9-ol;

4-(2-(2-(benzofuran-3-yl)allyloxy)phenyl)-1H-imidazole;

5-(3-chloro-4-fluorophenyl)-1H-imidazole;

-continued
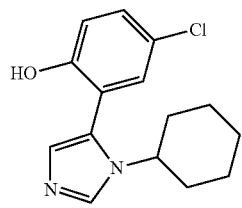 [SMILES: Oc1ccc(Cl)cc1-c1cncn1C1CCCCC1]
4-chloro-2-(1-cyclohexyl-1H-imidazol-5-yl)phenol;
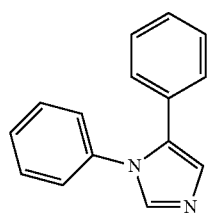 [SMILES: c1ccc(-c2cncn2-c2ccccc2)cc1]
1,5-diphenyl-1H-imidazole;
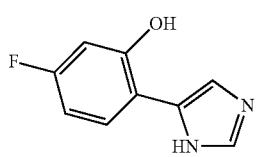 [SMILES: Oc1cc(F)ccc1-c1cnc[nH]1]
5-fluoro-2-(1H-imidazol-5-yl)phenol;
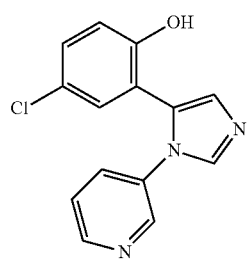
4-chloro-2-(1-(pyridin-3-yl)-1H-imidazol-5-yl)phenol;
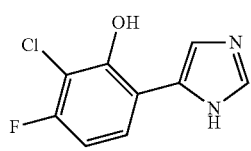 [SMILES: Oc1c(-c2cnc[nH]2)ccc(F)c1Cl]
2-chloro-3-fluoro-6-(1H-imidazol-5-yl)phenol;
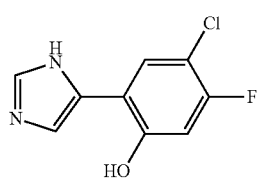 [SMILES: Oc1cc(F)c(Cl)cc1-c1cnc[nH]1]
4-chloro-5-fluoro-2-(1H-imidazol-5-yl)phenol;
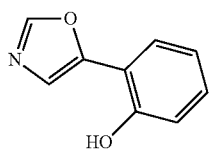 [SMILES: Oc1ccccc1-c1cnco1]
2-(oxazol-5-yl)phenol;
or a pharmaceutically acceptable salt thereof.

In another aspect, the invention provides compounds according to formula (VII),

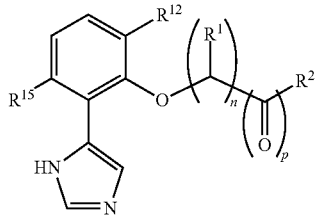

(VII)

a tautomer thereof, or a pharmaceutically acceptable salt thereof, wherein n is 1, 2, or 3;
p is 0 or 1;
each $R^1$ is independently hydrogen or methyl;
$R^{12}$ is hydrogen or halogen;
$R^{15}$ is hydrogen or hydroxy; and
$R^2$ is $C_3$-$C_8$cycloalkyl, $C_3$-$C_8$cycloalkenyl, heterocyclyl, aryl, or heteroaryl, each optionally substituted with one $R^{20}$ group and optionally substituted with one $R^{21}$ group, wherein $R^{20}$ is halogen, —C(O)R, —C(O)OR, —N(H)R, —N(H)C(O)C(H)($R^{22}$)R, —N(H)S(O)$_2$R, —N(H)C(O)R, —N(H)C(O)OR, —N(H)C(O)N(H)R, heteroaryl, heterocyclyl, wherein $R^{22}$ is —N($R^{23}$)$_2$ or —N(H)C(O)$R^{23}$, wherein $R^{23}$ is hydrogen or $C_1$-$C_6$ alkyl;
$R^{21}$ is halogen or trifluoromethyl; and
R is hydrogen, $C_1$-$C_6$ alkyl, aryl, heteroaryl, $C_3$-$C_8$cycloalkyl, heterocyclyl, aryl($C_1$-$C_6$)alkyl, heteroaryl($C_1$-$C_6$)alkyl, heterocyclyl($C_1$-$C_6$)alkyl, wherein the heterocyclyl, aryl, heteroaryl, cycloalkyl, heterocyclyl, heterocyclylalkyl, arylalkyl, and heteroarylalkyl are each optionally substituted with one group that is halogen, cyano, nitro, —O$R^{10}$, —N($R^{10}$)$_2$, —C(O)O$R^{10}$, —C(O)N($R^{10}$)$_2$, —C(O)$R^{10}$, or $C_1$-$C_6$ alkyl, wherein each $R^{10}$ is independently hydrogen, $C_1$-$C_6$ alkyl, $C_3$-$C_8$cycloalkyl, heterocyclyl, aryl, or heteroaryl, provided that the compound is not
4-(2-(2-bromophenethoxy)phenyl)-1H-imidazole;
3-(2-chlorophenethoxy)-2-(1H-imidazol-5-yl)phenol;
5-(2-(4-chlorobenzyloxy)phenyl)-1H-imidazole;
4-(2-(2-chlorophenethoxy)phenyl)-1H-imidazole;
4-(2-(2-cyclohexylethoxy)phenyl)-1H-imidazole;
4-(2-(2-cyclopropylethoxy)phenyl)-1H-imidazole;
5-(2-(2-cyclopentylethoxy)phenyl)-1H-imidazole;
4-(2-phenethoxyphenyl)-1H-imidazole;
5-(2-(3-chlorobenzyloxy)phenyl)-1H-imidazole;
4-(2-(3-chlorophenethoxy)phenyl)-1H-imidazole;
N-(4-(2-(2-(1H-imidazol-4-yl)phenoxy)ethyl)phenyl)acetamide;
N-(3-(2-(2-(1H-imidazol-4-yl)phenoxy)ethyl)phenyl)acetamide;
5-(2-(3-phenylpropoxy)phenyl)-1H-imidazole;
4-(2-(benzyloxy)phenyl)-1H-imidazole;
4-(3-bromo-2-(4-chlorobenzyloxy)phenyl)-1H-imidazole;
4-(2-(4-chlorophenethoxy)phenyl)-1H-imidazole;
3-(4-chlorobenzyloxy)-2-(1H-imidazol-5-yl)phenol;
4-(2-(2-chlorobenzyloxy)phenyl)-1H-imidazole;
3-((2-(1H-imidazol-4-yl)phenoxy)methyl)piperidine;
1-(4-((2-(1H-imidazol-4-yl)phenoxy)methyl)piperidin-1-yl)ethanone;
1-(3-((2-(1H-imidazol-4-yl)phenoxy)methyl)piperidin-1-yl)ethanone;
4-(2-(2-bromophenethoxy)phenyl)-1H-imidazole;
tert-butyl 4-(2-(2-(1H-imidazol-4-yl)phenoxy)ethyl)piperidine-1-carboxylate;
1-(4-(2-(2-(1H-imidazol-4-yl)phenoxy)ethyl)piperidin-1-yl)ethanone;
4-((2-(1H-imidazol-4-yl)phenoxy)methyl)piperidine;
N-(2-(2-(1H-imidazol-4-yl)phenoxy)ethyl)phenyl)acetamide;
4-((2-(1H-imidazol-5-yl)phenoxy)methyl)-7-methoxy-2H-chromen-2-one;
3-(2-(2-(1H-imidazol-5-yl)phenoxy)ethyl)-1H-indole;
2-(2-(1H-imidazol-5-yl)phenoxy)-1-(4-(pyrrolidin-1-yl)phenyl)ethanone;
2-(2-(1H-imidazol-5-yl)phenoxy)-1-(benzofuran-2-yl)ethanone;
2-(2-(1H-imidazol-5-yl)phenoxy)-1-(thiazol-2-yl)ethanone;
2-(2-(1H-imidazol-5-yl)phenoxy)-1-(benzofuran-5-yl)ethanone;
2-(3-(2-(1H-imidazol-5-yl)phenoxy)propyl)isoindoline-1,3-dione;
2-(2-(1H-imidazol-5-yl)phenoxy)-1-(4-(diethylamino)phenyl)ethanone;
2-(2-(1H-imidazol-5-yl)phenoxy)-1-(thiophen-3-yl)ethanone;
2-(2-(1H-imidazol-5-yl)phenoxy)-1-(thiophen-2-yl)ethanone;
2-(2-(1H-imidazol-5-yl)phenoxy)-1-(benzofuran-3-yl)ethanone;
2-(2-(1H-imidazol-5-yl)phenoxy)-1-(pyridin-2-yl)ethanone;
2-(2-(1H-imidazol-5-yl)phenoxy)-1-(pyridin-4-yl)ethanone;
1-(2-(2-(1H-imidazol-5-yl)phenoxy)ethyl)-1H-pyrazole;
2-(2-(1H-imidazol-5-yl)phenoxy)-1-(benzo[b]thiophen-5-yl)ethanone;
2-(2-(2-(1H-imidazol-5-yl)phenoxy)ethyl)isoindoline-1,3-dione;
2-(2-(1H-imidazol-5-yl)phenoxy)-1-(3-phenylisoxazol-5-yl)ethanone;
5-(2-(2-(2,3-dihydrobenzofuran-5-yl)ethoxy)phenyl)-1H-imidazole;
5-(2-(1-phenylpropan-2-yloxy)phenyl)-1H-imidazole;
3-(2-(2-(1H-imidazol-5-yl)phenoxy)acetyl)-2H-chromen-2-one;
2-(2-(1H-imidazol-5-yl)phenoxy)-2,3-dihydro-1H-inden-1-one;
5-(2-((2,3-dihydrobenzo[b][1,4]dioxin-2-yl)methoxy)phenyl)-1H-imidazole;
5-(2-(2-(1H-pyrrol-1-yl)ethoxy)phenyl)-1H-imidazole;
2-((2-(1H-imidazol-5-yl)phenoxy)methyl)-1H-benzo[d]imidazole;
6-(2-(2-(1H-imidazol-5-yl)phenoxy)acetyl)-2H-benzo[b][1,4]oxazin-3(4H)-one;
6-(2-(2-(1H-imidazol-5-yl)phenoxy)acetyl)benzo[d]oxazol-2(3H)-one;
2-((2-(1H-imidazol-5-yl)phenoxy)methyl)pyridine;
5-((2-(1H-imidazol-5-yl)phenoxy)methyl)-2-chloropyridine;
4-((2-(1H-imidazol-5-yl)phenoxy)methyl)pyridine;
2-((2-(1H-imidazol-5-yl)phenoxy)methyl)quinazolin-4(3H)-one;
2-((2-(1H-imidazol-5-yl)phenoxy)methyl)quinoline;
3-((2-(1H-imidazol-5-yl)phenoxy)methyl)quinoxalin-2(1H)-one;
3-((2-(1H-imidazol-5-yl)phenoxy)methyl)benzo[d]thiazol-2(3H)-one;
5-(2-(naphthalen-2-ylmethoxy)phenyl)-1H-imidazole; and
5-(2-(2-(naphthalen-1-yl)ethoxy)phenyl)-1H-imidazole.

The invention further comprises subgenera of formula (VII) in which the substituents are selected as any and all combinations of one or more of structural formula (VII), R, $R^1$, $R^2$, $R^{12}$, $R^{15}$, $R^{20}$, and $R^{21}$, as defined herein, including without limitation, the following:

Structural Formula VII is One of Formulae (VIIa)-(VIIe):

(VIIa)

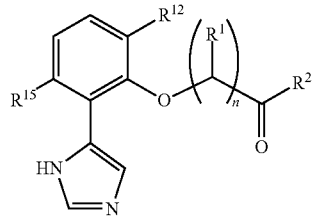

(VIIb)

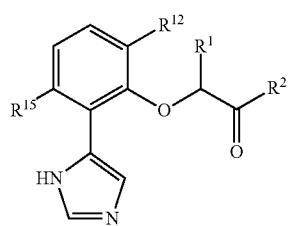

(VIIc)

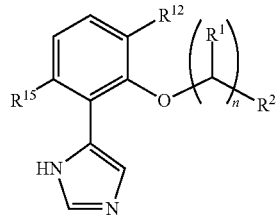

(VIId)

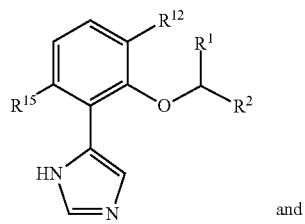

and (VIIe)

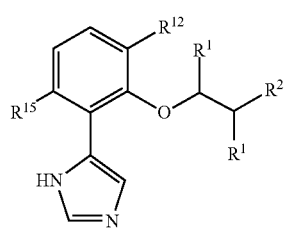

$R^1$ is Selected from One of the Following Groups (1a)-(1b):
(1a) at least one $R^1$ group is methyl, and the remaining $R^1$ groups are each independently hydrogen or methyl.
(1b) each $R^1$ group is hydrogen.

$R^{12}$ is Selected from One of the Following Groups (2a)-(2b):
(2a) hydrogen.
(2b) halogen.

$R^{15}$ is Selected from One of the Following Groups (3a)-(3b):
(3a) hydrogen.
(3b) hydroxy.

$R^2$ is Selected from One of the Following Groups (4a)-(4q):
(4a) $C_3$-$C_8$cycloalkyl, $C_3$-$C_8$cycloalkenyl, or heterocyclyl, each optionally substituted with one $R^{20}$ group and optionally substituted with one $R^{21}$ group.
(4b) $C_3$-$C_8$cycloalkyl, or $C_3$-$C_8$cycloalkenyl, each optionally substituted with one $R^{20}$ group and optionally substituted with one $R^{21}$ group.
(4c) cyclohexyl or cyclohexenyl, each optionally substituted with one $R^{20}$ group and optionally substituted with one $R^{21}$ group.
(4d) cyclohexyl or cyclohex-3-en-1-yl, each optionally substituted with one $R^{20}$ group and optionally substituted with one $R^{21}$ group.
(4e) heterocyclyl optionally substituted with one $R^{20}$ group and optionally substituted with one $R^{21}$ group.
(4f) piperidinyl optionally substituted with one $R^{20}$ group and optionally substituted with one $R^{21}$ group.
(4g) piperidin-4-yl optionally substituted with one $R^{20}$ group and optionally substituted with one $R^{21}$ group.
(4h) aryl or heteroaryl, each optionally substituted with one $R^{20}$ group and optionally substituted with one $R^{21}$ group.
(4i) aryl optionally substituted with one $R^{20}$ group and optionally substituted with one $R^{21}$ group.
(4j) phenyl or benzodioxolyl, optionally substituted with one $R^{20}$ group and optionally substituted with one $R^{21}$ group.
(4k) phenyl or benzo[d][1,3]dioxol-5-yl, each optionally substituted with one $R^{20}$ group and optionally substituted with one $R^{21}$ group.
(4l) phenyl optionally substituted with one $R^{20}$ group and optionally substituted with one $R^{21}$ group.
(4m) heteroaryl optionally substituted with one $R^{20}$ group and optionally substituted with one $R^{20}$ group.
(4n) benzothienyl, benzofuranyl, thienyl, benzoxazolyl, or pyridyl, each optionally substituted with one $R^{20}$ group and optionally substituted with one $R^{21}$ group.
(4o) benzothien-6-yl, benzofuran-5-yl, benzofuran-3-yl, thien-2-yl, thien-3-yl, benzo[d]xazol-2-yl, or pyrid-3-yl, each optionally substituted with one $R^{20}$ group and optionally substituted with one $R^{21}$ group.
(4p) any of groups (4a)-(4o), wherein $R^2$ is substituted with one $R^{20}$ group and optionally substituted with one $R^{21}$ group.
(4q) any of groups (4a)-(4o), wherein $R^2$ is substituted with one $R^{20}$ group and substituted with one $R^{21}$ group $R^{20}$, when Present, is Selected from One of the Following Groups (5a)-(5o):
(5a) —C(O)R, —C(O)OR, —N(H)R, —N(H)C(O)C(H)($R^{22}$)R, —N(H)S(O)$_2$R, —N(H)C(O)R, —N(H)C(O)OR, —N(H)C(O)N(H)R, heteroaryl, or heterocyclyl.
(5b) —C(O)R or —C(O)OR.
(5c) —N(H)C(O)C(H)($R^{22}$)R, —N(H)S(O)$_2$R, —N(H)C(O)R, —N(H)C(O)OR, or —N(H)C(O)N(H)R.
(5d) —N(H)S(O)$_2$R, —N(H)C(O)R, —N(H)C(O)OR, or —N(H)C(O)N(H)R.
(5e) —C(O)R.
(5f) —C(O)OR.
(5 g) —N(H)R.
(5h) —N(H)C(O)C(H)($R^{22}$)R.
(5i) —N(H)S(O)$_2$R.
(5j) —N(H)C(O)R.
(5k) —N(H)C(O)OR.
(5l) —N(H)C(O)N(H)R.
(5m) heteroaryl or heterocyclyl.
(5n) a 5-membered heteroaryl or a 5-membered heterocyclyl.
(5o) thienyl or pyrrolidinyl.

$R^{21}$, when Present, is Selected from One of the Following Groups (6a)-(6c):
(6a) halogen.
(6b) trifluoromethyl.
(6c) hydrogen (i.e., $R^2$ is not substituted with $R^{21}$).
R, when Present, is Selected from One of the Following Groups (7a)-(7u):
(7a) $C_1$-$C_6$ alkyl, aryl, heteroaryl, $C_3$-$C_8$cycloalkyl, heterocyclyl, aryl($C_1$-$C_6$)alkyl, heteroaryl($C_1$-$C_6$)alkyl, heterocyclyl($C_1$-$C_6$)alkyl, wherein the heterocyclyl, aryl, heteroaryl, cycloalkyl, heterocyclyl, heterocyclylalkyl, arylalkyl, and heteroarylalkyl are each optionally substituted with one group that is halogen, cyano, nitro, —$OR^{10}$, —$N(R^{10})_2$, or —$C(O)OR^{10}$, wherein each $R^{10}$ is independently hydrogen, $C_1$-$C_6$ alkyl, or heterocyclyl.
(7b) $C_1$-$C_6$ alkyl, aryl, heteroaryl, $C_3$-$C_8$cycloalkyl, heterocyclyl, aryl($C_1$-$C_6$)alkyl, heteroaryl($C_1$-$C_6$)alkyl, or heterocyclyl($C_1$-$C_6$)alkyl.
(7c) aryl($C_1$-$C_6$)alkyl, heteroaryl($C_1$-$C_6$)alkyl, or heterocyclyl($C_1$-$C_6$)alkyl, wherein the heterocyclylalkyl, arylalkyl, and heteroarylalkyl are each optionally substituted with one group that is halogen, cyano, nitro, —$OR^{10}$, —$N(R^{10})_2$, $C(O)OR^{10}$, —$C(O)NR^{10})_2$, —$C(O)R^{10}$, or $C_1$-$C_6$ alkyl, wherein each $R^{10}$ is independently hydrogen, $C_1$-$C_6$ alkyl, $C_3$-$C_8$cycloalkyl, heterocyclyl, aryl, or heteroaryl,
(7d) aryl($C_1$-$C_6$)alkyl, heteroaryl($C_1$-$C_6$)alkyl, or heterocyclyl($C_1$-$C_6$)alkyl, wherein the heterocyclylalkyl, arylalkyl, and heteroarylalkyl are each optionally substituted with one group that is halogen, cyano, nitro, —$OR^{10}$, —$N(R^{10})_2$, or —$C(O)OR^{10}$, wherein each $R^{10}$ is independently hydrogen, $C_1$-$C_6$ alkyl, or heterocyclyl.
(7e) aryl($C_1$-$C_6$)alkyl, heteroaryl($C_1$-$C_6$)alkyl, or heterocyclyl($C_1$-$C_6$)alkyl.
(7f) aryl($C_1$-$C_6$)alkyl optionally substituted with one group that is halogen, cyano, nitro, —$OR^{10}$, —$N(R^{10})_2$, or —$C(O)OR^{10}$, wherein each $R^{10}$ is independently hydrogen, $C_1$-$C_6$ alkyl, or heterocyclyl.
(7g) heteroaryl($C_1$-$C_6$)alkyl optionally substituted with one group that is halogen, cyano, nitro, —$OR^{10}$, —$N(R^{10})_2$, or —$C(O)OR^{10}$, wherein each $R^{10}$ is independently hydrogen, $C_1$-$C_6$ alkyl, or heterocyclyl.
(7h) heterocyclyl($C_1$-$C_6$)alkyl optionally substituted with one group that is halogen, cyano, nitro, —$OR^{10}$, —$N(R^{10})_2$, or —$C(O)OR^{10}$, wherein each $R^{10}$ is independently hydrogen, $C_1$-$C_6$ alkyl, or heterocyclyl.
(7i) methyl, ethyl, t-butyl, neopentyl, phenyl, thienyl, pyridyl, cyclohexyl, tetrahydropyranyl, piperidinyl, pyridonyl, pyrimidindionyl, benzyl, thienylmethyl, imidazolylmethyl, thiazolylmethyl, pyrimidinylmethyl, pyrazinylmethyl, tetrahydrofuranylmethyl, tetrahydropyranylmethyl, morpholinylmethyl, wherein each of the heterocyclyl, aryl, heteroaryl, cycloalkyl, heterocyclyl, heterocyclylalkyl, arylalkyl, and heteroarylalkyl groups are each optionally substituted with one group that is halogen, cyano, nitro, —$OR^{10}$, —$N(R^{10})_2$, or —$C(O)OR^{10}$, wherein each $R^{10}$ is independently hydrogen or $C_1$-$C_6$ alkyl.
(7j) methyl, ethyl, t-butyl, neopentyl, phenyl, 2-nitrophenyl, 3-nitrophenyl, 4-nitrophenyl, 2-aminophenyl, 3-aminophenyl, 4-aminophenyl, 2-carboxyphenyl, 3-carboxyphenyl, 4-carboxyphenyl, 4-methoxycarbonylphenyl, 3-methoxycarbonylphenyl, 3-(3-tetrahydrofur-3-yl)phenyl, 2-aminopyrid-3-yl, thien-2-yl, cyclohexyl, 2-aminocyclohexyl, trans-2-aminocyclohexyl, cis-2-aminocyclohexyl, tetrahydropyran-4-yl, piperidin-2-yl, pyrid-2-on-3-yl, pyrimidin-2,4-dion-5-yl, benzyl, thien-2-ylmethyl, imidazol-1-ylmethyl, thiazol-4-ylmethyl, 2-aminothiazol-4-ylmethyl, pyrimidin-2-ylmethyl, pyrimidin-5-ylmethyl, pyrazin-2-ylmethyl, tetrahydrofuran-2-ylmethyl, tetrahydropyran-4-ylmethyl, or morpholin-4-ylmethyl.
(7k) methyl, ethyl, t-butyl, or neopentyl.
(7l) phenyl, 2-nitrophenyl, 3-nitrophenyl, 4-nitrophenyl, 2-aminophenyl, 3-aminophenyl, 4-aminophenyl, 2-carboxyphenyl, 3-carboxyphenyl, 4-carboxyphenyl, 4-methoxycarbonylphenyl, 3-methoxycarbonylphenyl, 3-(3-tetrahydrofur-3-yl)phenyl, 2-aminopyrid-3-yl, thien-2-yl, cyclohexyl, 2-aminocyclohexyl, trans-2-aminocyclohexyl, cis-2-aminocyclohexyl, tetrahydropyran-4-yl, piperidin-2-yl, pyrid-2-on-3-yl, pyrimidin-2,4-dion-5-yl, benzyl, thien-2-ylmethyl, imidazol-1-ylmethyl, thiazol-4-ylmethyl, 2-aminothiazol-4-ylmethyl, pyrimidin-2-ylmethyl, pyrimidin-5-ylmethyl, pyrazin-2-ylmethyl, tetrahydrofuran-2-ylmethyl, tetrahydropyran-4-ylmethyl, or morpholin-4-ylmethyl.
(7m) 2-aminocyclohexyl.
(7n) trans-2-aminocyclohexyl.
(7o) cis-2-aminocyclohexyl.
(7p) phenyl, 2-nitrophenyl, 3-nitrophenyl, 4-nitrophenyl, 2-aminophenyl, 3-aminophenyl, 4-aminophenyl, 2-carboxyphenyl, 3-carboxyphenyl, 4-carboxyphenyl, 4-methoxycarbonylphenyl, 3-methoxycarbonylphenyl, 3-(3-tetrahydrofur-3-yl)phenyl, 2-aminopyrid-3-yl, or thien-2-yl.
(7q) cyclohexyl, 2-aminocyclohexyl, trans-2-aminocyclohexyl, cis-2-aminocyclohexyl, tetrahydropyran-4-yl, piperidin-2-yl, pyrid-2-on-3-yl, or pyrimidin-2,4-dion-5-yl.
(7r) benzyl, thien-2-ylmethyl, imidazol-1-ylmethyl, thiazol-4-ylmethyl, 2-aminothiazol-4-ylmethyl, pyrimidin-2-ylmethyl, pyrimidin-5-ylmethyl, pyrazin-2-ylmethyl, tetrahydrofuran-2-ylmethyl, tetrahydropyran-4-ylmethyl, or morpholin-4-ylmethyl.
(7s) benzyl.
(7t) thien-2-ylmethyl, imidazol-1-ylmethyl, thiazol-4-ylmethyl, 2-aminothiazol-4-ylmethyl, pyrimidin-2-ylmethyl, pyrimidin-5-ylmethyl, or pyrazin-2-ylmethyl.
(7u) tetrahydrofuran-2-ylmethyl, tetrahydropyran-4-ylmethyl, or morpholin-4-ylmethyl.

Particular embodiments of this aspect of the invention include compounds of any one of the formulae (VII) and (VIIa)-(VIIe), each as defined in each of the following rows, wherein each entry is a group number as defined above (e.g., (1b) refers to $R^1$ is hydrogen), and a dash "-" indicates that the variable is as defined for formula (VII) or defined according to any one of the applicable variable definitions (1a)-(7u) [e.g., when $R^1$ is a dash, it can be either as defined for Formula (VII) or any one of definitions (1a)-(1b)]:

|        | $R^1$ | $R^{12}$ | $R^{15}$ | $R^2$ | $R^{20}$ | $R^{21}$ | R |
|--------|-------|----------|----------|-------|----------|----------|---|
| (7)-1  | —     | —        | —        | 4a    | —        | 6c       | — |
| (7)-2  | —     | —        | —        | 4b    | —        | 6c       | — |
| (7)-3  | —     | —        | —        | 4c    | —        | 6c       | — |
| (7)-4  | —     | —        | —        | 4d    | —        | 6c       | — |
| (7)-5  | —     | —        | 3a       | 4a    | —        | 6c       | — |
| (7)-6  | —     | —        | 3a       | 4b    | —        | 6c       | — |
| (7)-7  | —     | —        | 3a       | 4c    | —        | 6c       | — |
| (7)-8  | —     | —        | 3a       | 4d    | —        | 6c       | — |
| (7)-9  | —     | —        | 3b       | 4a    | —        | 6c       | — |
| (7)-10 | —     | —        | 3b       | 4b    | —        | 6c       | — |
| (7)-11 | —     | —        | 3b       | 4c    | —        | 6c       | — |
| (7)-12 | —     | —        | 3b       | 4d    | —        | 6c       | — |

|  | R¹ | R¹² | R¹⁵ | R² | R²⁰ | R²¹ | R |
|---|---|---|---|---|---|---|---|
| (7)-13 | — | 2a | — | 4a | — | 6c | — |
| (7)-14 | — | 2a | — | 4b | — | 6c | — |
| (7)-15 | — | 2a | — | 4c | — | 6c | — |
| (7)-16 | — | 2a | — | 4d | — | 6c | — |
| (7)-17 | — | 2a | 3a | 4a | — | 6c | — |
| (7)-18 | — | 2a | 3a | 4b | — | 6c | — |
| (7)-19 | — | 2a | 3a | 4c | — | 6c | — |
| (7)-20 | — | 2a | 3a | 4d | — | 6c | — |
| (7)-21 | — | 2a | 3b | 4a | — | 6c | — |
| (7)-22 | — | 2a | 3b | 4b | — | 6c | — |
| (7)-23 | — | 2a | 3b | 4c | — | 6c | — |
| (7)-24 | — | 2a | 3b | 4d | — | 6c | — |
| (7)-25 | — | 2b | — | 4a | — | 6c | — |
| (7)-26 | — | 2b | — | 4b | — | 6c | — |
| (7)-27 | — | 2b | — | 4c | — | 6c | — |
| (7)-28 | — | 2b | — | 4d | — | 6c | — |
| (7)-29 | — | 2b | 3a | 4a | — | 6c | — |
| (7)-30 | — | 2b | 3a | 4b | — | 6c | — |
| (7)-31 | — | 2b | 3a | 4c | — | 6c | — |
| (7)-32 | — | 2b | 3a | 4d | — | 6c | — |
| (7)-33 | — | 2b | 3b | 4a | — | 6c | — |
| (7)-34 | — | 2b | 3b | 4b | — | 6c | — |
| (7)-35 | — | 2b | 3b | 4c | — | 6c | — |
| (7)-36 | — | 2b | 3b | 4d | — | 6c | — |
| (7)-37 | 1a | — | — | 4a | — | 6c | — |
| (7)-38 | 1a | — | — | 4b | — | 6c | — |
| (7)-39 | 1a | — | — | 4c | — | 6c | — |
| (7)-40 | 1a | — | — | 4d | — | 6c | — |
| (7)-41 | 1a | — | 3a | 4a | — | 6c | — |
| (7)-42 | 1a | — | 3a | 4b | — | 6c | — |
| (7)-43 | 1a | — | 3a | 4c | — | 6c | — |
| (7)-44 | 1a | — | 3a | 4d | — | 6c | — |
| (7)-45 | 1a | — | 3b | 4a | — | 6c | — |
| (7)-46 | 1a | — | 3b | 4b | — | 6c | — |
| (7)-47 | 1a | — | 3b | 4c | — | 6c | — |
| (7)-48 | 1a | — | 3b | 4d | — | 6c | — |
| (7)-49 | 1a | 2a | — | 4a | — | 6c | — |
| (7)-50 | 1a | 2a | — | 4b | — | 6c | — |
| (7)-51 | 1a | 2a | — | 4c | — | 6c | — |
| (7)-52 | 1a | 2a | — | 4d | — | 6c | — |
| (7)-53 | 1a | 2a | 3a | 4a | — | 6c | — |
| (7)-54 | 1a | 2a | 3a | 4b | — | 6c | — |
| (7)-55 | 1a | 2a | 3a | 4c | — | 6c | — |
| (7)-56 | 1a | 2a | 3a | 4d | — | 6c | — |
| (7)-57 | 1a | 2a | 3b | 4a | — | 6c | — |
| (7)-58 | 1a | 2a | 3b | 4b | — | 6c | — |
| (7)-59 | 1a | 2a | 3b | 4c | — | 6c | — |
| (7)-60 | 1a | 2a | 3b | 4d | — | 6c | — |
| (7)-61 | 1a | 2b | — | 4a | — | 6c | — |
| (7)-62 | 1a | 2b | — | 4b | — | 6c | — |
| (7)-63 | 1a | 2b | — | 4c | — | 6c | — |
| (7)-64 | 1a | 2b | — | 4d | — | 6c | — |
| (7)-65 | 1a | 2b | 3a | 4a | — | 6c | — |
| (7)-66 | 1a | 2b | 3a | 4b | — | 6c | — |
| (7)-67 | 1a | 2b | 3a | 4c | — | 6c | — |
| (7)-68 | 1a | 2b | 3a | 4d | — | 6c | — |
| (7)-69 | 1a | 2b | 3b | 4a | — | 6c | — |
| (7)-70 | 1a | 2b | 3b | 4b | — | 6c | — |
| (7)-71 | 1a | 2b | 3b | 4c | — | 6c | — |
| (7)-72 | 1a | 2b | 3b | 4d | — | 6c | — |
| (7)-73 | 1b | — | — | 4a | — | 6c | — |
| (7)-74 | 1b | — | — | 4b | — | 6c | — |
| (7)-75 | 1b | — | — | 4c | — | 6c | — |
| (7)-76 | 1b | — | — | 4d | — | 6c | — |
| (7)-77 | 1b | — | 3a | 4a | — | 6c | — |
| (7)-78 | 1b | — | 3a | 4b | — | 6c | — |
| (7)-79 | 1b | — | 3a | 4c | — | 6c | — |
| (7)-80 | 1b | — | 3a | 4d | — | 6c | — |
| (7)-81 | 1b | — | 3b | 4a | — | 6c | — |
| (7)-82 | 1b | — | 3b | 4b | — | 6c | — |
| (7)-83 | 1b | — | 3b | 4c | — | 6c | — |
| (7)-84 | 1b | — | 3b | 4d | — | 6c | — |
| (7)-85 | 1b | 2a | — | 4a | — | 6c | — |
| (7)-86 | 1b | 2a | — | 4b | — | 6c | — |
| (7)-87 | 1b | 2a | — | 4c | — | 6c | — |
| (7)-88 | 1b | 2a | — | 4d | — | 6c | — |
| (7)-89 | 1b | 2a | 3a | 4a | — | 6c | — |
| (7)-90 | 1b | 2a | 3a | 4b | — | 6c | — |
| (7)-91 | 1b | 2a | 3a | 4c | — | 6c | — |
| (7)-92 | 1b | 2a | 3a | 4d | — | 6c | — |
| (7)-93 | 1b | 2a | 3b | 4a | — | 6c | — |
| (7)-94 | 1b | 2a | 3b | 4b | — | 6c | — |
| (7)-95 | 1b | 2a | 3b | 4c | — | 6c | — |
| (7)-96 | 1b | 2a | 3b | 4d | — | 6c | — |
| (7)-97 | 1b | 2b | — | 4a | — | 6c | — |
| (7)-98 | 1b | 2b | — | 4b | — | 6c | — |
| (7)-99 | 1b | 2b | — | 4c | — | 6c | — |
| (7)-100 | 1b | 2b | — | 4d | — | 6c | — |
| (7)-101 | 1b | 2b | 3a | 4a | — | 6c | — |
| (7)-102 | 1b | 2b | 3a | 4b | — | 6c | — |
| (7)-103 | 1b | 2b | 3a | 4c | — | 6c | — |
| (7)-104 | 1b | 2b | 3a | 4d | — | 6c | — |
| (7)-105 | 1b | 2b | 3b | 4a | — | 6c | — |
| (7)-106 | 1b | 2b | 3b | 4b | — | 6c | — |
| (7)-107 | 1b | 2b | 3b | 4c | — | 6c | — |
| (7)-108 | 1b | 2b | 3b | 4d | — | 6c | — |
| (7)-109 | 1b | 2a | 3a | 4e | 5a | 6c | 7a |
| (7)-110 | 1b | 2a | 3a | 4f | 5a | 6c | 7a |
| (7)-111 | 1b | 2a | 3a | 4e | 5a | 6c | 7a |
| (7)-112 | 1b | 2a | 3a | 4f | 5b | 6c | 7a |
| (7)-113 | 1b | 2a | 3a | 4g | 5b | 6c | 7a |
| (7)-114 | 1b | 2a | 3a | 4e | 5b | 6c | 7a |
| (7)-115 | 1b | 2a | 3a | 4f | 5e | 6c | 7a |
| (7)-116 | 1b | 2a | 3a | 4g | 5e | 6c | 7a |
| (7)-117 | 1b | 2a | 3a | 4e | 5e | 6c | 7a |
| (7)-118 | 1b | 2a | 3a | 4f | 5a | 6c | 7c |
| (7)-119 | 1b | 2a | 3a | 4g | 5a | 6c | 7c |
| (7)-120 | 1b | 2a | 3a | 4e | 5a | 6c | 7c |
| (7)-121 | 1b | 2a | 3a | 4f | 5b | 6c | 7c |
| (7)-122 | 1b | 2a | 3a | 4g | 5b | 6c | 7c |
| (7)-123 | 1b | 2a | 3a | 4e | 5b | 6c | 7c |
| (7)-124 | 1b | 2a | 3a | 4f | 5e | 6c | 7c |
| (7)-125 | 1b | 2a | 3a | 4g | 5e | 6c | 7c |
| (7)-126 | 1b | 2a | 3a | 4e | 5e | 6c | 7c |
| (7)-127 | — | — | — | 4h | 5a | 6a | — |
| (7)-128 | — | — | — | 4i | 5a | 6a | — |
| (7)-129 | — | — | — | 4j | 5a | 6a | — |
| (7)-130 | — | — | — | 4m | 5a | 6a | — |
| (7)-131 | — | — | — | 4n | 5a | 6a | — |
| (7)-132 | — | — | — | 4h | 5b | 6a | — |
| (7)-133 | — | — | — | 4i | 5b | 6a | — |
| (7)-134 | — | — | — | 4j | 5b | 6a | — |
| (7)-135 | — | — | — | 4m | 5b | 6a | — |
| (7)-136 | — | — | — | 4n | 5b | 6a | — |
| (7)-137 | — | — | — | 4h | 5c | 6a | — |
| (7)-138 | — | — | — | 4i | 5c | 6a | — |
| (7)-139 | — | — | — | 4j | 5c | 6a | — |
| (7)-140 | — | — | — | 4m | 5c | 6a | — |
| (7)-141 | — | — | — | 4n | 5c | 6a | — |
| (7)-142 | — | — | — | 4h | 5d | 6a | — |
| (7)-143 | — | — | — | 4i | 5d | 6a | — |
| (7)-144 | — | — | — | 4j | 5d | 6a | — |
| (7)-145 | — | — | — | 4m | 5d | 6a | — |
| (7)-146 | — | — | — | 4n | 5d | 6a | — |
| (7)-147 | — | — | — | 4h | 5a | 6b | — |
| (7)-148 | — | — | — | 4i | 5a | 6b | — |
| (7)-149 | — | — | — | 4j | 5a | 6b | — |
| (7)-150 | — | — | — | 4m | 5a | 6b | — |
| (7)-151 | — | — | — | 4n | 5a | 6b | — |
| (7)-152 | — | — | — | 4h | 5b | 6b | — |
| (7)-153 | — | — | — | 4i | 5b | 6b | — |
| (7)-154 | — | — | — | 4j | 5b | 6b | — |
| (7)-155 | — | — | — | 4m | 5b | 6b | — |
| (7)-156 | — | — | — | 4n | 5b | 6b | — |
| (7)-157 | — | — | — | 4h | 5c | 6b | — |
| (7)-158 | — | — | — | 4i | 5c | 6b | — |
| (7)-159 | — | — | — | 4j | 5c | 6b | — |
| (7)-160 | — | — | — | 4m | 5c | 6b | — |
| (7)-161 | — | — | — | 4n | 5c | 6b | — |
| (7)-162 | — | — | — | 4h | 5d | 6b | — |
| (7)-163 | — | — | — | 4i | 5d | 6b | — |
| (7)-164 | — | — | — | 4j | 5d | 6b | — |
| (7)-165 | — | — | — | 4m | 5d | 6b | — |
| (7)-166 | — | — | — | 4n | 5d | 6b | — |
| (7)-167 | — | — | — | 4h | 5a | 6c | — |
| (7)-168 | — | — | — | 4i | 5a | 6c | — |

-continued

| | R¹ | R¹² | R¹⁵ | R² | R²⁰ | R²¹ | R |
|---|---|---|---|---|---|---|---|
| (7)-169 | — | — | — | 4j | 5a | 6c | — |
| (7)-170 | — | — | — | 4m | 5a | 6c | — |
| (7)-171 | — | — | — | 4n | 5a | 6c | — |
| (7)-172 | — | — | — | 4h | 5b | 6c | — |
| (7)-173 | — | — | — | 4i | 5b | 6c | — |
| (7)-174 | — | — | — | 4j | 5b | 6c | — |
| (7)-175 | — | — | — | 4m | 5b | 6c | — |
| (7)-176 | — | — | — | 4n | 5b | 6c | — |
| (7)-177 | — | — | — | 4h | 5c | 6c | — |
| (7)-178 | — | — | — | 4i | 5c | 6c | — |
| (7)-179 | — | — | — | 4j | 5c | 6c | — |
| (7)-180 | — | — | — | 4m | 5c | 6c | — |
| (7)-181 | — | — | — | 4n | 5c | 6c | — |
| (7)-182 | — | — | — | 4h | 5d | 6c | — |
| (7)-183 | — | — | — | 4i | 5d | 6c | — |
| (7)-184 | — | — | — | 4j | 5d | 6c | — |
| (7)-185 | — | — | — | 4m | 5d | 6c | — |
| (7)-186 | — | — | — | 4n | 5d | 6c | — |

In another embodiment, the compound of formula (VIIf),

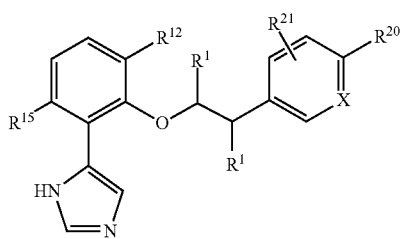

a tautomer thereof, or a pharmaceutically acceptable salt thereof, wherein

X is —C(H)═ or —N═;

each $R^1$ is independently hydrogen or methyl;

$R^{12}$ is hydrogen or halogen;

$R^{15}$ is hydrogen or hydroxy; and $R^{20}$ is —C(O)R, —C(O)OR, —N(H)R, —N(H)C(O)C(H)($R^{22}$)R, —N(H)S(O)$_2$R, —N(H)C(O)R, —N(H)C(O)OR, —N(H)C(O)N(H)R, heteroaryl, heterocyclyl, wherein $R^{22}$ is —N($R^{23}$)$_2$ or —N(H)C(O)$R^{23}$, wherein $R^{23}$ is hydrogen or $C_1$-$C_6$ alkyl;

$R^{21}$ is hydrogen, halogen, or trifluoromethyl; and each R is independently $C_1$-$C_6$ alkyl, aryl, heteroaryl, $C_3$-$C_8$cycloalkyl, heterocyclyl, aryl($C_1$-$C_6$)alkyl, heteroaryl($C_1$-$C_6$)alkyl, heterocyclyl($C_1$-$C_6$)alkyl, wherein the heterocyclyl, aryl, heteroaryl, cycloalkyl, heterocyclyl, heterocyclylalkyl, arylalkyl, and heteroarylalkyl are each optionally substituted with one group that is halogen, cyano, nitro, —OR¹⁰, —N(R¹⁰)$_2$, —C(O)OR¹⁰, —C(O)N(R¹⁰)$_2$, —C(O)R¹⁰, or $C_1$-$C_6$ alkyl, wherein each $R^{10}$ is independently hydrogen, $C_1$-$C_6$ alkyl, $C_3$-$C_8$cycloalkyl, heterocyclyl, aryl, or heteroaryl, provided that the compound is not N-(4-(2-(2-(1H-imidazol-4-yl)phenoxy)ethyl)phenyl)acetamide.

The invention further comprises subgenera of formula (VIIf) in which the substituents are selected as any and all combinations of one or more of X, R, R¹, R¹², R¹⁵, R²⁰, and R²¹, as defined herein, including without limitation, the following:

X is Selected from One of the Following Groups (8a)-(8b):
(8a) —C(H)═.
(8b) —N═.

R¹ is selected from one of the groups (1a)-(1b), as defined above.

R¹² is selected from one of the groups (2a)-(2b), as defined above.

R¹⁵ is selected from one of the groups (3a)-(3b), as defined above.

R²⁰ is selected from one of the groups (5a)-(5o); as defined above.

R²¹ is selected from one of the groups (6a)-(6c), as defined above.

R is selected from one of the groups (7a)-(7u), as defined above.

Additional particular embodiments of the compounds of formula (VIIf) are each as defined in each of the following rows, wherein each entry is a group number as defined above (e.g., (1b) refers to R¹ is hydrogen), and a dash "-" indicates that the variable is as defined for formula (VIIf) or defined according to any one of the applicable variable definitions (1a)-(8b) [e.g., when R¹⁵ is a dash, it can be either as defined for Formula (VIIf) or any one of definitions (3a)-(3b)]:

| | R¹ | R¹² | R¹⁵ | R²⁰ | R²¹ | R | X |
|---|---|---|---|---|---|---|---|
| (7f)-1 | 1b | 2a | — | 5c | — | — | 8a |
| (7f)-2 | 1b | 2a | — | 5c | — | 7c | 8a |
| (7f)-3 | 1b | 2a | — | 5c | — | 7e | 8a |
| (7f)-4 | 1b | 2a | — | 5c | — | 7i | 8a |
| (7f)-5 | 1b | 2a | — | 5c | — | 7l | 8a |
| (7f)-6 | 1b | 2a | — | 5c | 6a | — | 8a |
| (7f)-7 | 1b | 2a | — | 5c | 6a | 7c | 8a |
| (7f)-8 | 1b | 2a | — | 5c | 6a | 7e | 8a |
| (7f)-9 | 1b | 2a | — | 5c | 6a | 7i | 8a |
| (7f)-10 | 1b | 2a | — | 5c | 6a | 7l | 8a |
| (7f)-11 | 1b | 2a | — | 5c | 6b | — | 8a |
| (7f)-12 | 1b | 2a | — | 5c | 6b | 7c | 8a |
| (7f)-13 | 1b | 2a | — | 5c | 6b | 7e | 8a |
| (7f)-14 | 1b | 2a | — | 5c | 6b | 7i | 8a |
| (7f)-15 | 1b | 2a | — | 5c | 6b | 7l | 8a |
| (7f)-16 | 1b | 2a | — | 5c | 6c | — | 8a |
| (7f)-17 | 1b | 2a | — | 5c | 6c | 7c | 8a |
| (7f)-18 | 1b | 2a | — | 5c | 6c | 7e | 8a |
| (7f)-19 | 1b | 2a | — | 5c | 6c | 7i | 8a |
| (7f)-20 | 1b | 2a | — | 5c | 6c | 7l | 8a |
| (7f)-21 | 1b | 2a | 3a | 5c | — | — | 8a |
| (7f)-22 | 1b | 2a | 3a | 5c | — | 7c | 8a |
| (7f)-23 | 1b | 2a | 3a | 5c | — | 7e | 8a |
| (7f)-24 | 1b | 2a | 3a | 5c | — | 7i | 8a |
| (7f)-25 | 1b | 2a | 3a | 5c | — | 7l | 8a |
| (7f)-26 | 1b | 2a | 3a | 5c | 6a | — | 8a |
| (7f)-27 | 1b | 2a | 3a | 5c | 6a | 7c | 8a |
| (7f)-28 | 1b | 2a | 36 | 5c | 6a | 7e | 8a |
| (7f)-29 | 1b | 2a | 3a | 5c | 6a | 7i | 8a |
| (7f)-30 | 1b | 2a | 3a | 5c | 6a | 7l | 8a |
| (7f)-31 | 1b | 2a | 3a | 5c | 6b | — | 8a |
| (7f)-32 | 1b | 2a | 3a | 5c | 6b | 7c | 8a |
| (7f)-33 | 1b | 2a | 3a | 5c | 6b | 7e | 8a |
| (7f)-34 | 1b | 2a | 3a | 5c | 6b | 7i | 8a |
| (7f)-35 | 1b | 2a | 3a | 5c | 6b | 7l | 8a |
| (7f)-36 | 1b | 2a | 3a | 5c | 6c | — | 8a |
| (7f)-37 | 1b | 2a | 3a | 5c | 6c | 7c | 8a |
| (7f)-38 | 1b | 2a | 3a | 5c | 6c | 7e | 8a |
| (7f)-39 | 1b | 2a | 3a | 5c | 6c | 7i | 8a |
| (7f)-40 | 1b | 2a | 3a | 5c | 6c | 7l | 8a |
| (7f)-41 | 1b | 2a | 3b | 5c | — | — | 8a |
| (7f)-42 | 1b | 2a | 3b | 5c | — | 7c | 8a |
| (7f)-43 | 1b | 2a | 3b | 5c | — | 7e | 8a |
| (7f)-44 | 1b | 2a | 3b | 5c | — | 7i | 8a |
| (7f)-45 | 1b | 2a | 3b | 5c | — | 7l | 8a |
| (7f)-46 | 1b | 2a | 3b | 5c | 6a | — | 8a |
| (7f)-47 | 1b | 2a | 3b | 5c | 6a | 7c | 8a |
| (7f)-48 | 1b | 2a | 3b | 5c | 6a | 7e | 8a |
| (7f)-49 | 1b | 2a | 3b | 5c | 6a | 7i | 8a |
| (7f)-50 | 1b | 2a | 3b | 5c | 6a | 7l | 8a |
| (7f)-51 | 1b | 2a | 3b | 5c | 6b | — | 8a |
| (7f)-52 | 1b | 2a | 3b | 5c | 6b | 7c | 8a |

| | R$^1$ | R$^{12}$ | R$^{15}$ | R$^{20}$ | R$^{21}$ | R | X |
|---|---|---|---|---|---|---|---|
| (7f)-53 | 1b | 2a | 3b | 5c | 6b | 7e | 8a |
| (7f)-54 | 1b | 2a | 3b | 5c | 6b | 7i | 8a |
| (7f)-55 | 1b | 2a | 3b | 5c | 6b | 7l | 8a |
| (7f)-56 | 1b | 2a | 3b | 5c | 6c | — | 8a |
| (7f)-57 | 1b | 2a | 3b | 5c | 6c | 7c | 8a |
| (7f)-58 | 1b | 2a | 3b | 5c | 6c | 7e | 8a |
| (7f)-59 | 1b | 2a | 3b | 5c | 6c | 7i | 8a |
| (7f)-60 | 1b | 2a | 3b | 5c | 6c | 7l | 8a |
| (7f)-61 | 1b | 2a | — | 5d | — | — | 8a |
| (7f)-62 | 1b | 2a | — | 5d | — | 7c | 8a |
| (7f)-63 | 1b | 2a | — | 5d | — | 7e | 8a |
| (7f)-64 | 1b | 2a | — | 5d | — | 7i | 8a |
| (7f)-65 | 1b | 2a | — | 5d | — | 7l | 8a |
| (7f)-66 | 1b | 2a | — | 5d | 6a | — | 8a |
| (7f)-67 | 1b | 2a | — | 5d | 6a | 7c | 8a |
| (7f)-68 | 1b | 2a | — | 5d | 6a | 7e | 8a |
| (7f)-69 | 1b | 2a | — | 5d | 6a | 7i | 8a |
| (7f)-70 | 1b | 2a | — | 5d | 6a | 7l | 8a |
| (7f)-71 | 1b | 2a | — | 5d | 6b | — | 8a |
| (7f)-72 | 1b | 2a | — | 5d | 6b | 7c | 8a |
| (7f)-73 | 1b | 2a | — | 5d | 6b | 7e | 8a |
| (7f)-74 | 1b | 2a | — | 5d | 6b | 7i | 8a |
| (7f)-75 | 1b | 2a | — | 5d | 6b | 7l | 8a |
| (7f)-76 | 1b | 2a | — | 5d | 6c | — | 8a |
| (7f)-77 | 1b | 2a | — | 5d | 6c | 7c | 8a |
| (7f)-78 | 1b | 2a | — | 5d | 6c | 7e | 8a |
| (7f)-79 | 1b | 2a | — | 5d | 6c | 7i | 8a |
| (7f)-80 | 1b | 2a | — | 5d | 6c | 7l | 8a |
| (7f)-81 | 1b | 2a | 3a | 5d | — | — | 8a |
| (7f)-82 | 1b | 2a | 3a | 5d | — | 7c | 8a |
| (7f)-83 | 1b | 2a | 3a | 5d | — | 7e | 8a |
| (7f)-84 | 1b | 2a | 3a | 5d | — | 7i | 8a |
| (7f)-85 | 1b | 2a | 3a | 5d | — | 7l | 8a |
| (7f)-86 | 1b | 2a | 3a | 5d | 6a | — | 8a |
| (7f)-87 | 1b | 2a | 3a | 5d | 6a | 7c | 8a |
| (7f)-88 | 1b | 2a | 3a | 5d | 6a | 7e | 8a |
| (7f)-89 | 1b | 2a | 3a | 5d | 6a | 7i | 8a |
| (7f)-90 | 1b | 2a | 3a | 5d | 6a | 7l | 8a |
| (7f)-91 | 1b | 2a | 3a | 5d | 6b | — | 8a |
| (7f)-92 | 1b | 2a | 3a | 5d | 6b | 7c | 8a |
| (7f)-93 | 1b | 2a | 3a | 5d | 6b | 7e | 8a |
| (7f)-94 | 1b | 2a | 3a | 5d | 6b | 7i | 8a |
| (7f)-95 | 1b | 2a | 3a | 5d | 6b | 7l | 8a |
| (7f)-96 | 1b | 2a | 3a | 5d | 6c | — | 8a |
| (7f)-97 | 1b | 2a | 3a | 5d | 6c | 7c | 8a |
| (7f)-98 | 1b | 2a | 3a | 5d | 6c | 7e | 8a |
| (7f)-99 | 1b | 2a | 3a | 5d | 6c | 7i | 8a |
| (7f)-100 | 1b | 2a | 3a | 5d | 6c | 7l | 8a |
| (7f)-101 | 1b | 2a | 3b | 5d | — | — | 8a |
| (7f)-102 | 1b | 2a | 3b | 5d | — | 7c | 8a |
| (7f)-103 | 1b | 2a | 3b | 5d | — | 7e | 8a |
| (7f)-104 | 1b | 2a | 3b | 5d | — | 7i | 8a |
| (7f)-105 | 1b | 2a | 3b | 5d | — | 7l | 8a |
| (7f)-106 | 1b | 2a | 3b | 5d | 6a | — | 8a |
| (7f)-107 | 1b | 2a | 3b | 5d | 6a | 7c | 8a |
| (7f)-108 | 1b | 2a | 3b | 5d | 6a | 7e | 8a |
| (7f)-109 | 1b | 2a | 3b | 5d | 6a | 7i | 8a |
| (7f)-110 | 1b | 2a | 3b | 5d | 6a | 7l | 8a |
| (7f)-111 | 1b | 2a | 3b | 5d | 6b | — | 8a |
| (7f)-112 | 1b | 2a | 3b | 5d | 6b | 7c | 8a |
| (7f)-113 | 1b | 2a | 3b | 5d | 6b | 7e | 8a |
| (7f)-114 | 1b | 2a | 3b | 5d | 6b | 7i | 8a |
| (7f)-115 | 1b | 2a | 3b | 5d | 6b | 7l | 8a |
| (7f)-116 | 1b | 2a | 3b | 5d | 6c | — | 8a |
| (7f)-117 | 1b | 2a | 3b | 5d | 6c | 7c | 8a |
| (7f)-118 | 1b | 2a | 3b | 5d | 6c | 7e | 8a |
| (7f)-119 | 1b | 2a | 3b | 5d | 6c | 7i | 8a |
| (7f)-120 | 1b | 2a | 3b | 5d | 6c | 7l | 8a |
| (7f)-121 | 1b | 2a | — | 5c | — | — | 8b |
| (7f)-122 | 1b | 2a | — | 5c | — | 7c | 8b |
| (7f)-123 | 1b | 2a | — | 5c | — | 7e | 8b |
| (7f)-124 | 1b | 2a | — | 5c | — | 7i | 8b |
| (7f)-125 | 1b | 2a | — | 5c | — | 7l | 8b |
| (7f)-126 | 1b | 2a | — | 5c | 6a | — | 8b |
| (7f)-127 | 1b | 2a | — | 5c | 6a | 7c | 8b |
| (7f)-128 | 1b | 2a | — | 5c | 6a | 7e | 8b |
| (7f)-129 | 1b | 2a | — | 5c | 6a | 7i | 8b |
| (7f)-130 | 1b | 2a | — | 5c | 6a | 7l | 8b |
| (7f)-131 | 1b | 2a | — | 5c | 6b | — | 8b |
| (7f)-132 | 1b | 2a | — | 5c | 6b | 7c | 8b |
| (7f)-133 | 1b | 2a | — | 5c | 6b | 7e | 8b |
| (7f)-134 | 1b | 2a | — | 5c | 6b | 7i | 8b |
| (7f)-135 | 1b | 2a | — | 5c | 6b | 7l | 8b |
| (7f)-136 | 1b | 2a | — | 5c | 6c | — | 8b |
| (7f)-137 | 1b | 2a | — | 5c | 6c | 7c | 8b |
| (7f)-138 | 1b | 2a | — | 5c | 6c | 7e | 8b |
| (7f)-139 | 1b | 2a | — | 5c | 6c | 7i | 8b |
| (7f)-140 | 1b | 2a | — | 5c | 6c | 7l | 8b |
| (7f)-141 | 1b | 2a | 3a | 5c | — | — | 8b |
| (7f)-142 | 1b | 2a | 3a | 5c | — | 7c | 8b |
| (7f)-143 | 1b | 2a | 3a | 5c | — | 7e | 8b |
| (7f)-144 | 1b | 2a | 3a | 5c | — | 7i | 8b |
| (7f)-145 | 1b | 2a | 3a | 5c | — | 7l | 8b |
| (7f)-146 | 1b | 2a | 3a | 5c | 6a | — | 8b |
| (7f)-147 | 1b | 2a | 3a | 5c | 6a | 7c | 8b |
| (7f)-148 | 1b | 2a | 3a | 5c | 6a | 7e | 8b |
| (7f)-149 | 1b | 2a | 3a | 5c | 6a | 7i | 8b |
| (7f)-150 | 1b | 2a | 3a | 5c | 6a | 7l | 8b |
| (7f)-151 | 1b | 2a | 3a | 5c | 6b | — | 8b |
| (7f)-152 | 1b | 2a | 3a | 5c | 6b | 7c | 8b |
| (7f)-153 | 1b | 2a | 3a | 5c | 6b | 7e | 8b |
| (7f)-154 | 1b | 2a | 3a | 5c | 6b | 7i | 8b |
| (7f)-155 | 1b | 2a | 3a | 5c | 6b | 7l | 8b |
| (7f)-156 | 1b | 2a | 3a | 5c | 6c | — | 8b |
| (7f)-157 | 1b | 2a | 3a | 5c | 6c | 7c | 8b |
| (7f)-158 | 1b | 2a | 3a | 5c | 6c | 7e | 8b |
| (7f)-159 | 1b | 2a | 3a | 5c | 6c | 7i | 8b |
| (7f)-160 | 1b | 2a | 3a | 5c | 6c | 7l | 8b |
| (7f)-161 | 1b | 2a | 3b | 5c | — | — | 8b |
| (7f)-162 | 1b | 2a | 3b | 5c | — | 7c | 8b |
| (7f)-163 | 1b | 2a | 3b | 5c | — | 7e | 8b |
| (7f)-164 | 1b | 2a | 3b | 5c | — | 7i | 8b |
| (7f)-165 | 1b | 2a | 3b | 5c | — | 7l | 8b |
| (7f)-166 | 1b | 2a | 3b | 5c | 6a | — | 8b |
| (7f)-167 | 1b | 2a | 3b | 5c | 6a | 7c | 8b |
| (7f)-168 | 1b | 2a | 3b | 5c | 6a | 7e | 8b |
| (7f)-169 | 1b | 2a | 3b | 5c | 6a | 7i | 8b |
| (7f)-170 | 1b | 2a | 3b | 5c | 6a | 7l | 8b |
| (7f)-171 | 1b | 2a | 3b | 5c | 6b | — | 8b |
| (7f)-172 | 1b | 2a | 3b | 5c | 6b | 7c | 8b |
| (7f)-173 | 1b | 2a | 3b | 5c | 6b | 7e | 8b |
| (7f)-174 | 1b | 2a | 3b | 5c | 6b | 7i | 8b |
| (7f)-175 | 1b | 2a | 3b | 5c | 6b | 7l | 8b |
| (7f)-176 | 1b | 2a | 3b | 5c | 6c | — | 8b |
| (7f)-177 | 1b | 2a | 3b | 5c | 6c | 7c | 8b |
| (7f)-178 | 1b | 2a | 3b | 5c | 6c | 7e | 8b |
| (7f)-179 | 1b | 2a | 3b | 5c | 6c | 7i | 8b |
| (7f)-180 | 1b | 2a | 3b | 5c | 6c | 7l | 8b |
| (7f)-181 | 1b | 2a | — | 5d | — | — | 8b |
| (7f)-182 | 1b | 2a | — | 5d | — | 7c | 8b |
| (7f)-183 | 1b | 2a | — | 5d | — | 7e | 8b |
| (7f)-184 | 1b | 2a | — | 5d | — | 7i | 8b |
| (7f)-185 | 1b | 2a | — | 5d | — | 7l | 8b |
| (7f)-186 | 1b | 2a | — | 5d | 6a | — | 8b |
| (7f)-187 | 1b | 2a | — | 5d | 6a | 7c | 8b |
| (7f)-188 | 1b | 2a | — | 5d | 6a | 7e | 8b |
| (7f)-189 | 1b | 2a | — | 5d | 6a | 7i | 8b |
| (7f)-190 | 1b | 2a | — | 5d | 6a | 7l | 8b |
| (7f)-191 | 1b | 2a | — | 5d | 6b | — | 8b |
| (7f)-192 | 1b | 2a | — | 5d | 6b | 7c | 8b |
| (7f)-193 | 1b | 2a | — | 5d | 6b | 7e | 8b |
| (7f)-194 | 1b | 2a | — | 5d | 6b | 7i | 8b |
| (7f)-195 | 1b | 2a | — | 5d | 6b | 7l | 8b |
| (7f)-196 | 1b | 2a | — | 5d | 6c | — | 8b |
| (7f)-197 | 1b | 2a | — | 5d | 6c | 7c | 8b |
| (7f)-198 | 1b | 2a | — | 5d | 6c | 7e | 8b |
| (7f)-199 | 1b | 2a | — | 5d | 6c | 7i | 8b |
| (7f)-200 | 1b | 2a | — | 5d | 6c | 7l | 8b |
| (7f)-201 | 1b | 2a | 3a | 5d | — | — | 8b |
| (7f)-202 | 1b | 2a | 3a | 5d | — | 7c | 8b |
| (7f)-203 | 1b | 2a | 3a | 5d | — | 7e | 8b |
| (7f)-204 | 1b | 2a | 3a | 5d | — | 7i | 8b |
| (7f)-205 | 1b | 2a | 3a | 5d | — | 7l | 8b |
| (7f)-206 | 1b | 2a | 3a | 5d | 6a | — | 8b |
| (7f)-207 | 1b | 2a | 3a | 5d | 6a | 7c | 8b |
| (7f)-208 | 1b | 2a | 3a | 5d | 6a | 7e | 8b |

-continued

| | R¹ | R¹² | R¹⁵ | R²⁰ | R²¹ | R | X |
|---|---|---|---|---|---|---|---|
| (7f)-209 | 1b | 2a | 3a | 5d | 6a | 7i | 8b |
| (7f)-210 | 1b | 2a | 3a | 5d | 6a | 7l | 8b |
| (7f)-211 | 1b | 2a | 3a | 5d | 6b | — | 8b |
| (7f)-212 | 1b | 2a | 3a | 5d | 6b | 7c | 8b |
| (7f)-213 | 1b | 2a | 3a | 5d | 6b | 7e | 8b |
| (7f)-214 | 1b | 2a | 3a | 5d | 6b | 7i | 8b |
| (7f)-215 | 1b | 2a | 3a | 5d | 6b | 7l | 8b |
| (7f)-216 | 1b | 2a | 3a | 5d | 6c | — | 8b |
| (7f)-217 | 1b | 2a | 3a | 5d | 6c | 7c | 8b |
| (7f)-218 | 1b | 2a | 3a | 5d | 6c | 7e | 8b |
| (7f)-219 | 1b | 2a | 3a | 5d | 6c | 7i | 8b |
| (7f)-220 | 1b | 2a | 3a | 5d | 6c | 7l | 8b |
| (7f)-221 | 1b | 2a | 3b | 5d | — | — | 8b |
| (7f)-222 | 1b | 2a | 3b | 5d | — | 7c | 8b |
| (7f)-223 | 1b | 2a | 3b | 5d | — | 7e | 8b |
| (7f)-224 | 1b | 2a | 3b | 5d | — | 7i | 8b |
| (7f)-225 | 1b | 2a | 3b | 5d | — | 7l | 8b |
| (7f)-226 | 1b | 2a | 3b | 5d | 6a | — | 8b |
| (7f)-227 | 1b | 2a | 3b | 5d | 6a | 7c | 8b |
| (7f)-228 | 1b | 2a | 3b | 5d | 6a | 7e | 8b |
| (7f)-229 | 1b | 2a | 3b | 5d | 6a | 7i | 8b |
| (7f)-230 | 1b | 2a | 3b | 5d | 6a | 7l | 8b |
| (7f)-231 | 1b | 2a | 3b | 5d | 6b | — | 8b |
| (7f)-232 | 1b | 2a | 3b | 5d | 6b | 7c | 8b |
| (7f)-233 | 1b | 2a | 3b | 5d | 6b | 7e | 8b |
| (7f)-234 | 1b | 2a | 3b | 5d | 6b | 7i | 8b |
| (7f)-235 | 1b | 2a | 3b | 5d | 6b | 7l | 8b |
| (7f)-236 | 1b | 2a | 3b | 5d | 6c | — | 8b |
| (7f)-237 | 1b | 2a | 3b | 5d | 6c | 7c | 8b |
| (7f)-238 | 1b | 2a | 3b | 5d | 6c | 7e | 8b |
| (7f)-239 | 1b | 2a | 3b | 5d | 6c | 7i | 8b |
| (7f)-240 | 1b | 2a | 3b | 5d | 6c | 7l | 8b |

In another embodiment, the compound of formula (VIIg),

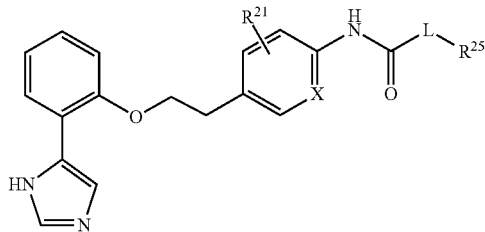

(VIIg)

a tautomer thereof, or a pharmaceutically acceptable salt thereof, wherein

X is —C(H)═ or —N═;

L is a bond, —CH$_2$, —O—, or —N(H)—;

R$^{25}$ is hydrogen, C$_1$-C$_6$ alkyl, aryl, heteroaryl, C$_3$-C$_8$cycloalkyl, or heterocyclyl, wherein the aryl, heteroaryl, cycloalkyl, and heterocyclyl, groups are each optionally substituted with one group that is halogen, cyano, nitro, —OR$^{11}$, —N(R$^{11}$)$_2$, —C(O)OR$^{11}$, —C(O)N(R$^{11}$)$_2$, —C(O)R$^{11}$, or C$_1$-C$_6$ alkyl, wherein each R$^{11}$ is independently hydrogen, C$_1$-C$_6$ alkyl, C$_3$-C$_8$cycloalkyl, heterocyclyl, aryl, or heteroaryl; and R$^{21}$ is hydrogen, halogen, or trifluoromethyl;

provided that R$^{25}$ can be hydrogen only when L is —CH$_2$—; and the compound is not N-(4-(2-(2-(1H-imidazol-4-yl)phenoxy)ethyl)phenyl)acetamide.

The invention further comprises subgenera of formula (VIIf) in which the substituents are selected as any and all combinations of one or more of L, X, R$^{21}$, and R$^{25}$, as defined herein, including without limitation, the following:

R$^{21}$ is selected from one of the groups (6a)-(6c), as defined above.

X is selected from one of the groups (8a)-(8b), as defined above.

L is Selected from One of the Following Groups (9a)-(9g):
(9a) a bond or —CH$_2$—.
(9b) —CH$_2$—, —O— or —N(H)—.
(9c) —O— or —N(H)—.
(9d) —CH$_2$—.
(9e) —O—.
(9f) —N(H)—
(9 g) a bond.

R$^{25}$ is Selected from One of the Following Groups (10a)-(10s)

(10a) C$_1$-C$_6$ alkyl, aryl, heteroaryl, C$_3$-C$_8$cycloalkyl, or heterocyclyl, wherein each is optionally substituted with one group that is halogen, cyano, nitro, —OR$^{10}$, —N(R$^{10}$)$_2$, or —C(O)OR$^{10}$, wherein each R$^{10}$ is independently hydrogen, C$_1$-C$_6$ alkyl, or heterocyclyl.

(10b) aryl, heteroaryl, or heterocyclyl, wherein each is each optionally substituted with one group that is halogen, cyano, nitro, —OR$^{10}$, —N(R$^{10}$)$_2$, —C(O)OR$^{10}$, —C(O)N(R$^{10}$)$_2$, —C(O)R$^{10}$, or C$_1$-C$_6$ alkyl, wherein each R$^{10}$ is independently hydrogen, C$_1$-C$_6$ alkyl, C$_3$-C$_8$cycloalkyl, heterocyclyl, aryl, or heteroaryl, (10c) aryl, heteroaryl, or heterocyclyl, wherein each is optionally substituted with one group that is halogen, cyano, nitro, OR$^{10}$, —N(R$^{10}$)$_2$, or —C(O)OR$^{10}$, wherein each R$^{10}$ is independently hydrogen, C$_1$-C$_6$ alkyl, or heterocyclyl.

(10d) aryl optionally substituted with one group that is halogen, cyano, nitro, —OR$^{10}$, —N(R$^{10}$)$_2$, or —C(O)OR$^{10}$, wherein each R$^{10}$ is independently hydrogen, C$_1$-C$_6$ alkyl, or heterocyclyl.

(10e) phenyl optionally substituted with one group that is halogen, cyano, nitro, —OR$^{10}$, —N(R$^{10}$)$_2$, or —C(O)OR$^{10}$, wherein each R$^{10}$ is independently hydrogen, C$_1$-C$_6$ alkyl, or heterocyclyl.

(10f) heteroaryl optionally substituted with one group that is halogen, cyano, nitro, —OR$^{10}$, —N(R$^{10}$)$_2$, or —C(O)OR$^{10}$, wherein each R$^{10}$ is independently hydrogen, C$_1$-C$_6$ alkyl, or heterocyclyl.

(10g) heterocyclyl optionally substituted with one group that is halogen, cyano, nitro, —OR$^{10}$, —N(R$^{10}$)$_2$, or —C(O)OR$^{10}$, wherein each R$^{10}$ is independently hydrogen, C$_1$-C$_6$ alkyl, or heterocyclyl.

(10h) hydrogen, methyl, ethyl, t-butyl, neopentyl, phenyl, thienyl, pyridyl, cyclohexyl, tetrahydropyranyl, piperidinyl, pyridonyl, pyrimidindionyl, imidazolyl; thiazolyl, pyrimidinyl, pyrazinyl, tetrahydrofuranyl, tetrahydropyranyl, morpholinyl, wherein each is optionally substituted with one group that is halogen, cyano, nitro, —OR$^{10}$, —N(R$^{10}$)$_2$, or —C(O)OR$^{10}$, wherein each R$^{10}$ is independently hydrogen or C$_1$-C$_6$ alkyl.

(10i) hydrogen, methyl, ethyl, t-butyl, neopentyl, phenyl, 2-nitrophenyl, 3-nitrophenyl, 4-nitrophenyl, 2-aminophenyl, 3-aminophenyl, 4-aminophenyl, 2-carboxyphenyl, 3-carboxyphenyl, 4-carboxyphenyl, 4-methoxycarbonylphenyl, 3-methoxycarbonylphenyl, 3-(3-tetrahydrofur-3-yl)phenyl, 2-aminopyrid-3-yl, thien-2-yl, cyclohexyl, 2-aminocyclohexyl, trans-2-aminocyclohexyl, cis-2-aminocyclohexyl, tetrahydropyran-4-yl, piperidin-2-yl, pyrid-2-on-3-yl, pyrimidin-2,4-dion-5-yl, imidazol-1-yl, thiazol-4-yl, 2-aminothiazol-4-yl, pyrimidin-2-yl, pyrimidin-5-yl, pyrazin-2-yl, tetrahydrofuran-2-yl, tetrahydropyran-4-yl, or morpholin-4-yl.

(10j) hydrogen, methyl, ethyl, t-butyl, or neopentyl.
(10k) phenyl, 2-nitrophenyl, 3-nitrophenyl, 4-nitrophenyl, 2-aminophenyl, 3-aminophenyl, 4-aminophenyl, 2-carboxyphenyl, 3-carboxyphenyl, 4-carboxyphenyl, 4-methoxycarbonylphenyl, 3-methoxycarbonylphenyl, 3-(3-tetrahydrofur-3-yl)phenyl, 2-aminopyrid-3-yl, thien-2-yl, cyclohexyl, 2-aminocyclohexyl, trans-2-aminocyclohexyl, cis-2-aminocyclohexyl, tetrahydropyran-4-yl, piperidin-2-yl, pyrid-2-on-3-yl, pyrimidin-2,4-dion-5-yl, imidazol-1-yl, thiazol-4-yl, 2-aminothiazol-4-yl, pyrimidin-2-yl, pyrimidin-5-yl, pyrazin-2-yl, tetrahydrofuran-2-yl, tetrahydropyran-4-yl, or morpholin-4-yl.
(10l) 2-aminocyclohexyl.
(10m) trans-2-aminocyclohexyl.
(10n) cis-2-aminocyclohexyl.
(10o) phenyl, 2-nitrophenyl, 3-nitrophenyl, 4-nitrophenyl, 2-aminophenyl, 3-aminophenyl, 4-aminophenyl, 2-carboxyphenyl, 3-carboxyphenyl, 4-carboxyphenyl, 4-methoxycarbonylphenyl, 3-methoxycarbonylphenyl, 3-(3-tetrahydrofur-3-yl)phenyl, 2-aminopyrid-3-yl, or thien-2-yl.
(10p) cyclohexyl, 2-aminocyclohexyl, trans-2-aminocyclohexyl, cis-2-aminocyclohexyl, tetrahydropyran-4-yl, piperidin-2-yl, pyrid-2-on-3-yl, or pyrimidin-2,4-dion-5-yl.
(10q) phenyl, thienyl, imidazol-1-yl, thiazol-4-yl, 2-aminothiazol-4-yl, pyrimidin-2-yl, pyrimidin-5-yl, pyrazin-2-yl, tetrahydrofuran-2-yl, tetrahydropyran-2-yl, or morpholin-4-yl.
(10r) phenyl, thien-2-yl, imidazol-1-yl, thiazol-4-yl, 2-aminothiazol-4-yl, pyrimidin-2-yl, pyrimidin-5-yl, or pyrazin-2-yl.
(10s) tetrahydrofuran-2-yl, tetrahydropyran-4-yl, or morpholin-4-yl.

Additional particular embodiments of the compounds of formula (VIIg) are each as defined in each of the following rows, wherein each entry is a group number as defined above (e.g., (1b) refers to $R^1$ is hydrogen), and a dash "-" indicates that the variable is as defined for formula (VIIg) or defined according to any one of the applicable variable definitions (1a)-(10s) [e.g., when $R^{21}$ is a dash, it can be either as defined for Formula (VIIg) or any one of definitions (6a)-(6c)]:

| | $R^{21}$ | X | L | $R^{25}$ |
|---|---|---|---|---|
| (7g)-1 | 6a | 8a | 9a | 10b |
| (7g)-2 | 6a | 8a | 9a | 10e |
| (7g)-3 | 6a | 8a | 9a | 10g |
| (7g)-4 | 6a | 8a | 9a | 10h |
| (7g)-5 | 6a | 8a | 9a | 10i |
| (7g)-6 | 6a | 8a | 9a | 10k |
| (7g)-7 | 6a | 8a | 9a | 10l |
| (7g)-8 | 6a | 8a | 9a | 10m |
| (7g)-9 | 6a | 8a | 9a | 10n |
| (7g)-10 | 6a | 8a | 9b | 10b |
| (7g)-11 | 6a | 8a | 9b | 10e |
| (7g)-12 | 6a | 8a | 9b | 10g |
| (7g)-13 | 6a | 8a | 9b | 10h |
| (7g)-14 | 6a | 8a | 9b | 10i |
| (7g)-15 | 6a | 8a | 9b | 10k |
| (7g)-16 | 6a | 8a | 9b | 10l |
| (7g)-17 | 6a | 8a | 9b | 10m |
| (7g)-18 | 6a | 8a | 9b | 10n |
| (7g)-19 | 6a | 8a | 9c | 10b |
| (7g)-20 | 6a | 8a | 9c | 10e |
| (7g)-21 | 6a | 8a | 9c | 10g |
| (7g)-22 | 6a | 8a | 9c | 10h |
| (7g)-23 | 6a | 8a | 9c | 10i |
| (7g)-24 | 6a | 8a | 9c | 10k |
| (7g)-25 | 6a | 8a | 9c | 10l |
| (7g)-26 | 6a | 8a | 9c | 10m |
| (7g)-27 | 6a | 8a | 9c | 10n |
| (7g)-28 | 6a | 8a | 9c | 10b |
| (7g)-29 | 6a | 8a | 9d | 10e |
| (7g)-30 | 6a | 8a | 9d | 10g |
| (7g)-31 | 6a | 8a | 9d | 10h |
| (7g)-32 | 6a | 8a | 9d | 10i |
| (7g)-33 | 6a | 8a | 9d | 10k |
| (7g)-34 | 6a | 8a | 9d | 10l |
| (7g)-35 | 6a | 8a | 9d | 10m |
| (7g)-36 | 6a | 8a | 9d | 10n |
| (7g)-37 | 6a | 8a | 9e | 10b |
| (7g)-38 | 6a | 8a | 9e | 10e |
| (7g)-39 | 6a | 8a | 9e | 10g |
| (7g)-40 | 6a | 8a | 9e | 10h |
| (7g)-41 | 6a | 8a | 9e | 10i |
| (7g)-42 | 6a | 8a | 9e | 10k |
| (7g)-43 | 6a | 8a | 9e | 10l |
| (7g)-44 | 6a | 8a | 9e | 10m |
| (7g)-45 | 6a | 8a | 9e | 10n |
| (7g)-46 | 6a | 8a | 9f | 10b |
| (7g)-47 | 6a | 8a | 9f | 10e |
| (7g)-48 | 6a | 8a | 9f | 10g |
| (7g)-49 | 6a | 8a | 9f | 10h |
| (7g)-50 | 6a | 8a | 9f | 10i |
| (7g)-51 | 6a | 8a | 9f | 10k |
| (7g)-52 | 6a | 8a | 9f | 10l |
| (7g)-53 | 6a | 8a | 9f | 10m |
| (7g)-54 | 6a | 8a | 9g | 10n |
| (7g)-55 | 6a | 8a | 9g | 10b |
| (7g)-56 | 6a | 8a | 9g | 10e |
| (7g)-57 | 6a | 8a | 9g | 10g |
| (7g)-58 | 6a | 8a | 9g | 10h |
| (7g)-59 | 6a | 8a | 9g | 10i |
| (7g)-60 | 6a | 8a | 9g | 10k |
| (7g)-61 | 6a | 8a | 9g | 10l |
| (7g)-62 | 6a | 8a | 9g | 10m |
| (7g)-63 | 6a | 8a | 9g | 10n |
| (7g)-64 | 6b | 8a | 9a | 10b |
| (7g)-65 | 6b | 8a | 9a | 10e |
| (7g)-66 | 6b | 8a | 9a | 10g |
| (7g)-67 | 6b | 8a | 9a | 10h |
| (7g)-68 | 6b | 8a | 9a | 10i |
| (7g)-69 | 6b | 8a | 9a | 10k |
| (7g)-70 | 6b | 8a | 9a | 10l |
| (7g)-71 | 6b | 8a | 9a | 10m |
| (7g)-72 | 6b | 8a | 9a | 10n |
| (7g)-73 | 6b | 8a | 9b | 10b |
| (7g)-74 | 6b | 8a | 9b | 10e |
| (7g)-75 | 6b | 8a | 9b | 10g |
| (7g)-76 | 6b | 8a | 9b | 10h |
| (7g)-77 | 6b | 8a | 9b | 10i |
| (7g)-78 | 6b | 8a | 9b | 10k |
| (7g)-79 | 6b | 8a | 9b | 10l |
| (7g)-80 | 6b | 8a | 9b | 10m |
| (7g)-81 | 6b | 8a | 9b | 10n |
| (7g)-82 | 6b | 8a | 9c | 10b |
| (7g)-83 | 6b | 8a | 9c | 10e |
| (7g)-84 | 6b | 8a | 9c | 10g |
| (7g)-85 | 6b | 8a | 9c | 10h |
| (7g)-86 | 6b | 8a | 9c | 10i |
| (7g)-87 | 6b | 8a | 9c | 10k |
| (7g)-88 | 6b | 8a | 9c | 10l |
| (7g)-89 | 6b | 8a | 9c | 10m |
| (7g)-90 | 6b | 8a | 9c | 10n |
| (7g)-91 | 6b | 8a | 9c | 10b |
| (7g)-92 | 6b | 8a | 9d | 10e |
| (7g)-93 | 6b | 8a | 9d | 10g |
| (7g)-94 | 6b | 8a | 9d | 10h |
| (7g)-95 | 6b | 8a | 9d | 10i |

| | $R^{21}$ | X | L | $R^{25}$ |
|---|---|---|---|---|
| (7g)-96 | 6b | 8a | 9d | 10k |
| (7g)-97 | 6b | 8a | 9d | 10l |
| (7g)-98 | 6b | 8a | 9d | 10m |
| (7g)-99 | 6b | 8a | 9d | 10n |
| (7g)-100 | 6b | 8a | 9e | 10b |
| (7g)-101 | 6b | 8a | 9e | 10e |
| (7g)-102 | 6b | 8a | 9e | 10g |
| (7g)-103 | 6b | 8a | 9e | 10h |
| (7g)-104 | 6b | 8a | 9e | 10i |
| (7g)-105 | 6b | 8a | 9e | 10k |
| (7g)-106 | 6b | 8a | 9e | 10l |
| (7g)-107 | 6b | 8a | 9e | 10m |
| (7g)-108 | 6b | 8a | 9e | 10n |
| (7g)-109 | 6b | 8a | 9f | 10b |
| (7g)-110 | 6b | 8a | 9f | 10e |
| (7g)-111 | 6b | 8a | 9f | 10g |
| (7g)-112 | 6b | 8a | 9f | 10h |
| (7g)-113 | 6b | 8a | 9f | 10i |
| (7g)-114 | 6b | 8a | 9f | 10k |
| (7g)-115 | 6b | 8a | 9f | 10l |
| (7g)-116 | 6b | 8a | 9f | 10m |
| (7g)-117 | 6b | 8a | 9g | 10n |
| (7g)-118 | 6b | 8a | 9g | 10b |
| (7g)-119 | 6b | 8a | 9g | 10e |
| (7g)-120 | 6b | 8a | 9g | 10g |
| (7g)-121 | 6b | 8a | 9g | 10h |
| (7g)-122 | 6b | 8a | 9g | 10i |
| (7g)-123 | 6b | 8a | 9g | 10k |
| (7g)-124 | 6b | 8a | 9g | 10l |
| (7g)-125 | 6b | 8a | 9g | 10m |
| (7g)-126 | 6b | 8a | 9g | 10n |
| (7g)-127 | 6c | 8a | 9a | 10b |
| (7g)-128 | 6c | 8a | 9a | 10e |
| (7g)-129 | 6c | 8a | 9a | 10g |
| (7g)-130 | 6c | 8a | 9a | 10h |
| (7g)-131 | 6c | 8a | 9a | 10i |
| (7g)-132 | 6c | 8a | 9a | 10k |
| (7g)-133 | 6c | 8a | 9a | 10l |
| (7g)-134 | 6c | 8a | 9a | 10m |
| (7g)-135 | 6c | 8a | 9a | 10n |
| (7g)-136 | 6c | 8a | 9b | 10b |
| (7g)-137 | 6c | 8a | 9b | 10e |
| (7g)-138 | 6c | 8a | 9b | 10g |
| (7g)-139 | 6c | 8a | 9b | 10h |
| (7g)-140 | 6c | 8a | 9b | 10i |
| (7g)-141 | 6c | 8a | 9b | 10k |
| (7g)-142 | 6c | 8a | 9b | 10l |
| (7g)-143 | 6c | 8a | 9b | 10m |
| (7g)-144 | 6c | 8a | 9b | 10n |
| (7g)-145 | 6c | 8a | 9c | 10b |
| (7g)-146 | 6c | 8a | 9c | 10e |
| (7g)-147 | 6c | 8a | 9c | 10g |
| (7g)-148 | 6c | 8a | 9c | 10h |
| (7g)-149 | 6c | 8a | 9c | 10i |
| (7g)-150 | 6c | 8a | 9c | 10k |
| (7g)-151 | 6c | 8a | 9c | 10l |
| (7g)-152 | 6c | 8a | 9c | 10m |
| (7g)-153 | 6c | 8a | 9c | 10n |
| (7g)-154 | 6c | 8a | 9c | 10b |
| (7g)-155 | 6c | 8a | 9d | 10e |
| (7g)-156 | 6c | 8a | 9d | 10g |
| (7g)-157 | 6c | 8a | 9d | 10h |
| (7g)-158 | 6c | 8a | 9d | 10i |
| (7g)-159 | 6c | 8a | 9d | 10k |
| (7g)-160 | 6c | 8a | 9d | 10l |
| (7g)-161 | 6c | 8a | 9d | 10m |
| (7g)-162 | 6c | 8a | 9d | 10n |
| (7g)-163 | 6c | 8a | 9e | 10b |
| (7g)-164 | 6c | 8a | 9e | 10e |
| (7g)-165 | 6c | 8a | 9e | 10g |
| (7g)-166 | 6c | 8a | 9e | 10h |
| (7g)-167 | 6c | 8a | 9e | 10i |
| (7g)-168 | 6c | 8a | 9e | 10k |
| (7g)-169 | 6c | 8a | 9e | 10l |
| (7g)-170 | 6c | 8a | 9e | 10m |
| (7g)-171 | 6c | 8a | 9e | 10n |
| (7g)-172 | 6c | 8a | 9f | 10b |
| (7g)-173 | 6c | 8a | 9f | 10e |
| (7g)-174 | 6c | 8a | 9f | 10g |
| (7g)-175 | 6c | 8a | 9f | 10h |
| (7g)-176 | 6c | 8a | 9f | 10i |
| (7g)-177 | 6c | 8a | 9f | 10k |
| (7g)-178 | 6c | 8a | 9f | 10l |
| (7g)-179 | 6c | 8a | 9f | 10m |
| (7g)-180 | 6c | 8a | 9g | 10n |
| (7g)-181 | 6c | 8a | 9g | 10b |
| (7g)-182 | 6c | 8a | 9g | 10e |
| (7g)-183 | 6c | 8a | 9g | 10g |
| (7g)-184 | 6c | 8a | 9g | 10h |
| (7g)-185 | 6c | 8a | 9g | 10i |
| (7g)-186 | 6c | 8a | 9g | 10k |
| (7g)-187 | 6c | 8a | 9g | 10l |
| (7g)-188 | 6c | 8a | 9g | 10m |
| (7g)-189 | 6c | 8a | 9g | 10n |
| (7g)-190 | 6a | 8b | 9a | 10b |
| (7g)-191 | 6a | 8b | 9a | 10e |
| (7g)-192 | 6a | 8b | 9a | 10g |
| (7g)-193 | 6a | 8b | 9a | 10h |
| (7g)-194 | 6a | 8b | 9a | 10i |
| (7g)-195 | 6a | 8b | 9a | 10k |
| (7g)-196 | 6a | 8b | 9a | 10l |
| (7g)-197 | 6a | 8b | 9a | 10m |
| (7g)-198 | 6a | 8b | 9a | 10n |
| (7g)-199 | 6a | 8b | 9b | 10b |
| (7g)-200 | 6a | 8b | 9b | 10e |
| (7g)-201 | 6a | 8b | 9b | 10g |
| (7g)-202 | 6a | 8b | 9b | 10h |
| (7g)-203 | 6a | 8b | 9b | 10i |
| (7g)-204 | 6a | 8b | 9b | 10k |
| (7g)-205 | 6a | 8b | 9b | 10l |
| (7g)-206 | 6a | 8b | 9b | 10m |
| (7g)-207 | 6a | 8b | 9b | 10n |
| (7g)-208 | 6a | 8b | 9c | 10b |
| (7g)-209 | 6a | 8b | 9c | 10e |
| (7g)-210 | 6a | 8b | 9c | 10g |
| (7g)-211 | 6a | 8b | 9c | 10h |
| (7g)-212 | 6a | 8b | 9c | 10i |
| (7g)-213 | 6a | 8b | 9c | 10k |
| (7g)-214 | 6a | 8b | 9c | 10l |
| (7g)-215 | 6a | 8b | 9c | 10m |
| (7g)-216 | 6a | 8b | 9c | 10n |
| (7g)-217 | 6a | 8b | 9c | 10b |
| (7g)-218 | 6a | 8b | 9d | 10e |
| (7g)-219 | 6a | 8b | 9d | 10g |
| (7g)-220 | 6a | 8b | 9d | 10h |
| (7g)-221 | 6a | 8b | 9d | 10i |
| (7g)-222 | 6a | 8b | 9d | 10k |
| (7g)-223 | 6a | 8b | 9d | 10l |
| (7g)-224 | 6a | 8b | 9d | 10m |
| (7g)-225 | 6a | 8b | 9d | 10n |
| (7g)-226 | 6a | 8b | 9e | 10b |
| (7g)-227 | 6a | 8b | 9e | 10e |
| (7g)-228 | 6a | 8b | 9e | 10g |
| (7g)-229 | 6a | 8b | 9e | 10h |
| (7g)-230 | 6a | 8b | 9e | 10i |
| (7g)-231 | 6a | 8b | 9e | 10k |
| (7g)-232 | 6a | 8b | 9e | 10l |
| (7g)-233 | 6a | 8b | 9e | 10m |
| (7g)-234 | 6a | 8b | 9e | 10n |
| (7g)-235 | 6a | 8b | 9f | 10b |
| (7g)-236 | 6a | 8b | 9f | 10e |
| (7g)-237 | 6a | 8b | 9f | 10g |
| (7g)-238 | 6a | 8b | 9f | 10h |
| (7g)-239 | 6a | 8b | 9f | 10i |
| (7g)-240 | 6a | 8b | 9f | 10k |
| (7g)-241 | 6a | 8b | 9f | 10l |
| (7g)-242 | 6a | 8b | 9f | 10m |
| (7g)-243 | 6a | 8b | 9g | 10n |
| (7g)-244 | 6a | 8b | 9g | 10b |
| (7g)-245 | 6a | 8b | 9g | 10e |
| (7g)-246 | 6a | 8b | 9g | 10g |
| (7g)-247 | 6a | 8b | 9g | 10h |
| (7g)-248 | 6a | 8b | 9g | 10i |
| (7g)-249 | 6a | 8b | 9g | 10k |
| (7g)-250 | 6a | 8b | 9g | 10l |
| (7g)-251 | 6a | 8b | 9g | 10m |

| | R²¹ | X | L | R²⁵ |
|---|---|---|---|---|
| (7g)-252 | 6a | 8b | 9g | 10n |
| (7g)-253 | 6b | 8b | 9a | 10b |
| (7g)-254 | 6b | 8b | 9a | 10e |
| (7g)-255 | 6b | 8b | 9a | 10g |
| (7g)-256 | 6b | 8b | 9a | 10h |
| (7g)-257 | 6b | 8b | 9a | 10i |
| (7g)-258 | 6b | 8b | 9a | 10k |
| (7g)-259 | 6b | 8b | 9a | 10l |
| (7g)-260 | 6b | 8b | 9a | 10m |
| (7g)-261 | 6b | 8b | 9a | 10n |
| (7g)-262 | 6b | 8b | 9b | 10b |
| (7g)-263 | 6b | 8b | 9b | 10e |
| (7g)-264 | 6b | 8b | 9b | 10g |
| (7g)-265 | 6b | 8b | 9b | 10h |
| (7g)-266 | 6b | 8b | 9b | 10i |
| (7g)-267 | 6b | 8b | 9b | 10k |
| (7g)-268 | 6b | 8b | 9b | 10l |
| (7g)-269 | 6b | 8b | 9b | 10m |
| (7g)-270 | 6b | 8b | 9b | 10n |
| (7g)-271 | 6b | 8b | 9c | 10b |
| (7g)-272 | 6b | 8b | 9c | 10e |
| (7g)-273 | 6b | 8b | 9c | 10g |
| (7g)-274 | 6b | 8b | 9c | 10h |
| (7g)-275 | 6b | 8b | 9c | 10i |
| (7g)-276 | 6b | 8b | 9c | 10k |
| (7g)-277 | 6b | 8b | 9c | 10l |
| (7g)-278 | 6b | 8b | 9c | 10m |
| (7g)-279 | 6b | 8b | 9c | 10n |
| (7g)-280 | 6b | 8b | 9c | 10b |
| (7g)-281 | 6b | 8b | 9d | 10e |
| (7g)-282 | 6b | 8b | 9d | 10g |
| (7g)-283 | 6b | 8b | 9d | 10h |
| (7g)-284 | 6b | 8b | 9d | 10i |
| (7g)-285 | 6b | 8b | 9d | 10k |
| (7g)-286 | 6b | 8b | 9d | 10l |
| (7g)-287 | 6b | 8b | 9d | 10m |
| (7g)-288 | 6b | 8b | 9d | 10n |
| (7g)-289 | 6b | 8b | 9e | 10b |
| (7g)-290 | 6b | 8b | 9e | 10e |
| (7g)-291 | 6b | 8b | 9e | 10g |
| (7g)-292 | 6b | 8b | 9e | 10h |
| (7g)-293 | 6b | 8b | 9e | 10i |
| (7g)-294 | 6b | 8b | 9e | 10k |
| (7g)-295 | 6b | 8b | 9e | 10l |
| (7g)-296 | 6b | 8b | 9e | 10m |
| (7g)-297 | 6b | 8b | 9e | 10n |
| (7g)-298 | 6b | 8b | 9f | 10b |
| (7g)-299 | 6b | 8b | 9f | 10e |
| (7g)-300 | 6b | 8b | 9f | 10g |
| (7g)-301 | 6b | 8b | 9f | 10h |
| (7g)-302 | 6b | 8b | 9f | 10i |
| (7g)-303 | 6b | 8b | 9f | 10k |
| (7g)-304 | 6b | 8b | 9f | 10l |
| (7g)-305 | 6b | 8b | 9f | 10m |
| (7g)-306 | 6b | 8b | 9g | 10n |
| (7g)-307 | 6b | 8b | 9g | 10b |
| (7g)-308 | 6b | 8b | 9g | 10e |
| (7g)-309 | 6b | 8b | 9g | 10g |
| (7g)-310 | 6b | 8b | 9g | 10h |
| (7g)-311 | 6b | 8b | 9g | 10i |
| (7g)-312 | 6b | 8b | 9g | 10k |
| (7g)-313 | 6b | 8b | 9g | 10l |
| (7g)-314 | 6b | 8b | 9g | 10m |
| (7g)-315 | 6b | 8b | 9g | 10n |
| (7g)-316 | 6c | 8b | 9a | 10b |
| (7g)-317 | 6c | 8b | 9a | 10e |
| (7g)-318 | 6c | 8b | 9a | 10g |
| (7g)-319 | 6c | 8b | 9a | 10h |
| (7g)-320 | 6c | 8b | 9a | 10i |
| (7g)-321 | 6c | 8b | 9a | 10k |
| (7g)-322 | 6c | 8b | 9a | 10l |
| (7g)-323 | 6c | 8b | 9a | 10m |
| (7g)-324 | 6c | 8b | 9a | 10n |
| (7g)-325 | 6c | 8b | 9b | 10b |
| (7g)-326 | 6c | 8b | 9b | 10e |
| (7g)-327 | 6c | 8b | 9b | 10g |
| (7g)-328 | 6c | 8b | 9b | 10h |
| (7g)-329 | 6c | 8b | 9b | 10i |
| (7g)-330 | 6c | 8b | 9b | 10k |
| (7g)-331 | 6c | 8b | 9b | 10l |
| (7g)-332 | 6c | 8b | 9b | 10m |
| (7g)-333 | 6c | 8b | 9b | 10n |
| (7g)-334 | 6c | 8b | 9c | 10b |
| (7g)-335 | 6c | 8b | 9c | 10e |
| (7g)-336 | 6c | 8b | 9c | 10g |
| (7g)-337 | 6c | 8b | 9c | 10h |
| (7g)-338 | 6c | 8b | 9c | 10i |
| (7g)-339 | 6c | 8b | 9c | 10k |
| (7g)-340 | 6c | 8b | 9c | 10l |
| (7g)-341 | 6c | 8b | 9c | 10m |
| (7g)-342 | 6c | 8b | 9c | 10n |
| (7g)-343 | 6c | 8b | 9c | 10b |
| (7g)-344 | 6c | 8b | 9d | 10e |
| (7g)-345 | 6c | 8b | 9d | 10g |
| (7g)-346 | 6c | 8b | 9d | 10h |
| (7g)-347 | 6c | 8b | 9d | 10i |
| (7g)-348 | 6c | 8b | 9d | 10k |
| (7g)-349 | 6c | 8b | 9d | 10l |
| (7g)-350 | 6c | 8b | 9d | 10m |
| (7g)-351 | 6c | 8b | 9d | 10n |
| (7g)-352 | 6c | 8b | 9e | 10b |
| (7g)-353 | 6c | 8b | 9e | 10e |
| (7g)-354 | 6c | 8b | 9e | 10g |
| (7g)-355 | 6c | 8b | 9e | 10h |
| (7g)-356 | 6c | 8b | 9e | 10i |
| (7g)-357 | 6c | 8b | 9e | 10k |
| (7g)-358 | 6c | 8b | 9e | 10l |
| (7g)-359 | 6c | 8b | 9e | 10m |
| (7g)-360 | 6c | 8b | 9e | 10n |
| (7g)-361 | 6c | 8b | 9f | 10b |
| (7g)-362 | 6c | 8b | 9f | 10e |
| (7g)-363 | 6c | 8b | 9f | 10g |
| (7g)-364 | 6c | 8b | 9f | 10h |
| (7g)-365 | 6c | 8b | 9f | 10i |
| (7g)-366 | 6c | 8b | 9f | 10k |
| (7g)-367 | 6c | 8b | 9f | 10l |
| (7g)-368 | 6c | 8b | 9f | 10m |
| (7g)-369 | 6c | 8b | 9g | 10n |
| (7g)-370 | 6c | 8b | 9g | 10b |
| (7g)-371 | 6c | 8b | 9g | 10e |
| (7g)-372 | 6c | 8b | 9g | 10g |
| (7g)-373 | 6c | 8b | 9g | 10h |
| (7g)-374 | 6c | 8b | 9g | 10i |
| (7g)-375 | 6c | 8b | 9g | 10k |
| (7g)-376 | 6c | 8b | 9g | 10l |
| (7g)-377 | 6c | 8b | 9g | 10m |
| (7g)-378 | 6c | 8b | 9g | 10n |

In another aspect, the invention provides the compound that is,
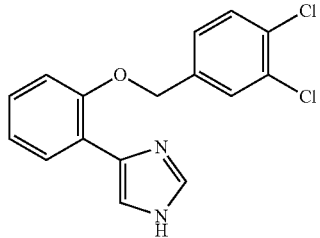 [SMILES: Clc1ccc(COc2ccccc2-c2c[nH]cn2)cc1Cl] 4-(2-(3,4-dichlorobenzyloxy)phenyl)-1H-imidazole;
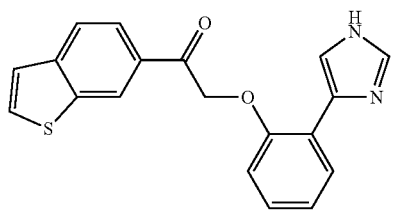 [SMILES: O=C(COc1ccccc1-c1c[nH]cn1)c1ccc2ccsc2c1] 2-(2-(1H-imidazol-4-yl)phenoxy)-1-(benzo[b]thiophen-6-yl)ethanone;
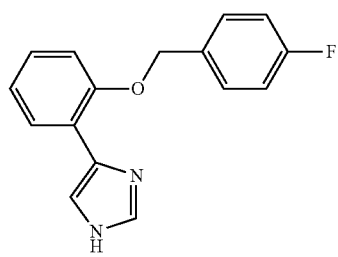 [SMILES: Fc1ccc(COc2ccccc2-c2c[nH]cn2)cc1] 4-(2-(4-fluorobenzyloxy)phenyl)-1H-imidazole;
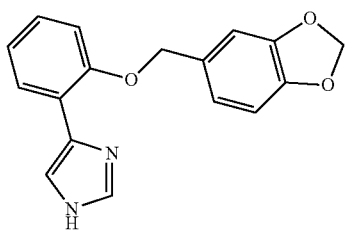 [SMILES: c1ccc(-c2c[nH]cn2)c(OCc2ccc3c(c2)OCO3)c1] 4-(2-(benzo[d][1,3]dioxol-5-ylmethoxy)phenyl)-1H-imidazole;
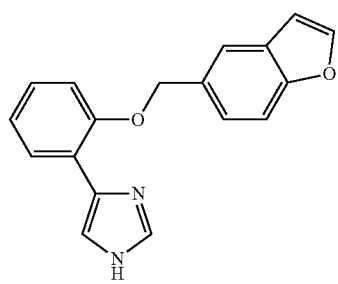 [SMILES: c1ccc(-c2c[nH]cn2)c(OCc2ccc3occc3c2)c1] 4-(2-(benzofuran-5-ylmethoxy)phenyl)-1H-imidazole;
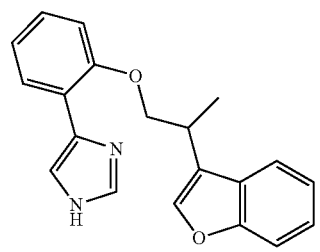 [SMILES: CC(COc1ccccc1-c1c[nH]cn1)c1coc2ccccc12] 4-(2-(2-(benzofuran-3-yl)propoxy)phenyl)-1H-imidazole;

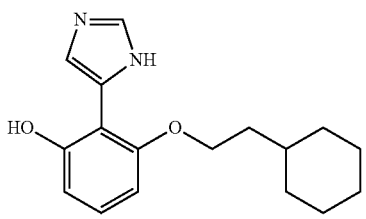 [SMILES: Oc1cccc(OCCC2CCCCC2)c1-c1cnc[nH]1] 3-(2-cyclohexylethoxy)-2-(1H-imidazol-5-yl)phenol;
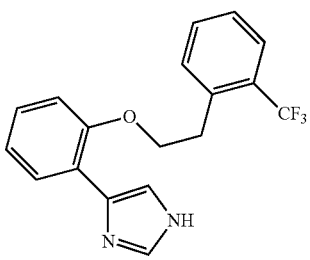 [SMILES: FC(F)(F)c1ccccc1CCOc1ccccc1-c1c[nH]cn1] 4-(2-(2-(trifluoromethyl)phenethoxy)phenyl)-1H-imidazole;
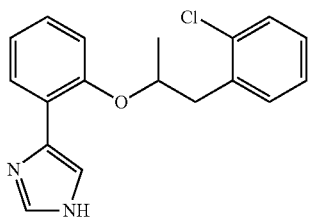 [SMILES: CC(Cc1ccccc1Cl)Oc1ccccc1-c1c[nH]cn1] 4-(2-(1-(2-chlorophenyl)propan-2-yloxy)phenyl)-1H-imidazole;
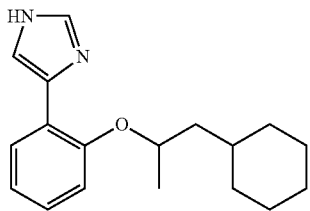 4-(2-(1-cyclohexylpropan-2-yloxy)phenyl)-1H-imidazole;
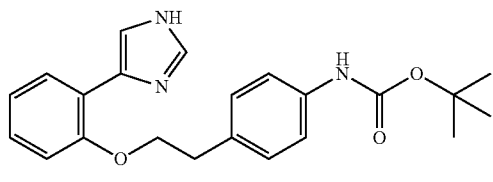 [SMILES: CC(C)(C)OC(=O)Nc1ccc(CCOc2ccccc2-c2c[nH]cn2)cc1] tert-butyl 4-(2-(2-(1H-imidazol-4-yl)phenoxy)ethyl)phenylcarbamate;
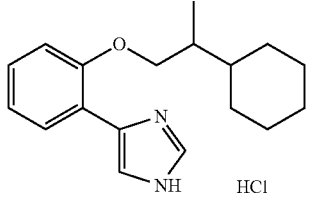 [SMILES: CC(COc1ccccc1-c1c[nH]cn1)C1CCCCC1 ; Cl] 4-(2-(2-cyclohexylpropoxy)phenyl)-1H-imidazole hydrochloride;
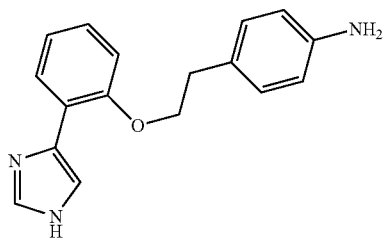 [SMILES: Nc1ccc(CCOc2ccccc2-c2c[nH]cn2)cc1] 4-(2-(2-(1H-imidazol-4-yl)phenoxy)ethyl)aniline;

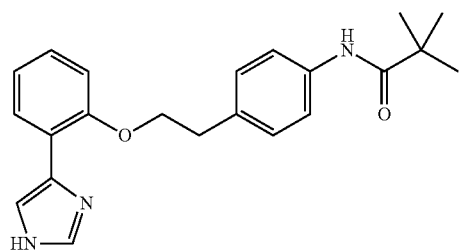 [SMILES: CC(C)(C)C(=O)Nc1ccc(CCOc2ccccc2-c2c[nH]cn2)cc1] N-(4-(2-(2-(1H-imidazol-4-yl)phenoxy)ethyl)phenyl)pivalamide;
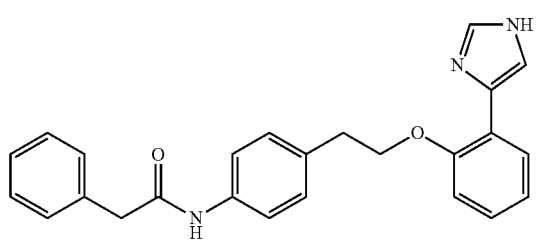 [SMILES: O=C(Cc1ccccc1)Nc1ccc(CCOc2ccccc2-c2c[nH]cn2)cc1] N-(4-(2-(2-(1H-imidazol-4-yl)phenoxy)ethyl)phenyl)-2-phenylacetamide;
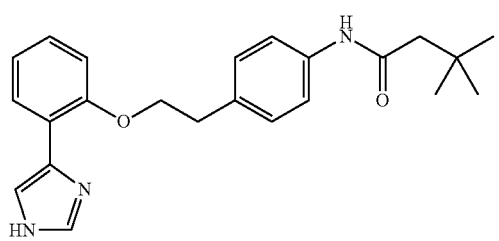 [SMILES: CC(C)(C)CC(=O)Nc1ccc(CCOc2ccccc2-c2c[nH]cn2)cc1] N-(4-(2-(2-(1H-imidazol-4-yl)phenoxy)ethyl)phenyl)-3,3-dimethylbutanamide;
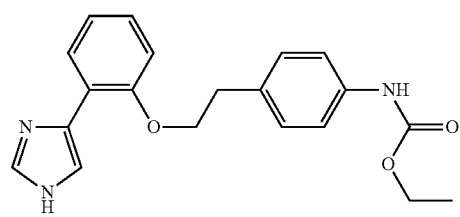 [SMILES: CCOC(=O)Nc1ccc(CCOc2ccccc2-c2c[nH]cn2)cc1] ethyl 4-(2-(2-(1H-imidazol-4-yl)phenoxy)ethyl)phenylcarbamate;
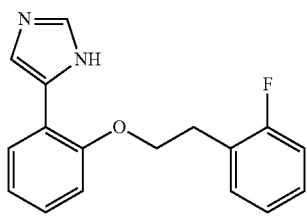 [SMILES: Fc1ccccc1CCOc1ccccc1-c1cnc[nH]1] 5-(2-(2-fluorophenethoxy)phenyl)-1H-imidazole;
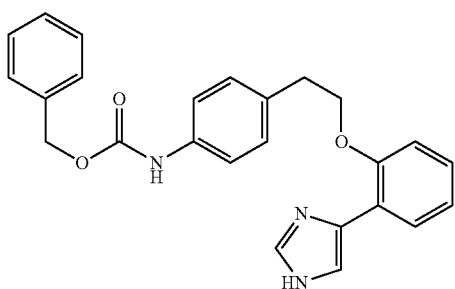 [SMILES: O=C(Nc1ccc(CCOc2ccccc2-c2c[nH]cn2)cc1)OCc1ccccc1] benzyl 4-(2-(2-(1H-imidazol-4-yl)phenoxy)ethyl)phenylcarbamate;

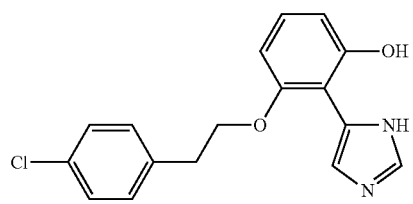 [SMILES: Oc1cccc(OCCc2ccc(Cl)cc2)c1-c1cnc[nH]1] 3-(4-chlorophenethoxy)-2-(1H-imidazol-5-yl)phenol;
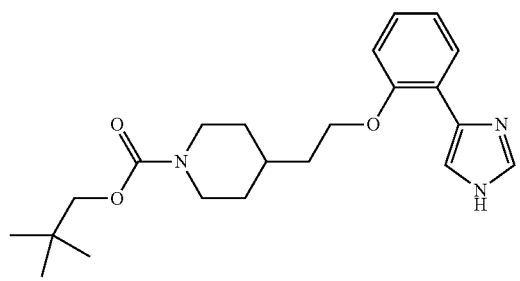 [SMILES: CC(C)(C)COC(=O)N1CCC(CCOc2ccccc2-c2c[nH]cn2)CC1] neopentyl 4-(2-(2-(1H-imidazol-4-yl)phenoxy)ethyl)piperidine-1-carboxylate;
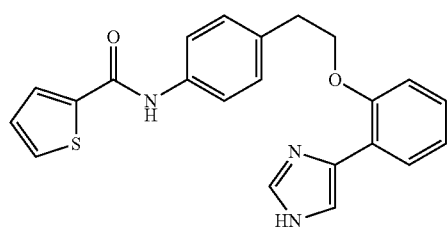 [SMILES: O=C(Nc1ccc(CCOc2ccccc2-c2c[nH]cn2)cc1)c1cccs1] N-(4-(2-(2-(1H-imidazol-4-yl)phenoxy)ethyl)phenyl)thiophene-2-carboxamide;
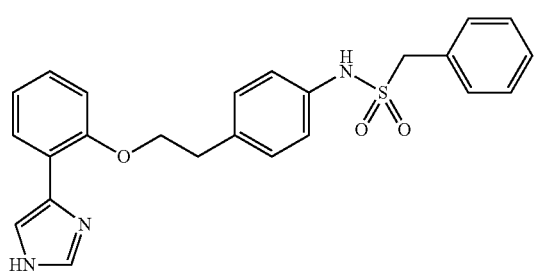 [SMILES: O=S(=O)(Cc1ccccc1)Nc1ccc(CCOc2ccccc2-c2c[nH]cn2)cc1] N-(4-(2-(2-(1H-imidazol-4-yl)phenoxy)ethyl)phenyl)-1-phenylmethanesulfonamide;
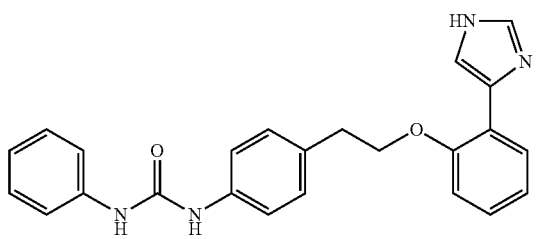 [SMILES: O=C(Nc1ccccc1)Nc1ccc(CCOc2ccccc2-c2c[nH]cn2)cc1] 1-(4-(2-(2-(1H-imidazol-4-yl)phenoxy)ethyl)phenyl)-3-phenylurea;
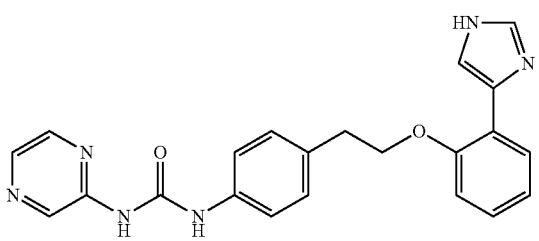 [SMILES: O=C(Nc1ccc(CCOc2ccccc2-c2c[nH]cn2)cc1)Nc1cnccn1] N-(4-(2-(2-(1H-imidazol-4-yl)phenoxy)ethyl)phenyl)-2-(pyrazin-2-yl)acetamide;

-continued

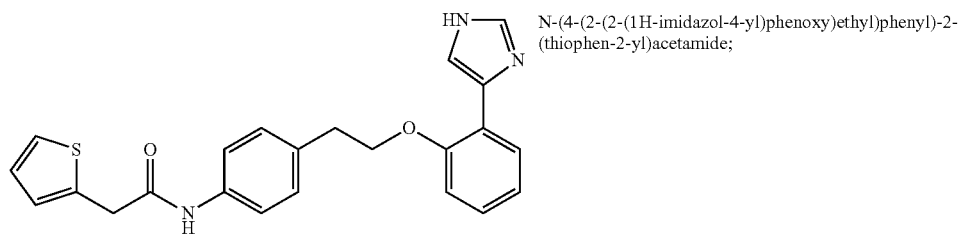

N-(4-(2-(2-(1H-imidazol-4-yl)phenoxy)ethyl)phenyl)-2-(thiophen-2-yl)acetamide;

or a pharmaceutically acceptable salt thereof.

In another aspect, the invention provides the compound that is,

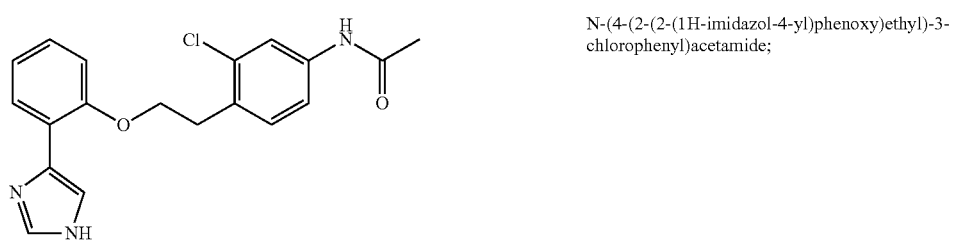

N-(4-(2-(2-(1H-imidazol-4-yl)phenoxy)ethyl)-3-chlorophenyl)acetamide;

3-(3-chlorophenethoxy)-2-(1H-imidazol-5-yl)phenol;

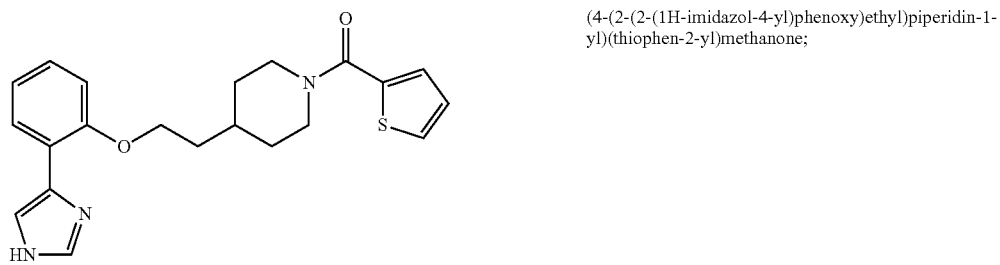

(4-(2-(2-(1H-imidazol-4-yl)phenoxy)ethyl)piperidin-1-yl)(thiophen-2-yl)methanone;

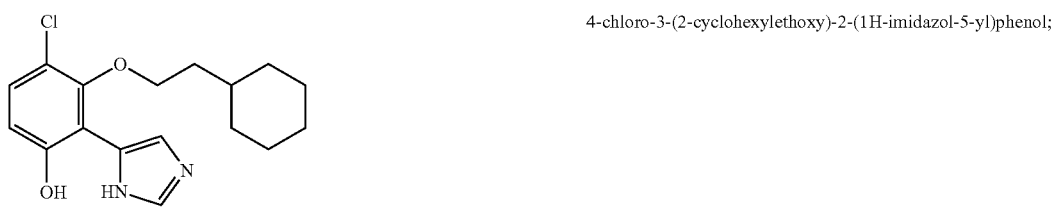

4-chloro-3-(2-cyclohexylethoxy)-2-(1H-imidazol-5-yl)phenol;

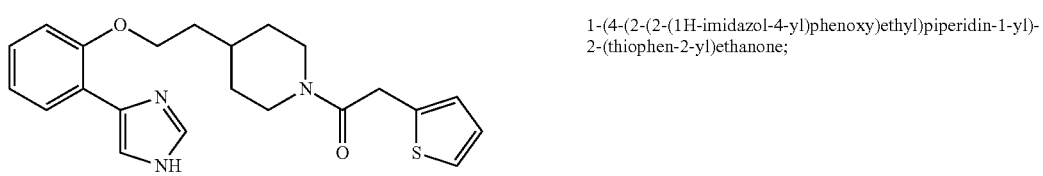

1-(4-(2-(2-(1H-imidazol-4-yl)phenoxy)ethyl)piperidin-1-yl)-2-(thiophen-2-yl)ethanone;

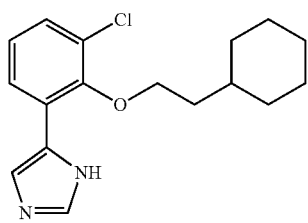 [SMILES: Clc1cccc(-c2cnc[nH]2)c1OCCC1CCCCC1]
5-(3-chloro-2-(2-cyclohexylethoxy)phenyl)-1H-imidazole;

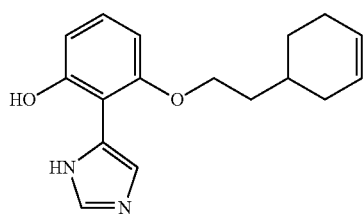 [SMILES: Oc1cccc(OCCC2CC=CCC2)c1-c1cnc[nH]1]
3-(2-(cyclohex-3-en-1-yl)ethoxy)-2-(1H-imidazol-5-yl)phenol;

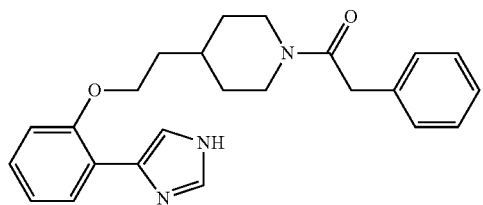 [SMILES: O=C(Cc1ccccc1)N1CCC(CCOc2ccccc2-c2c[nH]cn2)CC1]
1-(4-(2-(2-(1H-imidazol-4-yl)phenoxy)ethyl)piperidin-1-yl)-2-phenylethanone;

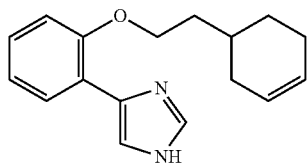 [SMILES: C1=CCC(CCOc2ccccc2-c2c[nH]cn2)CC1]
4-(2-(2-(cyclohex-3-en-1-yl)ethoxy)phenyl)-1H-imidazole;

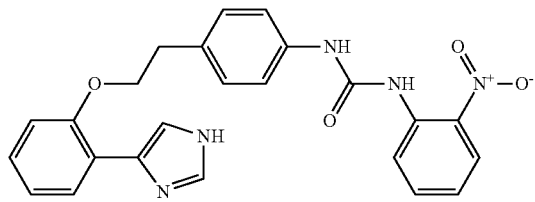 [SMILES: O=C(Nc1ccc(CCOc2ccccc2-c2c[nH]cn2)cc1)Nc1ccccc1[N+](=O)[O-]]
1-(4-(2-(2-(1H-imidazol-4-yl)phenoxy)ethyl)phenyl)-3-(2-nitrophenyl)urea;

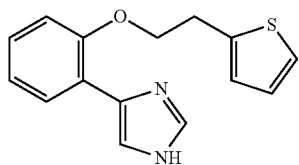 [SMILES: c1csc(CCOc2ccccc2-c2c[nH]cn2)c1]
4-(2-(2-(thiophen-2-yl)ethoxy)phenyl)-1H-imidazole;

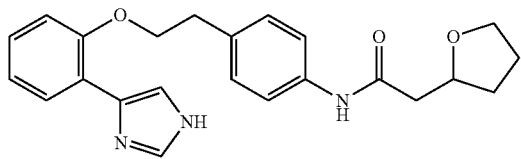 [SMILES: O=C(CC1CCCO1)Nc1ccc(CCOc2ccccc2-c2c[nH]cn2)cc1]
N-(4-(2-(2-(1H-imidazol-4-yl)phenoxy)ethyl)phenyl)-2-(tetrahydrofuran-2-yl)acetamide

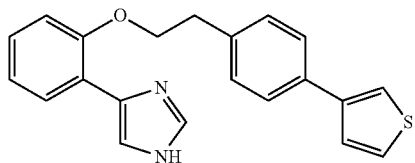 [SMILES: c1ccc(-c2c[nH]cn2)c(OCCc2ccc(-c3ccsc3)cc2)c1]
4-(2-(4-(thiophen-3-yl)phenethoxy)phenyl)-1H-imidazole;

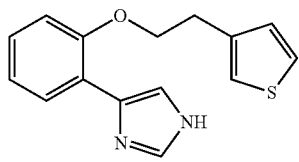 [SMILES: c1ccc(-c2c[nH]cn2)c(OCCc2ccsc2)c1] 4-(2-(2-(thiophen-3-yl)ethoxy)phenyl)-1H-imidazole;

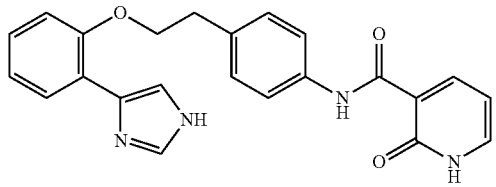 [SMILES: O=C(Nc1ccc(CCOc2ccccc2-c2c[nH]cn2)cc1)c1ccc[nH]c1=O] N-(4-(2-(2-(1H-imidazol-4-yl)phenoxy)ethyl)phenyl)-2-oxo-1,2-dihydropyridine-3-carboxamide;

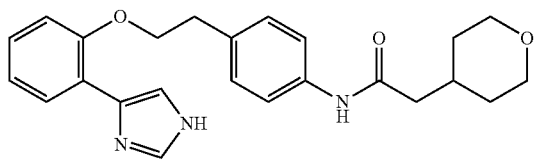 N-(4-(2-(2-(1H-imidazol-4-yl)phenoxy)ethyl)phenyl)-2-(tetrahydro-2H-pyran-4-yl)acetamide;

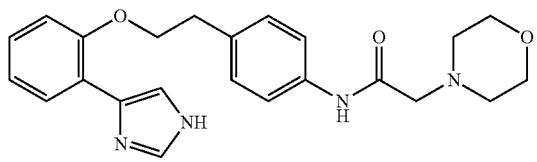 N-(4-(2-(2-(1H-imidazol-4-yl)phenoxy)ethyl)phenyl)-2-morpholinoacetamide;

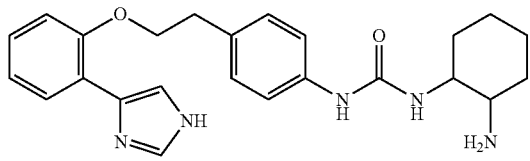 [SMILES: NC1CCCCC1NC(=O)Nc1ccc(CCOc2ccccc2-c2c[nH]cn2)cc1] 1-(4-(2-(2-(1H-imidazol-4-yl)phenoxy)ethyl)phenyl)-3-(2-aminocyclohexyl)urea;

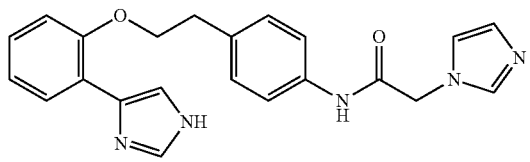 [SMILES: O=C(Cn1ccnc1)Nc1ccc(CCOc2ccccc2-c2c[nH]cn2)cc1] N-(4-(2-(2-(1H-imidazol-4-yl)phenoxy)ethyl)phenyl)-2-(1H-imidazol-1-yl)acetamide;

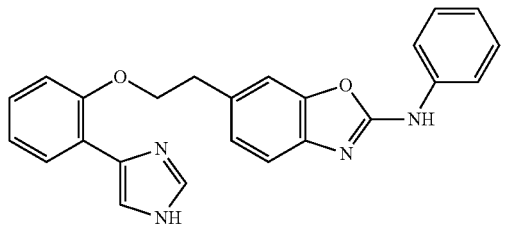 [SMILES: c1ccc(Nc2nc3ccc(CCOc4ccccc4-c4c[nH]cn4)cc3o2)cc1] 6-(2-(2-(1H-imidazol-4-yl)phenoxy)ethyl)-N-phenylbenzo[d]oxazol-2-amine;

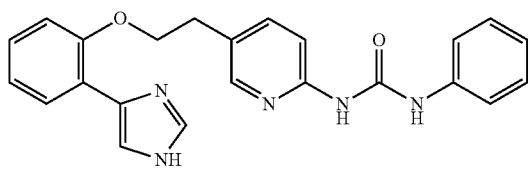 [SMILES: O=C(Nc1ccccc1)Nc1ccc(CCOc2ccccc2-c2c[nH]cn2)cn1] 1-(5-(2-(2-(1H-imidazol-4-yl)phenoxy)ethyl)pyridin-2-yl)-3-phenylurea;

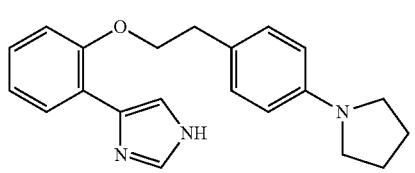 [SMILES: c1ccc(-c2c[nH]cn2)c(OCCc2ccc(N3CCCC3)cc2)c1] 4-(2-(4-(pyrrolidin-1-yl)phenethoxy)phenyl)-1H-imidazole;

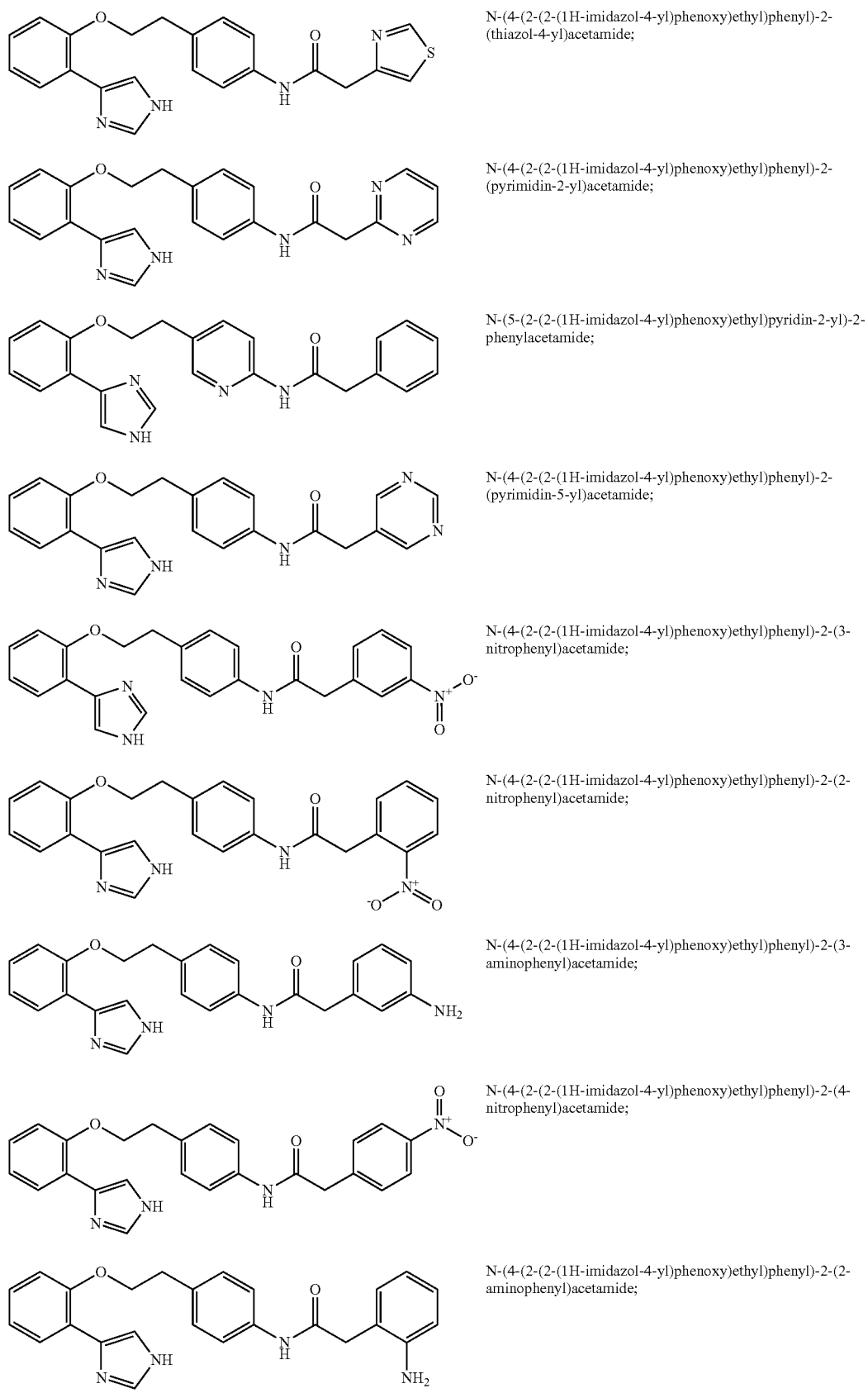

N-(4-(2-(2-(1H-imidazol-4-yl)phenoxy)ethyl)phenyl)-2-(thiazol-4-yl)acetamide;

N-(4-(2-(2-(1H-imidazol-4-yl)phenoxy)ethyl)phenyl)-2-(pyrimidin-2-yl)acetamide;

N-(5-(2-(2-(1H-imidazol-4-yl)phenoxy)ethyl)pyridin-2-yl)-2-phenylacetamide;

N-(4-(2-(2-(1H-imidazol-4-yl)phenoxy)ethyl)phenyl)-2-(pyrimidin-5-yl)acetamide;

N-(4-(2-(2-(1H-imidazol-4-yl)phenoxy)ethyl)phenyl)-2-(3-nitrophenyl)acetamide;

N-(4-(2-(2-(1H-imidazol-4-yl)phenoxy)ethyl)phenyl)-2-(2-nitrophenyl)acetamide;

N-(4-(2-(2-(1H-imidazol-4-yl)phenoxy)ethyl)phenyl)-2-(3-aminophenyl)acetamide;

N-(4-(2-(2-(1H-imidazol-4-yl)phenoxy)ethyl)phenyl)-2-(4-nitrophenyl)acetamide;

N-(4-(2-(2-(1H-imidazol-4-yl)phenoxy)ethyl)phenyl)-2-(2-aminophenyl)acetamide;

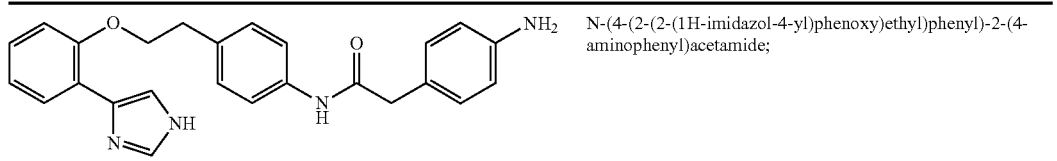 N-(4-(2-(2-(1H-imidazol-4-yl)phenoxy)ethyl)phenyl)-2-(4-aminophenyl)acetamide;

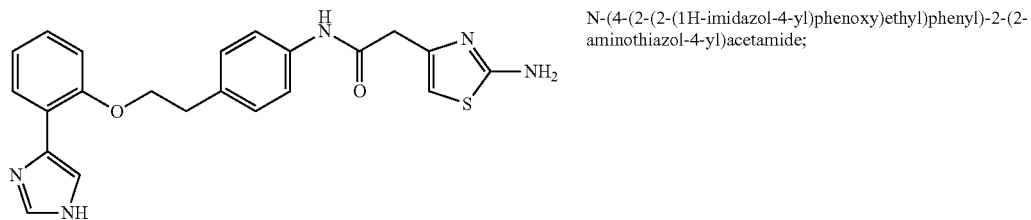 N-(4-(2-(2-(1H-imidazol-4-yl)phenoxy)ethyl)phenyl)-2-(2-aminothiazol-4-yl)acetamide;

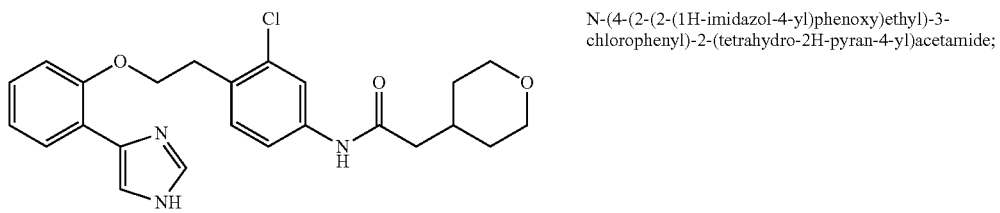 N-(4-(2-(2-(1H-imidazol-4-yl)phenoxy)ethyl)-3-chlorophenyl)-2-(tetrahydro-2H-pyran-4-yl)acetamide;

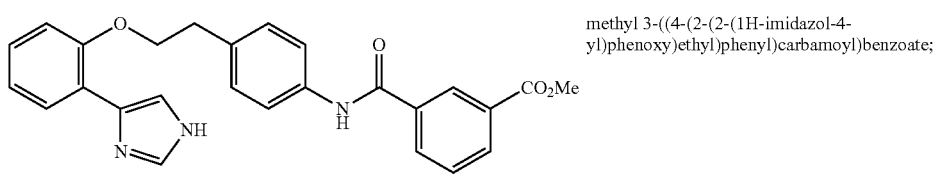 methyl 3-((4-(2-(2-(1H-imidazol-4-yl)phenoxy)ethyl)phenyl)carbamoyl)benzoate;

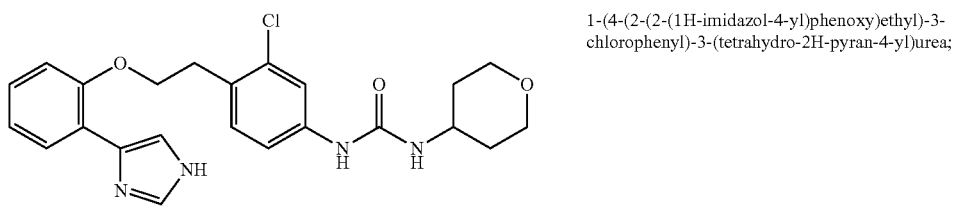 1-(4-(2-(2-(1H-imidazol-4-yl)phenoxy)ethyl)-3-chlorophenyl)-3-(tetrahydro-2H-pyran-4-yl)urea;

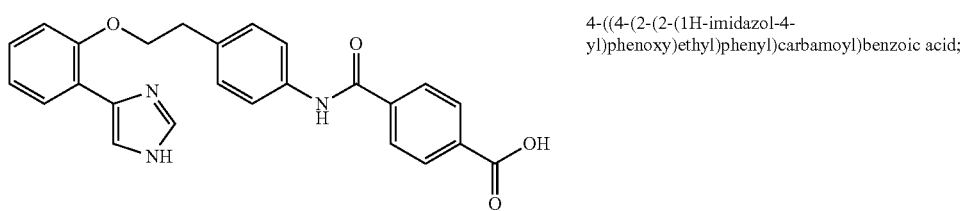 4-((4-(2-(2-(1H-imidazol-4-yl)phenoxy)ethyl)phenyl)carbamoyl)benzoic acid;

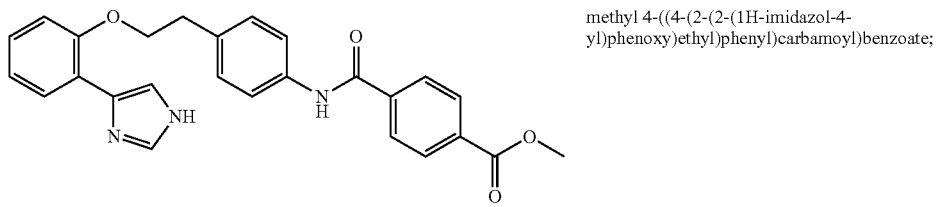 methyl 4-((4-(2-(2-(1H-imidazol-4-yl)phenoxy)ethyl)phenyl)carbamoyl)benzoate;

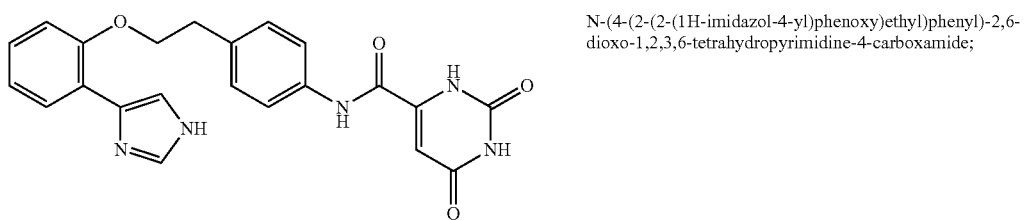 N-(4-(2-(2-(1H-imidazol-4-yl)phenoxy)ethyl)phenyl)-2,6-dioxo-1,2,3,6-tetrahydropyrimidine-4-carboxamide;

-continued

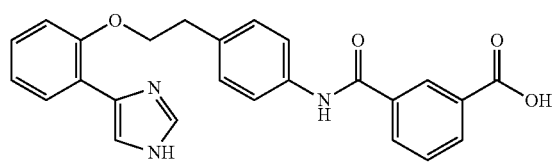 [SMILES: O=C(O)c1cccc(C(=O)Nc2ccc(CCOc3ccccc3-c3c[nH]cn3)cc2)c1]
3-((4-(2-(2-(1H-imidazol-4-yl)phenoxy)ethyl)phenyl)carbamoyl)benzoic acid;

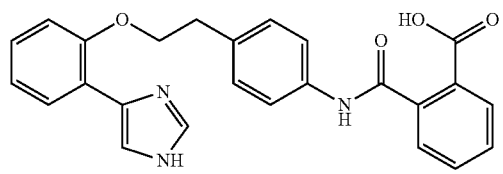 [SMILES: O=C(O)c1ccccc1C(=O)Nc1ccc(CCOc2ccccc2-c2c[nH]cn2)cc1]
2-((4-(2-(2-(1H-imidazol-4-yl)phenoxy)ethyl)phenyl)carbamoyl)benzoic acid;

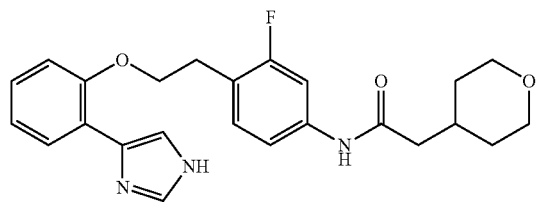 [SMILES: O=C(CC1CCOCC1)Nc1ccc(CCOc2ccccc2-c2c[nH]cn2)c(F)c1]
N-(4-(2-(2-(1H-imidazol-4-yl)phenoxy)ethyl)-3-fluorophenyl)-2-(tetrahydro-2H-pyran-4-yl)acetamide;

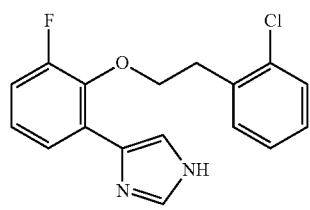 [SMILES: Fc1cccc(-c2c[nH]cn2)c1OCCc1ccccc1Cl]
4-(2-(2-chlorophenethoxy)-3-fluorophenyl)-1H-imidazole;

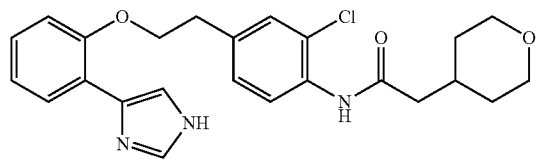 [SMILES: O=C(CC1CCOCC1)Nc1ccc(CCOc2ccccc2-c2c[nH]cn2)cc1Cl]
N-(4-(2-(2-(1H-imidazol-4-yl)phenoxy)ethyl)-2-chlorophenyl)-2-(tetrahydro-2H-pyran-4-yl)acetamide;

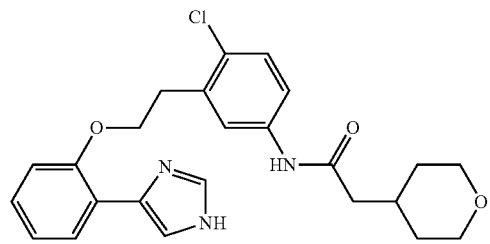
N-(3-(2-(2-(1H-imidazol-4-yl)phenoxy)ethyl)-4-chlorophenyl)-2-(tetrahydro-2H-pyran-4-yl)acetamide;

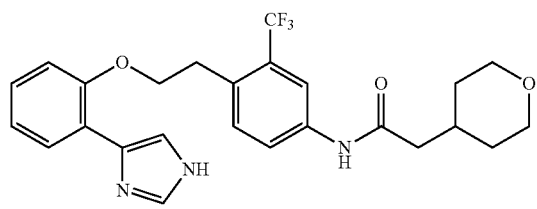 [SMILES: O=C(CC1CCOCC1)Nc1ccc(CCOc2ccccc2-c2c[nH]cn2)c(C(F)(F)F)c1]
N-(4-(2-(2-(1H-imidazol-4-yl)phenoxy)ethyl)-3-(trifluoromethyl)phenyl)-2-(tetrahydro-2H-pyran-4-yl)acetamide;

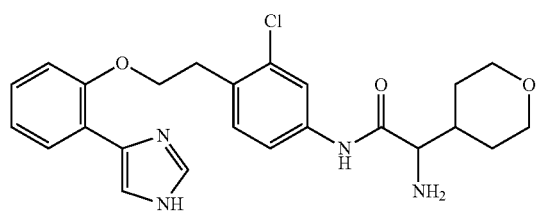 [SMILES: NC(C(=O)Nc1ccc(CCOc2ccccc2-c2c[nH]cn2)c(Cl)c1)C1CCOCC1]
N-(4-(2-(2-(1H-imidazol-4-yl)phenoxy)ethyl)-3-chlorophenyl)-2-amino-2-(tetrahydro-2H-pyran-4-yl)acetamide;

-continued

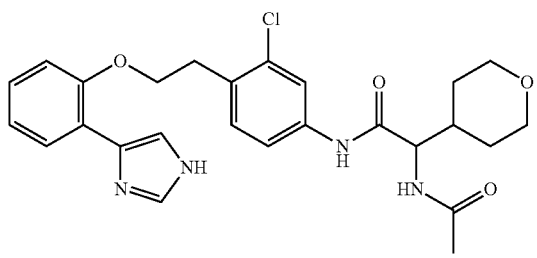 [SMILES: CC(=O)NC(C(=O)Nc1ccc(CCOc2ccccc2-c2c[nH]cn2)c(Cl)c1)C1CCOCC1]
N-(4-(2-(2-(1H-imidazol-4-yl)phenoxy)ethyl)-3-chlorophenyl)-2-acetamido-2-(tetrahydro-2H-pyran-4-yl)acetamide;

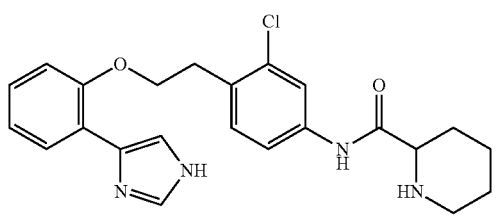 [SMILES: O=C(Nc1ccc(CCOc2ccccc2-c2c[nH]cn2)c(Cl)c1)C1CCCCN1]
N-(4-(2-(2-(1H-imidazol-4-yl)phenoxy)ethyl)-3-chlorophenyl)piperidine-2-carboxamide;

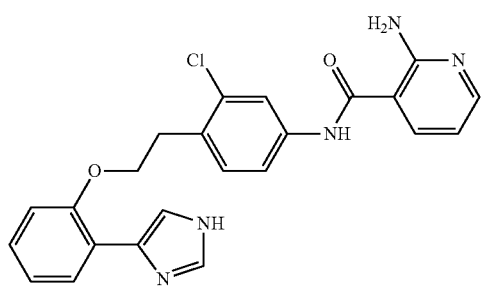 [SMILES: Nc1ncccc1C(=O)Nc1ccc(CCOc2ccccc2-c2c[nH]cn2)c(Cl)c1]
N-(4-(2-(2-(1H-imidazol-4-yl)phenoxy)ethyl)-3-chlorophenyl)-2-aminonicotinamide;

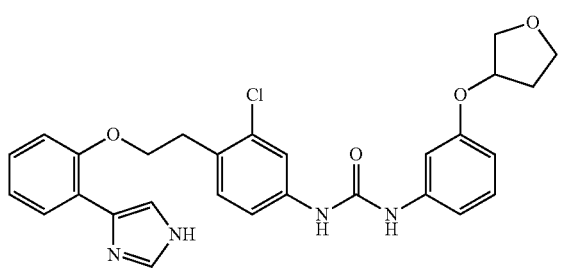 [SMILES: O=C(Nc1cccc(OC2CCOC2)c1)Nc1ccc(CCOc2ccccc2-c2c[nH]cn2)c(Cl)c1]
1-(4-(2-(2-(1H-imidazol-4-yl)phenoxy)ethyl)-3-chlorophenyl)-3-(3-((tetrahydrofuran-3-yl)oxy)phenyl)urea;

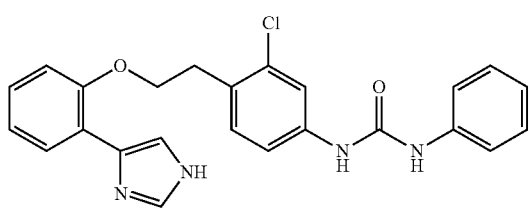 [SMILES: O=C(Nc1ccccc1)Nc1ccc(CCOc2ccccc2-c2c[nH]cn2)c(Cl)c1]
1-(4-(2-(2-(1H-imidazol-4-yl)phenoxy)ethyl)-3-chlorophenyl)-3-phenylurea;

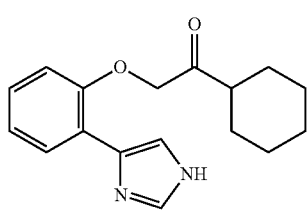
2-(2-(1H-imidazol-4-yl)phenoxy)-1-cyclohexylethanone;

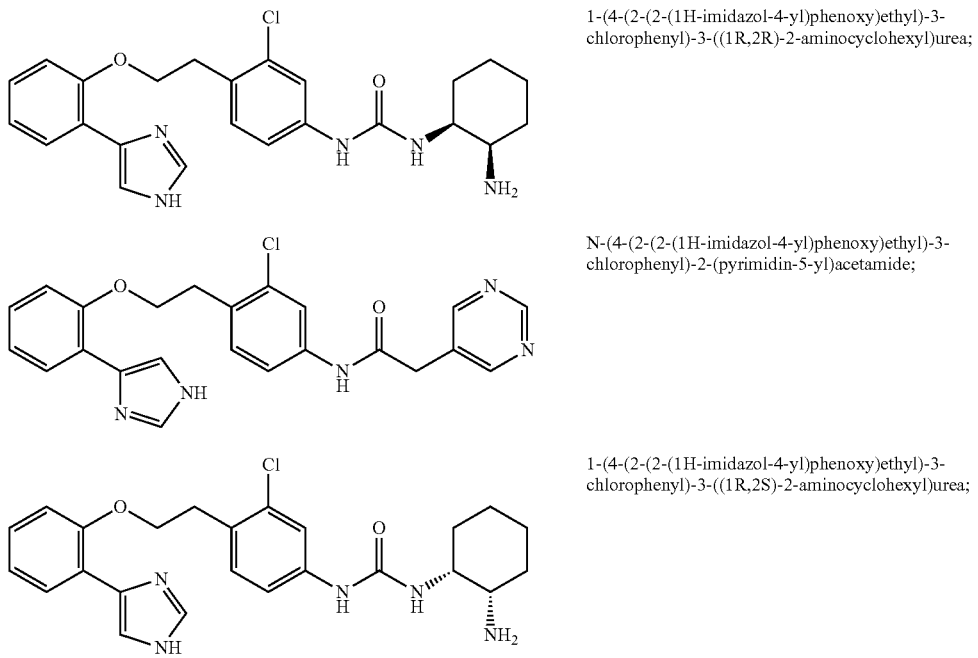

| | |
|---|---|
| | 1-(4-(2-(2-(1H-imidazol-4-yl)phenoxy)ethyl)-3-chlorophenyl)-3-((1R,2R)-2-aminocyclohexyl)urea; |
| | N-(4-(2-(2-(1H-imidazol-4-yl)phenoxy)ethyl)-3-chlorophenyl)-2-(pyrimidin-5-yl)acetamide; |
| | 1-(4-(2-(2-(1H-imidazol-4-yl)phenoxy)ethyl)-3-chlorophenyl)-3-((1R,2S)-2-aminocyclohexyl)urea; | or a pharmaceutically acceptable salt thereof.

In another aspect, the invention provides compounds according to formula (VIII),

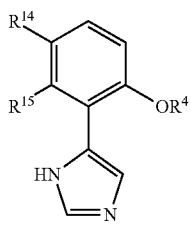

(VIII)

a tautomer thereof, or a pharmaceutically acceptable salt thereof, wherein $R^{14}$ is halogen;

$R^{15}$ is hydrogen or hydroxy, and $R^4$ is hydrogen or —C(O)$R^5$, wherein $R^5$ is (i) $C_1$-$C_6$ alkyl; or (ii) —N($R^2$)($R^3$), wherein $R^2$ is $C_1$-$C_6$ alkyl, aryl, —$C_1$-$C_6$ alkyl-OC(O)$R^6$, or —C(H)($R^{22}$)C(O)O$R^7$, wherein $R^{22}$ is hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with one group that is halo, cyano, —O$R^{23}$, —S$R^{23}$, —N($R^{23}$)$_2$, —C(O)O$R^{23}$, —C(O)N($R^{23}$)$_2$, —N($R^{23}$)C(=N$R^{23}$)N($R^{23}$)$_2$, or $C_1$-$C_6$alkyl, wherein each $R^{23}$ is hydrogen or $C_1$-$C_6$alkyl; and $R^6$ is $C_1$-$C_6$ alkyl;

$R^7$ is hydrogen or $C_1$-$C_6$ alkyl;

$R^3$ is hydrogen or $C_1$-$C_6$ alkyl;

or $R^2$ and $R^3$ taken together with the nitrogen to which they are attached form a heterocyclyl group, wherein the heterocyclyl group is optionally substituted with one or two groups that are each independently oxo or $C_1$-$C_6$ alkyl;

provided that the compound is not 4-chloro-2-(1H-imidazol-5-yl)phenol; and 4-bromo-2-(1H-imidazol-5-yl)phenol.

The invention further comprises subgenera of formula (VIII) in which the substituents are selected as any and all combinations of one or more of $R^4$, $R^{14}$, and $R^{15}$, as defined herein, including without limitation, the following:

$R^4$ is Selected from One of the Following Groups (11a)-(11b):

(11a) hydrogen.

(11b) —C(O)$R^5$.

(11c) —C(O)$R^5$, wherein $R^5$ is $C_1$-$C_6$ alkyl.

(11d) —C(O)N($R^2$)($R^3$).

(11e) —C(O)N($R^2$)($R^3$), wherein $R^2$ is $C_1$-$C_6$ alkyl or aryl; and $R^3$ is hydrogen or $C_1$-$C_6$ alkyl.

(11f) —C(O)N($R^2$)($R^3$), wherein $R^2$ is $C_1$-$C_6$ alkyl; and $R^3$ is $C_1$-$C_6$ alkyl.

(11g) —C(O)N($R^2$)($R^3$), wherein $R^2$ is —$C_1$-$C_6$ alkyl-OC(O)$R^6$ or —C(H)($R^{22}$)C(O)O$R^7$;

$R^3$ is hydrogen or $C_1$-$C_6$ alkyl;

$R^6$ is $C_1$-$C_6$ alkyl;

$R^7$ is hydrogen or $C_1$-$C_6$ alkyl;

and $R^{22}$ is hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with one group that is halo, cyano, —O$R^{23}$, —S$R^{23}$, —N($R^{23}$)$_2$, —C(O)O$R^{23}$, —C(O)N($R^{23}$)$_2$, —N($R^{23}$)C(=N$R^{23}$)N($R^{23}$)$_2$, or $C_1$-$C_6$alkyl, wherein each $R^{23}$ is hydrogen or $C_1$-$C_6$alkyl.

(11h) —C(O)N(R²)(R³), wherein R² is —$C_1$-$C_6$ alkyl-OC(O)R⁶ or —C(H)(R²²)C(O)OR⁷;
R³ is $C_1$-$C_6$ alkyl;
R⁶ is $C_1$-$C_6$ alkyl;
R⁷ is hydrogen or $C_1$-$C_6$ alkyl;
and R²² is hydrogen, $C_1$-$C_6$alkyl, aryl, heteroaryl, arylC₁-C₆alkyl, or heteroarylC₁-C₆alkyl, wherein the alkyl, arylalkyl, and heteroarylalkyl groups are optionally substituted with one group that is halo, cyano, —OR²³, —SR²³, —N(R²³)₂, —C(O)OR²³, —C(O)N(R²³)₂, —N(R²³)C(=NR²³)N(R²³)₂, or $C_1$-$C_6$alkyl, wherein each R²³ is hydrogen or $C_1$-$C_6$alkyl.

(11i) —C(O)N(R²)(R³), wherein R² is —$C_1$-$C_6$ alkyl-OC(O)R⁶ or —C(H)(R²²)C(O)OR⁷;
R³ is $C_1$-$C_6$ alkyl;
R⁶ is $C_1$-$C_6$ alkyl;
R⁷ is hydrogen or $C_1$-$C_6$ alkyl;
and R²² is hydrogen, $C_1$-$C_6$ alkyl, benzyl, 4-hydroxyphenylmethyl, indol-3-ylmethyl, wherein the alkyl group is optionally substituted with one group that is halo, —OH, —SH, —SCH₃, —NH₂, —C(O)OH, —C(O)NH₂, —NHC(=NH)N(H)₂.

(11j) —C(O)N(R²)(R³), wherein R² is $C_1$-$C_6$ alkyl or aryl; and R³ is $C_1$-$C_6$ alkyl; or R² and R³ taken together with the nitrogen to which they are attached form a heterocyclyl group, wherein the heterocyclyl group is optionally substituted with one or two groups that are each independently oxo or $C_1$-$C_6$ alkyl.

(11k) —C(O)N(R²)(R³), wherein R² and R³ taken together with the nitrogen to which they are attached form a heterocyclyl group, wherein the heterocyclyl group is optionally substituted with one or two groups that are each independently oxo or $C_1$-$C_6$ alkyl.

R¹⁴ is Selected from One of the Following Groups (12a)-(12e):
(12a) R¹⁴ is fluoro, chloro, or bromo.
(12b) R¹⁴ is chloro or bromo.
(12c) R¹⁴ is fluoro.
(12d) R¹⁴ is chloro.
(12e) R¹⁴ is bromo.

R¹⁵ is Selected from One of the Following Groups (13a)-(13b):
(13a) R¹⁵ is hydrogen.
(13b) R¹⁵ is hydroxy.

Particular embodiments of this aspect of the invention include compounds of formula (VIII), each as defined in each of the following rows, wherein each entry is a group number as defined above (e.g., (13a) refers to R¹⁵ is hydrogen), and a dash "-" indicates that the variable is as defined for formula (VIII) or defined according to any one of the applicable variable definitions 11(a)-13(b) [e.g., when R¹⁵ is a dash, it can be either as defined for Formula (VIII) or any one of definitions (13a)-(13b)]:

|        | R⁴  | R¹⁴ | R¹⁵ |
|--------|-----|-----|-----|
| (8)-1  | 11a | 12a | 13a |
| (8)-2  | 11a | 12b | 13a |
| (8)-3  | 11a | 12c | 13a |
| (8)-4  | 11a | 12d | 13a |
| (8)-5  | 11a | 12e | 13a |
| (8)-6  | 11a | 12a | 13b |
| (8)-7  | 11a | 12b | 13b |
| (8)-8  | 11a | 12c | 13b |
| (8)-9  | 11a | 12d | 13b |
| (8)-10 | 11a | 12e | 13b |
| (8)-11 | —   | 12a | 13a |
| (8)-12 | —   | 12b | 13a |
| (8)-13 | —   | 12c | 13a |
| (8)-14 | —   | 12d | 13a |
| (8)-15 | —   | 12e | 13a |
| (8)-16 | —   | 12a | 13b |
| (8)-17 | —   | 12b | 13b |
| (8)-18 | —   | 12c | 13b |
| (8)-19 | —   | 12d | 13b |
| (8)-20 | —   | 12e | 13b |

In another aspect, the invention provides compounds according to formula (VIIIa),

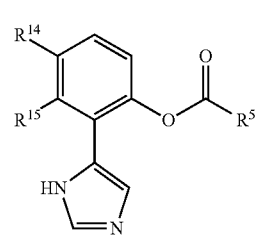

(VIIIa)

a tautomer thereof, or a pharmaceutically acceptable salt thereof, wherein

R¹⁴ is halogen;

R¹⁵ is hydrogen or hydroxy, and

R⁵ is (i) $C_1$-$C_6$ alkyl; or (ii) —N(R²)(R³), wherein

R² is $C_1$-$C_6$ alkyl, aryl, —$C_1$-$C_6$ alkyl-OC(O)R⁶, or —C(H)(R²²)C(O)OR⁷, wherein R²² is hydrogen, $C_1$-$C_6$alkyl, aryl, heteroaryl, arylC₁-C₆alkyl, or heteroarylC₁-C₆alkyl, wherein the alkyl, arylalkyl, and heteroarylalkyl groups are optionally substituted with one group that is halo, cyano, —OR²³, —SR²³, —N(R²³)₂, —C(O)OR²³, —C(O)N(R²³)₂, —N(R²³)C(=NR²³)N(R²³)₂, or $C_1$-$C_6$alkyl, wherein each R²³ is hydrogen or $C_1$-$C_6$alkyl; and R⁶ is $C_1$-$C_6$ alkyl;

R⁷ is hydrogen or $C_1$-$C_6$ alkyl;

R³ is hydrogen or $C_1$-$C_6$ alkyl;

or R² and R³ taken together with the nitrogen to which they are attached form a heterocyclyl group, wherein the heterocyclyl group is optionally substituted with one or two groups that are each independently oxo or $C_1$-$C_6$ alkyl; and each R is independently hydrogen or $C_1$-$C_6$ alkyl.

Particular embodiments of this aspect of the invention include compounds of formula (VIIIa), each as defined in each of the following rows, wherein each entry is a group number as defined above (e.g., (13a) refers to R¹⁵ is hydrogen), and a dash "-" indicates that the variable is as defined for formula (VIIIa) or defined according to any one of the applicable variable definitions 11(a)-13(b) [e.g., when R¹⁵ is a dash, it can be either as defined for Formula (VIIIa) or any one of definitions (13a)-(13b)]:

|  | R⁴ | R¹⁴ | R¹⁵ |
|---|---|---|---|
| (8a)-1 | 11a | 12a | — |
| (8a)-2 | 11b | 12a | — |
| (8a)-3 | 11c | 12a | — |
| (8a)-4 | 11d | 12a | — |
| (8a)-5 | 11e | 12a | — |
| (8a)-6 | 11f | 12a | — |
| (8a)-7 | 11g | 12a | — |
| (8a)-8 | 11h | 12a | — |
| (8a)-9 | 11i | 12a | — |
| (8a)-10 | 11j | 12a | — |
| (8a)-11 | 11k | 12a | — |
| (8a)-12 | 11a | 12b | — |
| (8a)-13 | 11b | 12b | — |
| (8a)-14 | 11c | 12b | — |
| (8a)-15 | 11d | 12b | — |
| (8a)-16 | 11e | 12b | — |
| (8a)-17 | 11f | 12b | — |
| (8a)-18 | 11g | 12b | — |
| (8a)-19 | 11h | 12b | — |
| (8a)-20 | 11i | 12b | — |
| (8a)-21 | 11j | 12b | — |
| (8a)-22 | 11k | 12b | — |
| (8a)-23 | 11a | 12c | — |
| (8a)-24 | 11b | 12c | — |
| (8a)-25 | 11c | 12c | — |
| (8a)-26 | 11d | 12c | — |
| (8a)-27 | 11e | 12c | — |
| (8a)-28 | 11f | 12c | — |
| (8a)-29 | 11g | 12c | — |
| (8a)-30 | 11h | 12c | — |
| (8a)-31 | 11i | 12c | — |
| (8a)-32 | 11j | 12c | — |
| (8a)-33 | 11k | 12c | — |
| (8a)-34 | 11a | 12d | — |
| (8a)-35 | 11b | 12d | — |
| (8a)-36 | 11c | 12d | — |
| (8a)-37 | 11d | 12d | — |
| (8a)-38 | 11e | 12d | — |
| (8a)-39 | 11f | 12d | — |
| (8a)-40 | 11g | 12d | — |
| (8a)-41 | 11h | 12d | — |
| (8a)-42 | 11i | 12d | — |
| (8a)-43 | 11j | 12d | — |
| (8a)-44 | 11k | 12d | — |
| (8a)-45 | 11a | 12e | — |
| (8a)-46 | 11b | 12e | — |
| (8a)-47 | 11c | 12e | — |
| (8a)-48 | 11d | 12e | — |
| (8a)-49 | 11e | 12e | — |
| (8a)-50 | 11f | 12e | — |
| (8a)-51 | 11g | 12e | — |
| (8a)-52 | 11h | 12e | — |
| (8a)-53 | 11i | 12e | — |
| (8a)-54 | 11j | 12e | — |
| (8a)-55 | 11k | 12e | — |
| (8a)-56 | 11a | 12a | 13a |
| (8a)-57 | 11b | 12a | 13a |
| (8a)-58 | 11c | 12a | 13a |
| (8a)-59 | 11d | 12a | 13a |
| (8a)-60 | 11e | 12a | 13a |
| (8a)-61 | 11f | 12a | 13a |
| (8a)-62 | 11g | 12a | 13a |
| (8a)-63 | 11h | 12a | 13a |
| (8a)-64 | 11i | 12a | 13a |
| (8a)-65 | 11j | 12a | 13a |
| (8a)-66 | 11k | 12a | 13a |
| (8a)-67 | 11a | 12b | 13a |
| (8a)-68 | 11b | 12b | 13a |
| (8a)-69 | 11c | 12b | 13a |
| (8a)-70 | 11d | 12b | 13a |
| (8a)-71 | 11e | 12b | 13a |
| (8a)-72 | 11f | 12b | 13a |
| (8a)-73 | 11g | 12b | 13a |
| (8a)-74 | 11h | 12b | 13a |
| (8a)-75 | 11i | 12b | 13a |
| (8a)-76 | 11j | 12b | 13a |
| (8a)-77 | 11k | 12b | 13a |
| (8a)-78 | 11a | 12c | 13a |
| (8a)-79 | 11b | 12c | 13a |
| (8a)-80 | 11c | 12c | 13a |
| (8a)-81 | 11d | 12c | 13a |
| (8a)-82 | 11e | 12c | 13a |
| (8a)-83 | 11f | 12c | 13a |
| (8a)-84 | 11g | 12c | 13a |
| (8a)-85 | 11h | 12c | 13a |
| (8a)-86 | 11i | 12c | 13a |
| (8a)-87 | 11j | 12c | 13a |
| (8a)-88 | 11k | 12c | 13a |
| (8a)-89 | 11a | 12d | 13a |
| (8a)-90 | 11b | 12d | 13a |
| (8a)-91 | 11c | 12d | 13a |
| (8a)-92 | 11d | 12d | 13a |
| (8a)-93 | 11e | 12d | 13a |
| (8a)-94 | 11f | 12d | 13a |
| (8a)-95 | 11g | 12d | 13a |
| (8a)-96 | 11h | 12d | 13a |
| (8a)-97 | 11i | 12d | 13a |
| (8a)-98 | 11j | 12d | 13a |
| (8a)-99 | 11k | 12d | 13a |
| (8a)-100 | 11a | 12e | 13a |
| (8a)-101 | 11b | 12e | 13a |
| (8a)-102 | 11c | 12e | 13a |
| (8a)-103 | 11d | 12e | 13a |
| (8a)-104 | 11e | 12e | 13a |
| (8a)-105 | 11f | 12e | 13a |
| (8a)-106 | 11g | 12e | 13a |
| (8a)-107 | 11h | 12e | 13a |
| (8a)-108 | 11i | 12e | 13a |
| (8a)-109 | 11j | 12e | 13a |
| (8a)-110 | 11k | 12e | 13a |
| (8a)-111 | 11a | 12a | 13b |
| (8a)-112 | 11b | 12a | 13b |
| (8a)-113 | 11c | 12a | 13b |
| (8a)-114 | 11d | 12a | 13b |
| (8a)-115 | 11e | 12a | 13b |
| (8a)-116 | 11f | 12a | 13b |
| (8a)-117 | 11g | 12a | 13b |
| (8a)-118 | 11h | 12a | 13b |
| (8a)-119 | 11i | 12a | 13b |
| (8a)-120 | 11j | 12a | 13b |
| (8a)-121 | 11k | 12a | 13b |
| (8a)-122 | 11a | 12b | 13b |
| (8a)-123 | 11b | 12b | 13b |
| (8a)-124 | 11c | 12b | 13b |
| (8a)-125 | 11d | 12b | 13b |
| (8a)-126 | 11e | 12b | 13b |
| (8a)-127 | 11f | 12b | 13b |
| (8a)-128 | 11g | 12b | 13b |
| (8a)-129 | 11h | 12b | 13b |
| (8a)-130 | 11i | 12b | 13b |
| (8a)-131 | 11j | 12b | 13b |
| (8a)-132 | 11k | 12b | 13b |
| (8a)-133 | 11a | 12c | 13b |
| (8a)-134 | 11b | 12c | 13b |
| (8a)-135 | 11c | 12c | 13b |
| (8a)-136 | 11d | 12c | 13b |
| (8a)-137 | 11e | 12c | 13b |
| (8a)-138 | 11f | 12c | 13b |
| (8a)-139 | 11g | 12c | 13b |
| (8a)-140 | 11h | 12c | 13b |
| (8a)-141 | 11i | 12c | 13b |
| (8a)-142 | 11j | 12c | 13b |
| (8a)-143 | 11k | 12c | 13b |
| (8a)-144 | 11a | 12d | 13b |
| (8a)-145 | 11b | 12d | 13b |
| (8a)-146 | 11c | 12d | 13b |
| (8a)-147 | 11d | 12d | 13b |
| (8a)-148 | 11e | 12d | 13b |
| (8a)-149 | 11f | 12d | 13b |
| (8a)-150 | 11g | 12d | 13b |
| (8a)-151 | 11h | 12d | 13b |
| (8a)-152 | 11i | 12d | 13b |
| (8a)-153 | 11j | 12d | 13b |
| (8a)-154 | 11k | 12d | 13b |
| (8a)-155 | 11a | 12e | 13b |
| (8a)-156 | 11b | 12e | 13b |

|        | R⁴  | R¹⁴ | R¹⁵ |
|--------|-----|-----|-----|
| (8a)-157 | 11c | 12e | 13b |
| (8a)-158 | 11d | 12e | 13b |
| (8a)-159 | 11e | 12e | 13b |
| (8a)-160 | 11f | 12e | 13b |
| (8a)-161 | 11g | 12e | 13b |
| (8a)-162 | 11h | 12e | 13b |

|        | R⁴  | R¹⁴ | R¹⁵ |
|--------|-----|-----|-----|
| (8a)-163 | 11i | 12e | 13b |
| (8a)-164 | 11j | 12e | 13b |
| (8a)-165 | 11k | 12e | 13b |

In another aspect, the invention provides the compound that is,

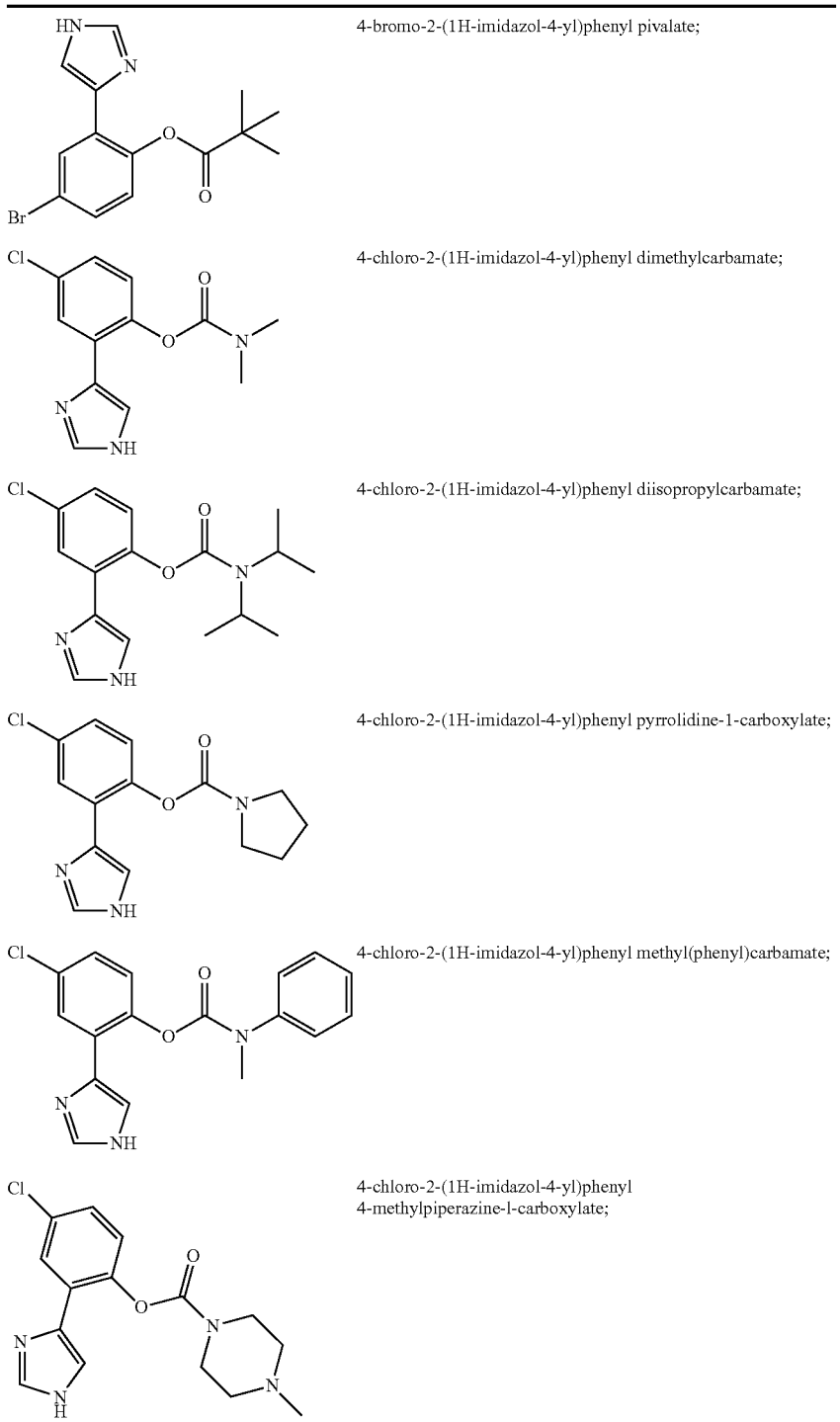

4-bromo-2-(1H-imidazol-4-yl)phenyl pivalate;

4-chloro-2-(1H-imidazol-4-yl)phenyl dimethylcarbamate;

4-chloro-2-(1H-imidazol-4-yl)phenyl diisopropylcarbamate;

4-chloro-2-(1H-imidazol-4-yl)phenyl pyrrolidine-1-carboxylate;

4-chloro-2-(1H-imidazol-4-yl)phenyl methyl(phenyl)carbamate;

4-chloro-2-(1H-imidazol-4-yl)phenyl 4-methylpiperazine-1-carboxylate;

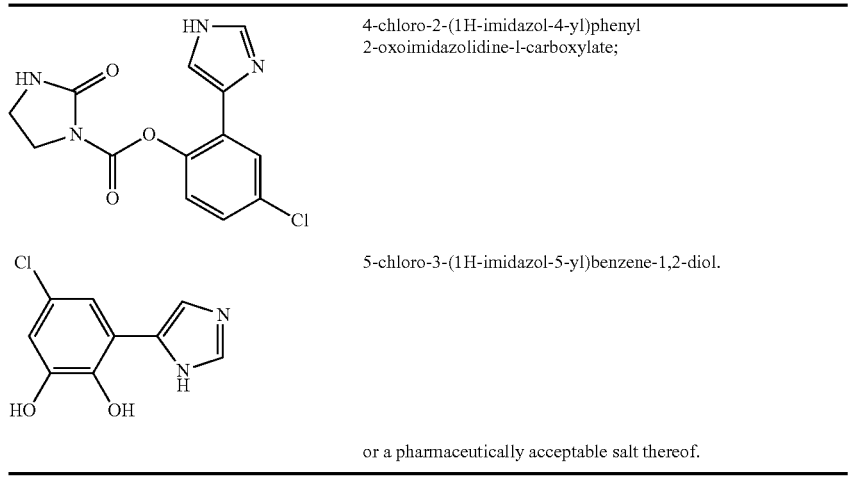

4-chloro-2-(1H-imidazol-4-yl)phenyl 2-oxoimidazolidine-1-carboxylate;

5-chloro-3-(1H-imidazol-5-yl)benzene-1,2-diol.

or a pharmaceutically acceptable salt thereof.

In another aspect, the invention provides the compound that is,

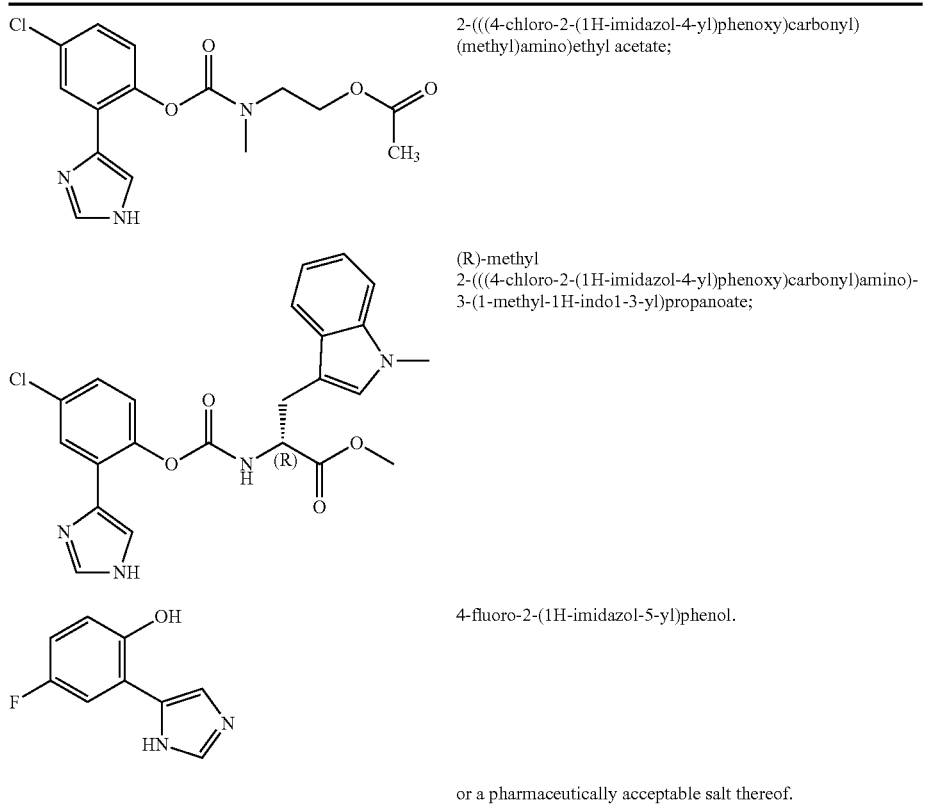

2-(((4-chloro-2-(1H-imidazol-4-yl)phenoxy)carbonyl)(methyl)amino)ethyl acetate;

(R)-methyl 2-(((4-chloro-2-(1H-imidazol-4-yl)phenoxy)carbonyl)amino)-3-(1-methyl-1H-indol-3-yl)propanoate;

4-fluoro-2-(1H-imidazol-5-yl)phenol.

or a pharmaceutically acceptable salt thereof.

In another aspect, the present disclosure provides compounds and pharmaceutical compositions comprising the compounds together with a pharmaceutically acceptable excipient, diluent, or carrier, wherein the compounds are according to any one of the preceding aspects of the invention or any embodiment thereof.

In another aspect, the invention provides methods for treating indoleamine 2,3-dioxygenase (IDO) mediated immunosuppression in a subject in need thereof, comprising administering an effective indoleamine 2,3-dioxygenase inhibiting amount of a compound or a pharmaceutical composition according to any of the preceding aspects.

In one embodiment, the immunosuppression is associated with an infectious disease, or cancer.

In another embodiment, the immunosuppression is associated with an infectious disease and the infectious disease is a viral infection selected from the group consisting of: hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

In another embodiment, the immunosuppression is immunosupression associated with HIV-1 infection.

In another embodiment, the immunosuppression is associated with a cancer.

In an embodiment, the immunosuppression is tumor-specific immunosuppression associated with cancer.

In another embodiment, the immunosuppression is associated with a cancer, wherein the cancer is colon, pancreas, breast, prostate, lung, brain, ovary, cervix, testes, renal, head, or neck cancer, or lymphoma, leukemia, or melanoma.

In another aspect, the invention provides the use of compounds described by any one of the preceding aspects (and any embodiment thereof), as defined above, for the preparation of a medicament for the treatment of medical conditions that benefit from the inhibition of enzymatic activity of indoleamine-2,3-dioxygenase. Medical conditions contemplated in this aspect include all the conditions described herein.

In another aspect, the invention provides a use of compounds described by any one of the preceding aspects (and any embodiment thereof), as defined above, for the preparation of a medicament to stimulate T cell proliferation or to reverse an immunologic state of anergy or immunosuppression.

In one embodiment, the anergy or immunosuppression is caused by expression of the enzyme indoleamine-2,3-dioxygenase.

In another aspect, the invention provides the use of compounds described by any one of the preceding aspects (and any embodiment thereof), as defined above, for the preparation of a medicament for the treatment of immunosuppression associated with cancer, infectious diseases, or viral infections.

In one embodiment, the invention provides the use of compounds described in to any one of the preceding aspects (and any embodiment thereof), as defined above, for the preparation of a medicament for the treatment of tumor-specific immunosuppression associated with cancer. Preferably, the cancer is cancer of the colon, pancreas, breast, prostate, lung, brain, ovary, cervix, testes, renal, or head and neck, lymphoma, leukemia, melanoma, and the like.

In another embodiment, the invention provides the use of compounds described in any of the preceding aspects (and any embodiment thereof), as defined above, and embodiments thereof as defined above, for the preparation of a medicament for the treatment of infectious diseases where the infectious disease is a viral infection. Preferably, the viral infection is selected from the group consisting of: influenza, hepatitis C virus (HCV), human papilloma virus (HPV), cytomegalovirus (CMV), Epstein-Barr virus (EBV), varicella zoster virus, poliovirus, coxsackie virus, and human immunodeficiency virus (HIV). More preferably, the viral infection is human immunodeficiency virus (HIV).

DEFINITIONS

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

The compounds described herein contain imidazole rings which, when one or the imidazolyl nitrogens is substituted by hydrogen, can exist in tautomeric forms as are familiar to one skilled in the art. The compounds described herein are understood to include all tautomeric forms thereof. For example, the following pairs of structures are merely tautomers of one another and represent the same chemical compound,

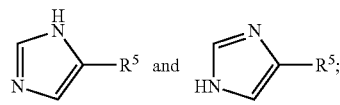

and

The term "alkenyl" as used herein, means a straight or branched chain hydrocarbon containing from 2 to 10 carbons, unless otherwise specified, and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl, and 3,7-dimethylocta-2,6-dienyl.

The term "alkoxy" as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkyl" as used herein, means a straight or branched chain hydrocarbon containing from 1 to 10 carbon atoms, unless otherwise specified. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl. When an "alkyl" group is a linking group between two other moieties, then it may also be a straight or branched chain; examples include, but are not limited to —CH$_2$—, —CH$_2$CH$_2$—, —CH$_2$CH$_2$CHC (CH$_3$)—, —CH$_2$CH(CH$_2$CH$_3$)CH$_2$—.

The term "alkyloxycarbonyl" as used herein means an —C(O)OR$^O$ group, where R$^O$ is an alkyl group as defined herein.

The term "alkylcarbonyloxy" as used herein means an —OC(O)R$^O$ group, where R$^O$ is an alkyl group as defined herein.

The term "alkylthio" as used herein, means an —SR$^O$ group, where R$^O$ is an alkyl group as defined herein.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino" as used herein, means a —NH$_2$ group.

The term "aryl," as used herein, means a phenyl (i.e., monocyclic aryl), or a bicyclic ring system containing at least one phenyl ring or an aromatic bicyclic ring containing only carbon atoms in the aromatic bicyclic ring system. The bicyclic aryl can be azulenyl, naphthyl, or a phenyl fused to a monocyclic cycloalkyl, a monocyclic cycloalkenyl, or a monocyclic heterocyclyl. The bicyclic aryl is attached to the parent molecular moiety through any carbon atom contained within the phenyl portion of the bicyclic system, or any carbon atom with the napthyl or azulenyl ring. The fused monocyclic cycloalkyl or monocyclic heterocyclyl portions of the bicyclic aryl are optionally substituted with one or two oxo and/or thia groups. Representative examples of the bicyclic aryls include, but are not limited to, azulenyl, naphthyl, dihydroinden-1-yl, dihydroinden-2-yl, dihydroinden-3-yl, dihydroinden-4-yl, 2,3-dihydroindol-4-yl, 2,3-dihydroindol-5-yl, 2,3-dihydroindol-6-yl, 2,3-dihydroindol-7-yl, inden-1-yl, inden-2-yl, inden-3-yl, inden-4-yl, dihydronaphthalen-2-yl, dihydronaphthalen-3-yl, dihydronaphthalen-4-yl, dihydronaphthalen-1-yl, 5,6,7,8-tetrahydronaphthalen-1-yl, 5,6,7,8-tetrahydronaphthalen-2-yl, 2,3-dihydrobenzofuran-4-yl, 2,3-dihydrobenzofuran-5-yl, 2,3-dihydrobenzofuran-6-yl, 2,3-dihydrobenzofuran-7-yl, benzo[d][1,3]dioxol-4-yl, benzo[d][1,3]dioxol-5-yl, 2H-chromen-2-on-5-yl, 2H-chromen-2-on-6-yl, 2H-chromen-2-on-7-yl, 2H-chromen-2-on-8-yl, isoindoline-1,3-dion-4-yl, isoindoline-1,3-dion-5-yl, inden-1-on-4-yl, inden-1-on-5-yl, inden-1-on-6-yl, inden-1-on-7-yl, 2,3-dihydrobenzo[b][1,4]dioxan-5-yl, 2,3-dihydrobenzo[b][1,4]dioxan-6-yl, 2H-benzo[b][1,4]oxazin3(4H)-on-5-yl, 2H-benzo[b][1,4]oxazin3(4H)-on-6-yl, 2H-benzo[b][1,4]oxazin3(4H)-on-7-yl, 2H-benzo[b][1,4]oxazin3(4H)-on-8-yl, benzo[d]oxazin-2(3H)-on-5-yl, benzo[d]oxazin-2(3H)-on-6-yl, benzo[d]oxazin-2(3H)-on-7-yl, benzo[d]oxazin-2(3H)-on-8-yl, quinazolin-4(3H)-on-5-yl, quinazolin-4(3H)-on-6-yl, quinazolin-4(3H)-on-7-yl, quinazolin-4(3H)-on-8-yl, quinoxalin-2(1H)-on-5-yl, quinoxalin-2(1H)-on-6-yl, quinoxalin-2(1H)-on-7-yl, quinoxalin-2(1H)-on-8-yl, benzo[d]thiazol-2(3H)-on-4-yl, benzo[d]thiazol-2(3H)-on-5-yl, benzo[d]thiazol-2(3H)-on-6-yl, and, benzo[d]thiazol-2(3H)-on-7-yl. In certain embodiments, the bicyclic aryl is (i) naphthyl or (ii) a phenyl ring fused to either a 5 or 6 membered monocyclic cycloalkyl, a 5 or 6 membered monocyclic cycloalkenyl, or a 5 or 6 membered monocyclic heterocyclyl, wherein the fused cycloalkyl, cycloalkenyl, and heterocyclyl groups are optionally substituted with one or two groups which are independently oxo or thia.

The term "arylalkyl" and "-alkylaryl" as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "carboxy" as used herein, means a —CO$_2$H group.

The terms "cyano" and "nitrile" as used herein, mean a —CN group.

The term "cycloalkyl" as used herein, means a monocyclic or a bicyclic cycloalkyl ring system. Monocyclic ring systems are cyclic hydrocarbon groups containing from 3 to 8 carbon atoms, where such groups can be saturated or unsaturated, but not aromatic. In certain embodiments, cycloalkyl groups are fully saturated. Examples of monocyclic cycloalkyls include cyclopropyl, cyclobutyl, cyclopentyl, cyclopentenyl, cyclohexyl, cyclohexenyl, cycloheptyl, and cyclooctyl. Bicyclic cycloalkyl ring systems are bridged monocyclic rings or fused bicyclic rings. Bridged monocyclic rings contain a monocyclic cycloalkyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Fused bicyclic cycloalkyl ring systems contain a monocyclic cycloalkyl ring fused to either a phenyl, a monocyclic cycloalkyl, a monocyclic cycloalkenyl, a monocyclic heterocyclyl, or a monocyclic heteroaryl. The bridged or fused bicyclic cycloalkyl is attached to the parent molecular moiety through any carbon atom contained within the monocyclic cycloalkyl ring. Cycloalkyl groups are optionally substituted with one or two groups which are independently oxo or thia. In certain embodiments, the fused bicyclic cycloalkyl is a 5 or 6 membered monocyclic cycloalkyl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused bicyclic cycloalkyl is optionally substituted by one or two groups which are independently oxo or thia.

"Cycloalkenyl" as used herein refers to a monocyclic or a bicyclic cycloalkenyl ring system. Monocyclic ring systems are cyclic hydrocarbon groups containing from 3 to 8 carbon atoms, where such groups are unsaturated (i.e., containing at least one annular carbon-carbon double bond), but not aromatic. Examples of monocyclic ring systems include cyclopentenyl and cyclohexenyl. Bicyclic cycloalkenyl rings are bridged monocyclic rings or a fused bicyclic rings. Bridged monocyclic rings contain a monocyclic cycloalkenyl ring where two non-adjacent carbon atoms of the monocyclic ring are linked by an alkylene bridge of between one and three additional carbon atoms (i.e., a bridging group of the form —(CH$_2$)$_w$—, where w is 1, 2, or 3). Representative examples of bicyclic cycloalkenyls include, but are not limited to, norbornenyl and bicyclo[2.2.2]oct-2-enyl. Fused bicyclic cycloalkenyl ring systems contain a monocyclic cycloalkenyl ring fused to either a phenyl, a monocyclic cycloalkyl, a monocyclic cycloalkenyl, a monocyclic heterocyclyl, or a monocyclic heteroaryl. The bridged or fused bicyclic cycloalkenyl is attached to the parent molecular moiety through any carbon atom contained within the monocyclic cycloalkenyl ring. Cycloalkenyl groups are optionally substituted with one or two groups which are independently oxo or thia.

The term "epoxy" as used herein, means a

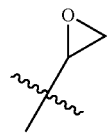 [SMILES: *C1CO1]

group.

The term "formyl" as used herein, means a —C(O)H group.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl," as used herein, means a monocyclic heteroaryl or a bicyclic ring system containing at least one heteroaromatic ring. The monocyclic heteroaryl can be a 5 or 6 membered ring. The 5 membered ring consists of two double bonds and one, two, three or four nitrogen atoms and optionally one oxygen or sulfur atom. The 6 membered ring consists of three double bonds and one, two, three or four nitrogen atoms. The 5 or 6 membered heteroaryl is connected to the parent molecular moiety through any carbon atom or any nitrogen atom contained within the heteroaryl. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, a monocyclic cycloalkyl, a monocyclic cycloalkenyl, a monocyclic heterocyclyl, or a monocyclic heteroaryl. The fused cycloalkyl or heterocyclyl portion of the bicyclic heteroaryl group is optionally substituted with one or two groups which are independently oxo or thia. When the bicyclic heteroaryl contains a fused cycloalkyl, cycloalkenyl, or heterocyclyl ring, then the bicyclic heteroaryl group is connected to the parent molecular moiety through any carbon or nitrogen atom contained within the monocyclic heteroaryl portion of the bicyclic ring system. When the bicyclic heteroaryl is a monocyclic heteroaryl fused to a phenyl ring or a monocyclic heteroaryl, then the bicyclic heteroaryl group is connected to the parent molecular moiety through any carbon atom or nitrogen atom within the bicyclic ring system. Representative examples of bicyclic heteroaryl include, but are not limited to, benzimidazolyl, benzofuranyl, benzothienyl, benzoxadiazolyl, benzoxathiadiazolyl, benzothiazolyl, cinnolinyl, 5,6-dihydroquinolin-2-yl, 5,6-dihydroisoquinolin-1-yl, furopyridinyl, indazolyl, indolyl, isoquinolinyl; naphthyridinyl, quinolinyl, purinyl, 5,6,7,8-tetrahydroquinolin-2-yl, 5,6,7,8-tetrahydroquinolin-3-yl, 5,6,7,8-tetrahydroquinolin-4-yl, 5,6,7,8-tetrahydroisoquinolin-1-yl, thienopyridinyl, 4,5,6,7-tetrahydrobenzo[c][1,2,5]oxadiazolyl, and 6,7-dihydrobenzo[c][1,2,5]oxadiazol-4(5H)-onyl. In certain embodiments, the fused bicyclic heteroaryl is a 5 or 6 membered monocyclic heteroaryl ring fused to either a phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the fused cycloalkyl, cycloalkenyl, and heterocyclyl groups are optionally substituted with one or two groups which are independently oxo or thia.

The term "heteroarylalkyl" and "-alkylheteroaryl" as used herein, means a heteroaryl, as defined herein, appended to the parent molecular moiety through an alkyl group, as defined herein. Representative examples of heteroarylalkyl include, but are not limited to, fur-3-ylmethyl, 1H-imidazol-2-ylmethyl, 1H-imidazol-4-ylmethyl, 1-(pyridin-4-yl)ethyl, pyridin-3-ylmethyl, pyridin-4-ylmethyl, pyrimidin-5-ylmethyl, 2-(pyrimidin-2-yl)propyl, thien-2-ylmethyl, and thien-3-ylmethyl.

The term "heterocyclyl" as used herein, means a monocyclic heterocycle or a bicyclic heterocycle. The monocyclic heterocycle is a 3, 4, 5, 6 or 7 membered ring containing at least one heteroatom independently selected from the group consisting of O, N, and S where the ring is saturated or unsaturated, but not aromatic. The 3 or 4 membered ring contains 1 heteroatom selected from the group consisting of O, N and S. The 5 membered ring can contain zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to either a phenyl, a monocyclic cycloalkyl, a monocyclic cycloalkenyl, a monocyclic heterocycle, or a monocyclic heteroaryl. The bicyclic heterocycle is connected to the parent molecular moiety through any carbon atom or any nitrogen atom contained within the monocyclic heterocycle portion of the bicyclic ring system. Representative examples of bicyclic heterocyclyls include, but are not limited to, 2,3-dihydrobenzofuran-2-yl, 2,3-dihydrobenzofuran-3-yl, indolin-1-yl, indolin-2-yl, indolin-3-yl, 2,3-dihydrobenzothien-2-yl, decahydroquinolinyl, decahydroisoquinolinyl, octahydro-1H-indolyl, and octahydrobenzofuranyl. Heterocyclyl groups are optionally substituted with one or two groups which are independently oxo or thia. In certain embodiments, the bicyclic heterocyclyl is a 5 or 6 membered monocyclic heterocyclyl ring fused to phenyl ring, a 5 or 6 membered monocyclic cycloalkyl, a 5 or 6 membered monocyclic cycloalkenyl, a 5 or 6 membered monocyclic heterocyclyl, or a 5 or 6 membered monocyclic heteroaryl, wherein the bicyclic heterocyclyl is optionally substituted by one or two groups which are independently oxo or thia.

The term "hydroxy" as used herein, means an —OH group.

The terms "mercapto" and "thiol" as used herein, mean a —SH group.

The term "nitro" as used herein, means a —$NO_2$ group.

The term "oxo" as used herein means a =O group.

The term "saturated" as used herein means the referenced chemical structure does not contain any multiple carbon-carbon bonds. For example, a saturated cycloalkyl group as defined herein includes cyclohexyl, cyclopropyl, and the like.

The term "thia" as used herein means a =S group.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the IDO enzyme with a compound includes the administration of a compound described herein to an individual or patient, such as a human, having IDO, as well as, for example, introducing a compound into a sample containing a cellular or purified preparation containing the IDO enzyme.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician, which includes one or more of the following:

(1) preventing the disease; for example, preventing a disease, condition or disorder in an individual who may be predisposed to the disease, condition or disorder but does not yet experience or display the pathology or symptomatology of the disease;

(2) inhibiting the disease; for example, inhibiting a disease, condition or disorder in an individual who is experiencing or displaying the pathology or symptomatology of the disease, condition or disorder; and (3) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease.

As used here, the terms "treatment" and "treating" means (i) ameliorating the referenced disease state, for example, ameliorating a disease, condition or disorder in an individual who is experiencing or displaying the pathology or symptomatology of the disease, condition or disorder (i.e., reversing or improving the pathology and/or symptomatology) such as decreasing the severity of disease; or (ii) eliciting the referenced biological effect (e.g., IDO modulation or tryptophan degradation inhibition).

Manifestation of amelioration of a disease condition with underlying IDO-mediated immunosuppression may require the concomitant or sequential administration of additional therapeutic agents, such as antineoplastic agents in the case of cancer, or antiretroviral agents in the case of viral diseases. For example, administration of IDO inhibitors for the treatment of cancer does not always produce a direct antitumor effect when used as a single agent. However, when combined with chemotherapeutic drugs (antineoplastic) the antitumor effect observed is higher than the sum of effects of each agent alone.

As used herein, the terms "catalytic pocket", "catalytic site", "active site" collectively and indistinctly refer to a region of the enzyme that contains amino acid residues responsible for the substrate binding (charge, hydrophobicity, steric hindrance) and catalytic amino acid residues which act as proton donors or acceptors or are responsible for binding a cofactor and participate in the catalysis of a chemical reaction.

As used herein, the phrase "pharmaceutically acceptable salt" refers to both pharmaceutically acceptable acid and base addition salts and solvates. Such pharmaceutically acceptable salts include salts of acids such as hydrochloric, phosphoric, hydrobromic, sulfuric, sulfinic, formic, toluenesulfonic, methanesulfonic, nitric, benzoic, citric, tartaric, maleic, hydroiodic, alkanoic such as acetic, $HOOC-(CH_2)_n-COOH$ where n is 0-4, and the like. Non-toxic pharmaceutical base addition salts include salts of bases such as sodium, potassium, calcium, ammonium, and the like. Those skilled in the art will recognize a wide variety of non-toxic pharmaceutically acceptable addition salts.

Methods of Use

The compounds and pharmaceutical compositions described herein can modulate activity of the enzyme indoleamine-2,3-dioxygenase (IDO). The term "modulate" is meant to refer to an ability to decrease activity of an enzyme or receptor. Accordingly, compounds described herein can be used in methods of modulating IDO by contacting the enzyme with any one or more of the compounds or compositions described herein. In some embodiments, the compounds described herein can act as inhibitors of IDO. In further embodiments, the compounds described herein can be used to modulate activity of IDO in cell or in an individual in need of modulation of the enzyme by administering a modulating (e.g., inhibiting) amount of a compound described herein.

Further provided are methods of inhibiting the degradation of tryptophan and preventing the production of N-formylkynurenine in a system containing cells expressing IDO such as a tissue, living organism, or cell culture. In some embodiments methods of altering (e.g., increasing) extracellular tryptophan levels in a mammal comprise administering an effective amount of a compound or pharmaceutical composition provided herein. Methods of measuring tryptophan levels and tryptophan degradation are routine in the art.

Further provided are methods of inhibiting immunosuppression such as IDO-mediated immunosuppression in a patient by administering to the patient an effective amount of a compound or composition recited herein. IDO-mediated immunosuppression has been associated with, for example, cancers, tumor growth, metastasis, infectious diseases (e.g., viral infection), viral replication, etc.

Further provided are methods for treating tumor-specific immunosuppression associated with cancer in a patient by administering to the patient an effective amount of a compound or composition recited herein. Example tumor-specific immunosuppression associated with cancers treatable by the methods herein include immunosuppression associated with cancer of the colon, pancreas, breast, prostate, lung, brain, ovary, cervix, testes, renal, head and neck, lymphoma, leukemia, melanoma, and the like.

For example, IDO-mediated immunosuppression associated with viral infection, is associated with a viral infection selected from the group consisting of: influenza, hepatitis C virus (HCV), human papilloma virus (HPV), cytomegalovirus (CMV), Epstein-Barr virus (EBV), poliovirus, varicella zoster virus, coxsackie virus, human immunodeficiency virus (HIV).

Further provided are methods for treating immunosupression associated with an infectious disease, e.g., HIV-1 infection, in a patient by administering to the patient an effective amount of a compound or composition recited herein.

For example, a patient undergoing or having completed a course of chemotherapy and/or radiation therapy for the treatment of a disease state, such as a cancer, can benefit from administering to the patient a therapeutically effective amount of a compound or composition recited herein for inhibiting immunosuppression resulting from the disease state and/or treatment thereof.

Further provided are methods of treating diseases associated with activity or expression, including abnormal activity and/or overexpression, of IDO in an individual (e.g., patient) by administering to the individual in need of such treatment a therapeutically effective amount or dose of a compound described herein or a pharmaceutical composition thereof. Example diseases can include any disease, disorder or condition that is directly or indirectly linked to expression or activity of the IDO enzyme, such as over expression or abnormal activity. An IDO-associated disease can also include any disease, disorder or condition that can be prevented, ameliorated, or cured by modulating enzyme activity.

Examples of IDO-associated diseases include cancer, viral infection such as HIV infection, depression, neurodegenerative disorders such as Alzheimer's disease and Huntington's disease, trauma, age-related cataracts, organ transplantation (e.g., organ transplant rejection), and autoimmune diseases including asthma, rheumatoid arthritis, multiple sclerosis, inflammatory bowel disease, psoriasis and systemic lupus erythematosusor. Example cancers treatable by the methods herein include cancer of the colon, pancreas, breast, prostate, lung, brain, ovary, cervix, testes, renal, head and neck, lymphoma, leukemia, melanoma, and the like.

Combination Therapy

One or more additional pharmaceutical agents for treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds and pharmaceutical compositions described herein for treatment of IDO-associated diseases, disorders or conditions (as noted above) or for enhancing the effectiveness of the treatment of a disease state or condition, such as cancer. The agents can be combined with the present compounds in a single dosage form, or the agents can be administered simultaneously or sequentially as separate dosage forms.

Suitable antiviral agents contemplated for use in combination with the compounds described herein can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddI); zalcitabine (ddC); stavudine (d4T); lamivudine (3TC); abacavir (1592U89); adefovir dipivoxil [bis (POM)-PMEA]; lobucavir (BMS-180194); BCH-10652; emitricitabine [(−)-FTC]; beta-L-FD4 (also called beta-L-D4C and named beta-L-2',3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2, 4(1H,3H)-pyrimid-inedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141 W94); lasinavir (BMS-234475); DMP-450; BMS-2322623; ABT-378; and AG-1549. Other antiviral agents include hydroxyurea, ribavirin, IL-2, IL-12, pentafuside and Yissum Project No. 11607.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol™), docetaxel, mithramycin, deoxyco-formycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB and PD-1, or antibodies to cytokines (IL-10, TGF-$\beta$, etc.).

Other anti-cancer agents also include those that block immune cell migration such as antagonists to chemokine receptors, including CCR2, CCR4 and CCR6.

Other anti-cancer agents also include those that augment the immune system such as adjuvants or adoptive T cell transfer.

Anti-cancer vaccines include dendritic cells, synthetic peptides, DNA vaccines and recombinant viruses.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

Pharmaceutical Formulations and Dosage Forms

The pharmaceutical compositions described herein generally comprise a combination of a compound described herein and a pharmaceutically acceptable carrier, diluent, or excipient. Such compositions are substantially free of non-pharmaceutically acceptable components, i.e., contain amounts of non-pharmaceutically acceptable components lower than permitted by US regulatory requirements at the time of filing this application. In some embodiments of this aspect, if the compound is dissolved or suspended in water, the composition further optionally comprises an additional pharmaceutically acceptable carrier, diluent, or excipient. In other embodiments, the pharmaceutical compositions described herein are solid pharmaceutical compositions (e.g., tablet, capsules, etc.).

These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also, pharmaceutical compositions can contain, as the active ingredient, one or more of the compounds described herein above in combination with one or more pharmaceutically acceptable carriers. In making the compositions described herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions described herein can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound described herein. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, 0.1 to about 500 mg of the active ingredient of a compound described herein.

The tablets or pills can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure, breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds can vary according to, for example, the particular use for which the treatment is made, the manner of administration of the compound, the health and condition of the patient, and the judgment of the prescribing physician. The proportion or concentration of a compound described herein in a pharmaceutical composition can vary depending upon a number of factors including dosage, chemical characteristics (e.g., hydrophobicity), and the route of administration. For example, the compounds described herein can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds described herein can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect relates to fluorescent dye, spin label, heavy metal or radio-labeled derivatives of the compounds described herein that would be useful not only in imaging but also in assays, both in vitro and in vivo, for localizing and quantitating the IDO enzyme in tissue samples, including human, and for identifying IDO enzyme ligands by inhibition binding of a labeled compound. Accordingly, further provided are IDO enzyme assays that contain such labeled compounds.

Further provided are isotopically-labeled compounds of the compounds described herein. An "isotopically" or "radio-labeled" compound is a compound described herein where one or more atoms are replaced or substituted by an atom having an atomic mass or mass number different from the atomic mass or mass number typically found in nature (i.e., naturally occurring). Suitable radionuclides that may be include but are not limited to 2H (also written as D for deuterium), 3H (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. The radionuclide that is incorporated in the instant radio-labeled compounds will depend on the specific application of that radio-labeled compound. For example, for in vitro IDO enzyme labeling and competition assays, compounds that incorporate $^3H$, $^{14}C$, $^{82}Br$, $^{125}I$, $^{131}I$, $^{35}S$ or will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labeled" or "labeled compound" is a compound that has incorporated at least one radionuclide. In some embodiments the radionuclide is selected from the group consisting of $^3H$, $^{14}C$, $^{125}I$, $^{35}S$ and $^{82}Br$.

Synthetic methods for incorporating radio-isotopes into organic compounds are applicable to compounds described herein and are well known in the art.

A radio-labeled compound described herein can be used in a screening assay to identify/evaluate compounds. In general terms, a newly synthesized or identified compound (i.e., test compound) can be evaluated for its ability to reduce binding of the radio-labeled compound described herein to the IDO enzyme. Accordingly, the ability of a test compound to compete with the radio-labeled compound for binding to the IDO enzyme directly correlates to its binding affinity.

Kits

Also included are pharmaceutical kits useful, for example, in the treatment or prevention of IDO-associated diseases or disorders, obesity, diabetes and other diseases referred to herein which include one or more containers containing a pharmaceutical composition comprising a therapeutically effective amount of a compound described herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The following examples are offered for illustrative purposes, and are not intended to limit the disclosure in any manner. Those of skill in the art will readily recognize a variety of noncritical parameters which can be changed or modified to yield essentially the same results. The example compounds below were found to be inhibitors of IDO according to one or more of the assays described herein.

EXAMPLES

All reagents and solvents were purchased from commercial sources. All commercial reagents and solvents were used as received without further purification. The reactions were monitored using analytical thin layer chromatography (TLC) with 0.25 mm EM Science silica gel plates (60E-254). The developed TLC plates were visualized by immersion in potassium permanganate solution followed by heating on a hot plate. Flash chromatography was performed with Selecto Scientific silica gel, 32-63 μm particle sizes. All reactions were performed in flame or oven-dried glassware under a nitrogen atmosphere. All reactions were stirred magnetically at ambient temperature unless otherwise indicated. $^1H$ NMR spectra were obtained with a Bruker DX 400, Varian VXR400 or VXR300. $^1H$ NMR spectra were reported in parts per million (δ) relative to TMS (0.0), DMSO-$d_6$ (2.50) or CD$_3$OD (4.80) as an internal reference. All spectra are recorded in CDCl$_3$ unless otherwise indicated.

Example 1

2-(4-(2-Hydroxyethyl)phenyl)isoindoline-1,3-dione

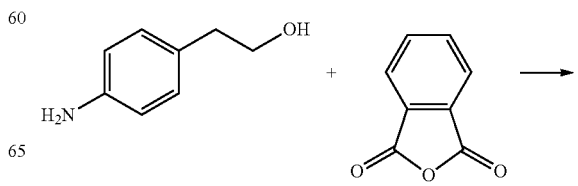

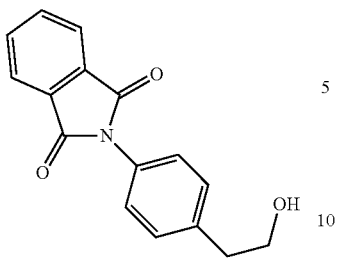

A flask containing 4-aminophenethyl alcohol (1 g, 7.29 mmol), phthalic anhydride (1.13 g, 7.65 mmol) and acetic acid (6 mL) was heated at 100° C. for 1 h. The reaction mixture was poured into water (50 mL) and the solid was filtered off and washed with water. The crude was purified by flash column chromatography to afford the desired product as white solid (1.2 g, 62%). ¹H NMR: 2.92 (t, 2H, J=6.6 Hz), 3.89 (t, 2H, J=6.6 Hz), 7.38 (s, 3H), 7.77-7.82 (m, 2H), 7.92-7.97 (m, 21-1).

Example 2

4-(1,3-Dioxoisoindolin-2-yl)phenethyl 4-methylbenzenesulfonate

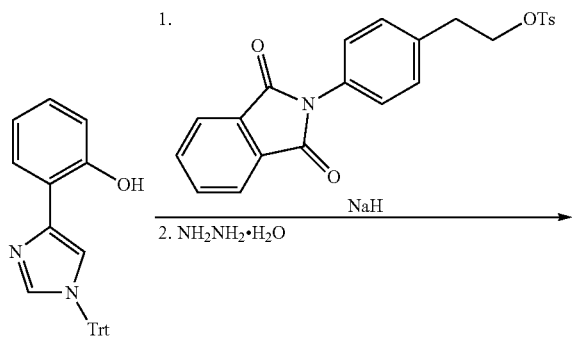

2-(4-(2-hydroxyethyl)phenyl)isoindoline-1,3-dione (926 mg, 3.46 mmol) was dissolved in dichloromethane (15 mL), cooled to 0° C. and p-toluenesulfonyl chloride (991 mg, 5.2 mmol) was added, followed by pyridine (0.56 ml, 6.93 mmol). The reaction was stirred at room temperature for 16 h and concentrated. The residue was dissolved in ethyl acetate (60 ml), washed with water (20 ml), saturated aqueous NaHCO₃ (2×15 ml), brine (20 mL), dried over sodium sulfate, filtered and concentrated. The crude tosylate was used without further purification.

Example 3

4-(2-(2-(1-Trityl-1H-imidazol-4-yl)phenoxy)ethyl) aniline

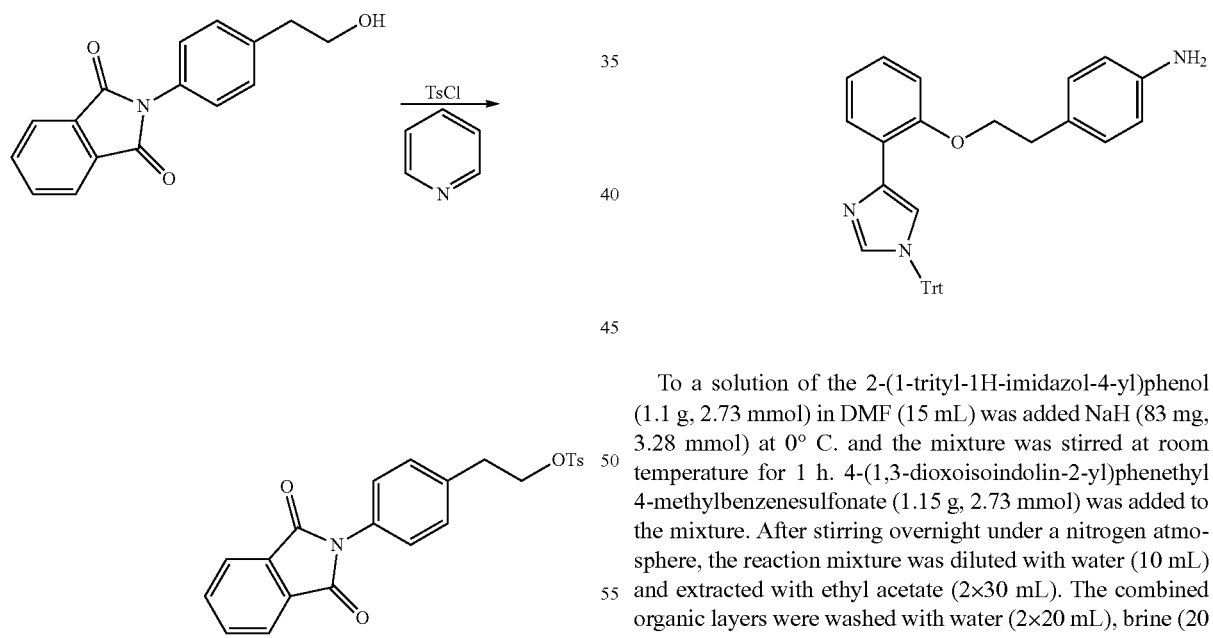

To a solution of the 2-(1-trityl-1H-imidazol-4-yl)phenol (1.1 g, 2.73 mmol) in DMF (15 mL) was added NaH (83 mg, 3.28 mmol) at 0° C. and the mixture was stirred at room temperature for 1 h. 4-(1,3-dioxoisoindolin-2-yl)phenethyl 4-methylbenzenesulfonate (1.15 g, 2.73 mmol) was added to the mixture. After stirring overnight under a nitrogen atmosphere, the reaction mixture was diluted with water (10 mL) and extracted with ethyl acetate (2×30 mL). The combined organic layers were washed with water (2×20 mL), brine (20 mL) and dried. The solvent was removed under reduced pressure and, the crude product was dissolved in ethanol (15 mL) and treated with hydrazine hydrate (0.3 mL, 5.46 mmol). The mixture was heated at 80° C. for 2 h and filtered. The solvent was removed under reduced pressure and the residue was purified by flash column chromatography (silica gel, 30%-50% EtOAc/hexanes as eluent) to afford the desired product as a yellow solid (862 mg, 60% over two steps). ¹H NMR: 2.63 (t, 2H, J=7.6 Hz), 4.03 (t, 2H, J=7.6 Hz), 6.46 (d, 1H, J=8.4 Hz), 6.80 (dd, 2H, J=12.4 Hz, 8 Hz), 6.99 (t, 1H, J=7.6

Hz), 7.10-7.19 (m, 7H), 7.28-7.31 (m, 9H), 7.41 (s, 1H), 7.52 (s, 1H), 8.18-8.21 (m, 1H), 8.63 (s, 1H), 9.11 (s, 1H).

Example 4

General Procedure for the Synthesis of Urea and Thiourea Analogs

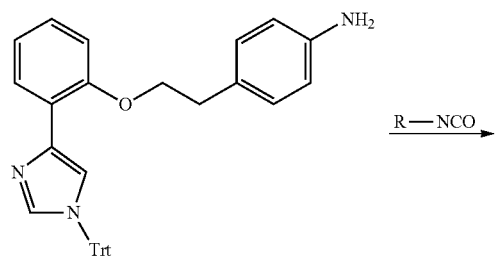

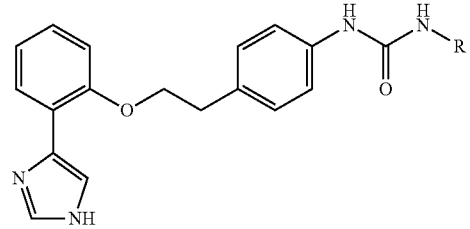

To a solution of 4-(2-(2-(1-trityl-1H-imidazol-4-yl)phenoxy)ethyl)aniline (80 mg, 0.153 mmol) in dichloromethane (3 mL) was added aryl isocyanate/isothiocyanate (0.161 mmol). The mixture was stirred at room temperature for 24 h and concentrated. The crude product was dissolved in AcOH/MeOH (1:4) and heated at 80° C. for 2 h. The reaction mixture was basified with aqueous 10% NaOH and aqueous layer was extracted with ethyl acetate (2×30 mL). The combined organic layers were washed with brine (15 mL), dried and concentrated. The crude product was purified by flash column chromatography.

The following compounds were prepared according to the general procedure of Example 4, by substituting the appropriate starting materials:

| No. | Compound | Name | Yield (%) | $^1$H NMR |
|---|---|---|---|---|
| 1152 | | 1-(4-(2-(2-(1H-imidazol-4-yl)phenoxy)ethyl)phenyl)-3-phenylurea | 82 | (DMSO-$d_6$) 3.08 (t, 2H, J = 5.6 Hz), 4.26 (t, 2H, J = 6.4 Hz), 6.91 (t, 2H, 7.6 Hz), 7.02 (d, 1H, J = 8 Hz), 7.11 (d, 1H, J = 7.2 Hz), 7.21-7.26 (m, 4H), 7.34-7.41 (m, 5H), 7.63 (s, 1H), 7.94 (s, 1H), 8.57 (d, 1H, J = 12.8 Hz) |
| 1197 | | 1-(4-(2-(2-(1H-imidazol-4-yl)phenoxy)ethyl)phenyl)-3-phenylthiourea | 85 | (DMSO-$d_6$) 3.12 (t, 2H, J = 6.4 Hz), 4.28 (t, 2H, J = 6.4 Hz), 6.92 (t, 1H, J = 7.2 Hz), 7.02-7.12 (m, 3H), 7.26-7.32 (m, 4H), 7.37-7.44 (m, 5H), 7.64 (s, 1H), 8.28 (s, 1H), 9.73 (s, 2H) |
| 1192 | | 1-(4-(2-(2-(1H-imidazol-4-yl)phenoxy)ethyl)phenyl)-3-(2-nitrophenyl)urea | 74 | 3.09 (t, 2H, J = 6.4 Hz), 4.26 (t, 2H, J = 6.4 Hz), 6.91 (t, 1H, J = 7.6 Hz), 7.01 (d, 1H, J = 8 Hz), 7.09 (d, 1H, J = 8 Hz), 7.16 (t, 1H, J = 7.2 Hz), 7.28 (d, 2H, J = 8.4 hz), 7.38-7.40 (m, 2H), 7.63-7.67 (m, 2H), 8.05 (d, 2H, J = 8 Hz), 8.26 (d, 1H, J = 8.4 Hz), 8.59 (s, 1H), 9.54 (s, 1H), 9.76 (s, 1H) |

Example 5

General Procedure for HATU Coupling

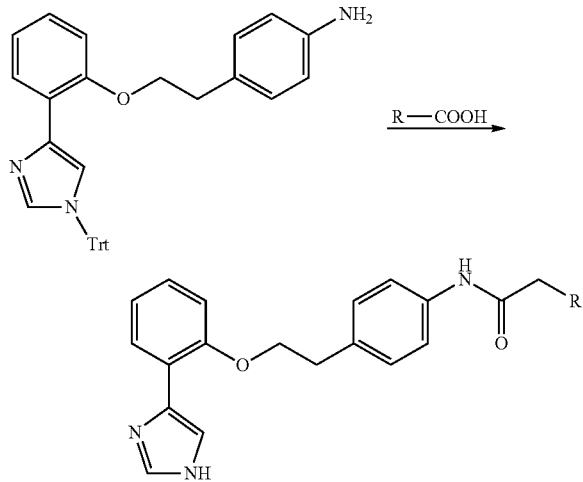

To a vial containing 4-(2-(2-(1-trityl-1H-imidazol-4-yl)phenoxy)ethyl)aniline (80 mg, 0.153 mmol) in DMF was added corresponding carboxylic acid (0.161 mmol), DIPEA (0.08 mL, 0.460 mmol) and HATU (64 mg, 0.169 mmol). The reaction was stirred at room temperature for 18 h and concentrated. The crude product was dissolved in AcOH:MeOH (1:4) and heated at 80° C. for 2 h. The reaction mixture was basified with aqueous 10% NaOH and the aqueous layer extracted with ethyl acetate (2×30 mL). The combined organic extracts were washed with brine (15 mL), dried over $Na_2SO_4$ and concentrated. The residue was purified by flash column chromatography.

The following compounds were prepared according to the general procedure of Example 5, by substituting the appropriate starting materials:

| No. | Compound | Name | Yield (%) | $^1$H NMR |
|---|---|---|---|---|
| 1199 |  | N-(4-(2-(2-(1H-imidazol-4-yl)phenoxy)ethyl)phenyl)-2-(tetrahydrofuran-2-yl)acetamide | 50 | 1.52-1.61 (m, 1H), 1.91-1.98 (m, 2H), 2.07-2.14 (m, 1H), 2.55-2.67 (m, 2H), 3.14 (t, 2H, J = 6 Hz), 3.84 (dd, 1H, J = 14 Hz, 8 Hz), 3.96 (dd, 1H, J = 15.2 Hz, 7.2 Hz), 4.24-4.26 (m, 1H), 4.36 (t, 2H, J = 6 Hz), 6.9 (s, 1H), 6.98-7.01 (m, 2H), 7.2 (dt, 1H, J = 8 Hz, 1.6 Hz), 7.27 (d, 1H, J = 6.8 Hz), 7.48 (d, 2H, J = 8.4 Hz), 7.54 (s, 1H), 7.76 (d, 1H, J = 7.6 Hz), 8.7 (s, 1H), 9.08 (br s, 1H) |
| 1156 |  | N-(4-(2-(2-(1H-imidazol-4-yl)phenoxy)ethyl)phenyl)-2-(pyrazin-2-yl)acetamide | 45 | 3.82 (s, 2H), 3.15 (t, 2H, J = 6 Hz), 4.37 (t, 2H, J = 6 Hz), 6.94 (s, 1H), 6.98-7.01 (m, 2H), 7.2 (dt, 1H, J = 8 Hz, 1.6 Hz), 7.4 (s, 1H), 7.47 (d, 2H, J = 8 Hz), 7.79 (d, 1H, J = 7.6 Hz), 8.35 (s, 1H), 8.51-8.58 (m, 3H) |
| 1157 |  | N-(4-(2-(2-(1H-imidazol-4-yl)phenoxy)ethyl)phenyl)-2-(thiophen-2-yl)acetamide | 35 | 3.11 (t, 2H, J = 6 Hz), 3.90 (s, 2H), 4.33 (t, 2H, J = 6 Hz), 6.84 (s, 1H), 6.95-6.99 (m, 4H), 7.18-7.24 (m, 4H), 7.35 (s, 1H), 7.40 (d, 2H, J = 8.4 Hz), 7.76 (d, 1H, J = 8 Hz), 8.22 (s, 1H). |

-continued

| No. | Compound | Name | Yield (%) | ¹H NMR |
|---|---|---|---|---|
| 1242 | 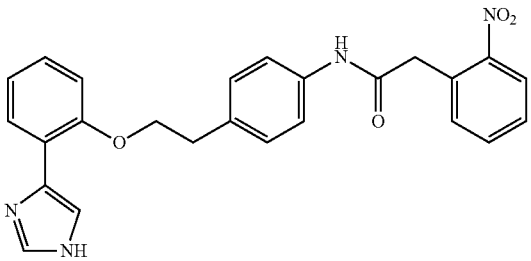 [SMILES: O=C(Cc1ccccc1[N+](=O)[O-])Nc1ccc(CCOc2ccccc2-c2c[nH]cn2)cc1] | N-(4-(2-(2-(1H-imidazol-4-yl)phenoxy)ethyl)phenyl)-2-(2-nitrophenyl)acetamide | 91 | (DMSO-$d_6$) 3.08 (t, 2H, J = 6.4 Hz), 4.07 (s, 2H), 4.25 (t, 2H, J = 6.4 Hz), 6.93 (t, 1H, J = 7.6 Hz), 7.03 (d, 1H, J = 7.6 Hz), 7.14 (t, 1H, J = 7.6 Hz), 7.25 (d, 2H, J = 8.4 Hz), 7.42-7.46 (m, 3H), 7.52-7.54 (m, 2H), 7.67 (t, 1H, J= 7.6 Hz), 7.82 (s, 1H), 7.92 (d, 1H, J = 6.8 Hz), 8.01 (d, 1H, J = 8.4 Hz), 10.14 (s, 1H) |
| 1248ᵃ | 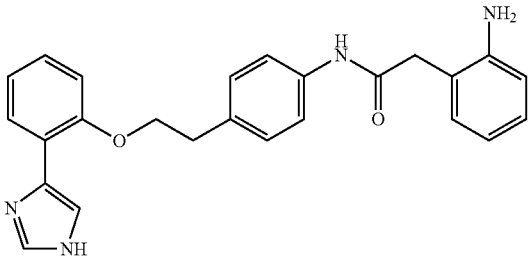 | N-(4-(2-(2-(1H-imidazol-4-yl)phenoxy)ethyl)phenyl)-2-(2-aminophenyl)acetamide | 90 | (DMSO-$d_6$) 3.07 (t, 2H, J = 6.4 Hz), 3.43 (s, 2H), 4.25 (t, 2H, J = 6.4 Hz), 5.06 (s, 2H), 6.48 (t, 1H, J = 7.2 Hz), 6.61 (d, 1H, J = 8 Hz), 6.91 (t, 2H, J = 7.6 Hz), 7.00 (d, 2H, J = 7.2 Hz), 7.08-7.12 (m, 1H), 7.26 (d, 2H, J = 8 Hz), 7.36 (s, 1H), 7.49 (d, 2H, J = 8.4 Hz), 7.62 (s, 1H), 8.01 (s, 1H), 10.12 (s, 1H) |
| 1241 | 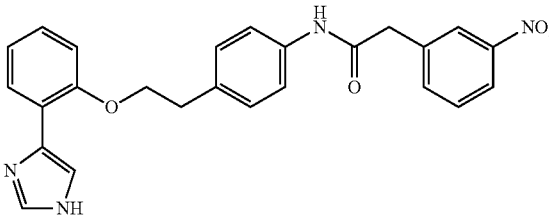 | N-(4-(2-(2-(1H-imidazol-4-yl)phenoxy)ethyl)phenyl)-2-(3-nitrophenyl)acetamide | 92 | 3.12 (t, 2H, J = 6 Hz), 3.74 (s, 2H), 4.36 (t, 2H, J = 6 Hz), 6.95-6.99 (m, 2H), 7.12 (s, 1H), 7.18-7.24 (m, 2H), 7.30 (t, 1H, J = 7.2 Hz), 7.38-7.46 (m, 3H), 7.54 (d, 2H, J = 8.4 Hz), 7.63 (d, 1H, J = 7.2 Hz), 7.68 (d, 1H, J = 7.6 Hz), 8.03 (d, 1H, J = 9.2 Hz), 8.11 (s, 1H), 9.4 (br s, 1H), 9.68 (s, 1H) |
| 1244ᵃ | 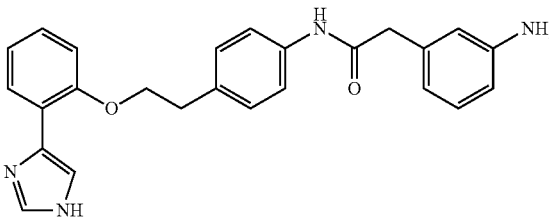 | N-(4-(2-(2-(1H-imidazol-4-yl)phenoxy)ethyl)phenyl)-2-(3-aminophenyl)acetamide | 94 | (DMSO-$d_6$) 3.07 (t, 2H, J = 6.4 Hz), 3.38 (s, 2H), 4.25 (t, 2H, J = 6.4 Hz), 4.98 (s, 2H), 6.39 (dd, 2H, J = 14.4 Hz, 8 Hz), 6.47 (s, 1H), 6.89 (q, 2H, J = 8 Hz), 7.00 (d, 1H, J = 8 Hz), 7.08-7.12 (m, 1H), 7.25 (d, 2H, J = 8 Hz), 7.37 (s, 1H), 7.50 (d, 2H, J = 8.4 Hz), 7.62 (s, 1H), 8.01 (s, 1H), 10.12 (s, 1H) |
| 1204 | 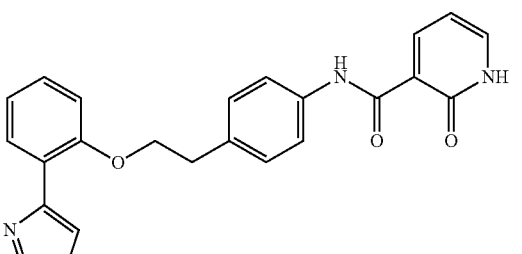 | N-(4-(2-(2-(1H-imidazol-4-yl)phenoxy)ethyl)phenyl)-2-oxo-1,2-dihydropyridine-3-carboxamide | 62 | (DMSO-$d_6$) 3.11 (t, 2H, J = 6.4 Hz), 4.29 (t, 2H, J = 6.4 Hz), 6.53 (t, 1H, J = 6.8 Hz), 6.93 (t, 1H, J = 7.2 Hz), 7.04 (d, 1H, J = 8 Hz), 7.12-7.16 (m, 1H), 7.33 (d, 2H, J = 8.4 Hz), 7.29 (s, 1H), 7.61 (d, 2H, J = 8.4 Hz), 7.78 (s, 2H), 7.94 (dd, 1H, J = 7.6 Hz, 1.6 Hz), 8.28 (s, 1H), 8.42 (dd, 1H, J = 1.2 Hz, 2 Hz) |
| 1227 | 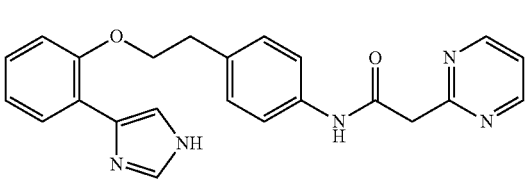 [SMILES: O=C(Cc1ncccn1)Nc1ccc(CCOc2ccccc2-c2c[nH]cn2)cc1] | N-(4-(2-(2-(1H-imidazol-4-yl)phenoxy)ethyl)phenyl)-2-(pyrimidin-2-yl)acetamide | 58 | 3.17 (t, 3H, J = 6.0 Hz), 4.16 (s, 1H), 4.39 (t, 2H, J = 6.0 Hz), 6.35 (br s, 1H), 6.88 (s, 1H), 7.02 (d, 2H, J = 8.0 Hz), 7.20-7.31 (m, 3H), 7.52-7.55 (m, 3H), 7.76 (d, 1H, J = 8.0 Hz), 8.77 (s, 2H), 9.83 (s, 1H) |

-continued

| No. | Compound | Name | Yield (%) | $^1$H NMR |
|---|---|---|---|---|
| 1217 | | N-(4-(2-(2-(1H-imidazol-4-yl)phenoxy)ethyl)phenyl)-2-(1H-imidazol-1-yl)acetamide | 76 | (CD$_3$OD) 3.14 (t, 2H, J = 6.6 Hz), 4.32 (t, 2H, J = 6.4 Hz), 4.90 (s, 2H), 6.96 (t, 1H, J = 7.0 Hz), 6.99 (s, 1H), 7.03 (d, 1H, J = 8.0 Hz), 7.19 (t, 1H, J = 7.2 Hz), 7.27-7.29 (m, 3H), 7.48 (s, 1H), 4.50 (s, 1H), 7.64 (s, 1H), 7.70 (s, 1H), 7.77 (d, 1H, J = 7.6 Hz) |
| 1226 | | N-(4-(2-(2-(1H-imidazol-4-yl)phenoxy)ethyl)phenyl)-2-(thiazol-4-yl)acetamide | 65 | 3.14 (t, 2H, J = 6.0 Hz), 3.95 (s, 2H), 4.36 (t, 2H, J = 6.2 Hz), 6.93 (s, 1H), 6.98-7.11 m, 2H), 7.16-7.29 (m, 4H), 7.77 (dd, 1H, J = 1.6, 8.0 Hz), 8.86 (d, 1H, J = 1.6 Hz), 9.28 (s, 1H) |
| 1219 | | N-(4-(2-(2-(1H-imidazol-4-yl)phenoxy)ethyl)phenyl)-2-(azepan-1-yl)acetamide | 77 | 1.67-1.72 (m, 8H), 2.79 (t, 4H, J = 4.0 Hz), 3.18 (t, 2H, J = 6.2 Hz), 3.28 (s, 2H), 4.38 (t, 2H, J = 6.0 Hz), 6.96-7.03 (m, 3H), 7.20 (t, 1H, J = 8.0 Hz), 7.32 (d, 2H, J = 8.0 Hz), 7.80 (d, 1H, J = 8.0 Hz), 8.79 (br s, 1H), 9.40 (s, 1H) |
| 1214 | | N-(4-(2-(2-(1H-imidazol-4-yl)phenoxy)ethyl)phenyl)-2-morpholinoacetamide | 87 | 2.62-2.64 (m, 4H), 3.16-3.19 (m, 4H), 3.77-3.79 (m, 4H), 4.38 (t, 2H, J = 6.0 Hz), 6.99-7.01 (m, 3H), 7.21 (t, 1H, J = 8.0 Hz), 7.32 (d, 2H, J = 8.0 Hz), 7.51-7.56 (m, 3H), 7.78 (d, 1H, J = 8.0 Hz), 9.09 (s, 1H), 9.21 (br s, 1H) |
| 1212 | | N-(4-(2-(2-(1H-imidazol-4-yl)phenoxy)ethyl)phenyl)-2-(4-methylpiperazin-1-yl)acetamide | 25 | 2.32 (s, 3H), 2.52 (s, 4H), 2.68 (s, 4H), 3.17 (singlet merged with triplet, 4H), 4.36 (t, 2H, J = 6.0 Hz), 7.00 (t, 2H, J = 7.4 Hz), 7.19 (t, 1H, J = 7.6 Hz), 7.26-7.31 (m, 3H), 7.45 (s, 1H), 7.50 (d, 2H, J = 8.0 Hz), 7.81 (d, 2H, J = 7.2 Hz), 9.14 (s, 1H) |
| 1211 | | N-(4-(2-(2-(1H-imidazol-4-yl)phenoxy)ethyl)phenyl)-2-(tetrahydro-2H-pyran-4-yl)acetamide | 93 | 1.34-1.42 (m, 2H), 1.66 (d, 2H, J = 12.4 Hz), 2.09-2.17 (m, 1H), 2.33 (d, 2H, J = 7.2 Hz), 3.14 (t, 2H, J = 5.4 Hz), 3.38 (t, 2H, J = 11.6 Hz), 3.90 (d, 2H, J = 8.0 Hz), 4.41 (t, 2H, J = 5.6 Hz), 6.98-7.05 (m, 2H), 7.25-7.30 (m, 4H), 7.56-7.60 (m, 3H), 7.89 (s, 1H), 8.09 (s, 1H), 10.09 (br s, 1H) |
| 1261 | | methyl 3-((4-(2-(2-(1H-imidazol-4-yl)phenoxy)ethyl)phenyl)carbamoyl)benzoate | 21 | 3.11 (t, 2H, J = 5.6 Hz), 3.87 (s, 3H), 4.38 (t, 2H, J = 6.0 Hz), 6.30 (s, 1H), 6.50-7.10 (m, 3H), 7.20-7.35 (m, 2H), 7.47 (t, 1H, J = 7.6 Hz), 7.63 (d, 2H, J = 8.0 Hz), 7.81 (d, 1H, J = 8.0 Hz), 8.10 (d, 1H, J = 8.0 Hz), 8.23 (s, 1H), 8.35 (d, 1H, J = 6.8 Hz), 8.70 (s, 1H), 9.74 (s, 1H) |

| No. | Compound | Name | Yield (%) | ¹H NMR |
|---|---|---|---|---|
| 1272 | | N-4-(2-(2-(1H-imidazol-4-yl)phenoxy)ethyl)phenyl)-2,6-dioxo-1,2,3,6-tetrahydro-pyrimidine-4-carboxamide | 30 | (MeOH-$d_4$) 3.18 (t, 2H, J = 6.2 Hz), 4.65 (t, 2H, J = 6.4 Hz), 6.29 (s, 1H), 6.97 (t, 1H, J = 7.6 Hz), 7.08 (d, 1H, J = 8.4 Hz), 7.23 (t, 1H, J = 7.6 Hz), 7.25-7.38 (m, 3H), 7.60 (d, 2H, J = 8.0 Hz), 7.75-7.82 (m, 2H) |
| 1271 | | methyl 4-((4-(2-(2-(1H-imidazol-4-yl)phenoxy)ethyl)phenyl)carbamoyl)benzoate | 28 | (MeOH-$d_4$) 3.10 (t, 2H, J = 5.2 Hz), 3.89 (s, 3H), 4.53 (t, 2H, J = 6.0 Hz), 6.85 (s, 1H), 6.92-7.20 (m, 2H), 7.19 (dt, 1H, J = 7.2, 1.2 Hz), 7.22-7.29 9m, 2H), 7.58 (d, 2H, J = 8.0 Hz), 7.63 (d, 1H, J = 1.2 Hz), 7.65 (s, 1H), 7.97 (d, 2H, J = 8.4 Hz), 7.97 (d, 2H, J = 8.4 Hz), 8.06 (d, 2H, J = 8.4 Hz) |
| 1150 | | N-(4-(2-(2-(1H-imidazol-4-yl)phenoxy)ethyl)phenyl)thiophene-2-carboxamide | 34 | 3.08 (t, 2H, J = 6.4 Hz), 4.31 (t, 2H, J = 6.0 Hz), 6.90 (s, 1H), 6.90-7.05 (m, 3H), 7.10-7.25 (m, 3H), 7.40-7.60 (m, 4H), 7.70-7.80 (m, 2H), 8.99 (s, 1H), 9.25 (s, 1H) |

*aObtained from compounds 1241 and 1242 by hydrogenation of nitro.

Example 6

4-(4-(2-(2-(1H-Imidazol-4-yl)phenoxy)ethyl)phenyl-carbamoyl)benzoic acid hydrochloride

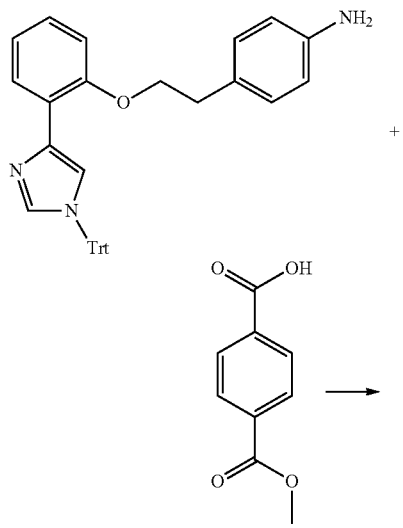

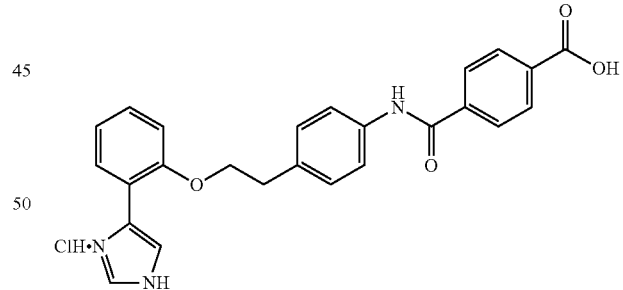

To a vial containing 4-(2-(2-(1-trityl-1H-imidazol-4-yl)phenoxy)ethyl)aniline (80 mg, 0.153 mmol) in DMF was added corresponding carboxylic acid (0.161 mmol), DIPEA (0.08 mL, 0.460 mmol) and HATU (64 mg, 0.169 mmol). The reaction was stirred at room temperature for 18 h and concentrated. The crude ester obtained from previous step was dissolved in MeOH (3 mL) and water (1 mL). LiOH (32 mg, 0.765 mmol) was added and the reaction mixture was stirred at room temperature for 18 h. Methanol was removed under reduced pressure and the aqueous layer acidified with 2M HCl. The aqueous layer was extracted with ethyl acetate (2×15 mL) and the combined organic layers were washed with brine, dried and concentrated. The crude product was dissolved in methanol (3 mL) and concentrated HCl was added (few drops). The reaction mixture was heated at 80° C. for 1 h. The solvent was removed under reduced pressure and the solid obtained was triturated with dichlormethane to afford the desired product as HCl salt (32 mg, 31%). $^1$H NMR (DMSO-d$_6$): 3.13 (t, 2H, J=6.6 Hz), 4.37 (t, 2H, J=6.6 Hz), 7.07 (t, 1H, J=7.5 Hz), 7.24 (d, 1H, J=8.7 Hz), 7.32 (d, 2H, J=8.4 Hz), 7.38-7.43 (m, 1H), 7.66-7.71 (m, 3H), 7.81 (d, 1H, J=7.2 Hz), 8.06 (d, 4H, J=7.8 Hz), 9.16 (d, 1H, J=6.3 Hz), 10.43 (d, 1H, J=9.9 Hz).

Example 7

3-(4-(2-(2-(1H-Imidazol-4-yl)phenoxy)ethyl)phenylcarbamoyl)benzoic acid hydrochloride

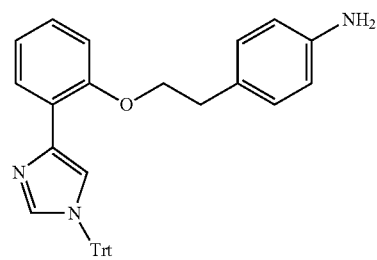

+

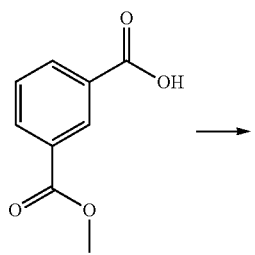

→

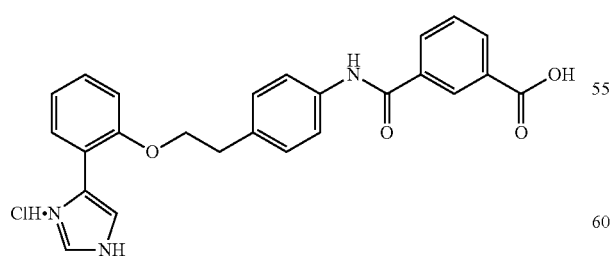

The reaction procedure of Example 6 was used to synthesize this compound. $^1$H NMR (DMSO-d$_6$): 3.13 (t, 2H, J=6 Hz), 4.37 (t, 2H, J=6 Hz), 7.06 (t, 1H, J=7.5 Hz), 7.23 (d, 1H, J=8.4 Hz), 7.32 (d, 2H, J=8.4 Hz), 7.40 (dt, 1H, J=8.4 Hz, 1.2 Hz), 7.61-7.72 (m, 4H), 7.87 (dd, 1H, J=7.8 Hz, 1.2 Hz), 8.11 (d, 1H, J=7.5 Hz), 8.21 (d, 1H, J=7.8 Hz), 8.50 (s, 1H), 9.2 (s, 1H), 10.4 (s, 1H).

Example 8

2-(4-(2-(2-(1-Trityl-1H-imidazol-4-yl)phenoxy)ethyl)phenylcarbamoyl)benzoic acid

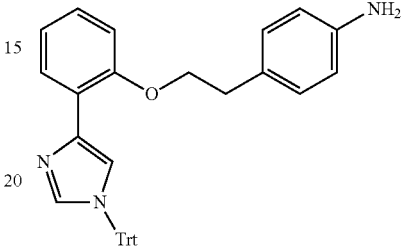

+

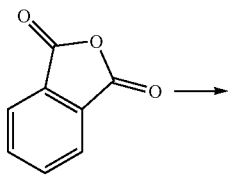

→

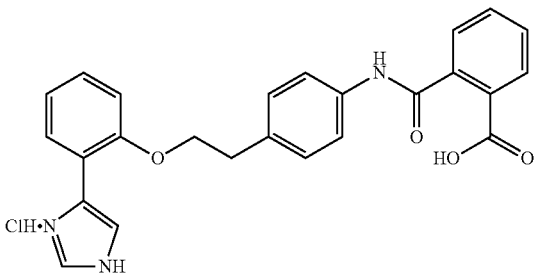

To a solution of 4-(2-(2-(1-trityl-1H-imidazol-4-yl)phenoxy)ethyl)aniline (59 mg, 0.113 mmol) in THF (3 mL) was added phthalic anhydride (16.75 mg, 0.113 mmol). The reaction mixture was stirred at room temperature for 18 h. THF was removed and the crude product dissolved in methanol (3 mL) and concentrated HCl was added (few drops). The reaction mixture was heated at 80° C. for 1 h. The solvent was removed under reduced pressure and the solid obtained was triturated with dichlormethane to afford the desired product as HCl salt (41 mg, 77%). $^1$H NMR (DMSO-d$_6$): 3.12 (t, 2H, J=6 Hz), 4.29 (t, 2H, J=6 Hz), 7.03-7.08 (m, 1H), 7.23 (t, 2H, J=10.4 Hz), 7.29-7.48 (m, 6H), 7.64 (s, 1H), 7.85-7.94 (m, 3H), 9.19 (s, 1H)

Example 9

(R)-methyl 2-(((2-(1H-imidazol-4-yl)phenoxy)carbonyl)amino)-3-(1-methyl-1H-indol-3-yl)propanoate

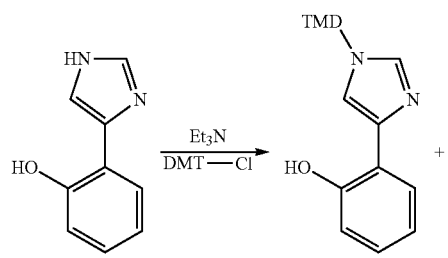

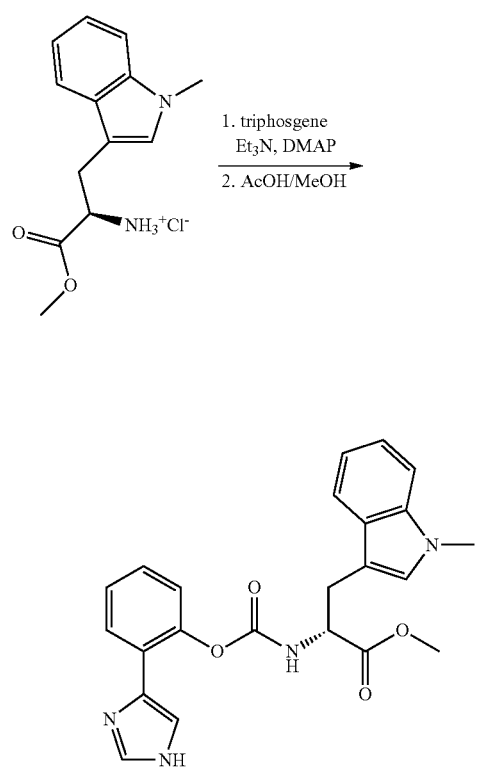

To a solution of phenyl imidazole (1.0 mmol) in DMF (3 mL) was added triethylamine (1.1 mmol). After stirred for 10 min, a solution of 4,4'-Dimethoxytrityl chloride (1.0 mmol) in DMF (2 mL) was added dropwise. After stirred overnight under a nitrogen atmosphere, the reaction mixture was poured into ice water (10 mL). The solid was filtered off, washed with cold water and dissolved in ethyl acetate. The organic layer was dried over $Na_2SO_4$ and concentrated the crude product was taken into next step without further purification. To a suspension of (R)-methyl 2-amino-3-(1-methyl-1H-indol-3-yl)propanoate (0.5 mmol) (prepared as described by Paul Cox, Donald Craig, Stephanos Ioannidis, Volker S. Rahn, *Tetrahedron Letters* 2005, 46, 4687) in DCM (3 mL) was added triphosgene (0.5 mmol) and $Et_3N$ (2.0 mmol) at 0° C. The solution was allowed to stir for 1 h and was concentrated to dryness. The crude residue was used immediately in the next step without purification. The crude residue was dissolved in DCM (5 mL), the phenyl imidazole derivative (0.5 mmol) and DMAP (1.5 mmol) were added. The resulting solution was allowed to stir at room temperature over night. The solvent was removed under reduced pressure and the crude residue was filtered through a plug of silica gel and concentrated. To the residue was added MeOH (3 mL) and AcOH (2 mL) and the solution was stirred at room temperature for 30 min. The solution was diluted with water and made basic with solid $K_2CO_3$ (pH~8-9). The aqueous was extracted with EtOAc and the combined organic layers were washed with water, brine and dried ($Na_2SO_4$). The crude residue was purified by column chromatography on silica gel afforded the compound (21% yield). $^1$H NMR: 3.20-3.48 (m, 2H), 3.66 (s, 3H), 3.70 (s, 3H), 4.61-4.75 (m, 1H), 6.57 (d, 1H, J=7.2 Hz), 6.90-7.30 (m, 7H), 7.50-7.58 (m, 1H), 7.10-7.76 (m, 2H).

Example 10

General Procedure for Benzyl Deprotection of Phenols

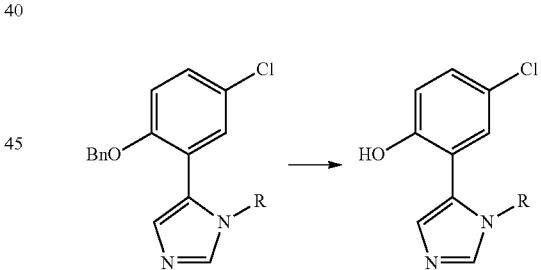

To a solution of the benzyloxy compound (0.44 mmol) in MeOH (5 mL) at room temperature was added an HCl solution (0.44 mmol) (1.25 M in MeOH) followed by 10% Pd/C (44.0 μmol) and the vial was evacuated and backfilled with hydrogen gas three times. A balloon of hydrogen was placed on the vial and the suspension was allowed to stir at room temperature overnight. The reaction mixture was filtered through a celite plug and the solvent was evaporated under reduced pressure to afford the crude product. The crude residue was purified by column chromatography using Hexanes/ EtOAc 50%→100% gradient to afford the product.

The following compounds were prepared according to the general procedure of Example 10, by substituting the appropriate starting materials:

| No. | Compound | Name | Yield (%) | $^1$H NMR |
|---|---|---|---|---|
| 1077 | | 4-chloro-2-(1-cyclohexyl-1H-imidazol-5-yl)phenol | 80 | (DMSO-$d_6$) 1.13-1.20 (m, 3H), 1.29-1.90 (m, 7 H), 3.61-3.68 (m, 1H), 6.79 (s, 1H), 6.95 (d, 1H, J = 8.6 Hz), 7.15 (d, 1H, J = 1.8 Hz), 7.29 (d, 1H, J = 8.5 Hz), 7.85 (s, 1H), 10.1 (brs, 1H) |
| 1249 | | 4-chloro-2-(1-cyclopentyl-1H-imidazol-5-yl)phenol | 75 | (DMSO-$d_6$) 1.52-1.57 (m, 2H), 1.67-1.74 (m, 4 H), 1.94-1.98 (m, 2H), 4.21-4.28 (m, 1H), 6.82 (s, 1H), 6.94 (d, 1H, J = 8.8 Hz), 7.16 (d, 1H, J = 1.6 Hz), 7.29 (dd, 1H, 2.0, 8.8 Hz), 7.83 (s, 1H), 10.07 (s, 1H) |

Example 11

N-(Tetrahydro-2H-pyran-4-yl)hydroxylamine

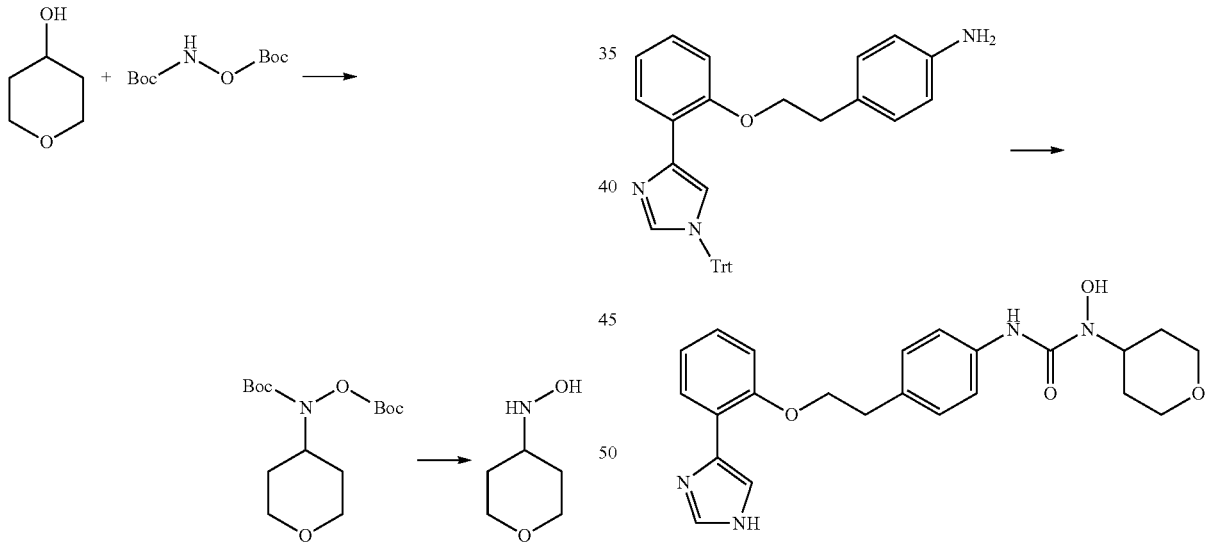

To a solution of triphenylphosphine (720 mg, 2.75 mmol), 4-hydroxytetrahydropyran (255 mg, 2.50 mmol) and tert-butyl tert-butoxycarbonyloxycarbamate (582 mg, 2.50 mmol) in THF (6 mL) was added DEAD (40 wt %, 1.25 mL, 2.75 mmol). The mixture was stirred at room temperature for 20 h and concentrated. The crude product was dissolved in dichloromethane (4 mL) and trifluoroacetic acid (1 mL) was added. The mixture was stirred at room temperature for 1 h and concentrated. The residue was dissolved in ethyl acetate (40 mL) and the organic layer washed with saturated aqueous NaHCO$_3$ (20 mL), brine (15 mL), dried, and concentrated. The crude was used without further purification.

Example 12

3-(4-(2-(2-(1H-Imidazol-4-yl)phenoxy)ethyl)phenyl)-1-hydroxy-1-(tetrahydro-2H-pyran-4-yl)urea A mixture of 4-(2-(2-(1-trityl-1H-imidazol-4-yl)phenoxy)ethyl)aniline (113 mg, 0.217 mmol), triphosgene (21 mg, 0.07 mmol) and triethylamine (0.04 mL, 0.260 mmol) in dry dichloromethane (6 mL) was heated at reflux for 2 h and then cooled with an ice bath. To this mixture was added N-(tetrahydro-2H-pyran-4-yl)hydroxylamine (76 mg, 0.650 mmol). The reaction mixture was stirred at room temperature for 2 h. The solvent was removed and the crude was dissolved in methanol (4 mL) and acetic acid (1 mL). The reaction mixture was heated at 80° C. for 2 h. The reaction mixture was basified with aqueous 10% NaOH and the aqueous layer extracted with ethyl acetate (2×30 mL). The combined organic extracts were washed with brine (15 mL), dried over Na$_2$SO$_4$ and concentrated. The residue was purified by flash column chromatography using 5% MeOH/dichloromethane as an eluent at afford the desired product as a yellowish solid (30 mg, 33%). $^1$H NMR: 1.63 (d, 2H, J=10.4 Hz), 1.98-2.07 (m, 2H), 3.15 (t, 3H, J=5.6 Hz), 3.46 (t, 2H, J=11.6 Hz), 3.78 (s, 1H), 4.02 (dd, 2H, J=11.2 Hz, 4 Hz), 4.36-4.45 (m, 4H), 6.98-7.03 (m, 3H), 7.19-7.27 (m, 3H), 7.30-7.42 (m, 3H), 7.66 (s, 1H), 8.14 (s, 1H).

Example 13

N-(3-(Hydroxymethyl)benzyl)acetamide

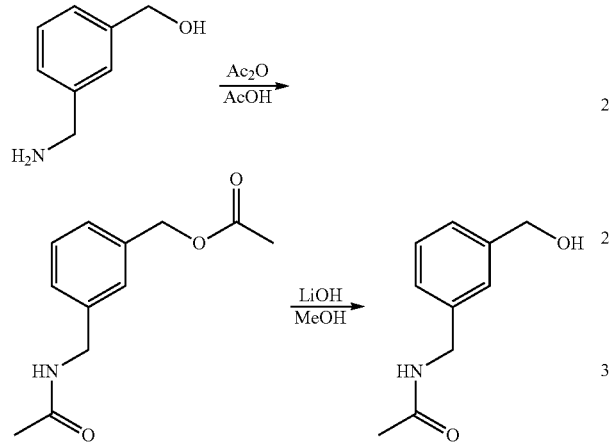

To a flask containing reflux condenser, 3-cyanobenzoic acid (5.0 mmol) and THF (15 ml) at 0° C. was added BH$_3$.Me$_2$S (6.0 mmol drop wise. The reaction was allowed to reflux for 12 h. After reaction was over MeOH was added drop wise at 0° C. and the resulting clear solution was concentrated in vacuum and taken to the next step without further purification. To the crude product obtained above glacial acetic acid (10 mL) and acetic anhydride (4 mL) was added. The reaction vial was sealed and heated at 110° C. for 12 h. The mixture was concentrated under reduced pressure. The crude product was dissolved in MeOH (10 mL) and LiOH (10.0 mmol) was added. The solution was allowed to stir overnight at room temperature. The solution was concentrated under reduced pressure and diluted with ethyl acetate. The organic phase was washed with water (2×5 mL), brine and dried (Na$_2$SO$_4$). The solvent was removed under reduced pressure and the crude mixture was purified by column chromatography to afford the desired product in 12% overall yield. $^1$H NMR: 1.93 (s, 3H), 2.85 (s, 1H), 4.32 (d, 2H, J=6 Hz), 6.15 (s, 1H), 7.12 (d, 1H, J=−6.8 Hz), 7.15-7.30 (m, 3H).

Example 14

(4-(2-Hydroxyethyl)piperidin-1-yl)(thiophen-2-yl)

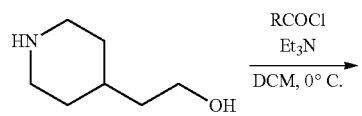

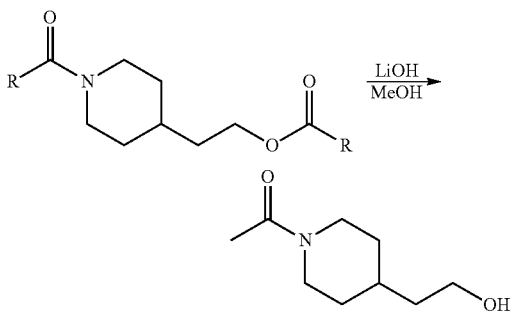

To the stirred solution of amino alcohol (1.0 mmol) in DCM at 0° C., Et$_3$N (2.2 mmol) was added. To this solution acid chloride (2.2 mmol) was added carefully dropwise. The reaction was allowed to stir overnight at room temperature. After reaction was over the reaction mixture was diluted with ethyl acetate and washed with water. The resulting organic layer was dried over sodium sulfate and concentrated under vacuum. The crude reaction product was dissolved in MeOH and LiOH was added. After 2 hours the mixture was concentrated and diluted with EtOAc and washed with water. The resulting organic layer was dried over sodium sulfate and concentrated under vacuum. The crude mixture after concentration under vacuum was purified by column chromatography to give desired product in 58% yield. $^1$H NMR: 1.00-1.20 (m, 2H), 1.41 (q, 2H, J=6.0 Hz), 1.60-1.75 (m, 3H), 2.84 (s, 1H), 3.06 (t, 1H, J=4.8 Hz), 3.54 (q, 2H, J=6.4 Hz), 4.29 (s, 1H), 6.90-6.96 (m, 1H), 7.16 (dd, 1H, J=3.6, 1,2 Hz), 7.32 (dd, 1H, J=5.2, 1.2 Hz).

The following compounds were prepared according to the general procedure of Example 14, by substituting the appropriate starting materials:

| | Yield (%) | $^1$H NMR |
|---|---|---|
| 1-(4-(2-Hydroxyethyl)piperidin-1-yl)-2-(thiophen-2-yl)ethanone | 63 | $^1$H NMR: 0.97-1.10 (m, 2H), 1.30-1.50 (m, 2H), 1.50-1.70 (m, 3H), 2.41 (s, 1H), 2.51 (t, 1H, J = 13.2), 2.95 (t, 1H, J = 13.2 Hz), 3.58 (t, 2H, J = 6.8 Hz), 3.75-3.90 (m, 3H), 4.51 (d, 1H, J = 12.8 Hz), 6.78-6.90 (m, 2H), 7.08-7.15 (m, 1H). |
| 1-(4-(2-Hydroxyethyl)piperidin-1-yl)-2-phenylethanone | 44 | $^1$H NMR: 0.70-1.10 (m, 2H), 1.37 (q, 2H, J = 6.8), 1.48-1.70 (m, 3H), 2.40-2.60 (m, 2H), 2.88 (dt, 1H, J = 13.6, 2.4 Hz), 3.55 (t, 2H, J = 6.4 Hz), 3.66 (s, 2H), 3.76 (d, 1H, J = 13.6 Hz), 4.53 (d, 1H, J = 13.2 Hz), 7.16-7.27 (m, 3H). |
| Benzyl (4-(2-hydroxyethyl)phenyl)carbamate | 40 | $^1$H NMR: 1.41 (t, 1H, J = 6.0 Hz), 2.82 (t, 2H, J = 6.4 Hz), 3.82 (q, 2H, J = 6.4 Hz), 5.19 (s, 2H), 6.66 (s, 1H), 7.16 (d, 1H, J = 8.4 Hz), 7.30-7.45 (m, 7H). |

Example 15

General Procedure for the Synthesis of N-(4-(Bromomethyl)benzyl)acetamide and tert-Butyl 4-(2-bromoethyl)piperidine-1-carboxylate To a stirred solution of the alcohol (1.0 mmol) and carbon tetrabromide (364.0 mg, 1.1 mmol) in dichloromethane (5 mL) at 0° C. was added triphenyl phosphine (288.0 mg, 1.1 mmol). The reaction mixture was allowed to stir 12 h at room temperature. The mixture was concentrated under reduced pressure, adsorbed on silica gel and purified by flash column chromatography.

The following compounds were prepared according to the general procedure of Example 15, by substituting the appropriate starting materials:

| Compound | Name | Yield (%) | $^1$H NMR |
|---|---|---|---|
|  | (4-(2-bromoethyl)piperidin-1-yl)(thiophen-2-yl)methanone | 67 | 1.10-1.30 (m, 2H), 1.70-1.90 (m, 5H), 2.80-3.00 (m, 2H), 3.42 (t, 2H, J = 6.4 Hz), 4.30-4.60 (m, 2H), 6.99 (dd, 1H, J = 3.6, 4.4 Hz), 7.23 (d, 1H, J = 3.6), 7.39 (d, 1H, J = 4.8) |
|  | 1-(4-(2-bromoethyl)piperidin-1-yl)-2-(thiophen-2-yl)ethanone | 73 | 0.80-1.15 (m, 2H), 1.60-1.70 (m, 5H), 2.55 (dd, 1H, J = 13.2, 2.0 Hz), 3.01 (dd, 1H, J = 13.2, 2.0 Hz), 3.90 (t, 2H, J = 6.8 Hz), 3.80-3.45 (m, 3H), 4.62 (d, 1H, J = 11.2 Hz), 6.81-6.95 (m, 2H), 7.15 (dd, 1H, J = 5.2, 0.8 Hz) |
|  | 1-(4-(2-bromoethyl)piperidin-1-yl)-2-phenylethanone | 64 | 0.78-1.12 (m, 2H(, 1.56 (s, 1H), 1.60 (s, 1H), 1.65-1.80 (m, 4H), 2.55 (t, 1H, J = 12.8 Hz), 2.93 (t, 1H, J = 12.8 Hz), 3.38 (t, 2H, J = 6.0 Hz), 3.71 (s, 2H), 3.85 (d, 1H, J = 14.0 Hz), 4.63 (d, 1H, J = 13.2 Hz), 7.20-7.33 (m, 5H) |

Example 16

1-(4-(2-Hydroxyethyl)piperidin-1-yl)-3,3-dimethylbutan-1-one

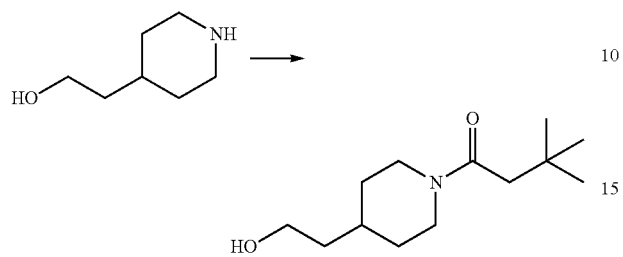

To a solution of 2-(piperidin-4-yl)ethanol (0.30 g, 2.32 mmol) in anhydrous dichloromethane (10 mL), NaHCO$_3$ (0.59 g, 6.97 mmol) was added. The suspension was cooled to 0° C. and then 3,3-dimethylbutanoyl chloride (0.38 g, 2.79 mmol) was added dropwise over a period of 15 min. The reaction was followed by TLC till the disappearance of the starting material (overnight) and was then filtered. The residue was then purified using column chromatography on a silica gel column eluting with a solution of ethyl acetate in hexane (50%) to produce the alcohol in a 45% yield.

The following compounds were prepared according to the general procedure of Example 16, by substituting the appropriate starting materials: Neopentyl 4-(2-hydroxyethyl)piperidine-1-carboxylate

Example 17

Ethyl 4-(2-hydroxyethyl)phenylcarbamate

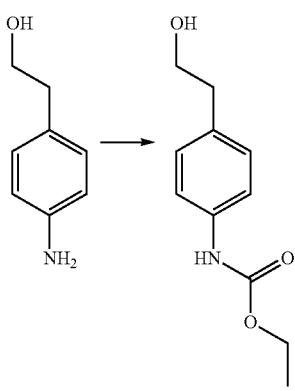

To a solution of the amine (500 mg, 3.64 mmol) in anhydrous dichloromethane (10 mL), NaHCO$_3$ (0.92 g, 10.92 mmol) was added. The suspension was cooled to 0° C. and then ethyl chloroformate (0.42 g, 3.83 mmol) was added dropwise over a period of 15 min. The reaction was followed by TLC till the disappearance of the starting material and was then filtered. The carbamate was then purified using column chromatography on a silica gel column eluting with a solution of 1:1 ethyl acetate in hexane (87% yield).

Example 18

General Procedure for the Preparation of Tosylates

A mixture of alcohol (1 equiv) and p-toluenesulfonyl chloride (1.5 equiv) in dichloromethane was cooled to 0° C. and pyridine (3 equiv) was added. The mixture was stirred at room temperature for 18 h and concentrated. The residue was suspended in ethyl acetate and the ethyl acetate layer was washed with water, saturated aqueous NaHCO$_3$, brine, dried over Na$_2$SO$_4$ and concentrated. The product obtained was used in the SN2 alkylation without further purification.

Example 19

General Procedure For the Alkylation of 2-(1H-Imidazol-4-yl)phenols

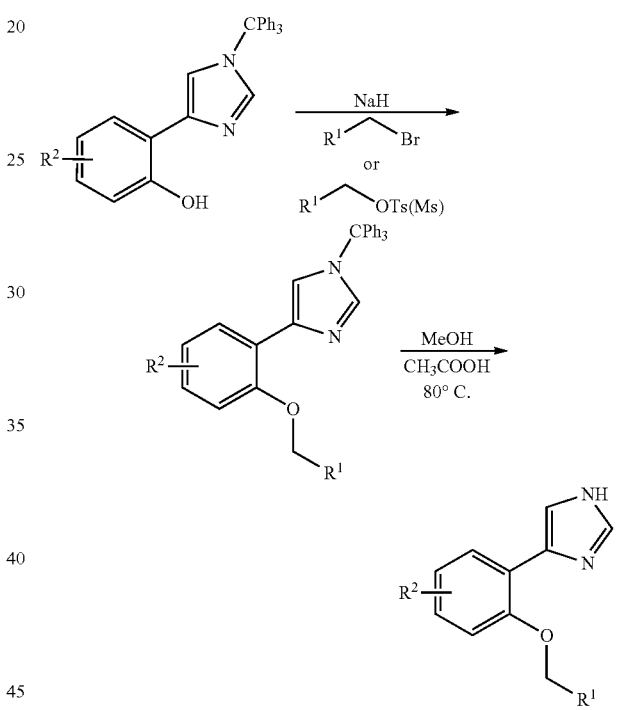

To a stirred solution of the appropriate phenol (0.5 mmol) in anhydrous DMF (3 mL) at 0° C. was added NaH (36.0 mg, 0.75 mmol). The resulting suspension was allowed to stir at room temperature for 45 min. To the resulting solution was added the appropriate alkylating reagent. After stirring overnight, the reaction mixture was carefully diluted with water and extracted with ethyl acetate (2×10 mL). The combined organic layers were washed with water, brine and dried (Na$_2$SO$_4$). The solvent was removed under reduced pressure and the crude product was taken to next step without further purification. To a solution of the crude ether was added acetic acid (1.0 mL) and MeOH (4.0 mL). The solution was stirred at 80° C. for 2 h. The solution was allowed to cool to room temperature and the pH was adjusted to ~10 with 10% NaOH (aq). The aqueous phase was extracted with EtOAc (3×20 mL). The combined organic layer were washed with water, brine, and dried. The solvent was removed in vacuo to afford the crude residue, which was purified by flash column chromatography on silica gel to afford the desired product.

The following compounds were prepared according to the general procedure of Example 19, by substituting the appropriate starting materials:

| | Products from Alkyl Tosylates | | | |
|---|---|---|---|---|
| No. | Compound | Name | Yield (%) | $^1$H NMR |
| 1368 | | 1-(4-(2-(2-(1H-imidazol-4-yl)phenoxy)ethyl)-3-chlorophenyl)-3-(±(1R,2S)-2-aminocyclohexyl)urea | 40 | 1.43-1.58 (m, 4H), 1.89 (t, 2H, J = 11.2 Hz), 2.03-2.05 (m, 1H), 2.94-2.98 (m, 1H), 3.22 (t, 1H, J = 11.2 Hz), 3.29 (t, 2H, J = 6.4 Hz), 3.51 (t, 1H, J = 11.2 Hz), 4.40 (t, 2H, J = 6.4 Hz), 5.17 (s, 1H), 6.99-7.03 (m, 2H), 7.18-7.33 (m, 4H), 7.56 (s, 1H), 7.67 (s, 1H), 7.80 (s, 1H), 10.24 (s, 1H) |
| 1361 | | 1-(4-(2-(2-(1H-imidazol-4-yl)phenoxy)ethyl)-3-chlorophenyl)-3-(±(1R,2R)-2-aminocyclohexyl)urea | 29 | 1.41-1.55 (m, 4H), 1.89 (t, 2H, J = 11.2 Hz), 2.03-2.05 (m, 1H), 2.94-2.98 (m, 1H), 3.22 (t, 1H, J = 11.2 Hz), 3.27 (t, 2H, J = 6.4 Hz), 3.51 (t, 1H, J = 11.2 Hz), 4.37 (t, 2H, J = 6.4 Hz), 5.02 (s, 1H), 6.99-7.03 (m, 2H), 7.18-7.33 (m, 4H), 7.56 (s, 1H), 7.67 (s, 1H), 7.80 (s, 1H), 10.27 (s, 1H) |
| 1347 | | 1-(4-(2-(2-(1H-imidazol-4-yl)phenoxy)ethyl)-3-chlorophenyl)-3-phenylurea | 31 | 3.22 (t, 2H, J = 6.4 Hz), 4.29 (t, 2H, J = 6.4 Hz), 6.95 (t, 2H, J = 7.2 Hz), 7.06 (d, 1H, J = 8 Hz), 7.14 (t, 1H, J = 8 Hz), 7.21 (d, 1H, J = 8.4 Hz), 7.26 (t, 2H, J = 7.6 Hz), 7.38-7.43 (m, 4H), 7.67 (s, 1H), 7.74 (d, 1H, J = 1.6 Hz), 7.99 (s, 1H), 8.71 (s, 1H), 8.80 (s, 1H), 12.04 (brs, 1H) |
| 1346 | | 1-(4-(2-(2-(1H-imidazol-4-yl)phenoxy)ethyl)-3-chlorophenyl)-3-(3-(tetrahydrofuran-3-yloxy)phenyl)urea | 47 | 2.04-2.10 (m, 2H), 3.17 (t, 2H, J = 6.4 Hz), 3.77-3.82 (m, 1H), 3.87-3.91 (m, 3H), 4.35 (d, 2H, J = 6.4 Hz), 4.79 (s, 1H), 6.44 (dd, 1H, J = 8 Hz, 2Hz), 6.80 (d, 1H, J = 8 Hz), 6.95-6.99 (m, 3H), 7.06-7.12 (m, 4H), 7.20 (t, 1H, J = 8 Hz), 7.52 (d, 1H, J = 5.2 Hz), 7.70 (d, 1H, J = 7.6 Hz), 8.47 (s, 1H), 8.83 (s, 1H) |
| 1333 | | N-(4-(2-(2-(1H-imidazol-4-yl)phenoxy)ethyl)-3-chlorophenyl)-2-amino-2-(tetrahydro-2H-pyran-4-yl)acetamide | 95 | 1.16-1.20 (m, 1H), 1.24-1.29 (m, 1H), 1.34-1.45 (m, 2H), 1.57-1.59 (m, 1H), 1.85-1.87 (m, 1H), 3.12-3.23 (m, 3H), 3.45 (d, 1H, J = 6.8 Hz), 3.81 (t, 2H, J = 6.8 Hz), 4.27 (t, 2H, J = 6.8 Hz), 6.92 (t, 1H, J = 7.6 Hz), 7.03 (d, 1H, J = 8 Hz), 7.10 (t, 1H, J = 6.8 Hz), 7.39-7.46 (m, 3H), 7.63 (s, 1H), 7.88 (d, 1H, J = 1.6 Hz), 7.98 (s, 1H) |

| No. | Compound | Name | Yield (%) | ¹H NMR |
|---|---|---|---|---|
| 1344 | | N-(4-(2-(2-(1H-imidazol-4-yl)phenoxy)ethyl)-3-chlorophenyl)piperidine-2-carboxamide | 92 | 1.68-1.75 (m, 3H), 1.85-1.95 (m, 2H), 2.28 (d, 1H, J = 8 Hz), 3.04-3.07 (m, 1H), 3.27 (t, 2H, J = 6.4 Hz), 3.41 (d, 1H, J = 12.8 Hz), 3.92 (dd, 1H, J = 11.6 Hz, 3.2 Hz), 4.35 (t, 2H, J = 6.4 Hz), 6.97 (t, 1H, J = 7.6 Hz), 7.05 (d, 1H, J = 8 Hz), 7.20 (dt, 1H, J = 8.4 Hz, 1.6 Hz), 7.33 (d, 1H, J = 8.4 Hz), 7.37 (d, 1H, J = 2 Hz), 7.39 (d, 1H, J = 2 Hz), 7.72 (s, 1H), 7.77 (dd, 1H, J = 8 Hz, 1.6 Hz), 7.83 (d, 1H, J = 2 Hz) |
| 1222 | | 6-(2-(2-(1H-imidazol-4-yl)phenoxy)ethyl)-N-phenylbenzo[d]oxazol-2-amine | 14 | 3.23 (t, 2H, J = 6.4 Hz), 4.38 (t, 2H, J = 6.4 Hz), 6.96-7.07 (m, 3H), 7.13-7.24 (m, 4H), 7.34-7.47 (m, 4H), 7.61-7.63 (m, 2H), 7.68-7.73 (m, 1H), 8.89 (br s, 1H) |
| 1021 | | 4-(5-bromo-2-(2-chlorophenethoxy)phenyl)-1H-imidazole | 27 | 3.33 (t, 2H, J = 6.8 Hz), 4.38 (2H, J = 6.8 Hz), 6.86 (d, 1H, J = 8.8 Hz), 7.22-7.32 (m, 4H), 7.40-7.42 (m, 1H), 7.45 (s, 1H), 7.57 (s, 1H), 7.99 (s, 1H) |
| 0978 | | 4-(2-(2-phenylpropoxy)phenyl)-1H-imidazole | 44 | 1.40 (d, 3H, J = 6.9 Hz), 3.33-3.40 (m, 1H), 4.18 (t, 1H, J = 9.3 Hz), 4.36 (dd, 1H, J = 9 Hz, 5.7 Hz), 6.80 (d, 1H, J = 8.4 Hz), 6.95 (dt, 1H, J = 8 Hz, 1.2 Hz), 7.05 (dt, 1H, J = 8 Hz, 1.6 Hz), 7.25-7.37 (m, 5H), 7.65 (s, 1H), 7.72 (s, 1H), 7.86 (d, 1H, J = 7.2 Hz) |
| 0936 | | 4-(2-(2-(1H-imidazol-4-yl)phenoxy)ethylidene)cyclohexanecarbonitrile | 41 | 1.43-1.52 (m, 4H), 1.79-1.86 (m, 4H), 2.17-2.20 (m, 1H), 4.05-4.11 (m, 2H), 6.69 (d, 1H, J = 10.5 Hz), 6.94 (t, m, J = 7.5 Hz), 7.02 (d, 1H, J = 8.1 Hz), 7.12 (d, 1H, J = 7.2 Hz), 7.50 (s, 1H), 7.67 (s, 1H), 8.07 (d, 1H, J = 7.5 Hz) |
| 1345 | | N-(4-(2-(2-(1H-imidazol-4-yl)phenoxy)ethyl)-3-chlorophenyl)-2-aminonicotinamide | 31 | (CD₃OD) 3.16 (t, 2H, J = 6.8 Hz), 4.28 (t, 2H, J = 6.8 Hz), 6.69 (dd, 1H, J = 8 Hz, 5.2 Hz), 6.98 (t, 1H, J = 7.6 Hz), 7.07 (d, 1H, J = 8 Hz), 7.18-7.22 (m, 2H), 7.34 (t, 1H, J = 4 Hz), 7.47 (dd, 1H, J = 8 Hz, 2 Hz), 7.65 (s, 1H), 7.67 (s, 1H), 7.85 (d, 1H, J = 2 Hz), 8.01 (dd, 1H, J = 8 Hz, 2 Hz), 8.07 (dd, 1H, J = 4.8 Hz, 1.6 Hz) |

-continued

| | Products from Alkyl Tosylates | | | |
|---|---|---|---|---|
| No. | Compound | Name | Yield (%) | $^1$H NMR |
| 1046 | | tert-butyl 4-(2-(2-(1H-imidazol-4-yl)phenoxy)ethyl)phenylcarbamate | 51 | 1.52 (s, 9H), 3.15 (t, 2H, J = 8.4 Hz), 4.36 (t, 2H, J = 8.4 Hz), 6.80 (br s, 1H), 6.97-7.02 (m, 2H), 7.15-7.24 (m, 3H), 7.35 (s, 1H), 7.38 (s, 1H), 7.44 (s, 1H), 7.78 (br s, 1H) |
| 1191 | | 4-(2-(2-(cyclohex-3-en-1-yl)ethoxy)phenyl)-1H-imidazole | 72 | 1.30-1.40 (s, 1H), 1.78-1.91 (m, 5H), 2.04-2.18 (m, 3H), 4.18 (t, 2H, J = 8.0 Hz) 5.64-5.71 (m, 2H), 6.97-7.04 (m, 2H), 7.22 (t, 1H, J = 8.0 Hz), 7.56 (s, 1H), 7.69 (s, 1H), 7.87 (d, 1H, J = 4.0 Hz) |
| 1296 | | 4-(2-(2-chlorophenethoxy)-3-fluorophenyl)-1H-imidazole | 57 | 3.26 (t, 2H, J = 6.6 Hz), 4.31 (t, 2H, J = 6.6 Hz), 6.94-6.99 (m, 1H), 7.02-7.07 (m, 1H), 7.23-7.25 (m, 2H), 7.34-7.41 (m, 4H), 7.54 (br s, 1H) |
| 1305 | | N-(4-(2-(2-(1H-imidazol-4-yl)phenoxy)ethyl)-3-(trifluoromethyl)phenyl)-2-(tetrahydro-2H-pyran-4-yl)acetamide | 22 | 1.31-1.40 (m, 2H), 1.69 (d, 2H, J = 12.4 Hz), 2.11-2.16 (m, 1H), 2.30 (d, 2H, J = 7.2 Hz), 3.34 (t, 2H, J = 6.2 Hz), 3.42 (t, 2H, J = 11.4 Hz), 3.94 (dd, 2H, J = 4.0, 11.2 Hz), 4.39 (t, 2H, J = 6.2 Hz), 6.99 (d, 1H, J = 8.0 Hz), 7.03 (d, 1H, J = 7.6 Hz), 7.24 (d, 2H, J = 7.6 Hz), 7.34 (d, 1H, J = 8.4), 7.53 (s, 1H), 7.62 (d, 1H, J= 8.0 Hz), 7.78 (d, 1H, J = 7.6 Hz), 7.93 (s, 1H), 8.46 (s, 1H) |
| 1295 | | N-(4-(2-(2-(1H-imidazol-4-yl)phenoxy)ethyl)-3-fluorophenyl)-2-(tetrahydro-2H-pyran-4-yl)acetamide | 58 | 1.32-1.41 (m, 2H), 1.68 (d, 2H, J = 12.8 Hz), 2.07-2.16 (m, 1H), 2.27 (d, 2H, J = 7.2 Hz), 3.17 (t, 2H, J = 6.0 Hz), 4.44 (t, 2H, J = 11.6 Hz), 3.67 (br s, 2H), 3.95 (dd, 2H, J = 3.4, 11.4 Hz), 4.35 (t, 2H, J = 6.2 Hz), 6.98 (d, 8.0 Hz), 7.02 (d, 1H, J = 7.6 Hz), 7.18-7.23 (m, 3H), 7.32 (s, 1H), 7.49 (s, 1H), 7.53 (s, 1H), 7.74 (d, 1H, 7.6 Hz) |
| 0958 | | N-(3-((2-(1H-imidazol-4-yl)phenoxy)methyl)benzyl)acetamide | 35 | 1.93 (s, 3H), 4.38 (d, 2H, J = 6.0 Hz), 5.08 (s, 2H), 6.96-7.05 (m, 2H), 7.15-7.35 (m, 4H), 7.36 (s, 1H), 7.47 (s, 1H), 7.53 (s, 1H) |

-continued

| Products from Alkyl Tosylates | | | | |
|---|---|---|---|---|
| No. | Compound | Name | Yield (%) | $^1$H NMR |
| 1136 | | benzyl (4-(2-(2-(1H-imidazol-4-yl)phenoxy)ethyl)phenyl)carbamate | 28 | 3.13 (t, 2H, J = 8.4 Hz), 4.35 (t, 2H, J = 8.4 Hz), 5.20 (s, 2H), 6.95-7.05 (m, 2H), 7.14 (s, 1H), 7.16-7.43 (m, 11H), 7.45 (s, 1H), 7.74 (dd, 1H, J = 10.8, 2.4 Hz) |
| 1229 | | 1-(4-(2-(2-(1H-imidazol-4-yl)phenoxy)ethyl)phenyl)pyrrolidin-2-one | 52 | 2.19 (m, 2H), 2.65 (t, 2H, J = 6.0 Hz), 3.19 (t, 2H, J = 6.0 Hz), 3.88 (t, 2H, J = 6.0 Hz), 4.37 (t, 2H, J = 6.0 Hz), 7.01 (m, 2H), 7.18 (m, 1H), 7.26 (s, 2H), 7.36 (d, 2H, J = 6.0 Hz), 7.46 (m, 3H) |
| 1225 | | 4-(2-(4-(pyrrolidin-1-yl)phenethoxy)phenyl)-1H-imidazole | 19 | 2.01 (m, 4H), 3.12 (t, 2H, J = 6.30 Hz), 3.28 (m, 4H), 4.37 (t, 2H, J = 6.60 Hz), 6.59 (d, 2H, J = 8.70 Hz), 6.96-7.02 (m, 2H), 7.17-7.21 (m, 3H), 7.32 (s, 1H), 7.38 (s, 1H), 7.65 (brs, 1H) |
| 1230 | | 1-(4-(2-(2-(1H-imidazol-4-yl)phenoxy)ethyl)phenyl)piperidin-2-one | 40 | DMS0-d6: 1.82 (m, 4H), 2.36 (t, 2H, J = 3.0 Hz), 3.14 (t, 2H, J = 3.0 Hz), 3.54 (m, 2H), 4.38 (t, 2H, J = 3.0 Hz), 7.06 (t, 1H, J = 6.0 Hz), 7.19 (d, 2H, J = 6.0 Hz), 7.24 (d, 1H, J = 6.0 Hz), 7.32-7.44 (m, 5H), 7.85 (d, 1H, J = 6.0 Hz), 9.19 (s, 1H). |
| 1223 | | 1-(4-(2-(2-(1H-imidazol-4-yl)phenoxy)ethyl)phenyl)piperidine | 60 | 1.23-1.28 (m, 7H), 3.15 (m, 6H), 4.39 (t, 2H, J = 6.0 Hz), 6.96-7.02 (m, 4H), 7.21-7.24 (m, 3H), 7.30 (s, 1H), 7.36 (s, 1H), 7.58 (m, 1H) |
| 1159 | | N-(4-(2-(2-(1H-imidazol-4-yl)phenoxy)ethyl)-3-chlorophenyl)acetamide | 17 | (MeOH, d$_4$), 2.00 (s, 3H), 3.26 (t, 2H, J = 6.9 Hz), 4.36 (t, 2H, J = 6.9 Hz), 6.96-7.08 (m, 2H), 7.20-7.31 (m, 4H), 7.75-7.78 (3H) |

| No. | Compound | Name | Yield (%) | $^1$H NMR |
|---|---|---|---|---|
| 1193 | 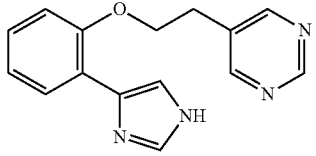 | 5-(2-(2-(1H-imidazol-4-yl)phenoxy)ethyl)pyrimidine | 42 | (MeOH, $d_4$), 3.24 (t, 2H, J = 6 Hz), 4.44 (t, 2H, J = 6 Hz), 7.02 (t, 1H, J = 7.5 Hz), 7.09 (t, 1H, J = 8.4 Hz), 7.21-7.26 (m, 1H), 7.30 (s, 2H), 7.71 (s, 1H), 7.78 (d, 1H, J = 7.8 Hz), 8.74 (s, 1H), 8.99 (s, 1H) |
| 1198 | 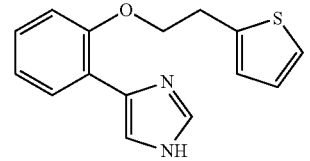 | 4-(2-(2-(thiophen-2-yl)ethoxy)phenyl)-1H-imidazole | 43 | (MeOH, $d_4$), 3.38 (t, 2H, J = 6.3 Hz), 4.34 (t, 2H, J = 6.3 Hz), 6.92-7.05 (m, 4H), 7.19-7.24 (m, 2H), 7.40 (s, 1H), 7.73 (s, 1H), 7.78-7.82 (m, 1H) |
| 1202 | 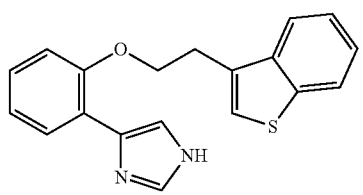 [SMILES: c1ccc(-c2c[nH]cn2)c(OCCc2csc3ccccc23)c1] | 4-(2-(2-(benzo[b]thiophen-3-yl)ethoxy)phenyl)-1H-imidazole | 39 | (MeOH, $d_4$), 3.39-3.43 (m, 2H), 4.44-4.48 (m, 2H), 6.98-7.07 (m, 2H), 7.17-7.40 (m, 5H), 7.64 (s, 1H), 7.79-7.87 (m, 3H) |
| 1203 | 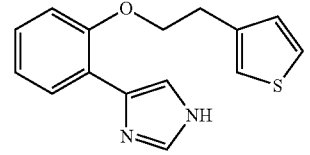 [SMILES: c1ccc(-c2c[nH]cn2)c(OCCc2ccsc2)c1] | 4-(2-(2-(thiophen-3-yl)ethoxy)phenyl)-1H-imidazole | 50 | (MeOH, $d_4$), 3.19 (t, 2H, J = 6.6 Hz), 4.34 (t, 2H, J = 6.3 Hz), 6.96-7.42 (m, 7H), 7.76-7.85 (m, 2H) |
| 1213 | 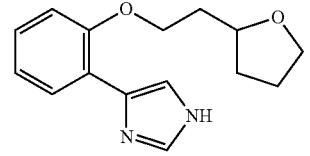 [SMILES: c1ccc(-c2c[nH]cn2)c(OCCC2CCCO2)c1] | 4-(2-(2-(tetrahydrofuran-2-yl)ethoxy)phenyl)-1H-imidazole | 41 | (MeOH, $d_4$), 1.55-2.15 (m, 6H), 3.75-4.26 (m, 5H), 6.96-7.07 (m, 2H), 7.22-7.27 (m, 1H), 7.59 (s, 1H), 7.77 (d, 2H, J = 7.8 Hz), 7.91 (s, 1H) |
| 1218 | 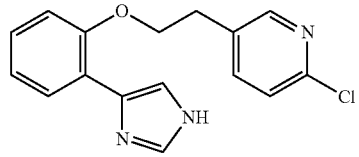 [SMILES: Clc1ccc(CCOc2ccccc2-c2c[nH]cn2)cn1] | 5-(2-(2-(1H-imidazol-4-yl)phenoxy)ethyl)-2-chloropyridine | 35 | (MeOH, $d_4$), 3.18 (t, 2H, J = 6.3 Hz), 4.37 (t, 2H, J = 6.3 Hz), 6.96-7.07 (m, 2H), 7.18-7.35 (m, 3H), 7.70-7.79 (m, 3H), 8.29-8.30 (m, 1H) |
| 1243 | 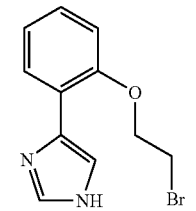 [SMILES: BrCCOc1ccccc1-c1c[nH]cn1] | 4-(2-(2-bromoethoxy)phenyl)-1H-imidazole | 40 | (MeOH, $d_4$), 3.82-3.85 (m, 2H), 4.44 (t, 2H, J = 5.1 Hz), 7.01-7.06 (m, 2H), 7.21-7.27 (m, 1H), 7.70-7.90 (m, 4H) |
| 1260 | 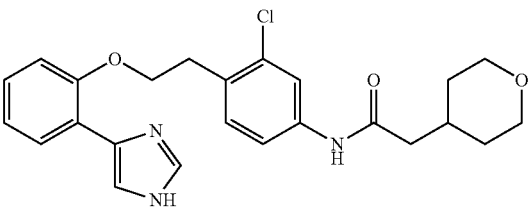 [SMILES: O=C(CC1CCOCC1)Nc1ccc(CCOc2ccccc2-c2c[nH]cn2)c(Cl)c1] | N-(4-(2-(2-(1H-imidazol-4-yl)phenoxy)ethyl)-3-chlorophenyl)-2-(tetrahydro-2H-pyran-4-yl)acetamide | 41 | (MeOH, $d_4$), 1.29-1.35 (m, 2H), 1.59-1.64 (m, 2H), 1.95-2.10 (m, 1H), 2.30 (s, 2H), 3.20 (t, 2H, J = 6.6 Hz), 3.30-3.42 (m, 2H), 3.86-3.90 (m, 2H), 4.29-4.33 (d, 2H, J = 6.6 Hz), 6.96-7.07 (m, 2H), 7.16-7.32 (m, 4H), 7.45 (s, 1H), 7.67-7.77 (m, 3H), 8.21 (s, 1H) |

-continued

| | | | Yield | |
|---|---|---|---|---|
| No. | Compound | Name | (%) | ¹H NMR |

Products from Alkyl Tosylates

| No. | Compound | Name | Yield (%) | ¹H NMR |
|---|---|---|---|---|
| 1265 | | 1-(4-(2-(2-(1H-imidazol-4-yl)phenoxy)ethyl)-3-chlorophenyl)-3-(tetrahydro-2H-pyran-4-yl)urea | 38 | (MeOH, $d_4$), 1.43-1.54 (m, 2H), 1.86-1.91 (m, 2H), 3.24 (t, 2H, J = 6.9 Hz), 3.54-3.53 (m, 2H), 3.76-3.79 (m, 1H), 3.90-3.94 (m, 2H), 4.35 (t, 2H, J = 6.9 Hz), 6.96-7.02 (m, 1H), 7.06-7.13 (m, 2H), 7.20-7.26 (m, 2H), 7.37 (s, 1H), 7.58 (d, 1H, J = 2.1 Hz), 7.76-7.79 (m, 1H), 7.82 (s, 1H) |
| 1297 | | N-(4-(2-(2-(1H-imidazol-4-yl)phenoxy)ethyl)-2-chlorophenyl)-2-(tetrahydro-2H-pyran-4-yl)acetamide | 46 | (MeOH, $d_4$), 1.30-1.42 (m, 2H), 1.70-1.74 (m, 2H), 2.03-2.20 (m, 1H), 2.37 (d, 2H, J = 7.2 Hz), 3.13-3.17 (t, 2H, J = 6.3 Hz), 3.39-3.48 (m, 2H), 3.91-3.96 (m, 2H), 4.33-4.37 (d, 2H, J = 6.3 Hz), 6.96-7.01 (m, 1H), 7.06-7.09 (m, 1H), 7.19-7.28 (m, 3H), 7.43 (s, 1H), 7.52-7.55 (m, 1H), 7.75-7.78 (m, 2H) |
| 1298 | | N-(3-(2-(2-(1H-imidazol-4-yl)phenoxy)ethyl)-4-chlorophenyl)-2-(tetrahydro-2H-pyran-4-yl)acetamide | 16 | (MeOH, $d_4$), 1.29-1.35 (m, 2H), 1.59-1.64 (m, 2H), 1.95-2.10 (m, 1H), 2.30 (s, 2H), 3.20 (t, 2H, J = 6.6 Hz), 3.30-3.42 (m, 2H), 3.86-3.90 (m, 2H), 4.31 (d, 2H, J = 6.6 Hz), 6.96-7.07 (m, 2H), 7.16-7.22 (m, 1H), 7.45 (s, 1H), 7.57-7.92 (m, 4H), 8.21 (s, 1H) |
| 1366 | | N-(4-(2-(2-(1H-imidazol-4-yl)phenoxy)ethyl)-3-chlorophenyl)-2-(pyrimidin-5-yl)acetamide | 18 | 3.25-3.31 (m, 2H), 3.79 (s, 2H), 4.36 (t, 2H, J = 6 Hz), 6.95-7.01 (m, 1H), 7.07 (d, 1H, J = 8.1 Hz), 7.18-7.23 (m, 1H), 7.30-7.37 (m, 3H), 7.71-7.80 (m, 3H), 8.77 (s, 1H), 9.06 (s, 1H) |
| 1143 | | 1-(4-(2-(2-(1H-imidazol-4-yl)phenoxy)ethyl)piperidin-1-yl)-3,3-dimethylbutan-1-one | 48 | 1.04 (s, 9H), 1.15-1.26 (m, 2H), 1.77-1.86 (m, 5H), 2.22-2.31 (m, 2H), 2.47-2.53 (m, 1H), 2.88-3.02 (m, 1H), 3.91-3.94 (m, 1H), 4.13-4.16 (m, 2H), 4.66-4.69 (m, 1H), 6.95 (d, 1H, J = 8.4 Hz), 7.20-7.23 (m, 1H), 7.57 (m, 1H), 7.71-7.76 (m, 1H), 7.90-7.92 (m, 1H) |
| 1149 | | neopentyl 4-(2-(2-(1H-imidazol-4-yl)phenoxy)ethyl)piperidine-1-carboxylate | 84 | 0.94 (s, 9H), 1.15-1.28 (m, 2H), 1.73-1.90 (m, 4H), 2.60-2.85 (m, 2H), 3.77 (s, 2H), 4.14-4.18 (m, 2H), 6.95-7.05 (m, 2H), 7.20-7.27 (m, 1H), 7.55 (s, 1H), 7.71 (s, 1H), 7.88 (d, 1H, J = 10 Hz) |

| | Products from Alkyl Tosylates | | | |
|---|---|---|---|---|
| No. | Compound | Name | Yield (%) | $^1$H NMR |
| 1104 | | ethyl 4-(2-(2-(1H-imidazol-4-yl)phenoxy)ethyl) phenylcarbamate | 51 | (MeOH-d$_4$) 1.27 (t, 3H, J = 6.9 Hz), 3.05-3.09 (t, 2H, J = 6.6 Hz), 4.14 (q, 2H, J = 6.9 Hz), 4.25-4.29 (m, 2H), 6.93-7.01 (m, 2H), 7.16-7.21 (m, 3H), 7.31-7.36 (m, 3H), 7.71 (s, 1H), 7.78 (dd, 1H, J = 7.8, 1.5 Hz) |

| | Products from Alkyl Bromides/Iodides/Chlorides | | | |
|---|---|---|---|---|
| No. | Compound | Name | Yield (%) | $^1$H NMR |
| 0968 | | 4-(2-((2,3-dihydrobenzo[b][1,4]dioxin-2-yl)methoxy) phenyl)-1H-imidazole | 12 | 4.24 (dd, 1H, J = 11.6 Hz, 6.8 Hz), 4.33 (dd, 1H, J = 10.4 Hz, 6.4 Hz), 4.39 (d, 1H, J = 2.8 Hz), 4.41-4.42 (m, 1H), 4.69-4.72 (m, 1H), 6.89-6.98 (m, 5H), 7.07 (dt, 1H, J = 7.6 Hz, 0.8 Hz), 7.21 (dt, 1H, J = 8.4 Hz, 1.6 Hz), 7.54 (s, 1H), 7.65 (s, 1H), 7.82 (s, 1H) |
| 0980 | | 5-((2-(1H-imidazol-4-yl)phenoxy) methyl)-2-chloropyridine | 69 | 5.15 (s, 2H), 7.00 (d, 1H, J = 8.4 Hz), 7.07 (dt, 1H, J = 7.5 Hz, 0.9 Hz), 7.23 (dt, 1H, J = 7.5 Hz, 1.2 Hz), 7.35 (d, 1H, J = 8.1 Hz), 7.44 (s, 1H), 7.64 (s, 1H), 7.73 (dd, 1H, J = 8.1 Hz, 2.4 Hz), 7.98 (d, 1H, J = 7.2 Hz), 8.49 (d, 1H, J = 2.1 Hz) |
| 0965 | | 4-((2-(1H-imidazol-4-yl)phenoxy) methyl)pyridine | 47 | 5.21 (s, 2H), 6.95 (dd, 1H, J = 8.4 Hz, 0.6 Hz), 7.07 (dt, 1H, J = 7.5 Hz, 0.9 Hz), 7.21 (dt, 1H, J = 7.5 Hz, 1.8 Hz), 7.37 (d, 2H, J = 5.7 Hz), 7.55 (d, 1H, J = 0.9 Hz), 7.69 (d, 1H, 0.6 Hz), 8.01 (dd, 1H, J = 7.5 Hz, 1.5 Hz), 8.61 (d, 1H, J = 2.7 Hz), 8.62 (d, 1H, J = 5.7 Hz) |
| 1289 | | 4-((2-(1H-imidazol-4-yl)phenoxy) methyl)thiazole | 94 | (MeOH, d$_4$), 5.34 (s, 2H), 7.00-7.28 (m, 3H), 7.54 (s, 1H), 7.66 (s, 1H), 7.80-7.85 (m, 2H), 9.07 (s, 1H) |
| 0966 | | 2-((2-(1H-imidazol-4-yl)phenoxy) methyl)pyridine | 43 | 5.33 (s, 2H), 7.01-7.07 (m, 2H), 7.19 (d, 1H, J = 1.8 Hz), 7.21 (d, 1H, J = 1.8 Hz), 7.24 (d, 1H, J = 1.8 Hz), 7.28-7.36 (m, 2H), 7.55 (d, 1H, J = 0.9 Hz), 7.70-7.80 (m, 3H), 8.69-8.71 (m, 1H) |

-continued

| No. | Compound | Name | Yield (%) | $^1$H NMR |
|---|---|---|---|---|
| 0963 | | 1-(3-(2-(1H-imidazol-4-yl)phenoxy)propyl)-4-(3-chlorophenyl)piperazine | 28 | 2.12 (t, 2H, J = 6.4 Hz), 2.59-2.68 (m, 6H), 3.18-3.22 (m, 4H), 4.20 (t, 2H, J = 6.4 Hz), 6.76-6.82 (m, 3H), 6.86-6.88 (m, 1H), 6.99-7.05 (m, 2H), 7.16 (t, 1H, J = 8 Hz), 7.22 (t, 1H, J = 8.4 Hz), 7.83 (s, 1H) |
| 0951 | | 4-((2-(1H-imidazol-4-yl)phenoxy)methyl)-7-methoxy-2H-chromen-2-one | 10 | 3.86 (s, 3H), 5.28 (s, 2H), 6.83 (d, 2H, J = 7.2 Hz), 6.98 (d, 1H, J = 8.4 Hz), 7.10 (t, 1H, J = 7.6 Hz), 7.23 (t, 1H, J = 7.2 Hz), 7.47 (d, 2H, J = 7.6 Hz), 7.69 (s, 1H), 7.97 (d, 1H, J = 7.2 Hz) |
| 0950 | | 4-(2-(naphthalen-2-ylmethoxy)phenyl)-1H-imidazole | 50 | 5.32 (s, 2H), 7.03-7.10 (m, 2H) 7.21-7.25 (m, 1H), 7.50-7.56 (m 5H), 7.83-7.91 (m, 5H) |
| 1354 | | 2-(2-(1H-imidazol-4-yl)phenoxy)-1-cyclohexyl-ethanone | 62 | 1.28-1.39 (m, 3H), 1.46-1.55 (m, 2H), 1.74 (d, 1H, J = 9.6 Hz), 1.84-1.93 (m, 4H), 2.49-2.54 (m, 1H), 4.91 (s, 2H), 6.87 (d, 1H, J = 8 Hz), 7.05 (dt, 1H, J = 7.6 Hz, 0.8 Hz), 7.20 (dt, 1H, J = 7.2 Hz, 1.6 Hz), 7.58 (s, 1H), 7.77 (d, 1H, J = 7.2 Hz), 7.80 (s, 1H) |
| 1016 | | 4-(5-bromo-2-(2-cyclohexyl-ethoxy)phenyl)-1H-imidazole | 55 | 0.91-1.02 (m, 2H), 1.12-1.27 (m, 3H), 1.46-1.52 (m, 1H), 1.65-1.82 (m, 7H), 4.10 (t, 2H, J = 6.8 Hz), 6.82 (d, 1H, J = 8.8 Hz), 7.28 (dd, 1H, J = 8.8 Hz, 2.4 Hz), 7.59 (s, 1H), 7.70 (s, 1H), 8.06 (s, 1H) |
| 0994 | | 2-(2-(1H-imidazol-4-yl)phenoxy)-1-(4-(pyrrolidin-1-yl)phenyl)ethanone | 55 | 2.04-2.07 (m, 4H), 3.38 (t, 4H, J = 6.4 Hz), 5.36 (s, 1H), 6.55 (d, 2H, J = 8.8 Hz), 6.99 (d, 1H, J = 8 Hz), 7.04 (t, 1H, J = 7.6 Hz), 7.21 (t, 1H, J = 7.6 Hz), 7.57 (s, 1H), 7.76 (d, 1H, J = 7.2 Hz), 7.88 (d, 3H, J = 8.8 Hz) |

-continued

| No. | Compound | Name | Yield (%) | ¹H NMR |
|---|---|---|---|---|
| 0993 | | 2-(2-(1H-imidazol-4-yl)phenoxy)-1-(4-(difluoromethoxy)phenyl)ethanone | 56 | 5.34 (s, 2H), 6.63 (t, 1H, J = 72.8 Hz, CHF$_2$), 6.92 (d, 1H, J = 8 Hz), 7.03 (t, 1H, J = 8 Hz), 7.17-7.27 (m, 3H), 7.58 (s, 1H), 7.77 (d, 2H, J = 10 Hz), 7.98 (d, 2H, J = 8.4 Hz) |
| 0981 | | 2-((2-(1H-imidazol-4-yl)phenoxy)methyl)quinoline | 61 | 5.41 (s, 2H), 6.98-7.05 (m, 2H), 7.20 (dd, 1H, J = 7.5 Hz, 1.2 Hz), 7.33 (d, 1H, J = 8.4 Hz), 7.55 (dt, 1H, J = 8.1 Hz, 0.9 Hz), 7.60 (s, 1H), 7.31-7.82 (m, 3H), 7.89 (s, 1H), 8..08 (d, 1H, J = 8.4 Hz), 8..14 (d, 1H, J = 8.4 Hz) |
| 0935 | | 2-(2-(1H-imidazol-4-yl)phenoxy)-2,3-dihydro-1H-inden-1-one | 25 | 3.30 (dd, 1H, J = 4.5, 16.4 Hz), 3.91 (dd, 1H, J = 7.6, 16.5 Hz), 5.08 (dd, 1H, J = 5.2, 7.5 Hz), 7.05 (d, 1H, J = 8.2 Hz), 7.11 (t, 1H, J = 7.5 Hz), 7.26 (dt, 1H, J = 1.6, 7.6 Hz) 7.47-7.53 (m, 3H), 7.72 (t, 2H, J = 7.5 Hz), 7.78 (s, 1H), 7.87 (d, 1H, J = 7.6 Hz) |
| 0973 | | 4-(2-(2-(1H-pyrrol-1-yl)ethoxy)phenyl)-1H-imidazole | 68 | 4.32-4.37 (m, 4H), 6.78 (s, 2H), 6.93 (d, 1H, J = 8.2 Hz), 7.03 (t, 1H, J = 7.4 Hz), 7.22 (t, 1H, J = 7.3 Hz), 7.33 (s, 1H), 7.49 (s, 1H), 7.75 (d, 1H, J = 7.4 Hz) |
| 0974 | | 1-(2-(2-(1H-imidazol-4-yl)phenoxy)ethyl)-1H-pyrazole | 15 | 4.35 (t, 2H, J = 4.5 Hz), 4.64 (t, 2H, J = 4.5 Hz), 6.33 (s, 1H), 6.85 (d, 1H, J = 8.2 Hz), 7.01 (t, 1H, J = 7.5 Hz), 7.45 (s, 1H), 7.49 (d, 1H, J = 1.6 Hz), 7.62 (1H), 7.70 (d, 1H, J = 7.6 Hz), 7.77 (s, 1H) |
| 0991 | | 2-(2-(1H-imidazol-4-yl)phenoxy)-N-phenylpropanamide | 32 | 1.75 (d, 3H, J = 6.7 Hz), 5.01 (q, 1H, J = 6.6 Hz), 7.00-7.12 (m, 3H), 7.25-7.33 (m, 4H), 7.41 (s, 1H), 7.59 (s, 1H), 7.61 (s, 1H), 7.66 (d, 1H, J = 7.0 Hz), 7.75 (s, 1H) |

| No. | Compound | Name | Yield (%) | $^1$H NMR |
|---|---|---|---|---|
| 0990 | | 2-(2-(1H-imidazol-4-yl)phenoxy)-N-(thiophen-2-ylmethyl)acetamide | 75 | 4.68 (s, 2H), 4.71 (d, 3H, J = 5.3 Hz), 6.90 (d, 1H, J = 8.1 Hz), 6.96 (t, 1H, J = 4.2 Hz), 7.01-7.06 (m, 2H), 7.24 (m, 2H), 7.32 (s, 2H), 7.61 (d, 1H, J = 6.8 Hz) |
| 0989 | | 2-(2-(1H-imidazol-4-yl)phenoxy)-N-(furan-2-ylmethyl)acetamide | 81 | 4.54 (d, 2H, J = 5.3 Hz), 4.67 (s, 2H), 6.26 (s, 1H), 6.33 (s, 1H), 6.89 (d, 1H, J = 8.1 Hz), 7.04 (t, 1H, J = 7.4 Hz), 7.23 (d, 1H, J = 7.6 Hz), 7.35 (d, 2H, J = 8.2 Hz), 7.50 (s, 1H), 7.62 (d, 1H, J = 7.6 Hz) |
| 1002 | | 2-(2-(1H-imidazol-4-yl)phenoxy)-1-(thiophen-3-yl)ethanone | 62 | 5.37 (s, 2H), 6.97 (t, 2H, J = 7.6 Hz), 7.06 (t, 1H, J = 7.5 Hz), 7.22 (t, 1H, J = 7.7 Hz), 7.52-7.54 (doublet merged with a singlet, 2H), 7.59 (s, 1H), 7.77 (d, 1H, J = 7.2 Hz), 7.83 (s, 1H) |
| 1003 | | 4-(2-(3,4-dichlorobenzyloxy)phenyl)-1H-imidazole | 39 | 5.13 (s, 2H), 6.97 (d, 1H, J = 8.2 Hz), 7.07 (t, 1H, J = 7.4 Hz), 7.22 (t, 1H, J = 7.8 Hz), 7.29 (s, 1H), 7.47 (d, 1H, J = 8.3 Hz), 7.50 (s, 1H), 7.55 (s, 1H), 7.66 (s, 1H), 7.95 (br s, 1H) |
| 1008 | | 3-(2-(1H-imidazol-4-yl)phenoxy)-1-phenylpyrrolidin-2-one | 50 | 2.39-2.50 (m, 1H), 2.94-3.00 (m, 1H), 3.91-3.99 (m, 2H), 4.98 (t, 1H, J = 9.1 Hz), 6.99 (d, 1H, J = 8.0 Hz), 7.11 (t, 1H, J = 7.4 Hz), 7.22-7.28 (m merged with CHCl$_3$, 2H), 7.43-7.50 (m, 3H), 7.69-7.73 (m, 3H), 7.78 (s, 1H) |
| 1086 | | 5-(3-chloro-2-(2-cyclohexylethoxy)phenyl)-1H-imidazole | 67 | 0.88-0.97 (m, 2H), 1.13-1.25 (m, 3H), 1.46-1.54 (m, 1H), 1.63-1.74 (m, 7H), 3.92 (t, 2H, J = 7.6 Hz), 7.09 (t, 1H, 8.0 Hz), 7.27 (doublet merged with CHCl$_3$, 1H), 7.58 (s, 1H), 7.74 (doublet merged with a singlet, 2H) |

-continued

| | Products from Alkyl Bromides/Iodides/Chlorides | | | |
|---|---|---|---|---|
| No. | Compound | Name | Yield (%) | $^1$H NMR |
| 0983 | | 2-(3-(2-(1H-imidazol-4-yl)phenoxy)propyl)isoindoline-1,3-dione | 50 | DMSO d$_6$: 2-10-2.20 (m, 2H), 3.78 (t, 2H, J = 6.8 Hz), 4.10 (t, 2H, J = 6.0 Hz), 6.90-7.00 (m, 2H), 7.10 (t, 1H, J = 7.6 Hz), 7.62 (s, 2H), 7.75-7.85 (m, 4H), 8.06 (d, 1H, J = 12.0 Hz) |
| 0960 | | (E)-4-(2-((3,7-dimethylocta-2,6-dien-1-yl)oxy)phenyl)-1H-imidazole | 37 | 1.58 (s, 3H), 1.65 (s, 3H), 1.71 (s, 3H), 2.05-2.15 (m, 4H), 4.63 (d, 2H, J = 5.1 Hz), 5.02-5.12 (m, 1H), 5.50-5.60 (m, 1H), 6.91-7.02 (m, 2H), 7.19 (dd, 1H, J = 6.0, 1.2 Hz), 7.53 (s, 1H), 7.7 (s, 1H), 7.79 (d, 1H, J = 6.0 Hz), 10.21 (s, 1H) |
| 1025 | | 4-(2-(2-(naphthalen-1yl)ethoxy)phenyl)-1H-imidazole | 15 | 3.66 (t, 2H, J = 6.4 Hz), 4.53 (t, 2H, J = 6.4 Hz), 6.95-7.0 (m, 2H), 7.18 (dt, 1H, J = 7.2, 1.6 Hz), 7.28 (s, 1H), 7.35 (s, 1H), 7.41-7.58 (m, 4H), 7.64 (d, 2H, J = 8.0 Hz), 7.75-7.85 (m, 1H), 7.90 (d, 1H, J = 7.2 Hz), 8.08 (d, 1H, J = 7.6 Hz) |
| 1165 | | (4-(2-(2-(1H-imidazol-4-yl)phenoxy)ethyl)piperidin-1-yl)(thiophen-2-yl)methanone | 56 | 1.10-1.40 (m, 2H), 1.70-1.90 (m, 5H), 2.70-3.0 (m, 2H), 4.05-4.15 (m, 2H), 4.20-4.60 (m, 2H), 6.91 (d, 1H, J = 8.0 Hz), 6.94-7.02 (m, 2H), 7.35-7.42 (m, 1H), 7.52 (s, 1H), 7.69 (s, 1H), 7.85 (d, 1H, J = 7.6 Hz |
| 1176 | | 1-(4-(2-(2-(1H-imidazol-4-yl)phenoxy)ethyl)piperidin-1-yl)-2-(thiophen-2-yl)ethanone | 74 | 0.90-1.30 (m, 2H), 1.60-1.90 (m, 5H), 2.52 (t, 1H, J = 12.0 Hz), 2.97 (t, 1H, J = 12.8 Hz), 3.80-3.95 (m, 3H), 4.07 (t, 2H, J = 6.0 Hz), 4.57 (d, 1H, J = 13.2 Hz), 6.84 (s, 1H), 6.85-6.95 (m, 2H), 6.97 (t, 1H, J = 7.6 Hz), 7.13 (d, 1H, J = 5.2 Hz), 7.19 (t, 1H, J = 7.2 Hz), 7.51 (s, 1H), 7.78 (s, 1H), 7.83 (d, 1H, J = 7.6 Hz), 8.82 (br, s, 2H) |

-continued

| No. | Compound | Name | Yield (%) | ¹H NMR |
|---|---|---|---|---|
| | Products from Alkyl Bromides/Iodides/Chlorides | | | |
| 1186 | | 1-(4-(2-(2-(1H-imidazol-4-yl)phenoxy)ethyl)piperidin-1-yl)-2-phenylethanone | 80 | 0.80-1.25 (m, 2H), 1.50-1.90 (m, 5H), 2.0-2.10 (m, 1H), 2.51 (t, 1H, J = 11.2 Hz), 2.80-3.00 (m, 1H), 3.69 (s, 2H), 3.81 (d, 1H, J = 12.8 Hz), 4.00-4.20 (m, 2H), 4.59 (d, 1H, J = 12.0 Hz), 6.85-7.05 (m, 2H), 7.10-7.30 (m, 6H), 7.50 (s, 1H), 7.68 (s, 1H), 7.85 (d, 1H, J = 6.4 Hz), 8.79 (br, s, 1H) |
| 1018 | | 2-(2-(1H-imidazol-4-yl)phenoxy)-1-(benzo[b]thiophen-6-yl)ethanone | 25 | 5.42 (s, 2H), 6.94 (d, 1H, J = 8.4 Hz), 7.00 (dt, 1H, J = 8.0, 0.8 Hz), 7.18 (dt, 1H, J = 7.2, 1.6 Hz), 7.43 (d, 1H, J = 5.2 Hz), 7.54 (d, 2H, J = 6.0 Hz), 7.72 (d, 1H, J = 7.6 Hz), 7.80 (s, 1H), 7.88 (dd, 1H, J = 8.4, 1.2 Hz), 7.96 (d, 1H, J = 8.8 Hz), 8.39 (d, 1H, J =0.8 Hz) |
| 1052 | | 4-(2-(2-cyclohexylpropoxy)phenyl)-1H-imidazole hydrochloride | 23 | 0.9327-1.27 (m, 9H), 1.43 (m, 1H), 1.69 (m, 5H), 1.92 (m, 1H), 3.93 (t, 1H, J = 8.67 Hz), 4.09 (m, 1H), 6.97 (d, 1H, J = 8.43 Hz), 7.02 (d, 1H, J = 7.56 Hz), 7.21 (t, 1H, J = 7.71 Hz), 7.54 (s, 1H), 7.69 (s, 1H), 7.82 (d, 1H, J = 7.23 Hz) |
| 0995 | | 2-(2-(1H-imidazol-4-yl)phenoxy)-1-(4-(diethylamino)phenyl)ethanone | 64 | 1.19 (t, 6H, J = 7.08 Hz), 3.41 (q, 4H, J = 7.08 Hz), 5.30 (s, 2H), 6.63 (2H, d, J = 9.15 Hz), 6.95 (d, 1H, J = 8.16 Hz), 7.01 (t, 1H, J = 7.59 Hz), 7.16-7.21 (m, 1H), 7.56 (s, 1H), 7.73 (d, 1H, J = 7.44 Hz), 7.83 (t, 3H, J = 4.26 Hz) |
| 0953 | | 2-(2-(1H-imidazol-4-yl)phenoxy)-1-(3-bromophenyl)ethanone | 47 | 5.44 (s, 2H), 6.99 (d, 1H, J = 8.19 Hz), 7.08 (t, 1H, J = 7.47 Hz), 7.22 (m, 1H), 7.45 (t, 1H, J = 7.83 Hz), 7.60 (br s, 1H), 7.80 (s, 1H), 7.82 (s, 2H), 7.94 (d, 1H, J = 7.83 Hz), 8.14 (s, 1H). |

-continued

| | | Products from Alkyl Bromides/Iodides/Chlorides | | |
|---|---|---|---|---|
| No. | Compound | Name | Yield (%) | ¹H NMR |
| 0992 | | 2-(2-(1H-imidazol-4-yl)phenoxy)-1-(benzofuran-3-yl)ethanone | 67 | 5.27 (s, 1H), 6.95 (d, 1H, J = 8.12 Hz), 7.06 (t, 1H, J = 6.88 Hz), 7.22 (t, 1H, J = 7.40 Hz), 7.42-7.44 (m, 2H), 7.55-7.60 (m, 2H), 7.79 (d, 1H, J = 7.48 Hz), 7.85 (s, 1H), 8.25 (dd, 1H, J = 3.28 Hz) |
| 1022 | | 4-(2-(4-fluorobenzyloxy)phenyl)-1H-imidazole | 30 | 5.14 (s, 2H), 7.02-7.13 (m, 4H), 7.21-7.26 (m, 1H), 7.40-7.45 (m, 2H), 7.49 (s, 1H), 7.65 (s, 1H), 7.87 (dd, 1H, J = 1.8 Hz, 7.5 Hz) |
| 1023 | | 4-(2-(4-(trifluoromethyl)benzyloxy)phenyl)-1H-imidazole | 15 | 5.25 (s, 1H), 7.00 (d, 1H, J = 8.1 Hz), 7.08 (t, 1H, J = 6.0 Hz), 7.20-7.26 (m, 1H), 7.51-7.58 (m, 3H), 7.68-7.69 (m, 3H), 7.93 (dd, 1H, J = 7.8 Hz, 1.8 Hz) |
| 1027 | | 4-(2-(benzo[d][1,3]dioxol-5-ylmethoxy)phenyl)-1H-imidazole | 30 | 5.06 (s, 2H), 5.99 (s, 2H), 6.79-6.93 (m, 4H), 7.02-7.07 (m, 2H), 7.20-7.26 (m, 1H), 7.50 (s, 1H), 7.64 (s, 1H), 7.84-7.87 (m, 1H) |
| 1028 | | 4-(2-(benzofuran-5-ylmethoxy)phenyl)-1H-imidazole | 31 | 5.25 (s, 2H), 6.78-6.80 (m, 1H), 7.04-7.10 (m, 2H), 7.22-7.26 (m, 1H), 7.40 (d, 1H, J = 8.4 Hz), 7.50-7.57 (m, 3H), 7.67-7.69 (2H), 7.87-7.89 (m, 1H) |

-continued

Products from Alkyl Bromides/Iodides/Chlorides

| No. | Compound | Name | Yield (%) | $^1$H NMR |
|---|---|---|---|---|
| 1029 | | ethyl 4-((2-(1H-imidazol-4-yl)phenoxy)methyl)benzoate | 59 | 1.38 (t, 3H, J = 7.2 Hz), 4.37 (q, 2H, J = 7.2 Hz), 5.21 (s, 2H), 6.96-7.05 (m, 2H), 7.18-7.26 (m, 2H), 7.48-7.50 (m, 2H), 7.68 (s, 1H), 7.88 (d, 2H, J = 6 Hz), 8.06 (d, 2H, J = 6 Hz), 8.31 (brs, 1H) |

Example 20

Lithium 4-((2-(1H-imidazol-4-yl)phenoxy)methyl)benzoate

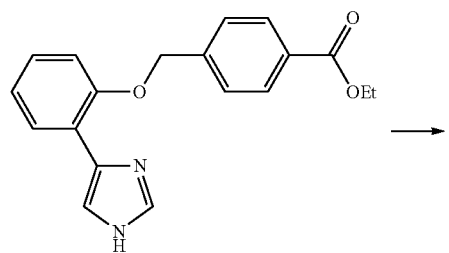

Ethyl 4-((2-(1H-imidazol-4-yl)phenoxy)methyl)benzoate (0.33 mmol, 105 mg) was diluted with MeOH (3 mL) and water (1 mL) followed by the addition of LiOH.H$_2$O (0.33 mmol, 14.35 mg). After stirring for 4 h at room temperature, the solvent was removed under vacuum to afford the product.

Example 21

2-(2-(2-(1H-Imidazol-4-yl)phenoxy)acetyl)benzoic acid

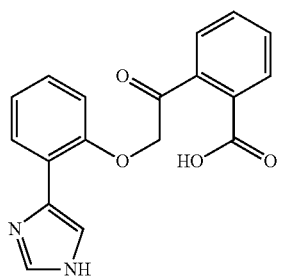

To a solution of ethyl 2-(2-(2-(1H-imidazol-4-yl)phenoxy)acetyl)benzoate (0.142 mmol) in a mixture of tetrahydrofuran (2 mL) and water (1 mL) was added LiOH.H20 (0.713 mmol). After stirring for 5 h the reaction mixture was acidified with 6N HCl and treated with NH$_3$ (solution in ethanol) till the pH was basic, the solution was concentrated under reduced pressure and subjected to column chromatography to afford the final product. Yield 46%. (CDCl$_3$+CD$_3$OD): 4.69 (s, 2H), 6.87 (d, 1H, J=6.18 Hz), 6.95 (t, 1H, J=5.55 Hz), 7.19 (t, 1H, J=5.79 Hz), 7.38 (d, 1H, J=5.10 Hz), 7.47-7.56 (m, 4H), 7.79 (d, 1H, J=5.00 Hz), 8.21 (br s, 1H).

Example 22

N-(3-((2-(1H-imidazol-4-yl)phenoxy)methyl)benzyl)-N-benzylacetamide

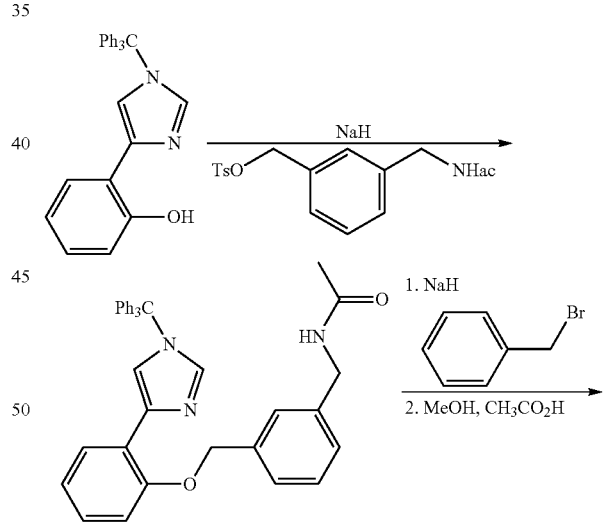

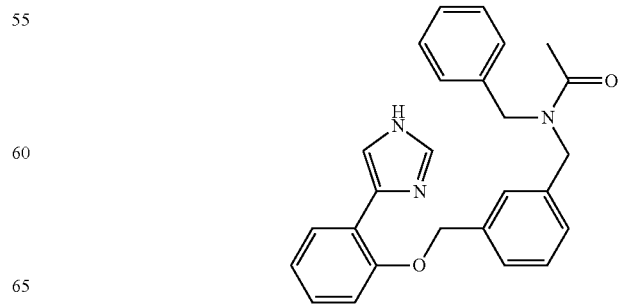

To a stirred solution of the 2-(1-trityl-1H-imidazol-4-yl) phenol (0.5 mmol) in anhydrous DMF (3 mL) at 0° C. was added NaH (36.0 mg, 0.75 mmol). The resulting suspension was allowed to stir for 10 min. To the resulting solution was added 3-(acetamidomethyl)benzyl 4-methylbenzenesulfonate (200.0 mg, 0.6 mmol). After stirring overnight, the reaction mixture was carefully diluted with water and extracted with ethyl acetate (2×10 mL). The combined organic layers were washed with water, brine and dried ($Na_2SO_4$). The solvent was removed under reduced pressure and the crude product purified using column chromatography. The product was isolated as white solid in 63% yield. $^1$H NMR: 1.95 (s, 3H), 4.21 (d, 2H, J=6.0 Hz), 4.95 (s, 2H), 5.65 (bis, 1H), 6.91 (d, 1H, J=7.6 Hz), 7.10-7.30 (m, 21H), 7.40-7.46 (m, 3H), 7.60-7.68 (m, 1H), 8.19 (dd, 1H, J=7.6, 1.6 Hz). To a stirred solution of the obtained imidazole (0.25 mmol) in anhydrous DMF (3 mL) at 0° C. was added NaH (18.0 mg, 0.37 mmol). The resulting suspension was allowed to stir for 10 min. To the resulting solution was added benzylbromide (51.0 mg, 0.30 mmol). After stirring overnight, the reaction mixture was carefully diluted with water and extracted with ethyl acetate (2×10 mL). The combined organic layers were washed with water, brine and dried ($Na_2SO_4$). The solvent was removed under reduced pressure and the crude product was taken to next step without further purification. To a solution of the crude product obtained above was added acetic acid (1.0 mL) and MeOH (4.0 mL). The solution was stirred at 80° C. for 2 h. The solution was allowed to cool to room temperature and the pH was adjusted to ~10 with 10% NaOH (aq). The aqueous phase was extracted with EtOAc (3×20 mL). The combined organic layer were washed with water, brine, and dried. The solvent was removed in vacuum to afford the crude residue, which was purified by flash column chromatography on silica gel to afford the desired product (1:1 rotamer) in 35% overall yield. $^1$H NMR: 2.15 (s, 3H), 2.18 (s, 3H), 4.18 (s, 2H), 4.47 (s, 2H), 4.60 (s, 2H), 5.15 (s, 2H), 5.18 (s, 2H), 7.00-7.50 (m, 22H), 7.56 (s, 2H), 7.66 (s, 2H), 7.93 (d, 2H, J=7.6 Hz), 8.07 (d, 2H, J=7.6 Hz)

Example 23

2-(1H-Imidazol-4-yl)benzoic acid

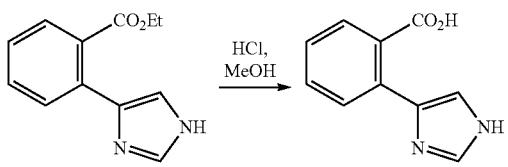 [SMILES: CCOC(=O)c1ccccc1-c1c[nH]cn1 ; O=C(O)c1ccccc1-c1c[nH]cn1]

To a stirred solution of ethyl 2-(1H-imidazol-5-yl)benzoate (0.25 mmol) in MeOH, 2 mL of HCl solution (2 mL, 1.0M in MeOH) was added. The solution was allowed to stir at 80° C. for 24 h and then the solution was evaporated and purified by column chromatography to give the pure desired product in 86% yield. $^1$H NMR: 7.31-7.44 (m, 2H), 7.50 (t, 1H, J=7.2 Hz), 7.59 (d, 1H, J=7.6 Hz), 7.85 (d, 1H, J=7.2 Hz), 8.04 (br s, 1H)

Example 24

1,5-Diphenyl-1H-imidazole

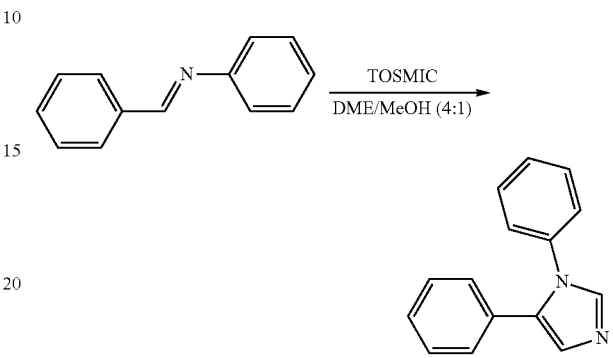

To a stirred solution of (E)-N-benzylideneaniline (1.0 mmol) in THF (5 mL) was added TOSMIC (1.1 mmol) and t-BuONa (2.2 mmol). The solution was allowed to stir at room temperature for 5 days. The solvent was evaporated under reduced pressure and the crude product was absorbed on silica gel. After purification by flash column chromatography on silica gel the desired product was obtained in 18% yield. $^1$H NMR: 7.10-7.16 (m, 2H), 7.16-7.23 (m, 2H), 7.23-7.31 (m, 4H), 7.36-7.42 (m, 3H), 7.73 (s, 1H)

Example 25

(1H-Imidazol-4-yl)(phenyl)methanol

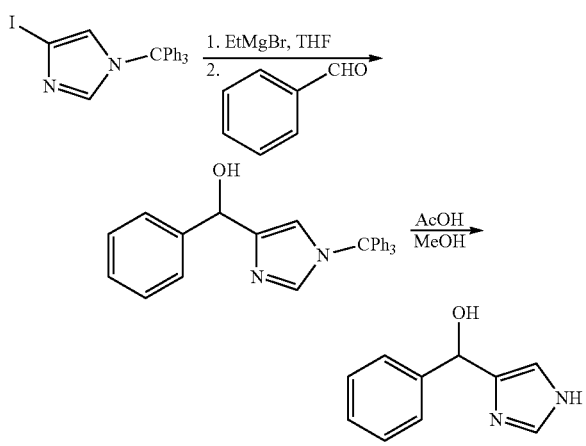

To the stirred solution of 4-iodo-1-trityl-1H-imidazole (0.5 mmol) in THF under anhydrous condition, EtMgBr (0.33 mL, 3M in diethyl ether) was added. The reaction was allowed to stir at room temperature. After 1.5 h benzaldehyde was added and the reaction was allowed to stir overnight. After the completion of reaction few drops of methanol was carefully added at 0° C. The crude residue was used in next step without further purification. To a solution of the crude imidazole from the previous step was added acetic acid (1.0 mL) and MeOH (4.0 mL). The solution was stirred at 80° C. for 2 h. The reaction mixture was allowed to cool to room temperature and the pH was adjusted to ~10 with 10% NaOH (aq). The aqueous phase was extracted with EtOAc (3×20 mL). The combined organic layers were washed with water, brine, and dried. The solvent was removed in vacuum to afford the crude residue, which was purified by flash column chromatography on silica gel to afford the desired product in 57% yield. $^1$H NMR: 1.27 (s, 1H), 5.78 (s, 1H), 6.80 (s, 1H), 7.07 (s, 1H), 7.25 (d, 1H, J=7.2 Hz), 7.32 (t, 1H, J=7.2 Hz), 7.40 (d, 1H, J=7.2 Hz), 7.64 (s, 1H), 7.74 (s, 1H)

Example 26

1-iodo-2-(2-(trifluoromethyl)phenethoxy)benzene

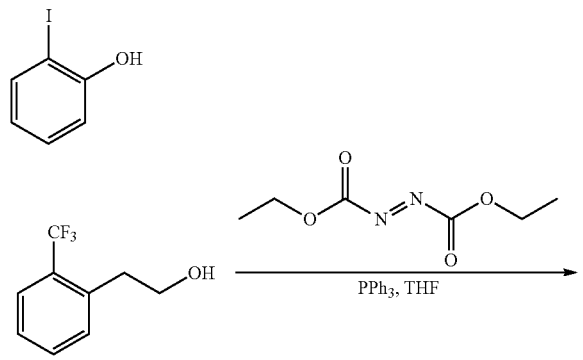

To a stirred solution of the 2-iodophenol (220.0 mg, 1.0 mmol), the 2-(2-(trifluoromethyl)phenyl)ethanol (228.0 mg, 1.2 mmol), and triphenyl phosphine (314.0 mg, 1.2 mmol) in anhydrous THF (5 mL) at 0° C. was added DEAD (40% in toluene, 1.20 mmol, 0.35 mL) dropwise. The yellow solution was allowed to warm to room temperature and stirring was continued overnite. After evaporating the solvent under reduced pressure the crude residue was dissolved in DCM (15 mL). The organic layer was washed with 10% NaOH (2×10 mL), water and brine. The organic phase was dried (Na$_2$SO$_4$), filtered and evaporated under reduced pressure. The crude residue was purified by column chromatography on silica gel using hexanes/EtOAc as the eluent. The compound was isolated in 56% yield as a white solid. $^1$H NMR: 3.17 (t, 2H, J=6.8 Hz), 4.22 (t, 2H, J=6.8 Hz), 6.90-7.10 (m, 4H), 7.15-7.23 (m 1H), 7.30-7.45 (m, 2H), 7.74 (dd, 1H, J=7.6, 1.6 Hz).

Example 27

4-Chloro-5-fluoro-2-iodophenol

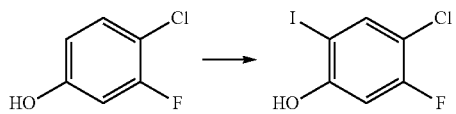 [SMILES: Oc1ccc(Cl)c(F)c1 ; Oc1cc(F)c(Cl)cc1I]

3-Fluoro-4-chlorophenol (1.78 g, 12.1 mmol) was dissolved in methanol (40 mL). Sodium iodide (3.63 g, 24.2 mmol) and sodium hydroxide (0.97 g, 24.2 mmol) was added, and the solution was cooled to 0° C. Aqueous sodium hypochlorite (6.0% NaOCl, 24.2 mmol) was added dropwise over 75 minutes at 0-3° C. The resulting slurry was stirred for 1 h at 0-2° C. and allowed to warm up to room temperature overnight. White precipitates were observed. The mixture was adjusted to pH 7 using 1M aqueous HCl while stirring. The aqueous layer was extracted with ether for three times and the ether layer was washed with aq sodium thiosulfate, brine, the organic layers were dried with MgSO$_4$. The solvent was removed under reduced pressure to afford the residue which was purified by flash column chromatography on silica gel (Hexanes:Ethyl acetate 1:1 to afford the desired product (1.60 g, 64% yield). $^1$H NMR: 6.84 (d, 1H, J=9.9 Hz), 7.67 (d, 1H, J=8.1 Hz).

Example 28

General Procedure for the Palladium-Catalyzed Cross-Coupling of Aryl Iodides with 1-Trityl-1H-imidazol-4-yl)zinc(II) chloride

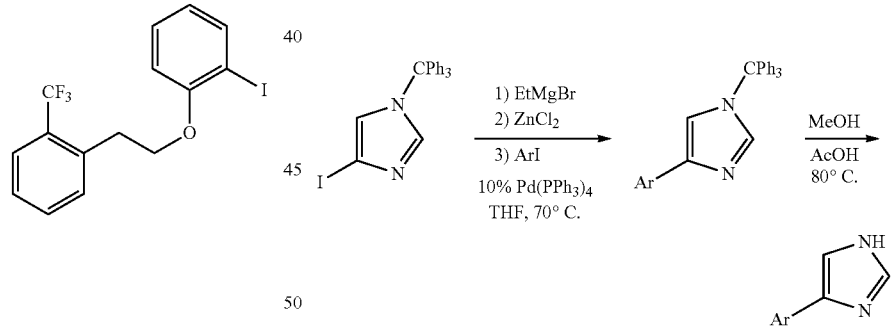

To a stirred solution of 4-iodo-1-trityl-1H-imidazole (218.0 mg, 0.5 mmol) in anhydrous THF (4 mL) at room temperature was added EtMgBr (1.0 M in THF, 0.5 mmol, 0.5 mL) dropwise, under an atmosphere of N$_2$. The resulting solution was allowed to stir for 90 min and anhydrous ZnCl$_2$ (0.5 mmol, 68.2 mg) was added. The resulting white suspension was allowed to stir for 90 min and a solution of the aryl iodide (0.5 mmol) in THF (1 mL) was added followed by the immediate addition of Pd(PPh$_3$)$_4$ (56 mg, 0.05 mmol). The reaction mixture was allowed to stir at 70° C. for 12 h under an atmosphere of N$_2$. After cooling to room temperature, the solution was diluted with CH$_2$Cl$_2$ (10 mL) and the organic layer was washed with an EDTA (aq) buffer (pH=9) (2×5 mL) and brine. The organic layer was dried (Na$_2$SO$_4$) and concentrated under reduced pressure. The crude residue was used in next step without further purification. To a solution of the crude imidazole from the previous step was added trifluoroacetic acid (1.0 mL) and MeOH (4.0 mL). The solution was stirred at 80° C. for 2 h. The reaction mixture was allowed to cool to room temperature and the pH was adjusted to ~10 with 10% NaOH (aq). The aqueous phase was extracted with EtOAc (3×20 mL). The combined organic layers were washed with water, brine, and dried. The solvent was removed in vacuo to afford the crude residue, which was purified by flash column chromatography on silica gel to afford the desired product.

The following compounds were prepared according to the general procedure of Example 28, by substituting the appropriate starting materials:

| No. | Compound | Name | Yield (%) | $^1$H NMR |
|---|---|---|---|---|
| 0972 | | 2-(1H-imidazol-4-yl)pyrimidine | 15 | 7.69 (s, 1H), 7.77 (s, 1H), 7.92 (s, 1H), 8.71 (d, 2H, J = 5.1 Hz) |
| 0961 | | 6-(1H-imidazol-4-yl)-1H-indole | 30 | 6.49 (s, 1H), 7.07-7.23 (m, 2H), 7.41 (s, 1H), 7.59 (d, 1H, J = 7.6 Hz), 7.74-7.76 (m, 2H), 8.75 (s, 1H) |
| 1024 | | 4-(2-(1-(4-chlorophenyl)ethoxy)phenyl)-1H-imidazole | 25 | 1.73 (d, 3H, J = 6.3 Hz), 5.45 (q, 1H, J = 6.3 Hz), 6.75 (dd, 1H, J = 7.5 Hz, 0.9 Hz), 6.99 (dt, 1H, J = 7.5 Hz, 1.2 Hz), 7.04 (dt, 1H, J = 7.2 Hz, 1.8 Hz), 7.24-7.32 (m, 4H), 7.64 (s, 1H), 7.73 (s, 1H), 7.88 (d, 1H, J = 7..5 Hz) |
| 1024 | | 4-(2-(1-phenylethoxy)phenyl)-1H-imidazole | 30 | 1.75 (d, 3H, J = 6.4 Hz), 5.47 (q, 1H, J = 6.4 Hz), 6.80 (d, 1H, J = 8.4 Hz), 6.95 (dt, 1H, J = 8 Hz, 1.2 Hz), 7.05 (dt, 1H, J = 8 Hz, 1.6 Hz), 7.25-7.37 (m, 5H), 7.65 (s, 1H), 7.72 (s, 1H), 7.86 (d, 1H, J = 7.2 Hz) |
| 0952 | | 8-(1H-imidazol-4-yl)quinoline | 29 | 7.46 (dd, 1H, J = 8.4 Hz, 4.2 Hz), 7.54-7.60 (m, 1H), 7.70 (dd, 1H, J = 8.1 Hz, 1.2 Hz), 7.77 (s, 1H), 7.80 (s, 1H), 8.16 (s, 1H), 8.21 (dd, 1H, J = 8.4 Hz, 1.8 Hz), 8.93 (dd, 1H, J = 4.2 Hz, 1.8 Hz) |
| 1014 | | (E)-ethyl 3-(2-(1H-imidazol-4-yl)phenyl)acrylate | 70 | 1.31 (t, 3H, J = 7.2 Hz), 4.26 (q, 2H, J = 7.2 Hz), 6.41 (d, 1H, J = 16 Hz), 7.1 (d, 1H, J = 0.8 Hz), 7.30-7.33 (m, 1H), 7.39-7.43 (m, 1H), 7.62 (d, 1H, J = 7.6 Hz), 7.68 (s, 1H), 7.69 (d, 1H, J = 0.8 Hz), 8.13 (d, 1H, J = 16 Hz) |

-continued

| No. | Compound | Name | Yield (%) | $^1$H NMR |
|---|---|---|---|---|
| 0949 | | 5-(1H-imidazol-4-yl)-1H-indole | 57 | (MeOH-d$_4$) 6.45 (d, 1H, J = 2.9 Hz), 7.23 (d, 1H, J = 3.0 Hz), 7.29 (s, 1H), 7.39 (d, 1H, J = 8.4 Hz), 7.44 (d, 1H, J = 8.4 Hz), 7.71 (s, 1H), 7.87 (s, 1H) |
| 0955 | | 4-(benzo[d][1,3]dioxol-5-yl)-1H-imidazole | 45 | 5.96 (s, 1H), 6.82 (d, 1H, J = 8.4 Hz), 7.21-7.23 (m, 3H), 7.65 (s, 1H) |
| 0948 | | 7-(1H-imidazol-4-yl)-1H-indole | 38 | 6.56 (s, 1H), 7.08-7.13 (m, 1H), 7.32 (s, 1H), 7.40-7.42 (d, 2H, J = 6.8 Hz), 7.55-7.59 (m, 1H), 7.70 (s, 1H), 10.79 (br s, 1H) |
| 0962 | | 4-(1H-imidazol-4-yl)benzo[c][1,2,5]thiadiazole | 32 | 7.68 (t, 1H, 7.9 Hz), 7.85 (s, 1H), 7.90 (d, 1H, J = 8.7 Hz), 8.07 (br s, 1H), 8.13 (d, 1H, J = 6.4 Hz) |
| 0956 | | 5-chloro-7-(1H-imidazol-4-yl)quinolin-8-ol | 30 | (MeOH-d$_4$) 7.57 (dd, 1H, J = 2.0, 9.1 Hz), 7.67-7.70 (m, 2H), 7.80 (s, 1H), 8.01 (d, 1H, J = 1.8 Hz), 8.59 (d, 1H, 6.5 Hz), 8.8 (d, 1H, 4.7 Hz) |
| 0964 | | 3-(1H-imidazol-4-yl)-1H-pyrrolo[2,3-b]pyridine | 4 | (MeOH-d$_4$) 7.08 (s, 1H), 7.19 (dd, 1H, 4.9, 7.9 Hz), 7.40 (s, 1H), 7.70 (s, 1H), 7.77 (s, 1H), 8.23 (d, 1H, J = 4.6 Hz), 8.28 (d, 1H, J = 7.3 Hz) |
| 0988 | | 4-(2-(1-phenylpropan-2-yloxy)phenyl)-1H-imidazole | 23 | 1.36 (d, 3H, J = 6.0 Hz), 3.03-3.15 (m, 2H), 4.83-4.88 (m, 1H), 6.99-7.03 (m, 2H), 7.17-7.37 (m, 7H), 7.45 (s, 1H), 7.50 (s, 1H), 7.76 (d, 1H, J = 7.2 Hz) |
| 1012 | | 3-(1H-imidazol-4-yl)-2-methoxypyridine | 53 | 3.96 (s, 3H), 6.60 (d, 1H, J = 8.2 Hz), 7.34 (d, 1H, J = 7.2 Hz), 7.58 (d, 3 1H, J = 8.0 Hz), 7.62 (s, 1H), 7.73 (s, 1H) |

| No. | Compound | Name | Yield (%) | ¹H NMR |
|---|---|---|---|---|
| 1009 | | 2-(1H-imidazol-4-yl)-6-methoxypyridine | 60 | 4.09 (s, 3H), 6.98 (t, 1H, J = 6.0 Hz), 7.63 (s, 1H), 7.72 (s, 1H), 8.07 (d, 1H, J = 4.7 Hz), 8.24 (br s, 1H) |
| 1109 | | 4-(2-(2-(2-chlorophenyl)propoxy)phenyl)-1H-imidazole | 48 | 1.40 (d, 3H, J = 6.6 Hz), 3.94-4.03 (m, 1H), 4.26-4.33 (m, 2H), 6.99-7.01 (m, 2H), 7.19-7.31 (m, 3H), 7.35-7.38 (m, 2H), 7.42 (s, 1H), 7.45 (d, 1H, J = 7.9 Hz), 7.73 (d, 1H, J = 7.3 Hz) |
| 1043 | | 4-(2-(1-(2-chlorophenyl)propan-2-yloxy)phenyl)-1H-imidazole | 39 | 1.38 (d, 3H, J = 6.0 Hz), 3.08 (dd, 1H, J = 6.2, 13.8 Hz), 3.35 (dd, 1H, J = 6.6, 13.8 Hz), 4.90-4.98 (m, 1H), 6.95-7.04 (m, 2H), 7.15-7.25 (m, 4H), 7.37-7.39 (m, 1H), 7.44-7.57 (m, 3H), 7.64-7.79 (m, 2H), 7.89 (d, 1H, J = 6.4 Hz) |
| 0996 | | 4-(3-(phenoxymethyl)phenyl)-1H-imidazole | 29 | 4.94 (s, 2H), 6.78 (d, 1H, J = 6.8 Hz), 6.90-7.02 (m, 2H), 7.05-7.18 (m, 2H), 7.20-7.40 (m, 6H) |
| 1004 | | 4-(1H-imidazol-4-yl)isoquinoline | 35 | 7.18 (s, 1H), 7.35-7.40 (m, 1H), 7.81 (t, 1H, J = 8.0 Hz), 7.98 (dt, 1H, J = 7.6, 1.2 Hz), 8.16 (d, 1H, J = 8.0 Hz), 8.21 (d, 1H, J = 8.8 Hz), 8.85 (s, 1H), 9.57 (s, 1H) |
| 1005 | | 3-(1H-imidazol-4-yl)-[1,1'-biphenyl]-4-ol | 56 | (MeOH-d₄) 7.15-7.28 (m, 4H), 7.28 (d, 1H, J = 4.4 Hz), 7.60-7.82 (m, 3H), 8.01 (m, 2H) |
| 1007 | | 4-(1H-imidazol-4-yl)quinoline | 15 | 7.40-7.51 (m, 4H), 7.50-7.58 (m, 2H), 7.60-7.68 (m, 3H) |

| No. | Compound | Name | Yield (%) | ¹H NMR |
|---|---|---|---|---|
| 1040 | | 4-(2-(2-(trifluoromethyl)phenethoxy)phenyl)-1H-imidazole | 17 | 3.38 (t, 2H, J = 6.4 Hz), 4.38 (t, 2H, J = 6.4 Hz), 6.97 (d, 1H, J = 8.4 Hz), 7.01 (t, 1H, J = 7.6 Hz), 7.20 (dt, 1H, J = 9.2, 1.6 Hz), 7.35 (t, 1H, J = 7.6 Hz), 7.39-7.50 (m, 3H), 7.53 (s, 1H), 7.68 (d, 1H, J = 8.0 Hz), 7.79 (d, 1H, J = 7.6 Hz) |
| 1044 | | 4-(2-((1-cyclohexylpropan-2-yl)oxy)phenyl)-1H-imidazole | 8 | 1.0-1.28 (m, 4H), 1.35 (d, 3H, J = 6.09 Hz), 1.42-1.82 (m, 9H), 4.65 (m, 1H), 6.96-7.01 (m, 2H), 7.17-7.23 (m, 1H), 7.43-7.54 (m, 2H), 7.63-7.70 (m, 1H), 7.79 (br s, 1H) |
| 0956 | | 5-chloro-7-(1H-imidazol-4-yl)quinolin-8-ol | 73 | 7.43-7.70 (m, 5H), 7.87 (s, 1H), 8.49 (dd, 1H, J = 8.55 Hz, 1.35 Hz), 8.81 (dd, 1H, J = 4.14 Hz, 1.20 Hz). |
| 1130 | | 4-chloro-5-fluoro-2-(1H-imidazol-5-yl)phenol | 35 | (MeOH-d₄), 6.68-6.72 (d, J = 9 Hz, 1H), 7.55 (s, 1H), 7.70-7.74 (m, 2H) |

Example 29

General Procedure for the Demethylation of Methoxypyridines

A mixture of the methoxypyridine (0.5 mmol) and 3 M aqueous HCl (5 mL) was heated at 90° C. overnight. After cooling to room temperature, the mixture was made basic by addition of solid $K_2CO_3$, and the precipitated crystals were collected by vacuum filtration. The solids were washed with distilled water and the crystals were dried under reduced pressure until a constant mass was achieved.

The following compounds were prepared according to the general procedure of Example 29, by substituting the appropriate starting materials:

| No. | Compound | Name | Yield (%) | ¹H NMR |
|---|---|---|---|---|
| 1011 | | 6-(1H-imidazol-4-yl)pyridin-2-ol | 38 | 6.27 (t, 1H, J = 6.6 Hz), 7.22-7.28 (m, 1H), 7.66 (s, 1H), 7.84 (s, 1H), 8.09 (d, 1H, J = 5.1 Hz), 11.68 (br s, 1H), 12.04 (br s, 1H) |
| 1015 | | 3-(1H-imidazol-4-yl)pyridin-2-ol | 84 | (DMSO-d₆) 6.16 (d, 1H, J = 9.0 Hz), 6.67 (d, 1H, J = 6.5 Hz), 7.44 (t, 1H, J = 8.0 Hz), 7.79 (s, 1H), 7.96 (s, 1H), 11.29 (br s, 1H), 12.4 (br s, 1H) |

Example 30

2-(1H-imidazol-4-yl)-1H-indole

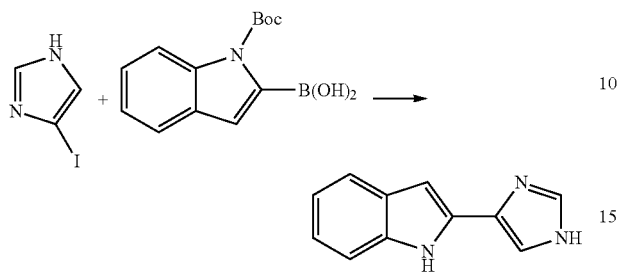

A mixture of DMF (3 mL) and 2M Na$_2$CO$_3$ (0.75 mL) was purged with nitrogen for 10 minutes. 4-iodo-1H-imidazole (145.5 mg, 0.75 mmol), (1-(tert-butoxycarbonyl)-1H-indol-2-yl)boronic acid (235.0 mg, 0.9 mmol) and Pd(PPh$_3$)$_4$ (86.7 mg, 75.0 µmol) were added followed by purging with nitrogen for an additional 2 minutes. The solution was heated at 85° C. over night. The solution was poured into water (20 mL) and the aqueous phase was extracted with ethyl acetate. The combined organic layers were washed with water (2×10 mL), brine and dried. The solvent was removed under reduced pressure and the crude residue was purified by column chromatography on silica gel using 10% MeOH/DCM as the eluent. The BOC protecting group was lost during the reaction sequence. Yield=37%. $^1$H NMR: 6.66 (s, 1H), 7.07-7.15 (m, 2H), 7.32 (s, 1H), 7.33 (d, 1H, J=7.8 Hz), 7.57 (d, 1H, J=7.5 Hz), 7.63 (s, 1H), 9.47 (s, 1H).

Example 31

1-(5-fluoro-2-phenethoxyphenyl)ethanone

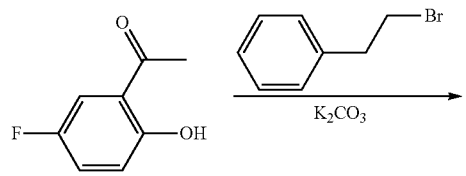

To a stirred solution of phenol (1.0 mmol) and K$_2$CO$_3$ (1.1 mmol) in DMF was added Phenethyl bromide (1.1 mmol) and resulting mixture was heated up to 80° C. for overnight. The resulting mixture was concentrated using rotavap and then diluted with ethyl acetate. The organic mixture was washed with water and dried over Na$_2$SO$_4$. The resulting solution was concentrated and purified using column chromatography. The product was obtained in 60% yield. $^1$H NMR: 2.50 (s, 3H), 3.16 (t, 2H, J=6 Hz), 4.29 (t, 2H, J=6 Hz), 6.86-6.94 (m, 1H), 7.07-7.16 (m, 1H), 7.25-7.37 (m, 5H), 7.41-7.48 (m, 1H).

Example 32

1-(5-Chloro-4-fluoro-2-methoxyphenyl)ethanone

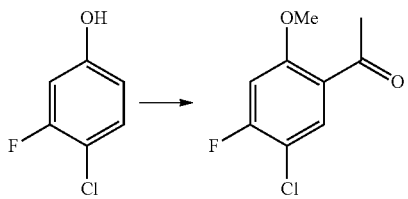

To a stirred solution of DMF (10 mL) and 4-chloro-3-fluorophenol (1 g, 6.84 mmol) at RT, K$_2$CO$_3$ (1.4 g, 10.3 mmol) was added and solution was allowed to stir at room temperature for additional 15 min. Methyl iodide (1.16 g, 8.21 mmol) was added to the mixture and mixture was allowed to stir for overnight at RT. After the completion of reaction 10 mL of water was added and was extracted with ethyl acetate (3×15 mL) and the resulting organic layer was washed with water, brine and dried. 1-chloro-2-fluoro-4-methoxybenzene was obtained via column chromatography (10/1 Hexanes/Ethyl acetate). To a stirred solution of 1-chloro-2-fluoro-4-methoxybenzene (1.09 g, 6.82 mmol) and AlCl$_3$ (1.36 g, 10.23 mmol) in CH$_3$NO$_2$ at 0° C., acetyl chloride (0.80 g, 10.23 mmol) was added and solution was allowed to warm up to room temperature and stir for overnight. After the completion of reaction 10 mL of water was added and was extracted with ethyl acetate (3×15 mL) and the resulting organic layer was washed with water, brine and dried. The solvent was removed in vacuo. The crude was purified by flash column chromatography using 10/1 Hexanes/Ethyl acetate to afford product (46%). $^1$H NMR: 2.59 (s, 3H), 3.91 (s, 3H), 6.78 (d, 1H, J=10.5 Hz), 7.85 (d, 1H, J=8.7 Hz).

Example 33

1-(5-Chloro-4-fluoro-2-hydroxyphenyl)ethanone and
1-(3-Chloro-4-fluoro-2-hydroxyphenyl)ethanone

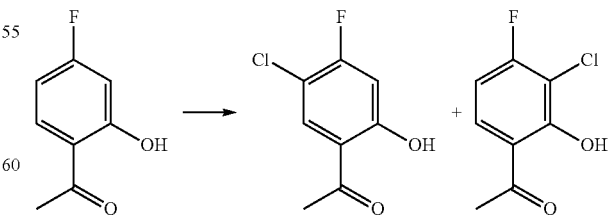

To 1-(4-fluoro-2-hydroxyphenyl)ethanone (1.7 g, 11.03 mmol) in glacial acetic acid (24 mL) at 10° C. was slowly added sulfuryl chloride (2.23 g, 16.54 mmol). The mixture was heated to 120° C. and was allowed to stir for overnight.

The solution was cooled down to room temperature and poured into water (30 mL). The water layer was extracted with EtOAc for three times. The EtOAc was washed with satd. Aq NaHCO$_3$, water, brine, dried (Na$_2$SO$_4$) and concentrated recrystallized The mix was purified by column chromatography using 1:10 Hexanes:Ethyl acetate to yield 234 mg of 1-(5-chloro-4-fluoro-2-hydroxyphenyl)ethanone and 400 mg of 1-(3-chloro-4-fluoro-2-hydroxyphenyl)ethanone. These compounds were used in the next step without characterization.

Example 34

General Procedure for the Condensation of α-Bromophenones with Formamide

A solution of α-bromophenone derivative (1.34 mmol) was heated (170-180° C.) in formamide (10 mL) for 5-10 h. The solution was allowed to cool to room temperature and the mixture was diluted with saturated NaHCO$_3$ (20 mL) and the aqueous phase was extracted with EtOAc (3×50 mL). The combined organic layers were washed with water, brine, dried (Na$_2$SO$_4$) and concentrated in vacuo to afford the crude residue which was purified by flash column chromatography on silica gel to yield the final product.

The following compounds were prepared according to the general procedure of Example 34, by substituting the appropriate starting materials:

| No. | Compound | Name | Yield (%) | $^1$H NMR |
|---|---|---|---|---|
| 1119 | | 5-(2-iodophenyl)-1H-imidazole | 52 | (set of peaks observed due to restricted rotation) 6.95 (dt, 1H, J = 7.6 Hz, 1.6 Hz), 7.10 (dt, 1H, J = 8 Hz, 2 Hz), 7.29-7.35 (m, 2H), 7.43 (d, 1H, J = 0.8 Hz), 7.55-7.63 (m, 5H), 7.79 (dd, 1H, J = 7.6 Hz, 1.6 Hz), 7.91 (dd, 1H, J = 7.6 Hz, 0.8 Hz) |
| 0957 | | 5-(naphthalen-1-yl)-1H-imidazole | 48 | 7.24 (d, 1H, J = 5.4 Hz), 7.45-7.49 (m, 3H), 7.57 (d, 1H, J = 7.0 Hz), 7.66 (s, 1H), 7.81 (d, 1H, J = 8.0 Hz), 7.86-7.89 (m, 1H), 8.29-8.31 (m, 1H) |
| 0982 | | 4-(1H-imidazol-4-yl)pyridine | 54 | 7.70-7.90 (m, 4H), 8.45 (d, 2H, J = 4.8 Hz) |
| 1026 | | 4-(benzofuran-2-yl)-1H-imidazole | 32 | 7.20-7.38 (m, 3H), 7.50 (d, 1H, J = 7.6 Hz), 7.21 (s, 1H), 7.79 (d, 1H, J = 6.8 Hz), 7.96 (s, 1H) |
| 1292 | | 4-(5-fluoro-2-phenethoxy-phenyl)-1H-imidazole | 42 | 3.18 (t, 2H, J = 6.4 Hz), 4.34 (t, 2H, J = 6.4 Hz), 6.85-6.95 (m, 2H), 7.25-7.40 (m, 6H), 7.49 (dd, 1H, J = 9.2, 1.6 Hz), 7.56 (s, 1H) |
| 1010 | | 2-(1H-imidazol-5-yl)-3-(3-phenylpropoxy)phenol | 4 | 2.24 (m, 2H), 2.86 (t, 2H, J = 7.68 Hz), 4.10 (t, 2H, J = 6.32 Hz), 6.42 (d, 1H, J = 8.04 Hz), 6.66 (d, 1H, J = 8.04 Hz), 7.07 (t, 1H, J = 8.24), 7.21-7.32 (m, 5H), 7.72 (s, 2H) |

-continued

| No. | Compound | Name | Yield (%) | ¹H NMR |
|---|---|---|---|---|
| 1105 | | 4-(benzyloxy)-2-(1H-imidazol-5-yl)phenol | 21 | 5.02 (s, 2H), 6.83 (dd, 1H, J = 2.92 Hz, 4.47 Hz), 6.91 (s, 1H, J = 8.88 Hz), 7.08 (d, 1H, J = 2.84 Hz), 7.26-7.45 (m, 6H), 7.67 (s, 1H) |
| | | 3-(5-chloro-2-methoxyphenyl)imidazo[1,2-a]pyrazine | 20 | 3.99 (s, 3H), 6.94 (d, 1H, J = 6.60 Hz), 7.29 (dd. 1H, J = 1.98 Hz, 4.62 Hz), 7.46-7.55 (m, 1H), 7.85 (d, 1H, J = 3.24 Hz), 8.06 (d, 1H, J = 2.88 Hz), 8.28 (s, 1H), 8.40 (d, 1H, J = 1.92 Hz) |
| | | 5-(5-chloro-2,3-dimethoxyphenyl)-1H-imidazole | 76 | 3.81 (s, 3H), 3.89 (s, 3H), 6.80 (s, 1H), 7.46 (s, 1H), 7.57 (s, 1H), 7.72 (s, 1H). |
| 1037 | | 5-(3-chloro-4-fluorophenyl)-1H-imidazole | 49 | 7.12-7.18 (t, J = 8.7 Hz, 1H), 7.30 (s, 1H), 7.62 (1H), 7.71 (1H), 7.82 (1H), 9.30-9.80 (br, 1H) |
| 1048 | | 2-(1H-imidazol-5-yl)-1H-indol-3-ol | 13 | 7.63-7.66 (d, J = 9 Hz, 1H), 7.87-7.91 (dd, 1H), 8.04 (s, 1H), 8.44 (s, 1H) |
| 1051 | | 5-(5-chloro-4-fluoro-2-methoxyphenyl)-1H-imidazole | 20 | 3.94 (s, 3H), 6.76-6.80 (d, J = 10.8 Hz, 1H), 7.91 (s, 1H), 8.13-8.17 (m, 2H) |
| 1120 | | 5-fluoro-2-(1H-imidazol-5-yl)phenol | 40 | 6.54-6.60 (m, 1H), 6.66-6.71 (m, 1H), 7.26-7.28 (m, 1H), 7.38-7.43 (m, 1H), 7.70 (s, 1H) |
| 1129 | | 2-chloro-3-fluoro-6-(1H-imidazol-5-yl)phenol | 11 | (MeOH-d₄), 7.17-7.26 (m, 1H), 7.63-7.67 (m, 1H), 8.41 (s, 1H), 8.44 (s, 1H) |

| No. | Compound | Name | Yield (%) | 1H NMR |
|---|---|---|---|---|
| 1130 | 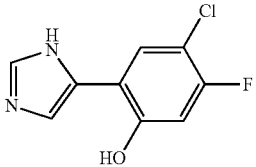 [SMILES: Oc1cc(F)c(Cl)cc1-c1cnc[nH]1] | 4-chloro-5-fluoro-2-(1H-imidazol-5-yl)phenol | 21 | (MeOH-d$_4$), 6.68-6.72 (d, J = 9 Hz, 1H), 7.55 (s, 1H), 7.70-7.74 (m, 2H) |
| 1113 | 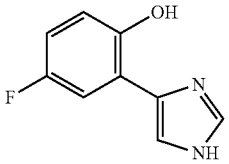 [SMILES: Oc1ccc(F)cc1-c1c[nH]cn1] | 4-fluoro-2-(1H-imidazol-4-yl)phenol | 33 | 6.84-6.95 (m, 2H), 7.13-7.17 (m, 1H), 7.36 (s, 1H), 7.76 (s, 1H) |

Example 35

2-(2-(1H-imidazol-4-yl)phenoxy)-1-(3-bromophenyl)ethanol

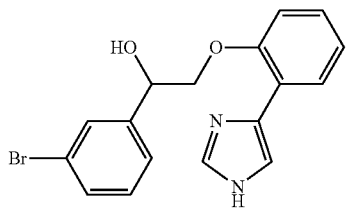 [SMILES: OC(COc1ccccc1-c1c[nH]cn1)c1cccc(Br)c1]

To a solution of 2-(2-(1H-imidazol-4-yl)phenoxy)-1-(3-bromophenyl)ethanone (0.025 g, 0.0699 mmol) in MeOH (2 mL) at room temperature, was added NaBH$_4$ (0.349 mmol) and the resulting suspension was stirred for 1.5 h. The reaction was quenched by adding 1N HCl followed by basification with saturated Na$_2$CO$_3$ solution. The product was extracted with EtOAc (3×10 mL), organic extract was dried (Na$_2$SO$_4$) and concentrated under reduced pressure to afford yellow solid. The crude was subjected to column chromatography to afford the final product. Yield 84%. $^1$H NMR: 3.48 (s, 1H), 4.08 (t, 1H, J=9.39 Hz), 4.40 (dd, 1H, J=3.06, 6.69 Hz), 5.18 (dd, 1H, J=3.48, 5.85 Hz), 6.97 (d, 1H, J=7.59 Hz), 7.04 (d, 1H, J=7.59 Hz), 7.19-7.28 (m, 3H), 7.40 (d, 1H, J=8.73 Hz), 7.46 (d, 1H, J=7.80 Hz), 7.55-7.59 (m, 2H), 7.66 (s, 1H).

Example 36

General Procedure to Addition of Grignard Reagent to Ketones

To a solution of 2-(2-(1H-imidazol-4-yl)phenoxy)-1-(thiophen-2-yl)ethanone (0.211 mmol) in tetrahydrofuran (3 mL) at room temperature, was added Grignard reagent (0.633 mmol) and the solution was stirred overnight at 50° C. After cooling to room temperature, the reaction was quenched by adding saturated NH$_4$Cl solution (5 mL) and the product was extracted with CH$_2$Cl$_2$ (3×20 mL). The combined organic extracts were dried over Na$_2$SO$_4$ and concentrated under reduced pressure to afford the crude oil. The crude was purified by column chromatography.

The following compounds were prepared according to the general procedure of Example 36, by substituting the appropriate starting materials:

| No. | Compound | Name | Yield (%) | 1H NMR |
|---|---|---|---|---|
| 0976 | 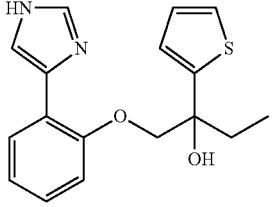 [SMILES: CCC(O)(COc1ccccc1-c1c[nH]cn1)c1cccs1] | 1-(2-(1H-imidazol-4-yl)phenoxy)-2-(thiophen-2-yl)butan-2-ol | 91 | 400 MHz, CDCl3: 0.85 (t, 3H, J = 6.93 Hz), 1.97 (m, 1H), 2.06 (m, 1H), 4.31 (d, 1H, J = 6.87 Hz), 4.37 (d, 1H, J = 6.87 Hz), 6.95-7.02 (m, 4H), 7.20 (t, 2H, J = 5.55 Hz), 7.27 (m, 1H), 7.37 (s, 1H), 7.54 (d, 1H, J = 5.58 Hz). |
| 0977 | 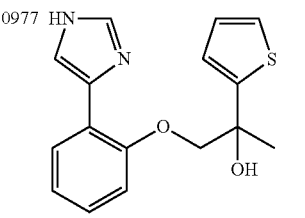 | 1-(2-(1H-imidazol-4-yl)phenoxy)-2-(thiophen-2-yl)propan-2-ol | 73 | 400 MHz, CDCl3 + CD3OD: 4.69 (s, 2H), 6.87 (d, 1H, J = 6.18 Hz), 6.95 (t, 1H, J = 5.55 Hz), 7.19 (t, 1H, J = 5.79 Hz), 7.38 (d, 1H, J = 5.10 Hz), 7.47-7.56 (m, 4H), 7.79 (d, 1H, J = 5.00 Hz), 8.21 (br s, 1H). |

Example 37

1-(2-iodo-3-methoxybenzyl)-1H-imidazole

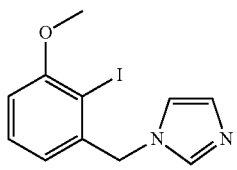

To a solution of (2-iodo-3-methoxyphenyl)methanol (0.350 g, 1.33 mmol), (Organic Letters, 2001, vol. 3, #21 p. 3245-3248) imidazole (0.181 g, 2.65 mmol) and triphenyl phosphine (0.382 g, 1.46 mmol) in tetrahydrofuran (5 mL) at 0° C. was added Diethyl azodicarboxylate (40% solution in toluene; 0.664 mL). The yellow solution was allowed to warm to room temperature and stirred at 60° C. overnight. After evaporating the solvent under reduced pressure, the crude was purified by column chromatography (5% EtOAc:hexanes, 20% EtOAc; Hexanes). Yield=43%. $^1$H NMR: 3.90 (s, 3H), 5.19 (s, 2H), 6.43 (d, 1H, J=5.70 Hz), 6.77 (d, 1H, J=6.09 Hz), 6.93 (s, 1H), 7.10 (s, 1H), 7.24 (t, 1H, J=6.03 Hz)

Example 38

9-methoxy-5-5H-imidazo[5,1-a]isoindole

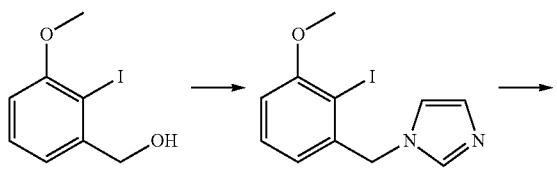

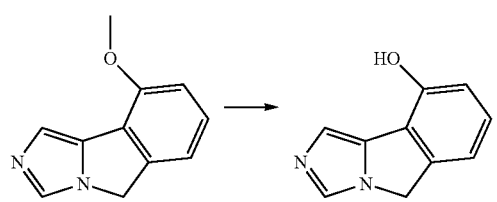

A mixture of 1-(2-iodo-3-methoxybenzyl)-1H-imidazole (0.180 g, 0.573 mmol), potassium carbonate (1.146 mmol) in dimethyl sulfoxide was purged with nitrogen for 5 min to which triphenylphosphine (0.057 mmol) and Pd(OAC)$_2$ (0.0286 mmol) was added. The mixture was stirred under nitrogen atmosphere at 110° C. for 36 h. After cooling to room temperature, the reaction mixture was diluted with water (15 mL) and the aqueous layer was extracted with EtOAc (3×25 mL). The combined organic extracts were dried and concentrated under reduced pressure to afford crude product. Chromatographic purification afforded the desired product in 37% yield. $^1$H NMR: 3.96 (s, 3H), 5.00 (s, 2H), 6.88 (d, 1H, J=8.32 Hz), 6.99 (d, 1H, J=7.52 Hz), 7.17 (s, 1H), 7.22 (t, 1H, J=7.96 Hz), 7.69 (s, 1H).

Example 39

N-(4-(2-(2-(1H-Imidazol-4-yl)phenoxy)ethyl)phenyl)-1-phenylmethanesulfonamide

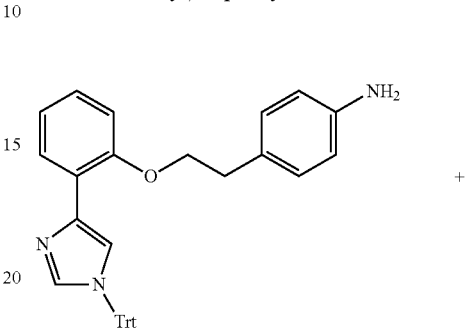

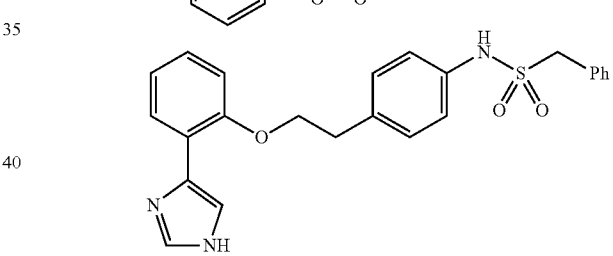

To a solution of 4-(2-(2-(1-trityl-1H-imidazol-4-yl)phenoxy)ethyl)aniline (80 mg, 0.153 mmol) in dichloromethane (4 mL) was added pyridine (24 µL, 0.307 mmol) followed by benzylsulfonyl chloride (32 mg, 0.169 mmol). The mixture was stirred at room temperature for 16 h and concentrated. The solvent was removed under reduced pressure and the crude was dissolved in methanol (4 mL) and acetic acid (1 mL). The reaction mixture was heated at 80° C. for 2 h. The reaction mixture was basified with aqueous 10% NaOH and the aqueous layer extracted with ethyl acetate (2×30 mL). The combined organic extracts were washed with brine (15 mL), dried over Na$_2$SO$_4$ and concentrated. The residue was purified by flash column chromatography using 5% MeOH/dichloromethane as an eluent at afford the desired product as a yellowish solid (52 mg, 0.120 mmol, 79%). $^1$H NMR: 3.16 (t, 2H, J=63.4 Hz), 4.28 (t, 2H, J=6.4 Hz), 4.36 (s, 2H), 6.92

(t, 1H, J=6.8 Hz), 7.02 (s, 1H), 7.11 (d, 3H, J=7.2 Hz), 7.19 (s, 2H), 7.28-7.31 (m, 5H), 7.41 (s, 1H), 7.62 (s, 1H), 8.04 (s, 1H), 9.71 (s, 1H).

Example 40

General Procedure for Suzuki Coupling

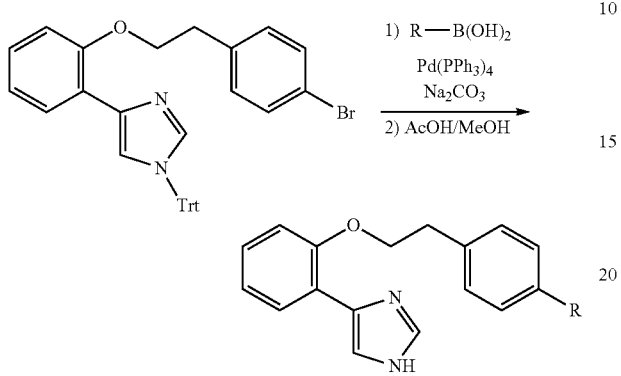

Pd(PPh$_3$)$_4$ (4.8 mg, 4.1 mol) was added to a solution of the aryl bromide (0.2 mmol), the boronic acid (0.3 mmol), and sodium carbonate (0.4 mmol) in 2:1 DME/water (6 mL). The mixture was heated at 85° C. overnight. The mixture was allowed to cool to room temperature, and was partitioned between EtOAc and water. The layers were separated and the aqueous layer was extracted with EtOAc (2×20 mL) and the combined organic layer washed with water, brine, and dried (Na$_2$SO$_4$). The solvent was removed under reduced pressure and the crude product was purified by silica gel flash column chromatography using EtOAc/hexanes as the eluent: gradient 10% EtOAc/hexanes to 100% EtOAc.

The following compounds were prepared according to the general procedure of Example 40, by substituting the appropriate starting materials:

Example 41

2-(((4-chloro-2-(1H-imidazol-4-yl)phenoxy)carbonyl)(methyl)amino)ethyl acetate

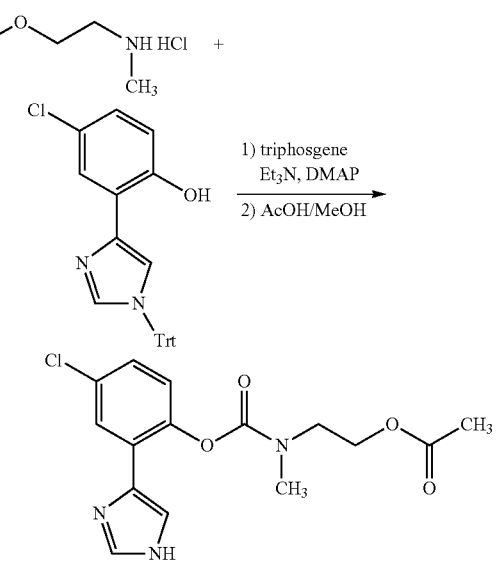

To a suspension 2-(methylamino)ethyl acetate hydrochloride (prepared as described by TAKEDA CHEMICAL INDUSTRIES, LTD. Patent: WO2003/105845 A1, 2003) (250.0 mg, 1.63 mmol) in DCM (5 mL) was added triphosgene (483.0 mg, 1.63 mmol) and Et$_3$N (907 μL, 6.51 mmol) at 0° C. The solution was allowed to stir for 1 h and was concentrated to dryness. The crude residue was used immediately in the next step without purification. The crude residue was dissolved in DCM (5 mL), the phenol derivative (568.9 mg, 1.30 mmol) and DMAP (397.7 mg, 3.26 mmol) were added.

| No. | Compound | Name | Yield (%) | $^1$H NMR |
|---|---|---|---|---|
| 1200 | | 4-(2-(4-(thiophen-2-yl)phenethoxy)phenyl)-1H-imidazole | 77 | 3.23 (t, 2H, J = 6.0 Hz), 4.43 (t, 2H, J = 6.2 Hz), 6.96-7.09 (m 3H), 7.18-7.39 (m, 6H), 4.79 (s, 1H), 7.62-7.68 (m, 2H), 9.57 (br s, 1H) |
| 1201 | | 4-(2-(4-(thiophen-3-yl)phenethoxy)phenyl)-1H-imidazole | 44 | 3.24 (t, 2H, J = 6.2 Hz), 4.45 (t, 2H, J = 6.4 Hz), 7.02 (d, 2H, J = 8.0 Hz), 7.21 (d, 1H, J = 8.0 Hz), 7.34 (s, 1H), 7.33-7.42 (m, 5H), 7.45-7.47 (m, 1H), 7.61-7.72 (m, 3H) |

The resulting solution was allowed to stir at room temperature over night. The solvent was removed under reduced pressure and the crude residue was filtered through a plug of silica gel and concentrated. To the residue was added MeOH (3 mL) and AcOH (2 mL) and the solution was heated at 80° C. for 30 min. The solution was diluted with water and made basic with solid $K_2CO_3$ (pH~8-9). The aqueous was extracted with EtOAc and the combined organic layers were washed with water, brine and dried ($Na_2SO_4$). The crude residue was purified by column chromatography on silica gel afforded the compound (115 mg, 21% yield). $^1$H NMR: mixture of rotational isomers: 2.02, 2.08 (two s, 3H), 3.07, 3.21 (two s, 3H), 3.62 (t, 1H, J=4.0 Hz), 3.75 (t, 1H, J=4.0 Hz), 4.27-4.32 (m, 2H), 7.05 (d, 1H, J=8.0 Hz), 7.21 (d, 2H, J=8.0 Hz), 7.58 (s, 1H), 7.86 (s, 1H).

Example 42

Prodrugs

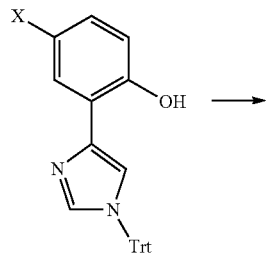

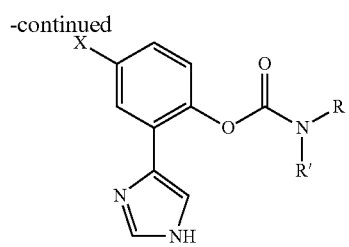

X = Br, Cl

To a stirred solution of the appropriate phenol (2.0 mmol), $Et_3N$ (3.0 mmol), and DMAP (0.2 mmol) in DCM (15 mL) was slowly added the appropriate carbamoyl chloride (3.0 mmol) at room temperature. The solution was allowed to stir at room temperature overnight. The solution was diluted with DCM (20 mL) and the organic layer washed with water, brine and dried ($Na_2SO_4$). The solution was concentrated under reduced pressure and the crude residue was dissolved in 3:2 MeOH/AcOH (5 mL). The solution was heated at 80° C. for 30 min. The solution was allowed to cool to room temperature and diluted with water (20 mL). The solution was made basic by the addition of solid $K_2CO_3$ until the approximate pH=9.0 and the aqueous was extracted with EtOAc. The combined organic layers were washed with water, brine and dried ($Na_2SO_4$). The solution was filtered and concentrated under reduced pressure to afford the crude residue, which was purified by column chromatography on silica gel using DCM:MeOH (0-10%) gradient as the eluent.

The following compounds were prepared according to the general procedure of Example 42, by substituting the appropriate starting materials:

| No. | Compound | Name | Yield (%) | $^1$H NMR |
|---|---|---|---|---|
| 1035 | Br-... | 4-bromo-2-(1H-imidazol-4-yl)phenyl dimethylcarbamate | 41 | 3.04 (s, 3H), 3.12 (s, 3H), 6.99 (d, 1H, J = 8.5 Hz), 7.33 (dd, 1H, J = 2.1, 7.5 Hz), 7.52 (s, 1H), 8.02 (br s, 1H), 10.37 (br s, 1H) |
| 1076 | Cl-... | 4-chloro-2-(1H-imidazol-4-yl)phenyl dimethylcarbamate | 53 | 3.00 (s, 3H), 3.16 (s, 3H), 7.04 (d, 1H, J = 8.6 Hz), 7.16 (dd, 1H, J = 2.2, 8.6 Hz), 7.43 (s, 1H), 7.79 (br s, 1H) |
| 1085 | Cl-... | 4-chloro-2-(1H-imidazol-4-yl)phenyl diisopropylcarbamate | 62 | 1.31 (d, 12H, J = 4.9 Hz), 3.94 (br s, 1H), 4.18 (br s, 1H), 7.01 (d, 1H, J = 7.9 Hz), 7.20 (d, 1H, J = 8.0 Hz), 7.52 (s, 1H), 7.77 (br s, 1H) |

| No. | Compound | Name | Yield (%) | $^1$H NMR |
|---|---|---|---|---|
| 1087 | 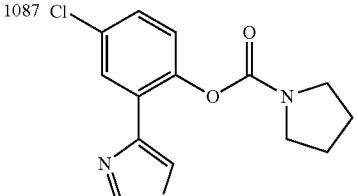 | 4-chloro-2-(1H-imidazol-4-yl)phenyl pyrrolidine-1-carboxylate | 42 | 1.91-1.99 (m, 4H), 3.49 (t, 2H, J = 6.2 Hz), 3.63 (t, 2H, J = 6.0 Hz), 7.08 (d, 1H, J = 8.6 Hz), 7.16 (dd, 1H, J = 1.9, 8.5 Hz), 7.25 (s, 1H), 7.43 (s, 1H), 7.84 (br s, 1H) |
| 1088 | 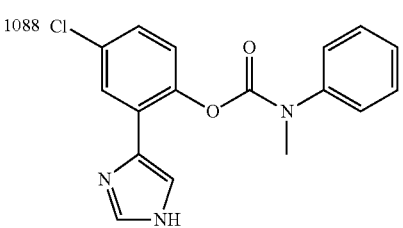 | 4-chloro-2-(1H-imidazol-4-yl)phenyl methyl(phenyl)carbamate | 48 | (dmso-d$_6$) 3.35 (s, 3H), 6.92 (br s, 1H), 7.27-7.31 (m, 3H), 7.43-7.52 (m, 4H), 7.76 (s, 1H), 8.0 (s, 1H), 12.26 (br s, 1H) |
| 1147 | 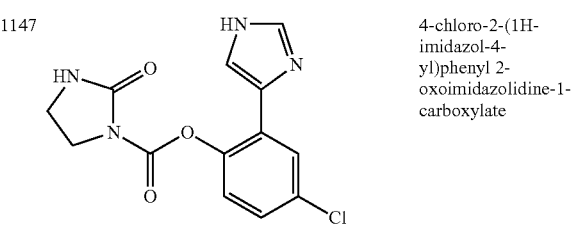 | 4-chloro-2-(1H-imidazol-4-yl)phenyl 2-oxoimidazolidine-1-carboxylate | 11 | (dmso-d$_6$) 3.39 (t, 2H, J = 7.8 Hz), 3.92 (t, 2H, J = 8.0 Hz), 7.25 (d, 1H, J = 8.6 Hz), 7.29 (dd, 1H, J = 2.5, 8.6 Hz), 7.70 (s, 1H), 7.78 (s, 1H), 7.82 (s, 1H), 8.05 (d, 1H, J = 2.4 Hz) |
| 1112 | 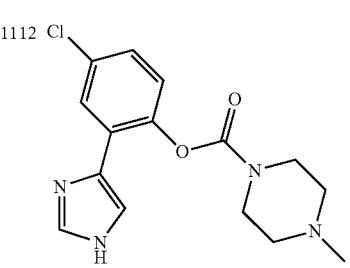 | 4-chloro-2-(1H-imidazol-4-yl)phenyl 4-methylpiperazine-1-carboxylate | 22 | (dmso-d$_6$) 1.87 (s, 3H), 2.34 (s, 2H), 2.42 (s, 2H), 3.41 (s, 2H), 3.69 (s, 2H) 7.14-7.31 (m, 3H), 7.78 (s, 1H), 8.01 s, 1H), 12.45 (br s, 1H) |
| 1245 | 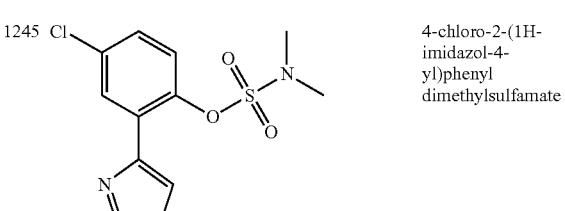 | 4-chloro-2-(1H-imidazol-4-yl)phenyl dimethylsulfamate | 61 | 2.77 (s, 6H), 7.24 (dd, 1H, J = 2.8, 8.8 Hz), 7.45 (d, 1H, J = 8.8 Hz), 7.61 (s, 1H), 7.76 (s, 1H), 7.99 (s, 1H) |

Example 43

General procedure for the Synthesis of Ethyl 2-(4-aminophenyl)acetates

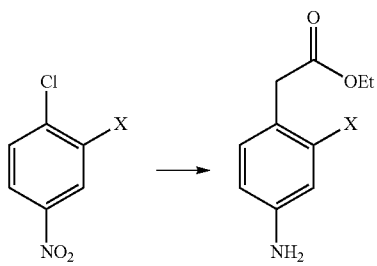

X = Cl, F, CF$_3$

To a suspension of 95% NaH (24.38 mmol) in anhydrous DMF (20 mL) at 0° C. under an atmosphere of nitrogen, was added dimethyl malonate (22.17 mmol) in DMF (3 mL) dropwise over a period of 20 min. and stirring was continued at 0° C. for 30 min. The appropriate 1-chloronitrobenzene (11.08 mmol) in DMF (3 mL) was added dropwise at 0° C. over a period of 20 min. The mixture was stirred at 70° C. for 15 h. The reaction mixture was cooled to room temperature and quenched with NH$_4$Cl. The aqueous was extracted with EtOAc (2×50 mL) and the combined organic layers were washed with water (2×20 mL), brine (10 mL) and dried (Na$_2$SO$_4$). The solution was filtered and concentrated under reduced pressure. The crude material was recrystallized from EtOH to give the dimethyl 2-(2-chloro-4-nitrophenyl)malonate as a solid.

To a stirred solution of concentrated HCl (18 mL) diluted to 72 mL with ethanol or methanol was added the appropriate dimethyl 2-(2-chloro-4-nitrophenyl)malonate (7.8 mmol). The resulting mixture was then heated at reflux under N$_2$ for 4 h. The reaction mixture was allowed to cool to room temperature and poured into H$_2$O (250 mL). This aqueous mixture was then extracted with EtOAc. The combined organic layers were extracted with H$_2$O and 5% NaHCO$_3$ washed with brine, dried and concentrated. The crude product was carried to the next step.

To a solution of the nitro compound (3.61 mmol) in methanol (25 mL) was added 5% Pd/C (0.36 mmol). The container was evacuated and backfilled with hydrogen three times. The reaction mixture was allowed to stir at room temperature overnight under an atmosphere of H$_2$. The suspension was filtered through a pad of celite/silica gel and the solvent removed under reduced pressure to afford the pure aniline.

The following compounds were prepared according to the general procedure of Example 43, by substituting the appropriate starting materials:

| Compound | Name | Yield (%) | $^1$H NMR |
|---|---|---|---|
| (structure with OEt, Cl, NH$_2$) | ethyl 2-(4-amino-2-chlorophenyl)acetate | 61 | 1.25 (t, 3H, J = 7.0 Hz), 3.64 (s, 2H), 3.66 (s, 2H), 4.18 (q, 2H, J = 7.0 Hz), 6.54 (dd, J = 2.4, 8.0 Hz), 6.72 (d, 1H, J = 2.4 Hz), 7.04 (d, 1H, J = 8.4 Hz) |
| (structure with OMe, F, NH$_2$) | methyl 2-(4-amino-2-fluorophenyl)acetate | 54 | 3.55 (s, 2H), 3.69 (s, 3H), 3.71 (br s, 2H), 6.67-6.43 (m, 2H), 7.00 (t, 1H, J = 8.2 Hz) |
| (structure with OEt, CF$_3$, NH$_2$) | ethyl 2-(4-amino-2-(trifluoromethyl)phenyl)acetate | 68 | 1.24 (t, 3H, J = 7.0 Hz), 3.67 (s, 2H), 3.83 (br s, 2H), 4.15 (q, 2H, J = 7.1 Hz), 6.78 (d, 1H, J = 8.4 Hz), 6.94 (s, 1H), 7.14 (d, 1H, J = 8.0 Hz) |

Example 44

Ethyl 4-(5-bromo-2-((ethoxycarbonyl)oxy)phenyl)-1H-imidazole-1-carboxylate

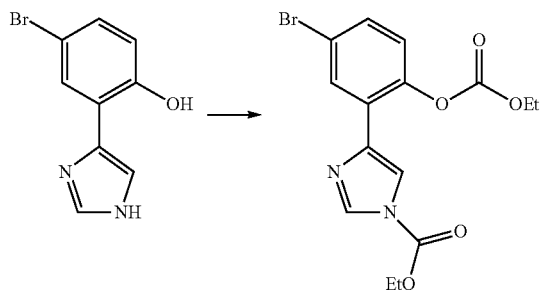 [SMILES: Oc1ccc(Br)cc1-c1c[nH]cn1 ; CCOC(=O)Oc1ccc(Br)cc1-c1cn(C(=O)OCC)cn1]

To a stirred solution of the appropriate imidazole (179.3 mg, 0.75 mmol), Et$_3$N (235.3 mg, 2.3 mmol), and DMAP (9.2 mg, 75.0 μmol) in DCM (5 mL) was slowly added ethyl chloroformate (252.3 mg, 2.3 mmol) at room temperature. The reaction was allowed to stir overnight at room temperature. The solution was poured into water and the organic layer was washed with water, brine and dried (Na$_2$SO$_4$). The crude residue was purified by column chromatography (30% EtOAc/hexanes) to afford the desired product as a solid (267 mg, 90% yield). $^1$H NMR: 1.39 (t, 3H, J=7.1 Hz), 1.17 (t, 3H, J=7.1 Hz), 4.33 (q, 2H, J=7.1 Hz), 4.51 (q, 2H, J=7.1 Hz), 7.14 (d, 1H, J=8.6 Hz), 7.43 (dd, 1H, J=2.3, 8.6 Hz), 7.85 (s, 1H), 8.19 (s, 1H), 8.33 (d, 1H, J=2.3 Hz)

Example 45

Ethyl 4-phenyl-1H-imidazole-1-carboxylate

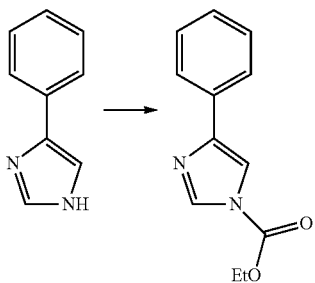 [SMILES: c1ccc(-c2c[nH]cn2)cc1 ; CCOC(=O)n1cnc(-c2ccccc2)c1]

To a stirred solution of 4-phenyl imidazole (245.1 mg, 1.7 mmol,), Et$_3$N (258.0 mg, 2.6 mmol), and DMAP (20.1 mg, 170.0 μmol) in DCM (5 mL) was slowly added ethyl chloroformate (276.7 mg, 2.6 mmol) at room temperature. The reaction was allowed to stir overnight at room temperature. The solution was poured into water and the organic layer was washed with water, brine and dried (Na$_2$SO$_4$). The crude residue was purified by column chromatography (30% EtOAc/hexanes) to afford a colorless solid (301.0 mg, 80% yield). $^1$H NMR: 1.47 (t, 3H, J=6.9 Hz), 4.50 (q, 2H, J=7.0 Hz), 7.30 (t, 1H, J=7.0 Hz), 7.41 (t, 2H, J=7.5 Hz), 7.69 (s, 1H), 7.80 (d, 2H, J=7.9 Hz), 8.2 (s, 1H)

Example 46

2-(2-chlorophenyl)propan-1-ol

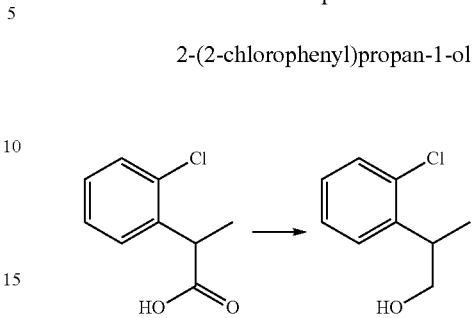

To a stirred solution of the carboxylic acid (1.0 g, 5.42 mmol) in THF at −20° C. was slowly added 95% BH$_3$.SMe$_2$ complex (1.39 g, 1.73 mL, 17.3 mmol) drop-wise under an atmosphere of N$_2$. The solution was slowly allowed to warm to room temperature under a swath of nitrogen gas where bubbling was observed. The solution was allowed to stir at room temperature overnight. Under a stream of nitrogen, MeOH (5 mL) was slowly added by syringe. Vigorous bubbling was observed and subsided after 15 min. The solution was concentrated to approx ¼ the original volume and diluted with EtOAc (25 mL). The organic layer was washed with water, brine and dried (Na$_2$SO$_4$). The solvent was removed under reduced pressure to provide the alcohol as colorless oil. $^1$H NMR: 1.29 (d, 3H, J=7.0 Hz), 3.51-3.57 (m, 1H), 3.70-3.74 (m, 1H), 3.77-3.81 (m, 1H), 7.14-7.18 (m, 1H), 7.23-7.30 (m, 1H), 7.37 (d, 1H, J=8.0 Hz)

Example 47

6-chloro-5-hydroxy-2,2-dimethyl-4H-benzo[d][1,3]dioxin-4-one

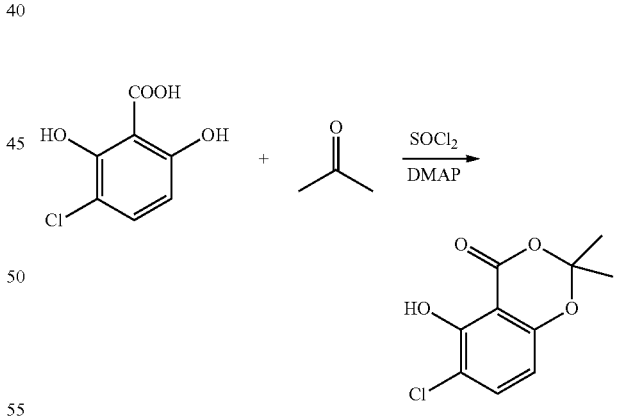

To a solution of 5-chloro-2,6-dihydroxybenzoic acid (Doyle, F. P. *J. Chem. Soc.*, 1963, p. 497-506) (500 mg, 2.65 mmol) in DME (2 mL) was added DMAP (16.2 mg, 0.13 mmol) and acetone (200.2 mg, 3.45 mmol). The solution was cooled to 10° C. and thionyl chloride (448 mg, 3.77 mmol) was added over 10 min. The solution was allowed to overnight. The solution was diluted with water and neutralized with solid K$_2$CO$_3$ and the aqueous phase was extracted w/EtOAc. The combined organic layers were washed with water, brine and dried (Na$_2$SO$_4$). The crude residue was purified by column chromatography on silica gel to afford the product as yellow solid (162 mg, 27% yield). ¹H NMR: 1.74 (s, 6H), 6.44 (d, 1H, J=8.0 Hz), 7.48 (d, 1H, J=8.0 Hz), 10.83 (s, 1H).

Example 48

6,8-dichloro-5-hydroxy-2,2-dimethyl-4H-benzo[d][1,3]dioxin-4-one

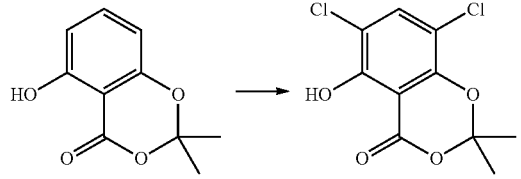 [SMILES: CC1(C)OC(=O)c2c(O)cccc2O1 ; CC1(C)OC(=O)c2c(O)c(Cl)cc(Cl)c2O1]

To a solution of the phenol (500 mg, 2.57 mmol), diisobutyl amine (26.6 mg, 0.21 mmol) in toluene (43 mL) at 70° C. was added sulfuryl chloride (695 mg, 5.14 mmol) for one hour. The solvent was removed under reduced pressure and the crude residue was purified by column chromatography on silica gel (20% EtOAc/Hexanes) to afford the product (426 mg, 63% yield). ¹H NMR: 1.81 (s, 6H), 7.60 (s, 1H), 10.83 (s, 1H)

Example 49

2-(2-(2-hydroxyethyl)phenyl)isoindoline-1,3-dione

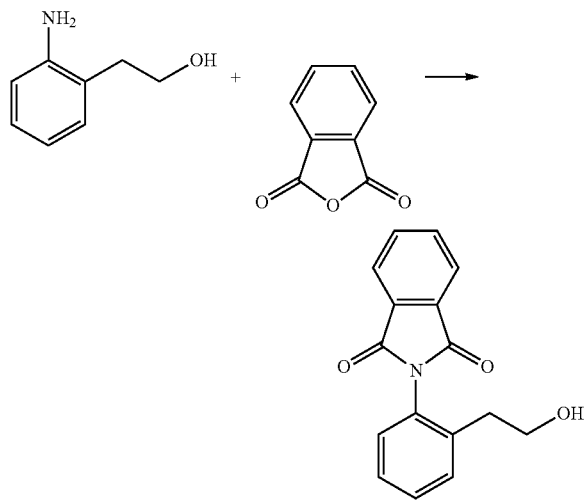

A flask containing 2-aminophenethyl alcohol (565 mg, 4.12 mmol), phthalic anhydride (641 mg, 4.32 mmol) and acetic acid (4 mL) was heated at 100° C. for 1 h. The reaction mixture was poured into water (30 mL) and the solid was filtered off and the solids were washed with water. The crude was purified by flash column chromatography to afford the desired product as white solid (435 mg, 1.63 mmol, 40%). ¹H NMR: 1.79 (br s, 1H), 2.78 (t, 2H, J=6.4 Hz), 3.81 (t, 2H, J=6.4 Hz), 7.20 (d, 1H, J=8 Hz), 7.36-7.41 (m, 1H), 7.46 (d, 2H, J=4 Hz), 7.79-7.83 (m, 2H), 7.94-7.97 (m, 21-1).

Example 50

N-(2-(2-(2-(1H-imidazol-4-yl)phenoxy)ethyl)phenyl)acetamide

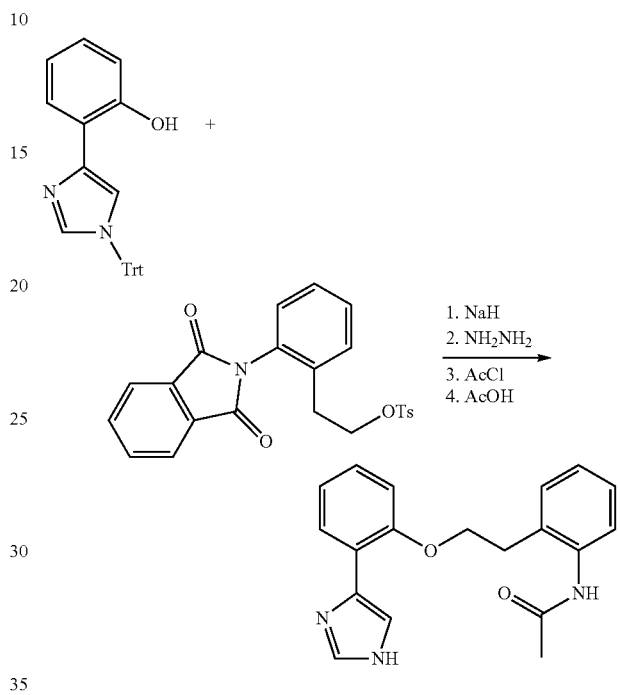

To a stirred solution of the 2-(1-trityl-1H-imidazol-4-yl)phenol (451 mg, 1.12 mmol) in anhydrous DMF (6 mL) at 0° C. was added NaH (30.0 mg, 1.23 mmol). The resulting suspension was allowed to stir at room temperature for 45 min. To the resulting solution was added the 2-(1,3-dioxoisoindolin-2-yl)phenethyl 4-methylbenzenesulfonate (520 mg, 1.23 mmol). After stirring overnight, the reaction mixture was carefully diluted with water (10 mL) and extracted with ethyl acetate (2×20 mL). The combined organic layers were washed with water, brine and dried (Na₂SO₄). The solvent was removed under reduced pressure and the crude product was taken to next step without further purification. To the stirred solution of the above obtained product in EtOH (5 mL), NH₂NH₂H₂O (0.05 mL, 1.60 mmol) was added. The reaction mixture was refluxed for 2 h, filtered over celite and concentrated to give crude aniline product. To a solution of crude aniline in dichloromethane (3 mL) was added pyridine (0.5 mL) followed by acetic anhydride (0.5 mL). The mixture was stirred at ambient temperature for 12 h. The mixture was diluted with dichloromethane (20 mL) and washed with water (2×10 mL), brine (10 mL) and dried over sodium sulfate. The solvent was removed under reduced pressure to afford the acylated product which was used directly in next step. To a solution of the crude product was added acetic acid (1.0 mL) and MeOH (4.0 mL). The solution was heated at 80° C. for 2 h. The solution was allowed to cool to room temperature and the pH was adjusted to ~10 with 10% NaOH (aq). The aqueous phase was extracted with EtOAc (3×20 mL). The combined organic layer were washed with water, brine, and dried. The solvent was removed in vacuo to afford the crude residue, which was purified by flash column chromatography on silica gel to afford the desired product as a white solid (40 mg, 0.125 mmol, 11% over 4 steps). ¹H NMR (DMSO-d₆): 2.05 (s, 3H), 3.17 (t, 2H, 6.6 Hz), 4.26 (t, 2H, J=6.9 Hz), 6.95 (t, 1H, J=7.5 Hz), 7.04 (d, 1H, J=8.1 Hz), 7.12-7.24 (m, 3H), 7.35-7.44 (m, 3H), 7.68 (s, 1H), 8.09 (d, 1H, J=7.2 Hz), 9.49 (s, 1H), 12.04 (br s, 1H).

Example 51

4-bromo-2-(1H-imidazol-4-yl)phenyl pivalate

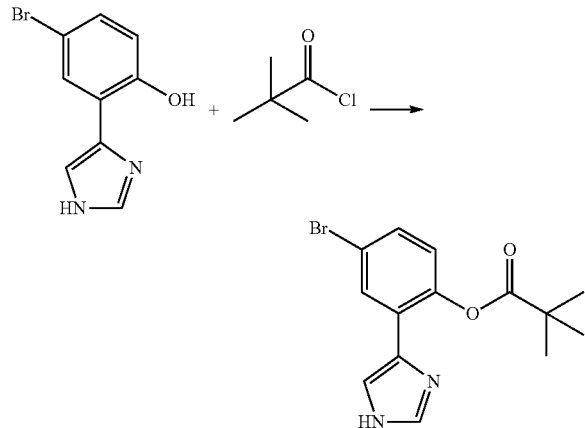

To a solution of 4-bromo-2-(1H-imidazol-4-yl)phenol (2.9 g, 12.13 mmol) in dichloromethane was added DMAP (296 mg, 2.43 mmol), triethylamine (5.1 mL, 36.4 mmol) and pivaloyl chloride (3.7 mL, 30.33 mmol). The reaction was stirred at room temperature for 16 h. The reaction mixture was poured into water (100 mL) and extracted with dichloromethane (2×100 mL). The combined organic layers were dried over sodium sulfate and concentrated. The crude product was dissolved in methanol (70 mL) and refluxed for 2 h. The solution was concentrated and the residue was purified by flash column chromatography (silica gel, 20%-70% EtOAc/hexanes as eluent) to afford the desired product as yellow solid (1.2 g, 3.72 mmol, 31%). ¹H NMR: 1.35 (s, 9H), 6.90 (d, 1H, J=8.4 Hz), 7.31 (s, 1H), 7.38 (dd, 1H, J=8.4 Hz, 2.4 Hz), 7.67 (s, 1H), 8.00 (d, 1H, J=2.4 Hz).

Example 52

N-(4-(2-(2-(1H-imidazol-4-yl)phenoxy)ethyl)-3-chlorophenyl)-2-acetamido-2-(tetrahydro-2H-pyran-4-yl)acetamide

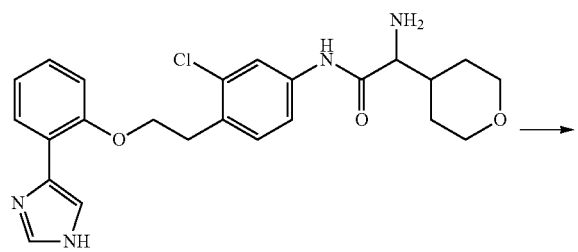

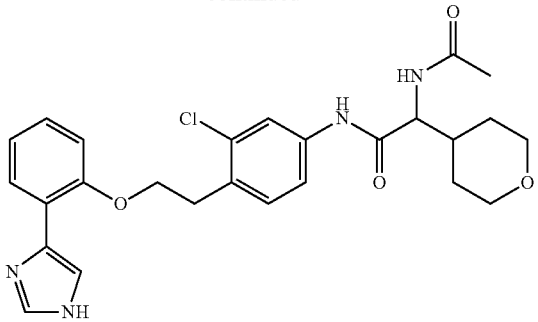

To a solution of N-(4-(2-(2-(1H-imidazol-4-yl)phenoxy)ethyl)-3-chlorophenyl)-2-amino-2-(tetrahydro-2H-pyran-4-yl)acetamide (40 mg, 0.088 mmol) in dichloromethane (3 mL) was added pyridine (29 μL, 0.352 mmol) and acetyl chloride (29 μL, 0.264 mmol). The reaction was stirred at room temperature for 16 h. The solvent was removed under reduced pressure. The crude product was dissolved in methanol (4 mL) and refluxed for 2 h. The solution was concentrated and the residue was purified by flash column chromatography (silica gel, 5%-10% MeOH/DCM as eluent) to afford the desired product as a white solid (27 mg, 0.054 mmol, 61%). ¹H NMR: 1.42-1.58 (m, 3H), 1.68 (d, 1H, J=12.8 Hz), 2.03-2.07 (m, 1H), 2.08 (s, 3H), 3.24-3.31 (m, 4H), 3.94 (t, 2H, J=11.2 Hz), 4.39 (t, 2H, J=6 Hz), 4.61 (t, 1H, J=8.4 Hz), 6.81 (d, 1H, J=8.4 Hz), 6.99 (d, 2H, J=8 Hz), 7.18-7.24 (m, 3H), 7.37 (dd, 1H, J=8 Hz, 1.6 Hz), 7.60 (s, 1H), 7.77 (s, 1H), Example 53

Ethyl 2-(4-(3-(2-(tert-butoxycarbonylamino)cyclohexyl)ureido)-2-chlorophenyl)acetate

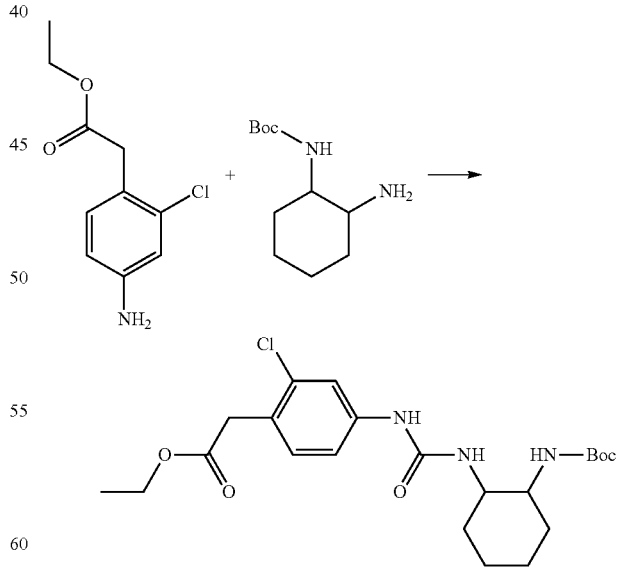

To a solution of ethyl 2-(4-amino-2-chlorophenyl)acetate (178 mg, 0.833 mmol) in dry dichloromethane (5 mL), was added triethylamine (2.32 mL, 16.66 mmol) followed by triphosgene (247 mg, 0.833 mmol) solution in dichloromethane (1 mL). The reaction mixture was stirred at room temperature for 1 h. To this mixture was then added tert-butyl 2-aminocyclohexylcarbamate (357 mg, 1.67 mmol) in dichloromethane (1 mL). The reaction mixture was stirred at room temperature for 4 h and concentrated. The residue was dissolved in ethyl acetate and washed with water (2×20 mL), brine (10 mL), dried and concentrated. The crude product was purified by flash column chromatography to afford the desired product as a mixture of cis and trans diastereomers (220 mg, 0.485 mmol, 58%). $^1$H NMR: 1.23-1.28 (m, 6H), 1.38 (s, 9H), 1.70-1.73 (m, 2H), 2.01-2.08 (m, 2H), 3.29-3.32 (m, 1H), 3.53-3.58 (m, 1H), 3.68 (s, 2H), 4.11-4.19 (m, 2H), 5.01 (d, 1H, J=8.8 Hz), 5.57 (d, 1H, J=8 Hz), 7.13 (d, 1H, J=8.4 Hz), 7.20 (d, 1H, J=6.8 Hz), 7.41 (s, 1H), 7.46 (s, 1H).

Example 54 tert-butyl 2-(3-(3-chloro-4-(2-hydroxyethyl)phenyl)ureido)cyclohexylcarbamate

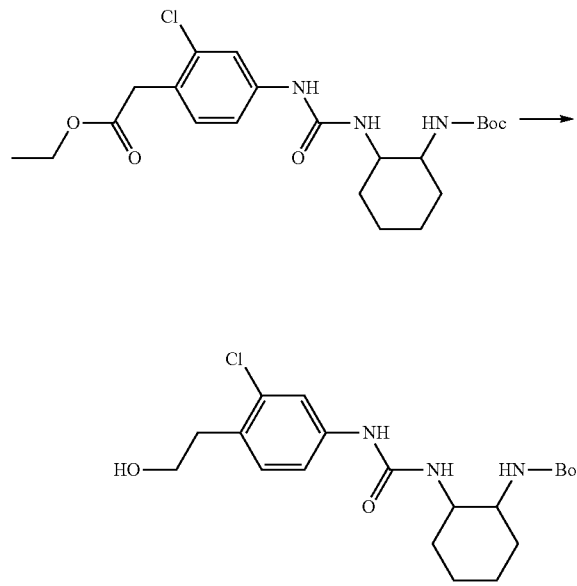

To a solution of ethyl 2-(4-(3-(2-(tert-butoxycarbonylamino)cyclohexyl)ureido)-2-chlorophenyl)acetate (452 mg, 0.996 mmol) in a mixture of THF:EtOH (1:2, 12 mL) at room temperature, was added NaBH$_4$ (124 mg, 3.29 mmol) and LiCl (139 mg, 3.29 mmol). The reaction mixture was stirred overnite. The solvents were distilled off and the crude was diluted with saturated aqueous NH$_4$Cl (20 mL), the product was extracted with ethyl acetate (2×20 mL). The combined organic extracts were dried over Na$_2$SO$_4$ and the solvent distilled off under reduced pressure. The crude product was purified by flash column chromatography to separate cis 964 mg, 0.155 mmol) and trans (83 mg, 0.201 mmol) diastereomers. These alcohols were converted into tosylates using general procedure for the preparation of tosylates. $^1$H NMR (cis): 1.23-1.26 (m, 3H), 1.36 (s, 9H), 1.70-1.74 (m, 2H), 1.99-2.06 (m, 2H), 2.41-2.43 (m, 1H), 2.92 (t, 2H, J=6.4 Hz), 3.25-3.29 (m, 1H), 3.51-3.54 (m, 1H), 3.83-3.86 (m, 2H), 5.03 (d, 1H, J=8.8 Hz), 5.62 (d, 1H, J=8.4 Hz), 7.04 (d, 1H, J=8.4 Hz), 7.09 (d, 1H, J=8 Hz), 7.32 (s, 2H). $^1$H NMR (trans): 1.26-1.29 (m, 1H), 1.37-1.42 (m, 12H), 1.69-1.72 (m, 2H), 1.97 (s, 1H), 2.53-2.55 (m, 1H), 2.85 (t, 2H, J=6.4 Hz), 3.75-3.77 (m, 3H), 3.97-3.99 (m, 1H), 5.15 (br s, 1H), 5.86 (br s, 1H), 6.98-7.05 (m, 2H), 7.30 (s, 1H), 7.41 (s, 2H).

Example 55

Ethyl 2-(2-chloro-4-(3-(3-(tetrahydrofuran-3-yloxy)phenyl)ureido)phenyl)acetate

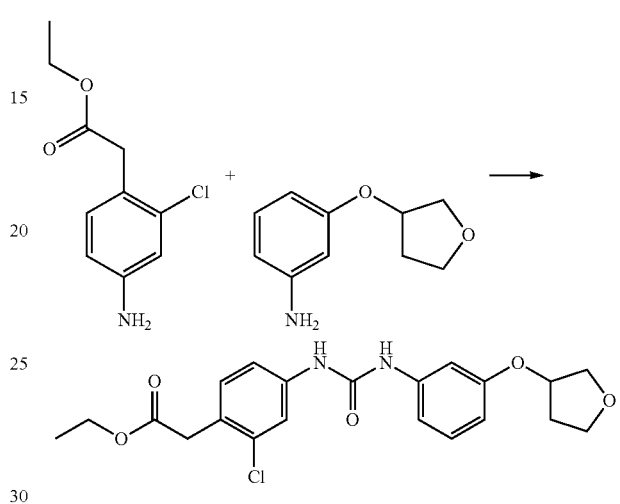

To a solution of ethyl 2-(4-amino-2-chlorophenyl)acetate (240 mg, 1.12 mmol) in dry dichloromethane (4 mL), was added triethylamine (3.13 mL, 22.47 mmol) followed by triphosgene (333 mg, 1.12 mmol) solution in dichloromethane (1 mL). The reaction mixture was stirred at room temperature for 1 h. To this mixture was then added 3-(tetrahydrofuran-3-yloxy)aniline (403 mg, 2.25 mmol) in dichloromethane (1 mL). The reaction mixture was stirred at room temperature for 4 h and concentrated. The residue was dissolved in ethyl acetate and washed with water (2×20 mL), brine (10 mL), dried and concentrated. The crude product was purified by flash column chromatography to afford the desired product as a clear oil (221 mg, 0.528 mmol, 47%). $^1$H NMR: 1.30 (t, 3H, J=7.2 Hz), 2.05-2.15 (m, 2H), 3.68 (s, 2H), 3.81-3.97 (m, 4H), 4.21 (q, 2H, J=7.2 Hz), 4.82 (d, 1H, J=1.6 Hz), 6.49 (dd, 1H, J=8 Hz, 1.6 Hz), 6.71 (d, 1H, J=7.6 Hz), 7.02-7.11 (m, 4H), 7.18 (s, 1H), 7.53 (s, 1H), 7.59 (s, 1H).

Example 56

2-(2-(2-(1H-imidazol-4-yl)phenoxy)ethyl)benzoic acid

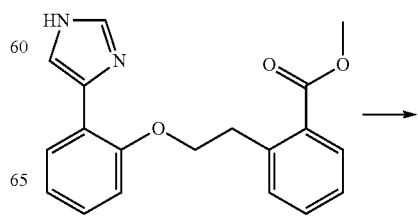

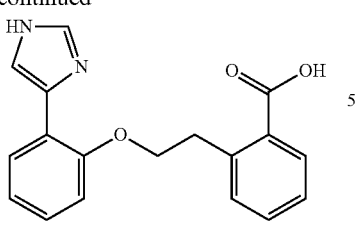

Methyl 2-(2-(2-(1H-imidazol-4-yl)phenoxy)ethyl)benzoate (30 mg, 0.093 mmol) was dissolved in methanol (3 mL) and aqueous NaOH (2M, 0.47 mL, 0.931 mmol) was added. The reaction mixture was heated at 60° C. for 16 h and methanol was evaporated under reduced pressure. The aqueous solution was neutralized to pH 7 and the aqueous layer was extracted with ethyl acetate (2×20 mL). The combined organic layers were dried and concentrated. The crude product was purified by flash column chromatography to give the desired acid as a white solid (23 mg, 0.075 mmol, 79%). $^1$H NMR (CD$_3$OD): 3.52 (t, 2H, J=6.4 Hz), 4.39 (t, 2H, J=6.4 Hz), 6.96 (t, 1H, J=7.4 Hz), 7.07 (d, 1H, J=8.4 Hz), 7.22 (t, 2H, J=7.8 Hz), 7.31 (d, 2H, J=6 Hz), 7.45 (s, 1H), 7.69-7.71 (m, 2H), 7.91 (d, 1H, J=4.8 Hz).

Example 57

2-(2-(2-(1H-imidazol-4-yl)phenoxy)ethyl)-N-methylbenzamide

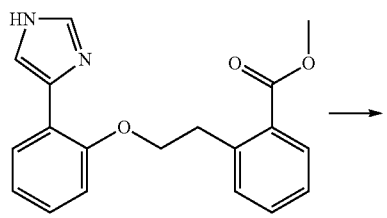

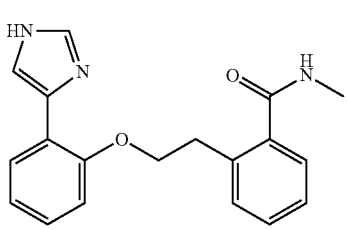

A mixture of methyl 2-(2-(2-(1H-imidazol-4-yl)phenoxy)ethyl)benzoate (30 mg, 0.093 mmol) and methylamine (2M, 3.3 mL, 6.51 mmol) in methanol was heated at 70° C. for 7 days. Methanol was removed under reduced pressure the crude product was purified by flash column chromatography to afford the desired product as a yellow solid (11 mg, 0.034 mmol, 37%). $^1$H NMR (CD$_3$OD): 2.69 (s, 3H), 3.29 (t, 2H, J=6.4 Hz), 4.36 (t, 2H, J=6.4 Hz), 6.96 (dt, 1H, J=7.6 Hz, 1.2 Hz), 7.04 (d, 1H, J=8 Hz), 7.17-7.41 (m, 6H), 7.63 (s, 1H), 7.76 (s, 1H).

Example 58

2-(2-phenylbenzo[d]oxazol-6-yl)ethanol

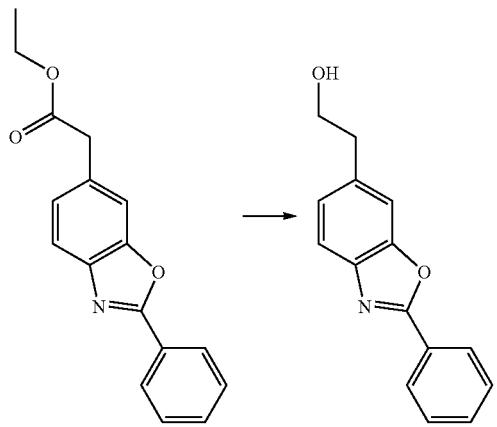 [SMILES: CCOC(=O)Cc1ccc2nc(-c3ccccc3)oc2c1 ; OCCc1ccc2nc(-c3ccccc3)oc2c1]

To the stirred solution of ethyl 2-(2-phenylbenzo[d]oxazol-6-yl)acetate (Daiichi Pharmaceuticals complay, Ltd, see EP1346982 A1, 2003)(407 mg, 1.37 mmol) in THF (12 mL) was added LAH at 10° C. The reaction mixture was allowed to stir at the same temperature for 2 h, water (0.07 mL), aqueous 15% NaOH (0.07 mL), and water (0.21 mL) were each carefully added to the mixture. The resulting slurry was filtered through a pad of Celite and concentrated in vacuo. The crude product was purified by flash column chromatography to afford the desired product as a clear gel (218 mg, 0.858 mmol, 63%). $^1$H NMR (DMSO-d$_6$): 2.75 (t, 2H, J=7 Hz), 3.59 (q, 2H, J=7 Hz), 4.62 (t, 1H, J=5.2 Hz), 6.98 (t, 1H, J=7.4 Hz), 7.03 (dd, 1H, J=7.8 Hz, 1.2 Hz), 7.29-7.34 (m, 4H), 7.71 (d, 2H, J=7.6 Hz), 10.51 (s, 1H).

Example 59

N-hydroxy-2-(1H-imidazol-4-yl)benzimidamide

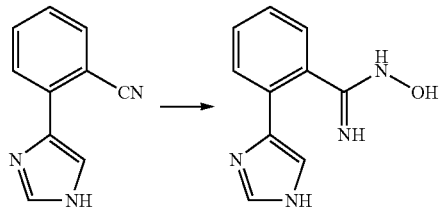 [SMILES: N#Cc1ccccc1-c1c[nH]cn1 ; N=C(NO)c1ccccc1-c1c[nH]cn1]

Hydroxylamine hydrochloride (56 mg, 0.804 mmol) was added to a solution of NaHCO$_3$ (68 mg, 0.804 mmol) in water (0.5 mL). Ethanol (1.5 mL) was added followed by 2-(1H-imidazol-4-yl)benzonitrile in THF (0.5 mL) and the reaction mixture was heated at 80° C. for 18 h. Solvents were removed under reduced pressure and the remaining solution poured into water and extracted with EtOAc (2×20 mL). The combined organic layers were washed with brine (10 mL), dried, and concentrated. The residue was purified by flash column chromatography (silica gel, 5%-30% MeOH/DCM) to afford the desired product as a white solid (20 mg, 0.099 mmol, 25%). $^1$H NMR (DMSO-d$_6$): 3.13 (s, 1H), 5.75 (s, 1H), 7.16-7.38 (m, 3H), 7.65 (s, 1H), 7.79 (s, 1H), 7.92 (d, 1H, J=7.6 Hz), 9.27 (s, 1H)

Example 60

N-(2-(1H-imidazol-4-yl)benzyl)acetamide

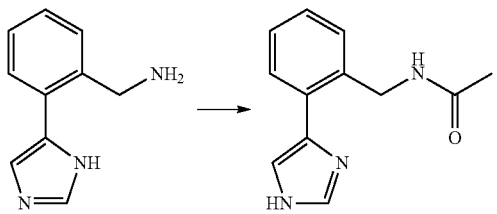 [SMILES: NCc1ccccc1-c1cnc[nH]1 ; CC(=O)NCc1ccccc1-c1c[nH]cn1]

To a solution of (2-(1H-imidazol-5-yl)phenyl)methanamine (77 mg, 0.445 mmol) in dichloromethane (3 mL) was added pyridine (0.11 mL, 1.33 mmol) and acetyl chloride (76 μL, 1.07 mmol). The reaction was stirred at room temperature for 16 h. The solvent was removed under reduced pressure. The crude product was dissolved in methanol (4 mL) and refluxed for 2 h. The solution was concentrated and the residue was purified by flash column chromatography (silica gel, 5%-20% MeOH/DCM as eluent) to afford the desired product as a white solid (12 mg, 0.056 mmol, 13%). $^1$H NMR: 2.01 (s, 3H), 4.44 (d, 2H, J=6.3 Hz), 7.21 (d, 1H, J=1.2 Hz), 7.27-7.30 (m, 2H), 7.41-7.48 (m, 2H), 7.73 (d, 1H, J=0.9 Hz), 7.96 (s, 1H).

Example 61

4-(2-(2-(1H-imidazol-4-yl)phenoxy)ethyl)-N,N-dimethylaniline

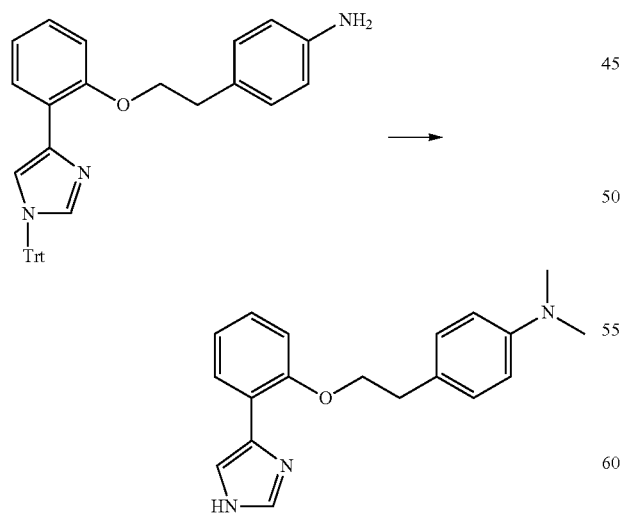

To a solution of 4-(2-(2-(1-trityl-1H-imidazol-4-yl)phenoxy)ethyl)aniline (100 mg, 0.192 mmol) in DMF (4 mL) was added NaH (15 mg, 0.575 mmol) followed by methyl iodide (24 μL, 0.383 mmol). The reaction was stirred at room temperature for 20 h and quenched with water. Methanol (3 mL) and acetic acid (1 mL) were added to the reaction mixture and heated at 80° C. for 2 h. The mixture was poured into water (10 mL) and the aqueous layer was extracted with ethyl acetate (2×30 mL). The combined organic layers were washed with water (10 mL), brine (10 mL), dried and concentrated. The crude product was purified by flash column chromatography (silica gel, 3%-7% MeOH/DCM as eluent) to afford the desired product as a gel (32 mg, 0.104 mmol, 54%). $^1$H NMR: 3.02 (s, 6H), 3.16 (t, 2H, J=6.4 Hz), 4.39 (t, 2H, J=6.4 Hz), 6.99 (t, 4H, J=7.8 Hz), 7.18-7.24 (m, 2H), 7.35 (d, 2H, J=10.8 Hz), 7.69 (s, 1H), 7.70 (d, 1H, J=7.2 Hz).

Example 62

N-(2-(1H-imidazol-4-yl)phenyl)acetamide

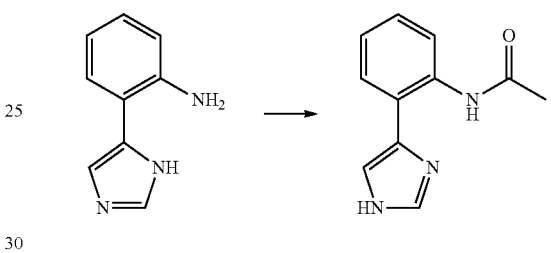

To a solution of 2-(1H-imidazol-5-yl)aniline (18 mg, 0.113 mmol) in dichloromethane (3 mL) was added pyridine (47 μL, 0.339 mmol) and acetyl chloride (19 μL, 0.271 mmol). The reaction was stirred at room temperature for 16 h. The solvent was removed under reduced pressure. The crude product was dissolved in methanol (4 mL) and refluxed for 2 h. The solution was concentrated and the residue was purified by flash column chromatography (silica gel, 5%-30% MeOH/DCM as eluent) to afford the desired product as a white solid (10 mg, 0.050 mmol, 44%). $^1$H NMR (MeOH-d$_4$): 2.17 (s, 3H), 7.05-7.26 (m, 2H), 7.46 (s, 1H), 7.62 (d, 1H, J=7.8 Hz), 7.78 (s, 1H), 8.18 (s, 1H).

Example 63

2-(1H-imidazol-4-yl)benzamide

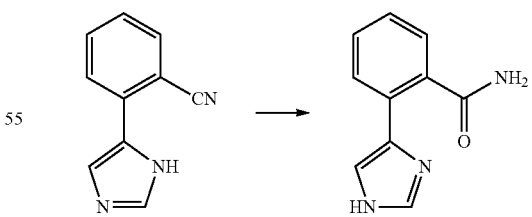

To a solution of 2-(1H-imidazol-5-yl)benzonitrile (85 mg, 0.502 mmol) in DMSO (3 mL) at room temperature was added K$_2$CO$_3$ (69 mg, 0.502 mmol) followed by H$_2$O$_2$ (30%, 1.1 mL, 10.04 mmol). After stirring for 16 h, the reaction was concentrated and the crude product was purified by flash column chromatography (silica gel, 10% MeOH/DCM followed by 10% MeOH/EtOAc) to yield the desired amide as a white solid (70 mg, 0.374 mmol, 75%). $^1$H NMR (DMSO-$d_6$): 7.20-7.35 (m, 5H), 7.66 (s, 1H), 7.75 (s, 1H), 7.83 (s, 1H), 12.01 (br s, 1H).

Example 64

4-(2-(2-(1H-imidazol-4-yl)phenoxy)ethylidene)cyclohexanecarboxamide

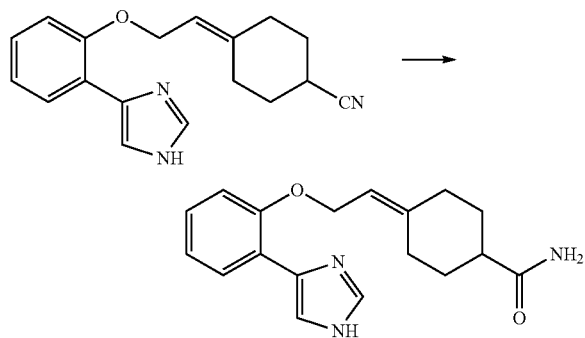

To a solution of 4-(2-(2-(1H-imidazol-4-yl)phenoxy)ethylidene)cyclohexanecarbonitrile (90 mg, 0.307 mmol) in DMSO (3 mL) at room temperature was added $K_2CO_3$ (42 mg, 0.307 mmol) followed by $H_2O_2$ (30%, 0.7 mL, 6.14 mmol). After stirring for 16 h, the reaction was concentrated and the crude product was purified by flash column chromatography (silica gel, 10% MeOH/DCM) to yield the desired amide as a white solid (40 mg, 0.129 mmol, 42%). $^1$H NMR (DMSO-$d_6$): 1.41-1.51 (m, 4H), 1.71-1.82 (m, 4H), 2.17-2.20 (m, 1H), 4.05-4.11 (m, 2H), 6.66 (d, 1H, J=10.5 Hz), 6.93 (t, 1H, J=7.5 Hz), 7.02 (d, 1H, J=8.1 Hz), 7.11 (d, 1H, J=7.2 Hz), 7.15 (s, 2H), 7.51 (s, 1H), 7.68 (s, 1H), 8.08 (d, 1H, J=7.5 Hz), 12.05 (br s, 1H).

Example 65

4-(2-(2-(1H-imidazol-4-yl)phenoxy)ethylidene)-N-(3-chlorobenzyl)cyclohexanecarboxamide

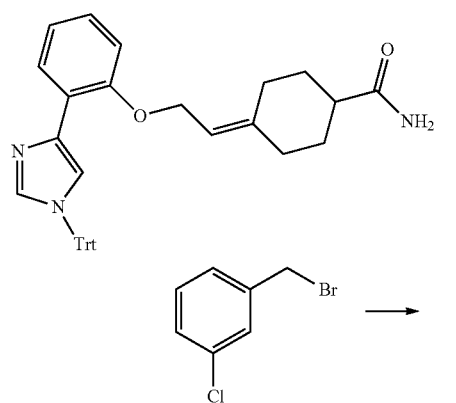

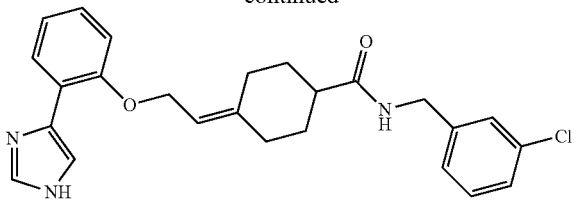

To a stirred solution of 4-(2-(2-(1-trityl-1H-imidazol-4-yl)phenoxy)ethylidene)cyclohexanecarboxamide (177 mg, 0.320 mmol) in anhydrous DMF (3 mL) at 0° C. was added NaH (9.0 mg, 0.384 mmol). The resulting suspension was allowed to stir at room temperature for 45 min. To the resulting solution was added 3-chlorobenzyl bromide (79 mg, 0.384 mmol). After stirring overnight, the reaction mixture was carefully diluted with water and extracted with ethyl acetate (2×10 mL). The combined organic layers were washed with water, brine and dried ($Na_2SO_4$). The solvent was removed under reduced pressure and the crude product was taken to next step without further purification. To a solution of the crude ether was added acetic acid (1.0 mL) and MeOH (4.0 mL). The solution was stirred at 80° C. for 2 h. The solution was allowed to cool to room temperature and the pH was adjusted to ~10 with 10% NaOH (aq). The aqueous phase was extracted with EtOAc (3×20 mL). The combined organic layer were washed with water, brine, and dried. The solvent was removed in vacuo to afford the crude residue, which was purified by flash column chromatography on silica gel to afford the desired product (47 mg, 0.108 mmol, 34%). $^1$H NMR (DMSO-$d_6$): 1.44-1.52 (m, 4H), 1.69-1.79 (m, 4H), 2.19-2.23 (m, 1H), 3.85 (s, 2H), 4.05-4.11 (m, 2H), 6.63 (d, 1H, J=10.5 Hz), 6.88-6.93 (m, 2H), 6.99 (t, 1H, J=6.8 Hz), 7.09-7.11 (m, 2H), 7.18 (d, 1H, J=7.6 Hz), 7.25 (t, 1H, J=7.6 Hz), 7.41-7.48 (m, 2H), 7.65 (s, 1H), 7.93 (s, 1H).

Example 66

(E)-N-benzylidene-2-(1H-imidazol-5-yl)aniline

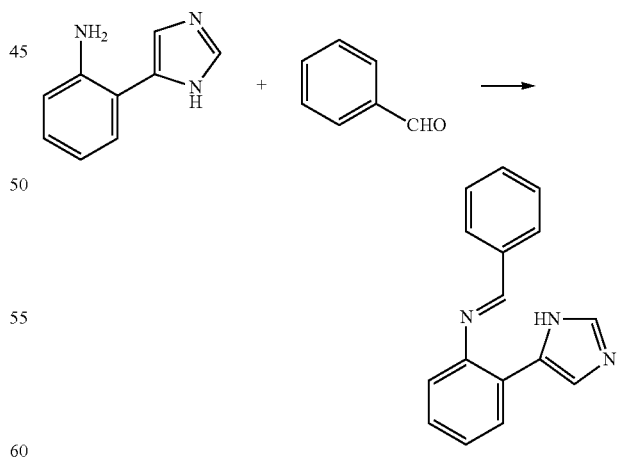

2-(1H-imidazol-5-yl)aniline 965 mg, 0.410 mmol) was dissolved in acetic acid (2 mL) and benzaldehyde (43 mg, 0.410 mmol) was added. The reaction was stirred for 1 h at room temperature, diluted with 30 mL ethyl acetate, and extracted with 5% HCl (56 mL from 50 mL water+6 mL 12N HCl). The aqueous layer was basified with $K_2CO_3$ (add solid portionwise until PH=7), then extracted with ethyl acetate (30 mL×2). The organic layer was evaporated under reduced pressure and the residue was separated by column chromatography to afford the desired product (9 mg, 0.036 mmol, 9%). $^1$H NMR (MeOH-d$_4$): 7.11-7.25 (m, 3H), 7.41-7.48 (m, 2H), 7.61-7.67 (m, 2H), 7.78 (s, 1H), 8.32 (s, 1H), 8.39 (s, 1H), 8.83 (s, 1H).

Example 67

(2S,5R)-2-(2-iodophenethyl)-5-isopropyl-3,6-dimethoxy-2,5-dihydropyrazine

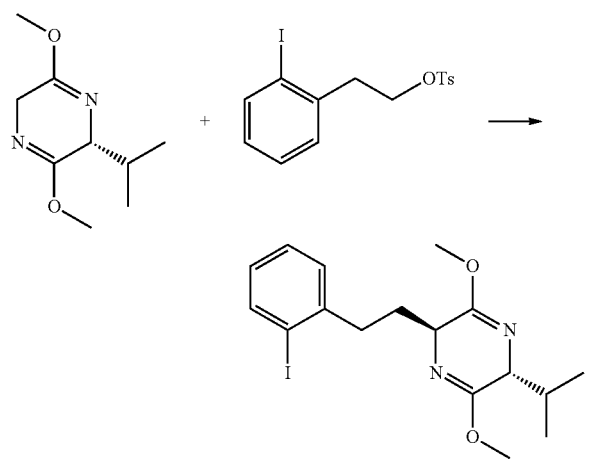

n-BuLi (2.5 M, 0.72 mL, 1.79 mmol) in hexane was added to a solution of Schollkopf chiral auxiliary (300 mg, 1.63 mmol) in anhydrous THF (8 mL) at −78° C. The solution was stirred at −78° C. for 45 min and 2-iodophenethyl 4-methylbenzenesulfonate (721 mg, 1.79 mmol) was added. The reaction mixture was stirred at this temperature for 3 h before it was allowed to reach ambient temperature overnight. The reaction was quenched by addition of saturated solution of ammonium chloride. The aqueous layer was extracted with ethyl acetate (2×30 mL). The combined organic layers were washed with brine, dried over Na$_2$SO$_4$ and concentrated. The crude product was used directly in the Negishi Coupling.

Example 68

(2R,5S)-2-isopropyl-3,6-dimethoxy-5-(2-(1-trityl-1H-imidazol-4-yl)phenethyl)-2,5-dihydropyrazine

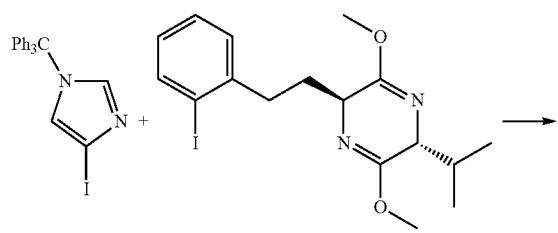

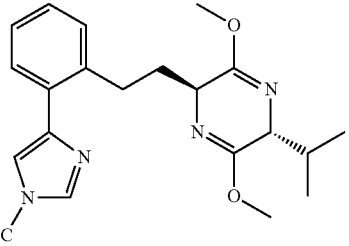

To a stirred solution of 4-iodo-1-trityl-1H-imidazole (300 mg, 0.688 mmol) in anhydrous THF (4 mL) at room temperature was added EtMgBr (1.0 M in THF, 0.802 mmol, 0.8 mL) dropwise, under an atmosphere of N$_2$. The resulting solution was allowed to stir for 90 min and anhydrous ZnCl$_2$ (109 mg, 0.802 mmol) was added. The resulting white suspension was allowed to stir for 90 min and a solution of the (2S,5R)-2-(2-iodophenethyl)-5-isopropyl-3,6-dimethoxy-2,5-dihydropyrazine (237 mg, 0.573 mmol) in THF (1 mL) was added followed by the immediate addition of Pd(PPh$_3$)$_4$ (33 mg, 0.029 mmol). The reaction mixture was allowed to stir at 70° C. for 12 h under an atmosphere of N$_2$. After cooling to room temperature, the solution was diluted with CH$_2$Cl$_2$ (10 mL) and the organic layer was washed with an EDTA (aq) buffer (pH=9) (2×5 mL) and brine. The organic layer was dried (Na$_2$SO$_4$) and concentrated under reduced pressure. The crude residue was purified by flash column chromatography to afford the desired product as yellow oil (87 mg, 0.146 mmol, 29%). $^1$H NMR: 0.70 (d, 3H, J=6 Hz), 1.02 (d, 3H, J=7.2 Hz), 1.72-1.81 (m, 1H), 2.01-2.08 (m, 1H), 2.15-2.24 (m, 1H), 2.80-3.09 (m, 2H), 3.54 (s, 3H), 3.56 (s, 3H), 3.86-3.91 (m, 214), 6.94 (d, 1H, J=1.2 Hz), 7.15-7.22 (m, 9H), 7.27 (d, 1H, J=1.6 Hz), 7.32-7.36 (m, 8H), 7.48 (d, 1H, J=1.2 Hz), 7.58-7.61 (m, 1H).

Example 69

Lithium (S)-4-(2-(1H-imidazol-4-yl)phenyl)-2-aminobutanoate

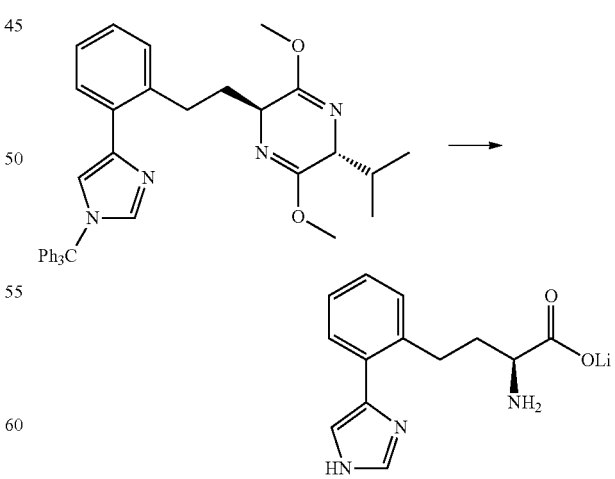

(2R,5S)-2-isopropyl-3,6-dimethoxy-5-(2-(1-trityl-1H-imidazol-4-yl)phenethyl)-2,5-dihydropyrazine (87 mg, 0.146 mmol) was dissolved in ethanol (3 mL) and concentrated HCl (few drops) was added. The mixture was heated at 70° C. for 2 h and concentrated. The residue was taken up in MeOH/water (3:1, 4 mL) and LiOH.H₂O (6 mg, 0.146 mmol) was added. The mixture was stirred at room temperature for 18 h and concentrated. The crude product was washed with dichloromethane, hexanes, suspended in methanol and filtered. The filtrate was concentrated to afford the desired product (30 mg, 0.120 mmol, 83%) as a white solid. ¹H NMR (MeOH-d₄): 0.84-1.00 (m, 2H), 1.86-1.94 (m, 1H), 2.77-2.85 (m, 1H), 4.26-4.28 (m, 1H), 7.10-7.19 (m, 3H), 7.23-7.28 (m, 1H), 7.41 (d, 1H, J=2.8 Hz), 7.64 (s, 1H).

Example 70

(E)-Ethyl 3-(2-iodophenyl)acrylate

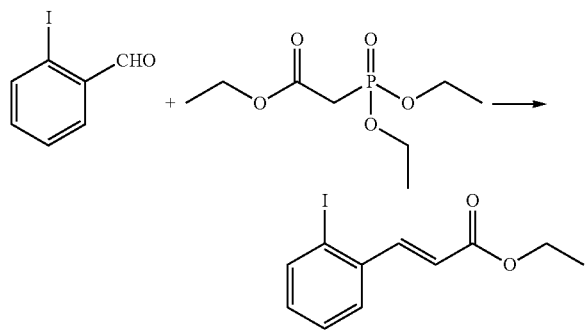

To a dispersion of sodium hydride (42 mg, 1.66 mmol) in THF (8 mL), triethyl phosphonoacetate (0.33 mL, 1.66 mmol) was added dropwise. The mixture was stirred until it was colorless before 2-iodobenzaldehyde (350 mg, 1.51 mmol) was added. The solution was stirred at ambient temperature until the reaction was complete (TLC). The reaction was quenched by the addition of saturated aqueous NH₄Cl and the aqueous layer was extracted with ethyl acetate (2×30 mL). The combined organic extracts were washed with brine, dried and concentrated. The crude product was purified by flash chromatography on silica gel to afford the desired product (421 mg, 1.39 mmol, 92%) as a white solid. ¹H NMR: 1.35 (t, 3H, J=7.2 Hz), 4.28 (d, 2H, J=7.2 Hz), 6.31 (d, 1H, J=15.9 Hz), 7.04 (dr, 1H, J=7.8 Hz, 1.5 Hz), 7.35 (t, 1H, J=7.5 Hz), 7.55 (dd, 1H, J=7.8 Hz, 1.5 Hz), 7.87-7.92 (m, 2H)

Example 71

General Procedure for the Synthesis of Ethers by the SN2 alkylation or Mitsunobu Reaction

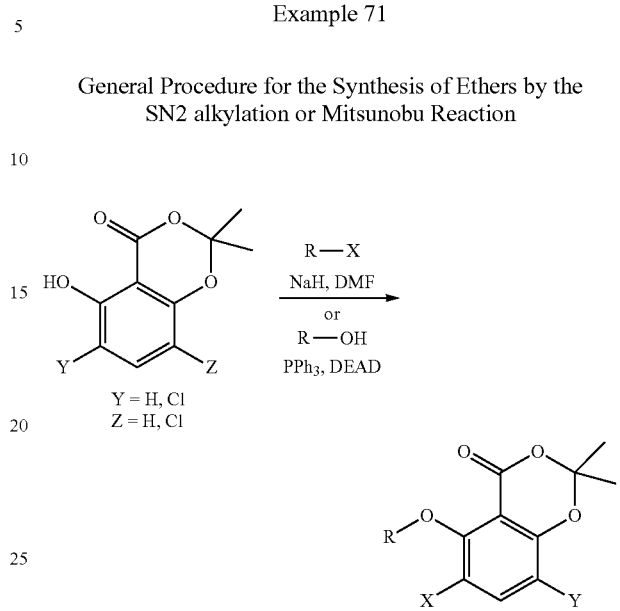

To a stirred solution of the phenol (3.89 mmol), the primary alcohol, (3.89 mmol), and triphenyl phosphine (4.28 mmol) in anhydrous THF (15 mL) at 0° C. was added DEAD (40% in toluene, 4.28 mmol, 1.95 mL) dropwise. The yellow solution was allowed to warm to room temperature and stirring was continued overnite. After evaporating the solvent under reduced pressure the crude residue was dissolved in DCM (15 mL). The organic layer was washed with 10% NaOH (2×10 mL), water and brine. The organic phase was dried (Na₂SO₄), filtered and evaporated under reduced pressure. The crude residue was purified by column chromatography on silica gel using hexanes/EtOAc as the eluent.

The following compounds were prepared according to the general procedure of Example 71, by substituting the appropriate starting materials:

| Compound | Name | Yield (%) | ¹H NMR |
|---|---|---|---|
| (structure) | 5-(4-chlorophenethoxy)-2,2-dimethyl-4H-benzo[d][1,3]dioxin-4-one | 59 | 1.68 (s, 6H), 3.14 (t, 2H, J = 6.6 Hz), 4.19 (t, 2H, J = 6.6 Hz), 6.50-6.54 (m, 2H), 7.24-7.26 (doublet merged with CHCl₃, 2H), 7.34 (d, 2H, J = 8.4 Hz), 7.38 (d, 1H, J = 8.4 Hz) |
| (structure) | 5-(2-(cyclohex-1-en-1-yl)ethoxy)-2,2-dimethyl-4H-benzo[d][1,3]dioxin-4-one | 65 | 1.56-1.62 (m, 4H), 1.75 (s, 6H), 2.00-2.05 (m, 4H), 2.54 (t, 2H, J = 6.8 Hz), 4.14 (t, 2H, J = 6.8 Hz), 5.55 (s, 1H), 6.53 (d, 1H, J = 8.2 Hz), 6.62 ((d, 1H, J = 8.0 Hz), 7.41 (t, 1H, J = 8.0 Hz) |

| Compound | Name | Yield (%) | ¹H NMR |
|---|---|---|---|
| | 6,8-dichloro-5-(2-cyclohexylethoxy)-2,2-dimethyl-4H-benzo[d][1,3]dioxin-4-one | 52 | 0.92-1.00 (m, 2H), 1.14-1.31 (m, 3H), 1.58-1.72 (m, 4H), 1.76 (s, 6H), 1.76-1.81 (m, 4H), 4.11 (t, 2H, J = 6.7 Hz), 7.64 (s, 1H) |
| | 6-chloro-5-(2-cyclohexylethoxy)-2,2-dimethyl-4H-benzo[d][1,3]dioxin-4-one | 68 | 0.94-1.01 (m, 2H), 1.14-1.28 (m, 3H), 1.45-1.63 (m, 4H), 1.70 (s, 6H), 1.75-1.82 (m, 4H), 4.12 (t, 2H, J = 6.6 Hz), 6.70 (d, 1H, J = 8.8 Hz), 7.52 (d, 1H, J = 8.8 Hz) |
| | 5-(2-cyclohexylethoxy)-2,2-dimethyl-4H-benzo[d][1,3]dioxin-4-one | 69 | 1.10-2.20 (m, 13H) 1.70 (s, 6H), 4.06 (t, 2H, J = 6.8 Hz), 6.47 (dd, 1H, J = 8.4, 0.8 Hz), 6.56 (d, 1H, J = 7.6 Hz), 6.47 (t, 1H, J = 7.6 Hz), |
| | 2,2-dimethyl-5-(2-(pyridin-4-yl)ethoxy)-4H-benzo[d][1,3]dioxin-4-one | 96 | 1.68 (s, 6H), 3.17 (t, 2H, J = 6.36 Hz), 4.24 (t, 2H, J = 6.36 Hz), 6.53 (d, 2H, J = 8.40 Hz), 7.33-7.67 (m, 3H), 8.51 (d, 2H, J = 5.68) |

Example 72

5-(3,3-dimethylbutoxy)-2-hydroxybenzaldehyde

To a solution of the 2,5-dihydroxybenzaldehyde in DMF was added K₂CO₃ at room temperature and the mixture was stirred for 10 min. To this solution 1-iodo-3,3-dimethylbutane was added. After stirring at 70° C. for 4 h, the solvent was removed under reduced pressure and reaction mixture was diluted with ethyl acetate. After washing with water, the organic layer was dried over Na₂SO₄ and concentrated under vacuum. The crude product was purified by column chromatography to give desired product in 65% yield. ¹H NMR: 0.97 (s, 9H), 1.73 (t, 2H, J=7.2 Hz), 4.05 (t, 2H, J=7.2 Hz), 6.88 (d, 1H, J=9.2 Hz), 7.09 (dd, 1H, J=9.2, 3.2 Hz), 7.35 (d, 1H, J=3.2 Hz), 10.39 (s, 1H)

Example 73

General Procedure for the Synthesis of 3-Substituted-2-(1H-imidazol-5-yl)phenols

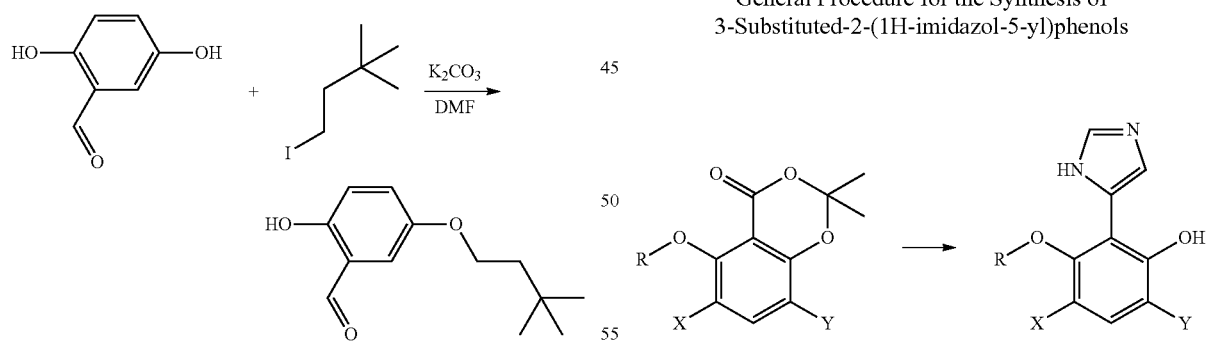

To a solution of the appropriate acetonide (0.627 mmol) in CH₂Cl₂ (6 mL) at −78° C. was added DIBAL-H (1.88 mmol, 1M in CH₂Cl₂). After stirring for 2 h at −78° C. the reaction was quenched by adding 1M HCl (2 mL) and MeOH (2 mL) and the reaction was allowed to warm to room temperature. H₂O (10 mL) was added and the aqueous phase was extracted with CH₂Cl₂ (3×35 mL). The combined organic layers were dried over Na₂SO₄ and concentrated under reduced pressure to afford the crude residue which was purified by flash column chromatography on silica gel using hexanes/EtOAc as the eluent. To a stirred solution of the appropriate aldehyde (0.38 mmol) in THF (2 mL) at room temperature was added NH₃ (2.0 mL, 2.0 M in EtOH). The solution was allowed to stir overnight and 1-(isocyanomethylsulfonyl)-4-methylbenzene (0.38 mmol) and piperazine (0.57 mmol) were added. Stirring was continued for an additional 48 h. The solvent was removed under reduced pressure and the crude residue was purified by column chromatography on silica gel afford the desired product.

The following compounds were prepared according to the general procedure of Example 73, by substituting the appropriate starting materials:

| No. | Compound | Name | Yield (%) | ¹H NMR |
|---|---|---|---|---|
| 1111 | | 4,6-dichloro-3-(2-chlorophenethoxy)-2-(1H-imidazol-5-yl)phenol | 59 | 3.29 (t, 2H, J = 6.7 Hz), 4.12 (t, 2H, J = 6.7 Hz), 7.21-7.25 (m, 3H), 7.37-7.38 (m, 2H), 7.70 (s, 1H), 9.54 (br s, 1H) |
| 1086 | | 4,6-dichloro-3-(2-cyclohexylethoxy)-2-(1H-imidazol-5-yl)phenol | 49 | 0.95 (q, 2H, J = 11.1 Hz), 1.13-1.28 (m, 2H), 1.48-1.56 (m, 1H), 1.64-1.76 (m, 8H), 3.93 (t, 2H, J = 6.9 Hz), 7.29 (s, 1H), 7.79 (s, 2H) |
| 1182 | | 3-(2-(cyclohex-3-en-1-yl)ethoxy)-2-(1H-imidazol-5-yl)phenol hydrochloride | 35 | (dmso-d₆) 1.16-1.26 (m, 1H), 1.65-1.73 (m, 5H), 1.98-2.09 (m, 3H), 4.11 (t, 2H, J = 6.5 Hz), 5.59-5.66 (m, 2H), 6.64-6.68 (m, 2H), 7.21 (t, 1H, J = 8.4 Hz), 7.70 (s, 1H), 8.99 (s, 1H), 10.59 (br s, 1H) |
| 1170 | | 2-chloro-6-(1H-imidazol-5-yl)phenol | 41 | 6.79 (t, 1H, J = 7.8 Hz), 7.24 (doublet merged with CHCl₃, 1H), 7.40 (s, 2H), 7.76 (s, 1H), 9.36 (br s, 1H), 12.96 (br s, 1H) |
| 1160 | | 3-(3-chlorophenethoxy)-2-(1H-imidazol-5-yl)phenol | 42 | 3.20 (t, 2H, J = 6.6 Hz), 4.36 (t, 2H, J = 6.8 Hz), 6.47 (d, 1H, J = 8.4 Hz), 6.68 (d, 1H, J = 8.4 Hz), 7.09 (t, 1H, J = 8.2 Hz), 7.14-7.26 (m, 4H), 7.33 (s, 1H), 7.39 (s, 1H), 7.70 (1H), 9.02 (br s, 1H) |
| 1172 | | 4-chloro-3-(2-cyclohexylethoxy)-2-(1H-imidazol-5-yl)phenol | 38 | 0.92-1.00 (m, 2H), 1.15-1.30 (m, 3H), 1.49-1.55 (m, 1H), 1.65-1.81 (m, 7H), 3.94 (t, 2H, J = 7.0 Hz), 6.72 (d, 1H, J = 8.8 Hz), 7.13 (d, 1H, J = 8.8 Hz), 7.77 (s, 1H), 7.78 (s, 1H), 9.46 (br s, 1H), 13.22 (br s, 1H) |
| 1235 | | 2-(1H-imidazol-5-yl)-3-(2-(tetrahydrofuran-2-yl)ethoxy)phenol | 32 | 1.52-1.63 (m, 2H), 1.90-2.21 (m, 4H), 3.72-3.78 (m, 1H), 3.88-3.91 (m, 1H), 4.18 (t, 2H, J = 7.0 Hz), 6.41 (d, 1H, J = 8.0 Hz), 6.64 (d, 1H, J = 8.0 Hz), 7.07 (t, 1H, J = 8.4 Hz), 7.67 (s, 1H), 7.70 (s, 1H), 10.03 (br s, 1H) |

-continued

| No. | Compound | Name | Yield (%) | $^1$H NMR |
|---|---|---|---|---|
| 1232 | | N-(4-(2-(3-hydroxy-2-(1H-imidazol-5-yl)phenoxy)ethyl)phenyl)acetamide | 39 | 2.21 (s, 3H), 3.16 (t, 2H, J = 6.0 Hz), 4.36 (t, 2H, J = 6.0 Hz), 6.52 (d, 1H, J = 8.4 Hz), 6.62 (d, 1H, J = 8.0 Hz), 7.03 (t, 1H, J = 8.2 Hz), 7.25-7.40 (m, 5H), 7.48 (s, 1H), 7.49 (s, 1H), 10.77 (br s, 1H) |
| 1231 | | 2-(1H-imidazol-5-yl)-3-(2-morpholinoethoxy)phenol | 24 | 2.57 (s, 4H), 2.87 (t, 2H, J = 5.6 Hz), 3.73 (t, 4H, J = 4.6 Hz), 4.20 (t, 2H, J = 5.6 Hz), 6.45 (d, 1H, J = 8.4 Hz), 6.66 (d, 1H, J = 8.0 Hz), 7.08 (t, 1H, J = 8.2 Hz), 7.68 (s, 1H), 8.03 (s, 1H) |
| 1240 | | tert-butyl 4-(2-(3-hydroxy-2-(1H-imidazol-5-yl)phenoxy)ethyl)piperidine-1-carboxylate | 41 | 1.47 (s, 9H), 1.70-1.87 (m, 7H), 2.62 (t, 2H, J = 6.2 Hz), 3.10-3.13 (m, 2H), 4.13 (t, 2H, J = 6.0 Hz), 6.44 (d, 1H, J = 8.0 Hz), 6.65 (d, 1H, J = 8.0 Hz), 7.05-7.10 (m, 1H), 7.67 (s, 1H), 7.70 (s, 1H) |
| 1148 | | 3-(4-chlorophenethoxy)-2-(1H-imidazol-5-yl)phenol | 25 | 3.18 (t, 2H, J = 6.6 Hz), 4.34 (t, 2H, J = 6.6 Hz), 6.46 (d, 1H, J = 8.0 Hz), 6.66 (d, 1H, J = 8.0 Hz), 7.08 (t, 1H, J = 8.0 Hz), 7.21-7.29 (m, 5H), 7.37 (s, 1H), 9.48 (br s, 1H) |
| 1039 | | 3-(2-cyclohexylethoxy)-2-(1H-imidazol-5-yl)phenol | 46 | 0.90-1.05 (m, 2H), 1.10-1.30 (m, 3H), 1.42-1.58 (m, 1H), 1.66-1.82 (m, 7H), 4.09 (t, 2H, J = 6.8 Hz), 6.45 (d, 1H, J = 8.4 Hz), 6.63 (d, 1H, J = 8.4 Hz), 7.06 (t, 1H, J = 8.4 Hz), 7.66 (s, 1H), 7.69 (s, 1H), 9.69 (br s, 1H) |
| 1107 | | 3-(2-cyclohexylethoxy)-2-(1H-imidazol-5-yl)phenol | 26 | 0.93 (s, 9H), 1.72 (t, 2H, J = 7.2 Hz), 3.97 (t, 2H, J = 7.6 Hz), 6.66-6.79 (m, 2H), 7.30 (s, 1H), 7.41 (s, 1H), 7.59 (s, 1H), 7.94 (s, 2H) |
| 1106 | | 4-(2-(2-fluorophenethoxy)phenyl)-1H-imidazole | 37 | 3.22 (t, 1H, J = 6.4 Hz), 4.36 (t, 1H, J = 6.4 Hz), 6.91-7.34 (m, 7H), 7.40 (s, 1H), 7.50 (s, 1H), 7.44 (d, 1H, J = 6.4 Hz) |

| No. | Compound | Name | Yield (%) | $^1$H NMR |
|---|---|---|---|---|
| 1238 | 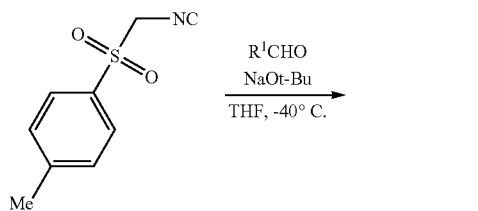 | 2-(1H-imidazol-5-yl)-3-(2-(pyridin-4-yl)ethoxy)phenol | 11 | 3.23 (t, 2H, J = 4.80 Hz), 4.45 (t, 2H, J = 6.03 Hz), 6.49 (d, 1H, J = 6.0 Hz), 6.68 (d, 1H, J = 6.30 Hz), 7.10 (t, 1H, J = 6.0 Hz), 7.19 (s, 1H), 7.26 (s, 1H), 7.27 (s, 1H), 7.68 (s, 1H), 8.50 (d, 1H, J = 3.60 Hz), 9.86 (s, 1H) |

Example 74

General Procedure for the Synthesis of 3-Substituted 5-phenyl-1H-imidazoles by the Van Leusen Reaction

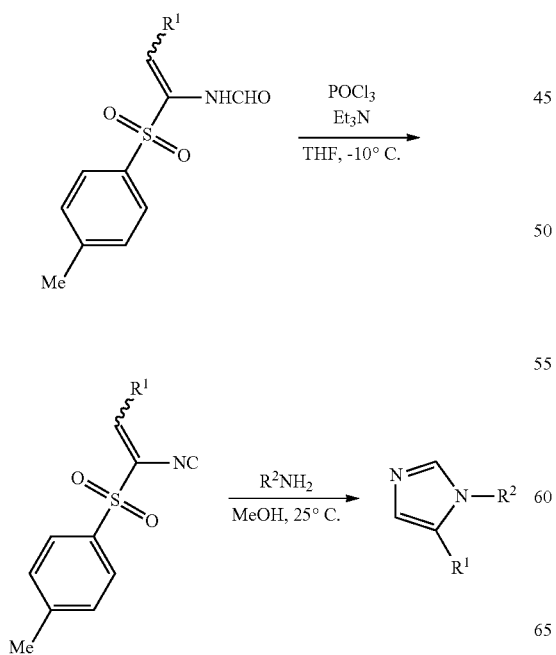

To a stirred solution of NaOt-Bu (124.0 mg, 1.3 mmol) in THF (12 mL) at −40° C., was added a solution of tosylmethyl isocyanide (390.0 mg, 2.0 mmol) in THF (6.0 mL). The solution was allowed to stir at −40° C. for 20 min and a solution of the aldehyde (1.1 mmol) in THF (6.0 mL) was added while maintaining the temperature at −40° C. The resulting mixture was allowed to stir for an additional 30 min and was poured into ice water (20 mL). The solution was neutralized with acetic acid (pH=7) and the aqueous phase was extracted with DCM (2×20 mL). The combined organic layers were dried (Na$_2$SO$_4$) and concentrated under reduced pressure to afford the crude product, which was filtered through a small plug of silica gel and used in next step.

To a stirred solution of the resulting crude formamide in THF (10 mL) at −5° C. was added Et$_3$N (1.39 mL, 10.0 mmol). The reaction mixture was cooled to −10° C. and POCl$_3$ (0.27 mL, 3.0 mmol) was added after 15 min. The solution was allowed to stir at −10° C. for an additional 30 min. The reaction mixture was poured into ice water (15 mL) and the aqueous layer was extracted with DCM (2×20 mL). The combined organic layers were dried (Na$_2$SO$_4$) and concentrated under reduced pressure. The crude residue was dissolved in MeOH (5 mL). The appropriate amine (2.0 mmol) was added and the reaction mixture was stirred for 12 h at 25° C. The solvent was removed under reduced pressure and the resulting residue was purified by column chromatography on silica gel.

The following compounds were prepared according to the general procedure of Example 74, by substituting the appropriate starting materials:

| No. | Compound | Name | Yield (%) | $^1$H NMR |
|---|---|---|---|---|
| 1060 | 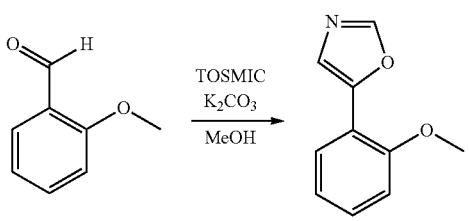 | 5-(2-(benzyloxy)-5-chlorophenyl)-1-cyclohexyl-1H-imidazole | 95 | 1.13-1.19 (m, 3H), 1.44-1.52 (m, 2H),. 1.63-1.85 (m, 5H), 3.64-3.70 (m, 1H), 5.01 (s, 2H), 6.96 (s, 1H), 7.21 (d, 2H, J = 6.0 Hz), 7.25 (d, 1H, J = 2.5 Hz), 7.29-7.33 (m, 4H), 7.61 (s, 1H) |
| 1115 | 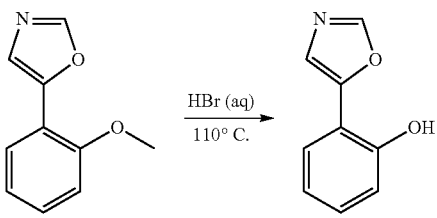 | 5-phenyl-1H-imidazol-1-amine | 22 | CD$_3$OD: 6.99 (s, 1H), 7.08 (s, 1H), 7.25-7.45(m, 5H) |

Example 75

5-(2-methoxyphenyl)oxazole

To a solution of Anisaldehyde (2.0 mmol) in MeOH (5.0 mL), was added K$_2$CO$_3$ (2.2 mmol) and TOSMIC (1.10 mmol) and the reaction was allowed to stir at 80° C. in a sealed vial. After the reaction was over, the methanol was removed and the crude product was absorbed in silica gel and purified by column chromatography. The product was isolated in 83% yield as colorless oil. $^1$H NMR: 3.91 (s, 3H), 6.94 (d, 1H, J=8.4 Hz), 7.01 (t, 1H, J=7.6 Hz), 6.94 (t, 1H, J=8.4 Hz), 7.53 (s, 1H), 7.75 (d, 1H, J=8.0 Hz), 7.53 (s, 1H).

Example 76

2-(oxazol-5-yl)phenol

A solution of the appropriate anisole derivative (2.52 mmol) in 48% HBr (5 mL) was stirred at 110° C. for 16 h. The solution was allowed to cool to room temperature and was poured into saturated NaHCO$_3$ (10 mL). The aqueous phase was extracted with ethyl acetate (3×30 mL). The combined organic layers were dried over sodium sulfate and concentrated under reduced pressure to afford the crude residue, which was purified by column chromatography on silica gel to afford the desired product in 24% yield. $^1$H NMR: 6.94 (d, 1H, J=8.4 Hz), 7.01 (t, 1H, J=7.6 Hz), 6.94 (t, 1H, J=8.4 Hz), 7.53 (s, 1H), 7.75 (d, 1H, J=8.0 Hz), 7.53 (s, 1H).

Example 77

Ethyl 2-(4-cyanocyclohexylidene)acetate

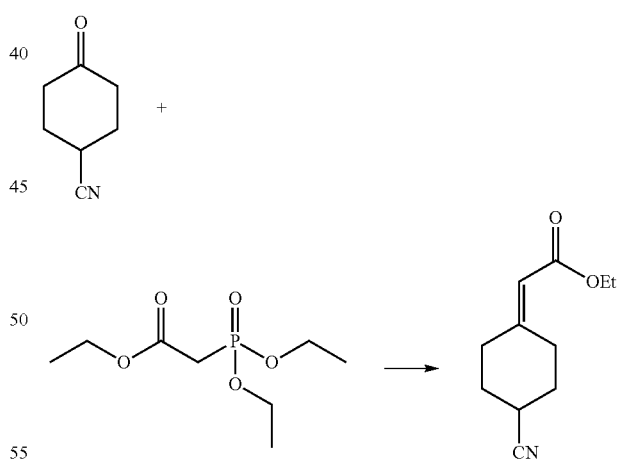

To a dispersion of sodium hydride (132 mg, 5.51 mmol) in THF (15 mL), triethyl phosphonoacetate (1.10 mL, 5.51 mmol) was added dropwise. The mixture was stirred until it was colorless before 4-oxocyclohexanecarbonitrile (Astrazeneca AB, see WO2007/13848 A1, 2007) (617 mg, 5.01 mmol) was added. The solution was stirred at ambient temperature until the reaction was complete (TLC). The reaction was quenched by the addition of saturated aqueous NH$_4$Cl and the aqueous layer was extracted with ethyl acetate (2×40

Example 78

4-(2-Hydroxyethylidene)cyclohexanecarbonitrile

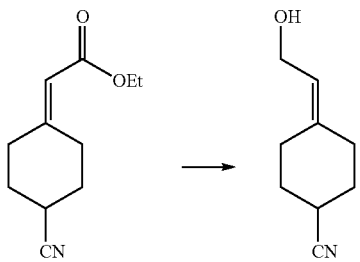 [SMILES: CCOC(=O)C=C1CCC(C#N)CC1 ; N#CC1CCC(=CCO)CC1]

To the stirred solution of crude ethyl 2-(4-cyanocyclohexylidene)acetate in THF (12 mL) was added LAH (187 mg, 4.91 mmol) at 10° C. The reaction mixture was allowed to stir at the same temperature for 2 h, water (1.2 mL), aqueous 15% NaOH (1.2 mL), and water (4.0 mL) were each carefully added to the mixture. The resulting slurry was filtered through a pad of Celite and concentrated in vacuo. The crude product was purified by flash column chromatography to afford the desired product as a mixture of isomers. (216 mg, 1.43 mmol, 32%). $^1$H NMR: 0.94-1.02 (m, 1H), 1.31-1.41 (m, 5H), 1.46-1.61 (m, 9H), 1.73-2.00 (m, 11H), 2.09-2.23 (m, 3H), 2.34-2.48 (m, 3H), 2.78-2.82 (m, 1H), 2.92-2.94 (m, 1H), 3.67-3.72 (m, 3H), 4.15 (d, 2H, J=6.8 Hz), 5.45 (t, 1H, J=6.8 Hz).

Example 79

2-(2-(1H-imidazol-4-yl)phenoxy)-1-cyclohexylethanol

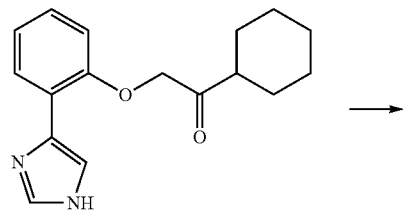

To a mixture 2-(2-(1H-imidazol-4-yl)phenoxy)-1-cyclohexylethanone (130 mg, 0.457 mmol) in MeOH (4 mL) at 0° C., was added NaBH$_4$ (52 mg, 1.37 mmol) and the solution was allowed to stir at room temperature for 1 h. The solvent was distilled off and the crude was acidified with dil HCl (2 N) and again basified by saturated aqueous NaHCO$_3$ solution, the product was extracted with EtOAc (3×15 mL). The combined organic extracts were washed with brine, dried, and concentrated under reduced pressure to afford the final product (118 mg, 0.413 mmol, 90%). $^1$H NMR (DMSO-d$_6$): 1.04-1.21 (m, 5H), 1.49-1.50 (m, 1H), 1.61-1.68 (m, 4H), 1.85 (d, 1H, J=12.4 Hz), 3.62-3.65 (m, 1H), 3.96 (d, 1H, J=9.6 Hz, 6.4 Hz), 4.07 (dd, 1H, J=10 Hz, 3.2 Hz), 4.97 (br s, 1H), 6.93 (t, 1H, J=7.2 Hz), 7.03 (d, 1H, J=7.6 Hz), 7.12 (d, 1H, J=7.2 Hz), 7.67 (s, 1H), 7.70 (s, 1H), 8.03 (s, 1H), 12.01 (br s, 1H).

Example 80

General Procedure for De-Methylation with Hydrobromic Acid

A solution of ether (0.198 mmol) in hydrobromic acid (48% aq, 2 mL) was stirred at 100° C. overnight (14 h). After cooling to room temperature, the excess of hydrobromic acid was distilled off and the crude was diluted with 10% aq NaOH solution and washed with toluene to remove unreacted methyl ether. The aqueous layer was acidified with HCl and then basified with said. K$_2$CO$_3$ solution. The product was extracted with EtOAc (3×15 mL). The combined organic extract was dried over sodium sulfate and concentrated under reduced pressure to afford the final product.

The following compounds were prepared according to the general procedure of Example 80, by substituting the appropriate starting materials:

| No. | Compound | Name | Yield (%) | $^1$H NMR |
|---|---|---|---|---|
| 1017 | (structure) | 5H-imidazo[5,1-a]isoindol-9-ol | 68 | CD$_3$OD: 5.07 (s, 2H), 6.80 (d, 1H, J = 8.07 Hz), 6.94 (dd, 1H, J = 6.84 Hz, 0.72 Hz), 7.0 (s, 1H), 7.12 (t, 1H, J = 7.80 Hz), 7.80 (s, 1H) |

| No. | Compound | Name | Yield (%) | $^1$H NMR |
|---|---|---|---|---|
| 1038 | | 4-chloro-2-(imidazo[1,2-a]pyrazin-3-yl)phenol | 11 | 7.07 (d, 1H, J = 6.57 Hz), 7.23 (dd, 1H, J = 1.8 Hz, 4.8 Hz), 7.58 (d, 1H, J = 1.77 Hz), 7.98 (s, 1H), 8.00 (d, 1H, J = 3.36 Hz), 8.13 (d, 1H, J = 3.30 Hz), 9.11 (s, 1H), 12.10 (s, 1H) |

Example 81

1-(benzofuran-3-yl)-2-(2-(1-trityl-1H-imidazol-4-yl)phenoxy)ethanone

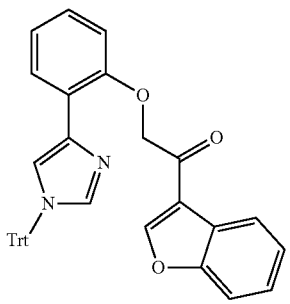

To a stirred solution of 2-(1-trityl-1H-imidazol-4-yl)phenol (0.5 mmol) in anhydrous DMF (3 mL) at 0° C. was added NaH (36.0 mg, 0.75 mmol). The resulting suspension was allowed to stir for 10 min. To the resulting solution was added 1-(benzofuran-3-yl)-2-bromoethanone (0.50 mmol). After stirring overnight, the reaction mixture was carefully diluted, with water and extracted with ethyl acetate (2×10 mL). The combined organic layers were washed with water, brine and dried (Na$_2$SO$_4$). The solvent was removed under reduced pressure and the crude product was purified by column chromatography. Yield 60%. $^1$H NMR: 5.16 (s, 2H), 6.88 (d, 1H, J=8.10 Hz), 7.06-7.47 (m, 20H), 7.54 (d, 2H, J=7.92 Hz), 8.22 (dd, 2H, J=7.60 Hz, 1.35 Hz), 8.33 (s, 1H).

Example 82

4-(2-((2-(benzofuran-3-yl)allyl)oxy)phenyl)-1H-imidazole

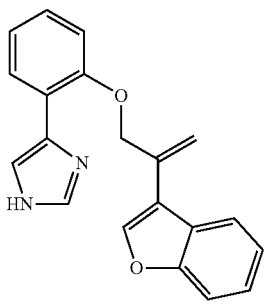 [SMILES: C=C(COc1ccccc1-c1c[nH]cn1)c1coc2ccccc12]

To a solution of triphenylphosphine methyl bromide (0.486 mmol) in diethyl ether (15 mL) at room temperature was added nBuLi (0.486 mmol, 2.5 M) and the suspension was stirred for 2.5 h. 1-(benzofuran-3-yl)-2-(2-(1-trityl-1H-imidazol-4-yl)phenoxy)ethanone (0.442 mmol) was added as a solution in diethyl ether (2 mL) at room temperature. After stirring overnight the reaction mixture was diluted with water (10 mL) and the product was extracted with EtOAC (3×30 mL). The combined organic extracts were dried (Na$_2$SO$_4$) and concentrated under reduced pressure to afford the crude product. The crude was stirred in a mixture of acetic acid (1.5 mL) and MeOH at 80° C. for 2 h. After cooling to room temperature the mixture was stripped off the solvents and the crude was diluted with satd. Na$_2$CO$_3$ solution and the product was extracted with EtOAc (3×30 mL). The combined organic extract was dried over Na2SO4 and concentrated to afford the crude. Chromatographic purification afforded the final product. Yield 44%. $^1$H NMR: 5.01 (s, 2H), 5.63 (s, 1H), 5.89 (s, 1H), 7.06 (d, 1H, J=6.69 Hz), 7.08 (d, 1H, J=5.10 Hz), 7.23-7.44 (m, 5H), 7.54 (d, 1H, J=7.59 Hz), 7.74 (s, 1H), 7.81 (s, 1H), 7.84 (s, 1H)

Example 83

4-(2-(2-(benzofuran-3-yl)propoxy)phenyl)-1H-imidazole

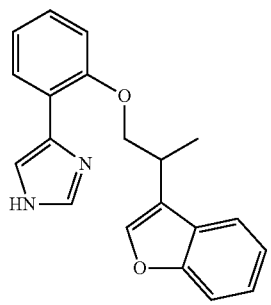 [SMILES: CC(COc1ccccc1-c1c[nH]cn1)c1coc2ccccc12]

To a solution of 4-(2-((2-(benzofuran-3-yl)allyl)oxy)phenyl)-1H-imidazole (0.126 mmol) in MeOH (3 mL) at room temperature was added 10% Pd/C (0.019 mmol) and the mixture was flushed with hydrogen gas after evacuating under vacuum. After stirring overnight the solution was filtered through a celite bed and the solvent was evaporated under reduced pressure to afford the crude product. Chromatographic purification afforded the final product. Yield 75%. $^1$H NMR: 1.55 (d, 3H, J=5.22 Hz), 3.60 (m, 1H), 4.36 (m, 2H), 7.01 (t, 2H J=5.97 Hz), 7.19-7.36 (m, 5H), 7.38 (s, 1H), 7.53 (d, 1H, J=6.09 Hz), 7.58 (s, 1H), 7.64 (d, 1H, J=5.76 Hz), 7.75 (d, 1H, J=5.01 Hz)

Example 84

Alkylation of 4-(2-(2-(1-trityl-1H-imidazol-4-yl)phenoxy)ethyl)aniline

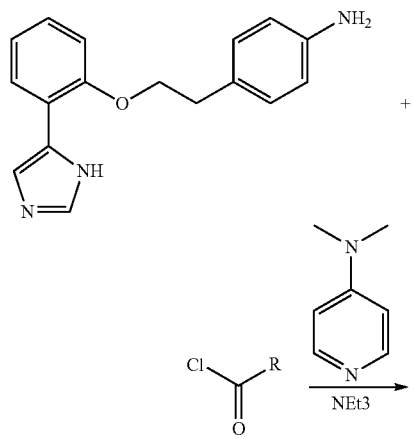

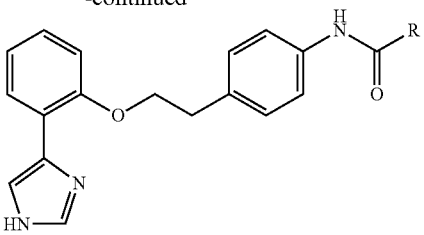

To a solution of 4-(2-(2-(1H-imidazol-5-yl)phenoxy)ethyl)aniline (0.429 mmol) in dichloromethane at 0° C. was added 4-N,N-dimethylamino pyridine (0.085 mmol), triethylamine (1.07 mmol) and appropriate acid chloride (0.945 mmol). The reaction was allowed to warm to room temperature and stirred for 16 h. The reaction mixture was concentrated and the crude was stirred in MeOH at 80° C. for 90 min. After cooling to room temperature, the solvent was evaporated under reduced pressure and the crude was purified by flash column chromatography.

The following compounds were prepared according to the general procedure of Example 84, by substituting the appropriate starting materials:

| No. | Compound | Name | Yield (%) | $^1$H NMR |
|---|---|---|---|---|
| 1101 | ![structure] | N-(4-(2-(2-(1H-imidazol-4-yl)phenoxy)ethyl)phenyl)pivalamide | 18 | 1.33 (s, 9H), 3.16 (t, 3H, J = 4.59 Hz), 4.36 (t, 2H, J = 4.53 Hz), 7.00 (t, 2H, J = 5.91 Hz), 7.18 (t, 1H, J = 5.67 Hz), 7.28 (s, 1H), 7.30 (s, 1H), 7.45 (m, 4H), 7.84 (br s, 1H) |
| 1102 | ![structure] | N-(4-(2-(2-(1H-imidazol-4-yl)phenoxy)ethyl)phenyl)-2-phenylacetamide | 27 | 3.14 (t, 2H, J = 4.47 Hz), 3.69 (s, 2H), 4.35 (t, 2H, J = 4.53 Hz), 6.87 (s, 1H), 7.00 (t, 2H, J = 5.91 Hz), 7.18 (m, 1H, J = 5.79 Hz), 7.25 (s, 1H), 7.33-7.42 (m, 8H), 7.59 (s, 1H), 7.79 (d, 1H, J = 5.49 Hz) |
| 1103 | ![structure] | N-(4-(2-(2-(1H-imidazol-4-yl)phenoxy)ethyl)phenyl)-3,3-dimethylbutanamide | 15 | 1.10 (s, 9H), 2.24 (s, 2H), 3.16 (t, 2H, J = 6.09 Hz), 4.37 (t, 2H, J = 6.21 Hz), 6.98-7.03 (m, 2H), 7.16-7.30 (m, 3H), 7.42-7.46 (m, 3 H), 7.58 (s, 1H), 7.81 (br s, 1H) |

Example 85

4-(benzyloxy)-2-(1-trityl-1H-imidazol-4-yl)phenol

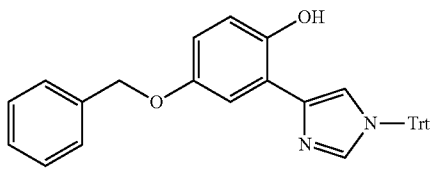

To a solution of 4-(benzyloxy)-2-(1H-imidazol-5-yl)phenol (0.488 mmol) in DMF (5 mL) was added triethylamine (0.585 mmol). After stirring for 10 min, chlorotriphenylmethane (0.512 mmol) was added and continued stirring for 16 h. The reaction mixture was diluted with water (25 mL) and the precipitated product was filtered and washed with water (3×10 mL). The solid cake was dissolved in $CH_2Cl_2$, washed with water, brine and dried over $Na_2SO_4$ and concentrated under reduced pressure to afford the crude product. The crude was purified by column chromatography to afford the final product (0.230 g, 47%).

Example 86

4-(5-(benzyloxy)-2-(3,3-dimethylbutoxy)phenyl)-1-trityl-1H-imidazole

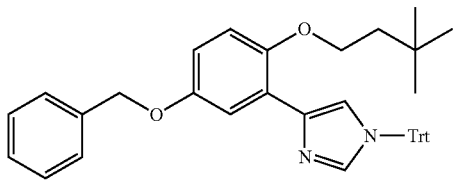

To a solution of 4-(benzyloxy)-2-(1H-imidazol-5-yl)phenol (0.452 mmol) in DMF (3 mL) was added NaH (0.497 mmol) at room temperature and the mixture was stirred for 45 minutes followed by the addition of 1-iodo-3,3-dimethylbutane (0.542 mmol). After stirring overnight, the reaction mixture was diluted with water (35 mL) and the product was extracted with ethyl acetate (3×45 mL). The combined organic extract was dried ($Na_2SO_4$) and concentrated under reduced pressure to afford the crude reside which was passed through a short pad of silica to afford off-white solid. Yield 60%. $^1$H NMR: 0.85 (s, 9H), 1.40 (t, 2H, J=7.41 Hz), 3.89 (t, 2H, J=7.41 Hz), 5.11 (s, 2H), 6.80 (s, 2H), 7.17-7.21 (m, 7H), 7.29-7.39 (m, 11H), 7.44-7.48 (m, 3H), 7.58 (d, 1H, J=1.35 Hz), 7.94 (s, 1H).

Example 87

General Procedure for De-Benzylation Using Hydrogen Pd/C

To a solution of substrate (0.256 mmol) in MeOH (5 mL) at room temperature was added methanolic HCl (0.256 mmol, 1.25 M in MeOH) followed by 10% Pd/C (0.025 mmol) and the solution was evacuated and purged with $H_2$ (balloon). The solution was stirred under a positive pressure of $H_2$ balloon overnight. After purging the reaction with nitrogen, the reaction mixture was filtered through a celite plug and the solvent was evaporated under reduced pressure to afford the crude product, the crude product was basified with satd. $K_2CO_3$ solution and the product was extracted with EtOAc (3×25 mL). The combined organic extract was dried ($Na_2SO_4$) and concentrated under reduced pressure to afford crude. Chromatographic purification afforded the desired product.

The following compounds were prepared according to the general procedure of Example 88, by substituting the appropriate starting materials:

| No. | Structure | Name | Yield | $^1$H NMR |
|---|---|---|---|---|
| 1110 | 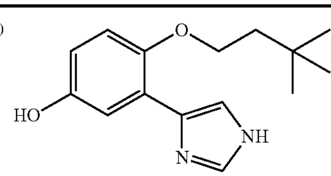 | 4-(3,3-dimethylbutoxy)-3-(1H-imidazol-4-yl)phenol | 53 | 1.0 (s, 9H), 1.81 (t, 2H, J = 7.56 Hz), 4.09 (t, 2H, J = 7.44 Hz), 6.75 (dd, 1H, J = 2.7 Hz, 6.21 Hz), 6.87 (d, 1H, J = 8.91 Hz), 7.35 (d, 1H, J = 2.34 Hz), 7.49 (s, 1H), 7.70 (s, 1H) |
| 1122 | 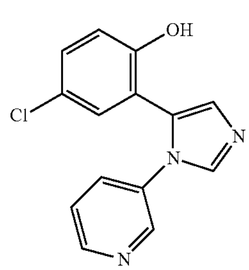 [SMILES: Oc1ccc(Cl)cc1-c1cncn1-c1cccnc1] | 4-chloro-2-(1-(pyridin-3-yl)-1H-imidazol-5-yl)phenol | 71 | 6.76 (d, 1H, J = 9.30 Hz), 7.14-7.17 (m, 3H), 7.26-7.31 (m, 1H), 7.48-7.51 (m, 1H), 7.67 (s, 1H), 8.43 (dd, 1H, J = 1.5 Hz, 3.3 Hz), 8.46 (d, 1H, J = 2.4 Hz) |

Example 88

N-(2-(benzyloxy)-5-chlorobenzylidene)pyridin-3-amine

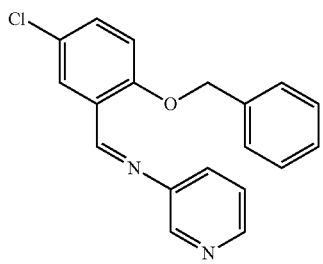 [SMILES: Clc1ccc(OCc2ccccc2)c(C=Nc2cccnc2)c1]

A mixture of pyridin-3-amine (2.13 mmol), 2-(benzyloxy)-5-chlorobenzaldehyde (1.93 mmol) and Mg(ClO$_4$)$_2$ (0.579 mmol) was stirred at 50° C. in dichloromethane (10 mL) for 4 h. After cooling to room temperature, the solution was filtered through 0.45 micron filter and the solvent was evaporated to afford solid. Yield 96%. $^1$H NMR: 5.16 (s, 2H), 6.97 (d, 1H, J=8.96 Hz), 7.28-7.40 (m, 8H), 7.48-7.52 (m, 1H), 8.15 (d, 1H, J=2.70 Hz), 8.45-8.48 (m, 2H).

Example 89

3-(5-(2-(benzyloxy)-5-chlorophenyl)-1H-imidazol-1-yl)pyridine

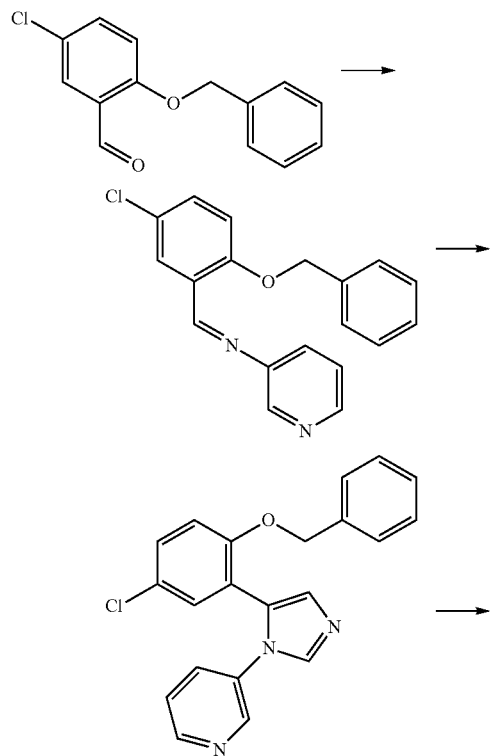

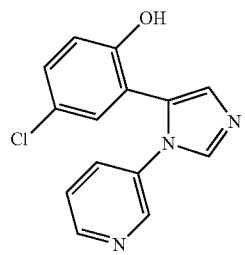

To a solution of N-(2-(benzyloxy)-5-chlorobenzylidene)pyridin-3-amine (0.929 mmol) in DMF (3 mL) at room temperature, was added NaH (1.12 mmol) and the solution was stirred for 1 h, followed by the addition of imine (0.929 mmol). After stirring for 4 d, the reaction mixture was diluted with satd. NH$_4$Cl solution and the product was extracted with EtOAc. The combined organic extract was dried (Na2SO4) and concentrated to afford the crude. Chromatographic purification afforded the final product. Yield 21%. $^1$H NMR: 4.64 (s, 2H), 6.70 (d, 1H), 6.96 (m, 2H), 7.16-7.30 (m, 8H), 7.71 (s, 1H), 8.31 (d, 1H, J=2.4 Hz), 8.53 (dd, 1H, J=1.8 Hz, 3.0 Hz)

Example 90

5-(2-(1H-imidazol-4-yl)phenoxy)-3,3-dimethylpentan-1-ol

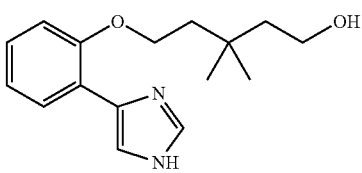 [SMILES: CC(C)(CCO)CCOc1ccccc1-c1c[nH]cn1]

The above product was isolated as a side product in the following reaction: To a solution of benzo[d][1,3]dioxol-5-amine (0.447 mmol) in N,N-dimethylformamide (2 mL) was added NaH (0.447 mmol) at room temperature and after stirring for 15 min 3,3-dimethyl-5-(2-(1-trityl-1H-imidazol-4-yl)phenoxy)pentyl 4-methylbenzenesulfonate (0.223 mmol) was added as a solution in N,N-dimethylformamide (1 mL). The reaction was stirred at 80° C. overnite. After cooling to room temperature, the reaction mixture was diluted with methanol (2 mL) and acetic acid (2 mL). The reaction was heated to 80° C. for 3 h, after cooling to room temperature, the reaction mixture was partitioned between dichloromethane (30 mL) and 20% sodium bicarbonate solution (10 mL), the organic layer was separated and the aqueous phase extracted with dichloromethane (3×25 mL). The combined organic extract was dried (Na2SO4) and concentrated to afford the crude. Yield 7%. $^1$H NMR: 1.10 (s, 6H), 1.24 (s, 1H), 1.62 (t, 2H, J=7.32 Hz), 1.89 (t, 2H, J=7.24 Hz), 3.75 (t, 2H, J=7.44 Hz), 4.16 (t, 2H, J=7.24 Hz), 6.97 (d, 1H, J=8.52 Hz), 7.01 (d, 1H, J=7.52 Hz), 7.21 (m, 1H), 7.51 (s, 1H), 7.69 (s, 1H), 7.78 (d, 1H, J=7.60 Hz).

Example 91

5-chloro-3-(1H-imidazol-5-yl)benzene-1,2-diol

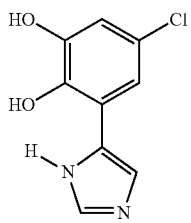

To a suspension of 5-(5-chloro-2,3-dimethoxyphenyl)-1H-imidazole (0.080 g, 0.335 mmol) in dichloromethane (4 mL) at −78° C. was added BBr$_3$ (1.01 mmol) and the reaction mixture was allowed to warm to room temperature. After stirring overnight, the reaction was quenched by cautious addition of satd. NH$_4$Cl solution (3 mL). The product was extracted with CH$_2$Cl$_2$ (3×10 mL), the combined organic extract was washed with water, brine and dried (MgSO$_4$) and concentrated in vacuum to afford the crude product. The crude was passed through a short pad of silica gel to afford the final product. Yield 62%. $^1$H NMR: 6.82 (d, 1H, J=2.40 Hz), 6.99 (d, 1H, J=2.40 Hz), 7.34 (s, 1H), 7.75 (s, 1H)

Example 92

1-(4-(2-Hydroxyethyl)phenyl)pyrrolidin-2-one

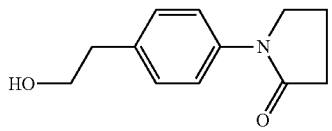

A mixture of CuI (0.198 mmol), N,N-dimethylethylamine (0.398 mmol), K$_2$CO$_3$ (3.98 mmol) and pyrrolidin-2-one (3.98 mmol) was purged with nitrogen gas. 2-(4-bromophenyl)ethanol (1.99 mmol) was added and the mixture was purged with purged again with nitrogen. The reaction mixture was stirred at 130° C. overnight. After cooling to room temperature, the reaction mixture was diluted with water (25 mL), NH$_4$OH (5 mL) and the aqueous layer was extracted with dichloromethane (3×40 mL). The combined organic extracts were dried over sodium sulfate and evaporated under reduced pressure; the crude was purified by column chromatography to afford the final product. Yield=37%.

The following compounds were prepared according to the general procedure of Example 92, by substituting the appropriate starting materials:

| | Name | Yield |
|---|---|---|
| (2-(4-(pyrrolidin-1-yl)phenyl)ethanol structure) | 2-(4-(pyrrolidin-1-yl)phenyl)ethanol | 54% |
| (1-(4-(2-hydroxyethyl)phenyl)piperidin-2-one structure) | 1-(4-(2-hydroxy-ethyl)phenyl)piperidin-2-one | 23% |
| (2-(4-(piperidin-1-yl)phenyl)ethanol structure) | 2-(4-(piperidin-1-yl)phenyl)ethanol | 49% |

Example 93

N-(3-chloro-4-(2-hydroxyethyl)phenyl)acetamide

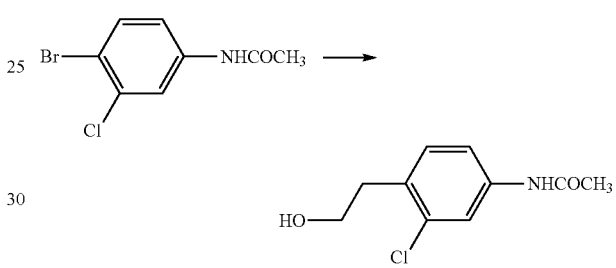

A solution of potassium vinyltrifluoroborate (2.00 mmol), PdCl$_2$ (0.04 mmol), PPh$_3$ (0.12 mmol), Cs$_2$CO$_3$ (6.00 mmol), and N-(4-bromo-3-chlorophenyl)acetamide (2.00 mmol) in THF/H$_2$O (9:1) (4 mL) was heated at 85° C. under an N$_2$ atmosphere in a sealed tube. The reaction mixture was stirred at 85° C. for 22 h, then cooled to room temperature and diluted with H$_2$O (3 mL) followed by extraction with CH$_2$Cl$_2$ (10 mL*3). The solvent was removed in vacuo, and the crude product was purified by silica gel chromatography (eluting with mixture of Hexanes and Ethyl acetate) to yield the vinylic arene. A solution of vinyl arene (2 mmol) in dry THF (10 mL) was treated with BH$_3$-Me$_2$S (1.6 mmol, 0.8 equiv) at 0° C. and the reaction mixture was warmed at room temperature and stirred for overnight, after which time 10 mL water was added to dilute the solution. Then 3M NaOH solution (0.93 mL) and 30% (w/w) hydrogen peroxide solution (1.54 mL) was added sequentially to the reaction at 0° C. The mixture was allowed to stir overnight at room temperature and was extracted with CH$_2$Cl$_2$ (20×3 mL). The organic layer was dried with MgSO$_4$ and concentrated in vacuum. Column chromatography was run using mixture of hexanes and ethyl acetate to afford corresponding alcohols.

The following compounds were prepared according to the general procedure of Example 93, by substituting the appropriate starting materials:

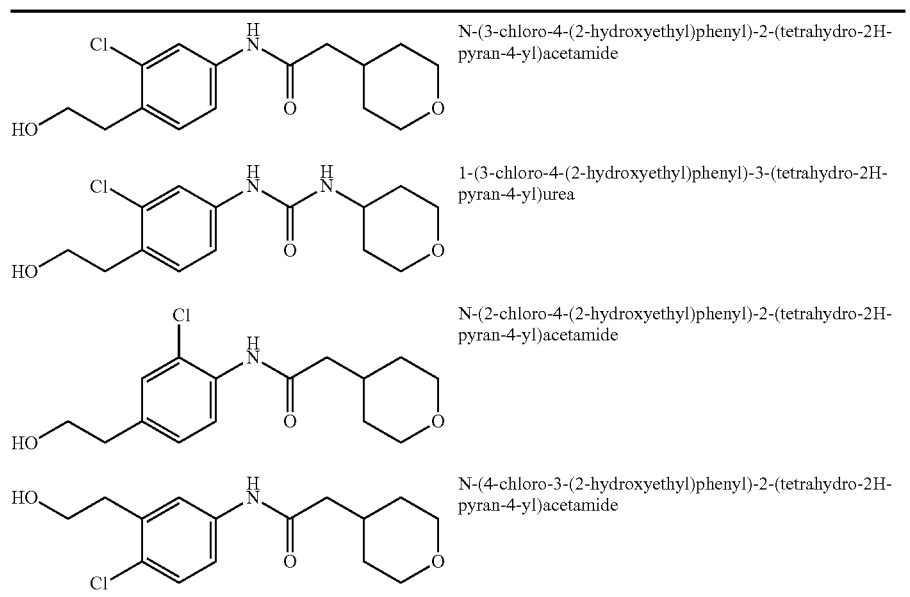

| | |
|---|---|
| | N-(3-chloro-4-(2-hydroxyethyl)phenyl)-2-(tetrahydro-2H-pyran-4-yl)acetamide |
| | 1-(3-chloro-4-(2-hydroxyethyl)phenyl)-3-(tetrahydro-2H-pyran-4-yl)urea |
| | N-(2-chloro-4-(2-hydroxyethyl)phenyl)-2-(tetrahydro-2H-pyran-4-yl)acetamide |
| | N-(4-chloro-3-(2-hydroxyethyl)phenyl)-2-(tetrahydro-2H-pyran-4-yl)acetamide |

Example 94

2-(benzo[b]thiophen-3-yl) ethanol

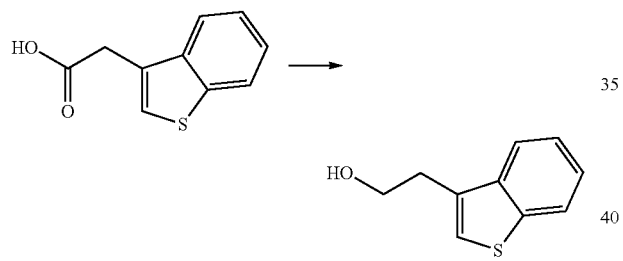

A solution of 3-benzothienylacetic acid (5.2 mmol) in 10 mL of anhydrous THF was slowly added to a stirred solution of LAH (10.4 mmol) in 50 mL of THF at 0° C. The ice bath was removed and the solution was stirred overnight, while it was allowed to warm to room temperature. The reaction was quenched by addition of water, 10% aqueous NaOH. The mixture was filtered over Celite and the filtrate was concentrated to give 2-(benzo[b]thiophen-3-yl)ethanol, which was used for tosylation.

The following compounds were prepared according to the general procedure of Example 94, by substituting the appropriate starting materials (carboxylic acid or alkyl ester):

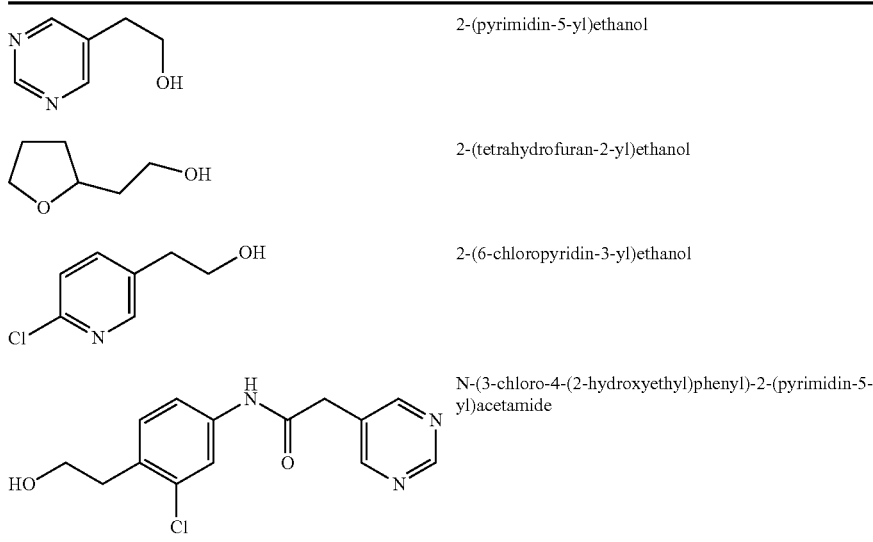

| | |
|---|---|
| | 2-(pyrimidin-5-yl)ethanol |
| | 2-(tetrahydrofuran-2-yl)ethanol |
| | 2-(6-chloropyridin-3-yl)ethanol |
| | N-(3-chloro-4-(2-hydroxyethyl)phenyl)-2-(pyrimidin-5-yl)acetamide |

Example 95

1-(5-(2-(2-(1H-imidazol-4-yl)phenoxy)ethyl)pyridin-2-yl)-3-phenylurea

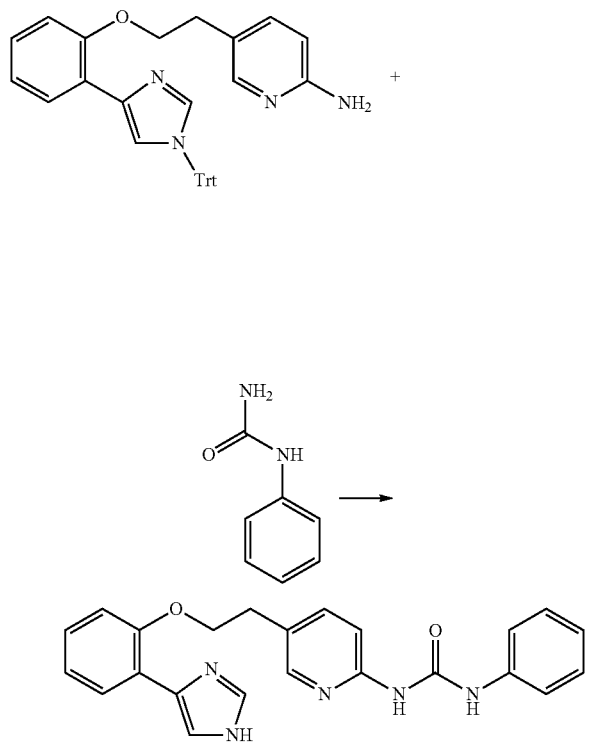

A vial was charged under N₂ with Pd(OAc)₂ (2 mg, 0.0087 mmol), xantphos (10.3 mg, 0.175 mmol) and dioxane (1 mL), and the mixture was degassed through several freeze-thaw cycles. The 2-chloro-5-(2-(2-(1-trityl-1H-imidazol-4-yl)phenoxy)ethyl)pyridine (94 mg, 0.173 mmol), phenylurea (23.6 mg, 0.173 mmol), NaOt-Bu (24.16 mg, 0.251 mmol) and previously degassed water (10 µL) were successively added to the flask. The reaction mixture was heated at 100° C. while stirring until TLC analysis showed the absence of starting reactants (2.5 h, most of starting material are gone). After cooling to room temperature, the mixture was filtered over Celite and the filtrate was concentrated. The residue was dissolved in MeOH/AcOH (4:1, 4 mL) and heated at 80° C. for 2 h. The reaction mixture was basified with aqueous 10% NaOH and the aqueous layer extracted with ethyl acetate (2×30 mL). The combined organic extracts were washed with brine (15 mL), dried over Na₂SO₄ and concentrated. The residue was purified by flash column chromatography. Yield=36%. ¹H NMR (MeOH-d₄): 3.10-3.21 (m, 2H), 4.36-4.38 (m, 2H), 7.00-7.13 (m, 4H), 7.20-7.37 (m, 4H), 7.49-7.52 (m, 2H), 7.69-7.80 (m, 3H), 8.22 (s, 1H).

The following compounds were prepared according to the general procedure of Example 95, by substituting the appropriate starting materials: N-(5-(2-(2-(1H-imidazol-4-yl)phenoxy)ethyl)pyridin-2-yl)-2-phenylacetamide. Yield: 25%. ¹H NMR (MeOH-d₄): 3.15 (t, 2H, J=6.6 Hz), 3.72 (s, 2H), 4.35 (t, 2H, J=6.3 Hz), 6.95-7.06 (m, 2H), 7.17-7.39 (m, 6H), 7.65 (s, 1H), 7.69-7.81 (m, 2H), 7.90 (s, 1H), 7.96-7.98 (m, 1H), 8.22 (s, 1H).

Example 96

1-(2-(2-(1H-imidazol-4-yl)phenoxy)ethyl)-4-methylpiperazine

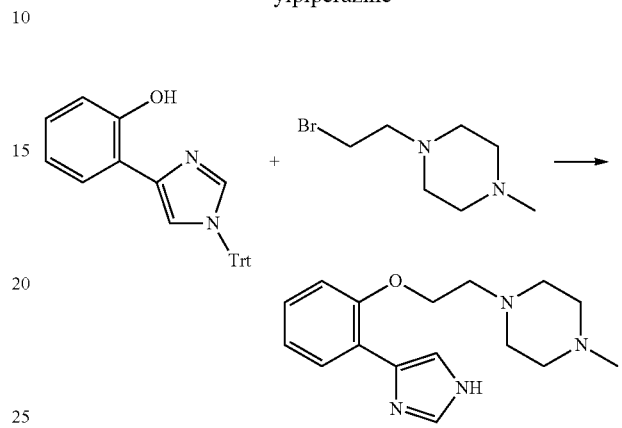

The mixture of 4-(2-(2-bromoethoxy)phenyl)-1-trityl-1H-imidazole (35.56 mg, 0.07 mmol), potassium carbonate (19.35 mg, 0.14 mmol) and 1-methylpiperazine (14.1 mg, 0.14 mmol) was stirred at in 3 mL CH₃CN at 75° C. for 3 h. After the completion of reaction, solid was filtered off and washed with DCM. The filtrate was collected and the solvent was removed. The residue was dissolved in MeOH/AcOH (4:1, 4 mL) and heated at 80° C. for 2 h. The reaction mixture was basified with aqueous 10% NaOH and the aqueous layer extracted with ethyl acetate (2×30 mL). The combined organic extracts were washed with brine (15 mL), dried over Na₂SO₄ and concentrated. The residue was purified by flash column chromatography. Yield=71%. ¹H NMR (MeOH-d₄): 1.94 (s. 3H), 2.59-2.62 (m, 8H), 2.89 (t, 2H, J=5.4 Hz), 4.28 (t, 2H, J=5.4 Hz), 6.97-7.01 (m, 1H), 7.09 (d, 1H, J=7.8 Hz), 7.22-7.27 (m, 1H), 7.70-7.86 (m, 3H).

The following compounds were prepared according to the general procedure of Example 96, by substituting the appropriate starting materials: 4-(2-(2-(1H-imidazol-4-yl)phenoxy)ethyl)morpholine. Yield: 37%. ¹H NMR (MeOH-d₄): 2.59-2.62 (m, 4H), 2.87-2.90 (t, 2H, J=5.4 Hz), 3.72-3.75 (m, 4H), 4.26-4.29 (t, 2H, J=5.4 Hz), 6.98-7.09 (m, 2H), 7.21-7.26 (m, 1H), 7.66 (s, 1H), 7.69-7.80 (m, 21-1).

Example 97

1-(4-(2-(2-(1H-imidazol-4-yl)phenoxy)ethyl)phenyl)-3-(tetrahydro-2H-pyran-4-yl)urea

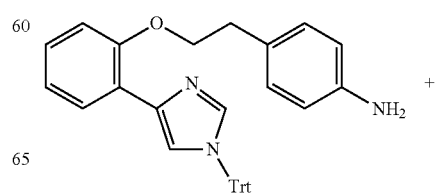

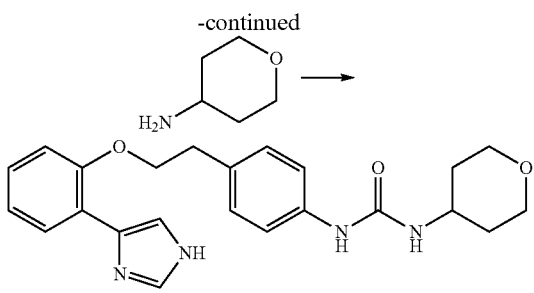

4-(2-(2-(1-trityl-1H-imidazol-4-yl)phenoxy)ethyl)aniline (50.0 mg. 0.096 mmol) was dissolved in dichloromethane (DCM, 5 ml) and triethylamine (1 ml), and a solution of triphosgene (0.105 mmol) in DCM (5 ml) was then added to the solution at 0° C. The mixture was stirred at room temperature under N₂ for 2 h. Next, tetrahydro-2H-pyran-4-amine (20.0 mg, 0.192 mmol) was added to the reaction solution, and the mixture was stirred at room temperature under N₂ for overnight. A saturated aqueous sodium bicarbonate solution was added to the reaction solution, followed by extraction with DCM (3×15 ml). The DCM layer was dried over Na₂SO₄. The solvent was removed by distillation under the reduced pressure. The residue was dissolved in MeOH/AcOH (4:1, 4 mL) and heated at 80° C. for 2 h. The reaction mixture was basified with aqueous 10% NaOH and the aqueous layer extracted with ethyl acetate (2×30 mL). The combined organic extracts were washed with brine (15 mL), dried over Na₂SO₄ and concentrated. The residue was purified by flash column chromatography. Yield=78%. ¹H NMR (MeOH-d₄): 1.40-1.54 (m, 2H), 1.81-1.92 (m, 2H), 3.11-3.15 (m, 2H), 3.46-3.53 (m, 2H), 3.55-3.80 (m, 1H), 3.85-3.95 (m, 2H), 4.35 (t, 2H, J=6.6 Hz), 6.95-7.00 (m, 1H), 7.05-7.13 (m, 2H), 7.19-7.30 (m, 5H), 7.70 (s, 1H), 7.78 (d, 1H, J=7.8 Hz).

Example 98

2-Chloro-4-fluoro-6-(1H-imidazol-5-yl)phenol

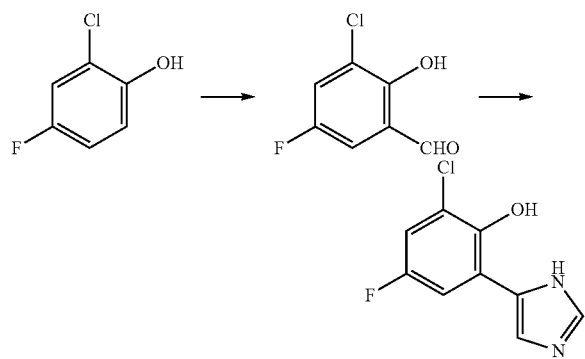

Paraformaldehyde (0.35 g) was added in portions to a mixture of phenol (487.8 mg, 3.33 mmol), triethylamine (1.3 mL, 9.33 mmol), and anhydrous MgCl₂ (0.98 g, 10.3 mmol) in acetonitrile (30 mL). The mixture was refluxed for 48 h, cooled to room temperature, acidified with aqueous 3 N HCl solution, and extracted with ether. The ether layer was washed with water, and brine, and dried (MgSO₄). Removal of solvent yielded a crude material which was purified by column chromatography (SiO₂) to yield 3-chloro-5-fluoro-2-hydroxybenzaldehyde. To this aldehyde (0.25 mmol) in at room temperature was added 3 mL of NH₃ (2.0 M solution in EtOH) solution and the solution was stirred overnite (upon addition of NH₃ in ethanol, the solution changed to yellow). TosMIC (0.30 mmol equiv) and piperazine (0.38 mmol) were then added directly to the solution at room temperature in solid form. The solution were stirred at room temperature for 3 h until completion confirmed by TLC monitor. The solvent was evaporated mostly under reduced pressure and the crude was purified by column chromatography using 1:1 Hexanes and Ethyl acetate mixtures to afford the desired product as a light yellow solid. Yield=65%. ¹H NMR (MeOH-d₄): 6.95-6.99 (m, 1H), 7.29-7.33 (m 1H), 7.61 (s, 1H), 7.84 (s, 1H).

Example 99

5,6-dihydroimidazo[1,5-c]quinazoline

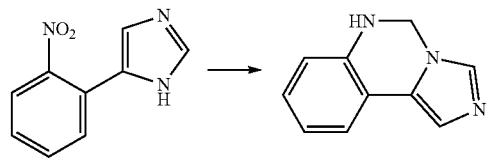 [SMILES: O=[N+]([O-])c1ccccc1-c1cnc[nH]1 ; c1ccc2c(c1)NCn1cncc1-2]

To a vial were added 5-(2-nitrophenyl)-1H-imidazole (200 mg, 1.06 mmol), ferric chloride (8.6 mg, 0.35 mmol), activated carbon (2.2 mg, 1.80 mmol) and hydrazine (1.1 ml, 21.2 mmol) and methanol (9 mL). The resulting mixture was stirred at r.t. for 5 min then was heated to 70° C. for two days. The reaction was cooled to room temperature and filtered. The filtrate was concentrated and purified to give 2-(1H-imidazol-5-yl)aniline. The intermediate was dissolved in acetic acid (2 ml) and formaldehyde (37% in water, 0.3 ml) was added. The reaction was stirred for 1 h at room temperature, diluted with 30 ml ethyl acetate, and extracted with 5% HCl. The aqueous layer was basified with K₂CO₃ (add gradually until PH=7), then extracted with ethyl acetate (30 mL*2). The organic layer was evaporated under reduced pressure and product was obtained by column chromatography using ethyl acetate as eluent (26% yield). ¹H NMR: 4.70 (s, 1H), 4.93 (s, 2H), 7.50-7.56 (m, 1H), 7.73-7.82 (m, 3H), 8.24-8.31 (m, 2H).

The following compounds where synthesized using the method described in the literature:

| No. | Name | Ref. |
|-----|------|------|
| 1131 | 1-allyl-5-phenyl-1H-imidazole | Horvath, Andras; Synthesis, 1995, 1183-1189. |
| 1137 | 6-methyl-5,6-dihydroimidazo[5,1-a]isoquinoline | Horvath, Andras; Synthesis, 1995, 1183-1189). |
|      | 2-(benzyloxy)-5-chlorobenzaldehyde | WO2003/101959 A1, 2003 |
|      | 1-(2-chlorophenyl)propan-2-ol | Kuwabe et al., J. Am. Chem. Soc., 2001, 123, 12202-12206 |
|      | 3-chloro-2,6-dihydroxybenzoic acid | Doyle, F.P. et al. J. Chem. Soc. 1963, 497-506 |

Biological Example 1

Human IDO Protein Cloning, Expression and Purification

Expression vectors for human indoleamine-2,3-dioxygenase (IDO) protein were prepared by amplification of a 1219 bp fragment of the sequence present in vector phIDO6H is cDNA with primers 5'-ggagcatgctaATGGCACACGCTATG-GAAAAC-3' and 5'-gagagatctACCTTCCTTCAAAAGGGA'TTTC-3' and cloning the SphI-BglII 1213 bp fragment into pQE70 (Qiagen), to yield vector pQE70-hIDO. This construct adds 2 extra amino acids and a 6-Histidine tag to the C-terminus of the natural human IDO protein while preserving intact the natural start codon and N-terminus amino acid sequence. The amplified allele of human IDO shows two polymorphisms with respect to the sequence deposited in accession file P14902 of SwissProt database. These polymorphisms result in a P110S and E119G amino acid changes.

Plasmid pQE70-hIDO was transformed into M15(pREP4) cells (Qiagen) and clones were selected in LB-agar plates supplemented with carbenicillin 50 μg/mL and kanamycin 30 μg/mL. Protein expression was carried out by growing an overnight culture of the M15pREP4/pQE70-hIDO clone in 100 mL LB supplemented with 100 μg/mL carbenicillin, 50 μg/mL kanamycin and 50 μg/mL of L-tryptophan (LBCKT medium). 40 mL of this culture were inoculated into 750 mL of LBCKT for 4 hours at 37° C. This culture was diluted 1:10 into LBCKT medium and cultured for another 2 hours at 37° C. until OD600 was higher than 0.8. At this point the cultures were inoculated with Hemin to 7 μM and L-Tryptophan to 75 μg/mL and incubated at 37° C. for 2 h. Induction of protein expression was carried out by supplementing the cultures with IPTG to 1 mM, PMSF to 200 μM, EDTA to 1 mM and L-tryptophan to 50 μg/mL. Incubation was continued for additional 16 h at 25° C. Cells were collected by centrifugation, and the cell pellets were washed with PBS buffer supplemented with 200 μM PMSF and 1 mM EDTA and stored at −80° C. until protein purification.

The equivalent of 16 L of culture were processed in one batch of purification. Cell pellets were thawed, resuspended in 50 mM potassium phosphate buffer pH 7.0, 200 μM PMSF, 1 mM EDTA, 1 mg/mL lysozyme to 10 mL per liter of bacterial culture and incubated 30 minutes on ice. Cells were then lysed by sonication. Cell lysates were centrifuged 20 min at 20000 g and the supernatant was filtered through 0.45 μm filters. The filtered supernatant was loaded onto a 60 mL phosphocellulose column equilibrated with 50 mM potassium phosphate buffer pH 6.5 (KPB) at 1-3 mL/min. The column was washed with 3 volumes of 50 mM KPB, 3 volumes of 100 mM KPB and the protein was eluted with 15 volumes of a linear gradient of 100-500 mM KPB. Fractions were collected and IDO activity assay was performed by measuring kynurenine production. This was carried out by mixing 50 µL of each fraction with 100 µL of reaction mix to yield a final concentration of 50 mM KPB buffer, 20 mM ascorbic acid, 200 µg/mL catalase, 20 µM methylene blue and 400 µM L-tryptophan. Fractions demonstrating IDO activity were loaded onto a Ni-NTA purification column (15 mL). This affinity purification column was washed with 10 volumes of 250 mM KPB, 150 mM NaCl, 50 mM imidazole pH 8, and eluted with 10 volumes of buffer containing 250 mM KPB, 150 mM NaCl and a 50 to 250 mM imidazole linear gradient. Collected fractions were assayed by IDO enzymatic assay described above and the positive fractions were pooled and concentrated by ultrafiltration and dialyzed against a buffer containing 250 mM KPB, 50% glycerol. This process yields ~8-10 mg of pure protein (>98%) with a specific activity of 170 µmol/h/mg.

Biological Example 2

Testing of IDO Inhibitory Compounds by Enzymatic IDO Assay

The $IC_{50}$ values for each compound were determined by testing the activity of IDO in a mixture containing 50 mM potassium phosphate buffer at pH 6.5; 70 nM purified human IDO protein, 200 µM L-tryptophan, 20 mM ascorbate, 20 µM methylene blue, 0.1% DMSO. The inhibitors were initially diluted in DMSO at 100 mM and were diluted in potassium phosphate 50 mM, added to the reaction mixture at final concentrations raging from 1 mM to 5 nM and preincubated with the enzyme for 5 min at 25° C. The reaction was started by addition of L-tryptophan to 200 µM and incubated 15 min at 37° C. The reaction was stopped by addition of 0.5 vol of 30% trichloroacetic acid and incubated 30 min at 60° C. to hydrolyze N-formylkynurenine to kynurenine. The reaction was centrifuged at 3400 g for 5 min to remove precipitated protein and the supernatant was reacted with 2% (w/v) of p-dimethylaminobenzaldehyde in acetic acid. The reaction was incubated 10 min at 25° C. and read at 480 nm in a spectrophotometer. Control samples with no IDO inhibitor, or with no IDO enzyme or with the reference inhibitors 1-methyl-tryptophan (200 µM) and menadione (1.2 µM) were used as controls to set the parameters for the non-linear regressions necessary for determination of the $IC_{50}$ for each compound. Nonlinear regressions and determination of the $IC_{50}$ values were performed using the GraphPad Prism 4 software. Compounds with an $IC_{50}$ of less than 500 µM were considered as active inhibitors in this assay.

Biological Example 3

Determination of IDO Inhibitory Activity and Toxicity in Cell Based IDO/Kynurenine Assay 293-T-REx™ cells (Invitrogen) constitutively express a tet operator binding repressor protein and are maintained in DMEM, 10% FBS, 1× Penicillin+Streptomycin, 2 mM L-glutamine, 5 µg/mL blasticidin at 37° C. with a 5% $CO_2$ in air atmosphere and typically split prior to confluency. Cells were passed by splitting the culture 1/10—by removing media by aspiration, washing 1× with PBS, incubating with 0.25% trypsin/EDTA until the cells detach, disbursing the cells in fresh growth media, and plating at 1/10 dilutions in fresh growth media. For long term cryopreservation, cells are detached from the plate as described above, collected by centrifugation, resuspended in freeze medium (growth medium, 10% DMSO), stored in 1.8 mL cyropreservation vials (~2-5×106 cells per vial), in liquid nitrogen vapor storage tanks.

IDO1—expressing 293-T-Rex™ cell lines were generated by stable transfection of plasmid pcDNA-tetO-IDO expressing human IDO or murine IDO under the control of the doxycycline-inducible CMV-tet promoter. Transfected cells were selected in DBZ medium (DMEM, 10% FBS, 1× Penicillin+Streptomycin, 2 mM L-glutamine, 5 µg/mL blasticidin and 25 µg/ml Zeocin) at 37° C. with a 5% $CO_2$ in air atmosphere. Individual clones were isolated by limiting dilution cloning from these populations. These clones were assayed for IDO activity and the clones that showed the highest levels of IDO activity inducible by doxycycline were used for subsequent cell based IDO assays.

To setup an IDO cell based activity assay, IDO-293-T-Rex cells were harvested and resuspended in DBZ media at $10^6$ cells/mL, and split into poly-D-lysine coated 96-well plates at 100,000 cells per well. 100 µL of Neutral medium (DBZ medium, 200 µM L-tryptophan) or Induction media (Neutral medium supplemented with 5 µM doxycycline) are added to the cells and incubated 28 h at 37° C. After the IDO induction period, medium is removed and replaced with Induction or Neutral medium containing different concentrations of each inhibitor (1 mM to 0.5 nM). The cells incubated in Neutral medium serve as negative control of the assay. The cells incubated in Induction medium and without inhibitor serve as the positive control of the assay. The incubation is carried out for 16 h at 37° C. in a cell culture incubator. 200 µL of medium are transferred to U-bottom polypropylene 96-well plates containing 25 µL of 30% TCA, incubated 30 minutes at 60° C. and centrifuged at 3400 g for 5 minutes. 150 µL of the clear supernatant is transferred to a polystyrene 96-well plate containing 50 µL of 4% (w/v) of p-dimethylaminobenzaldehyde in acetic acid, incubated for 10 min. Kynurenine concentration is determined by measuring the absorbance at 480 nm.

To measure the toxicity of each compound after 16 h incubation with cells, cell viability is measured via a WST-1 assay (Roche) according to instructions from the manufacturer. Briefly, after the incubation with each compound, medium is aspirated and replaced with 100 mL of WST-1 reagent, and incubated 30 min at 37° C. Absorbance at 540 nm is correlated with the number of viable cells. Determination of $IC_{50}$ (Kynurenine assay) or $LD_{50}$ (WST-1 assay) is performed via non-linear regression analysis using GraphPad Prism software.

Biological Example 4

Reversal of IDO-Mediated Suppression of T-Cell Proliferation by IDO Inhibitors

Human monocytes were collected from peripheral mononuclear cells by leukoapheresis and cultured overnight at $10^6$ cells/well in a 96-well plate in RPMI 1640 medium supplemented with 10% fetal calf serum and 2 mM L-glutamine. Adherent cells were retained and cultured for 7 days with 200 ng/ml IL-4, 100 ng/ml GM-CSF. Cells were matured for 2 days with a cytokine cocktail containing TNF-α, IL-1β and PGE2 for additional 2 days to induce dendritic cell maturation. At the end of maturation, loosely adherent cells were detached by gentle aspiration and plated in V-bottom 96 well plates, at 5000 cells/well. These cells are >80% IDO+ dendritic cells. Human allogeneic T cells ($3\times10^5$) from normal donors were resuspended in RPMI 1640 supplemented with 100-200 U/mL IL-2 and 100 ng/mL anti-CD3 antibody and added to the wells. Serial dilutions of IDO compounds dissolved in phenol red-free RPMI was added to yield a final concentration of IDOi between 500 and 1 µM. After incubation for 2-4 days, T cell proliferation was measured by BrdU incorporation assay after an overnight pulse with BrdU labeling mix (Roche Molecular Biochemicals). At the en of the pulse, the cells were fixed and incubated with 100 µL/well anti-BrdU-POD antibody following the instructions from the manufacturer. Plates were read in a microplate reader.

Alternatively, testing of IDO inhibitors in an in vitro mouse model of IDO-mediated suppression of T cell proliferation is performed by the following procedure. C57bl6 mice are inoculated with $1 \times 10^6$ B78H-GMCSF tumor cells in the right flank. After 10-12 days, tumor draining lymph nodes are collected and cells are stained with anti-CD11c and anti-B220 monoclonal antibodies. Cells are sorted by high-speed fluorescence activated cell sorting and the CD11c+/B220+ plasmacytoid dendritic cells are collected and seeded at 2000 cells/well in 96 well V-bottom plates. Splenocytes are collected from BM3 transgenic mice (in CBA background) and collected by nylon wool enrichment. BM3 T cells ($10^5$ cells/well) are added to each well in 200 µL of RPMI, 10% FCS, 50 µM β-mercaptoetanol. Alternatively, T cells are obtained from spleens of OT-I transgenic mice and added to the culture in combination with OVA peptide. IDO inhibitors are added dissolved in RPMI at final concentrations ranging from 1 mM to 10 nM. After 3 days of stimulation, cells are pulsed by 16 h with BrdU or $^3$H-thymidine. Cells are collected, fixed and tested for BrdU incorporation following the instructions from the BrdU labeling kit manufacturer (Roche Diagnostics). If $^3$H-tymidine is used to measure T cell proliferation, cells are harvested and dpm counts are measured in a scintillation counter following procedures widely known in the art. Control CD11c$^+$ cells taken from the contralateral lymph node or CD11c$^+$/B220$^-$ cells (IDO$^-$ population) from the TDLN are used as positive control for proliferation.

Biological Example 5

In Vivo Testing of IDO Inhibitors for Antitumor Activity in Combination with Chemotherapeutic Agents In vivo anti-tumor efficacy can be tested using modified tumor allograft protocols. For instance, it has been described in the literature that IDO inhibition can syngerize with cytotoxic chemotherapy in immune-competent mice. Due to different susceptibilities of different tumor cell lines to chemotherapeutic drugs and to immune mediated rejection, each IDO inhibitor is tested alone and in combination with 2 different chemotherapeutic drugs in 4 different animal tumor models, represented by 4 different mouse tumor cell lines, of different tissue origin (colorectal, bladder, mammary and lung carcinoma), implanted subcutaneously in syngeneic strains of mice. These cell lines have been selected based on their known susceptibility to chemotherapeutic drugs, their partial response to IDO inhibitors as single agents, their presumed pattern of IDO expression according to their tissue of origin, and their ability to elicit an immune reaction.

For every animal tumor model, 2 different chemotherapeutic drugs are tested in separate groups of mice according to the following list: 1] LLC tumor: cyclophosphamide and paclitaxel; 2] EMT6 tumor: cyclophosphamide and paclitaxel; 3] CT26 tumor: cyclophosphamide and doxorubicin; and 4] MB49 tumor: cyclophosphamide and gemcitabine.

The following chemotherapeutic drugs are used, at the indicated doses. The maximum tolerated dose for the following chemotherapeutic agents in mice depends on the formulation, concentration, frequency of administration, route of administration and number of doses. The chemotherapeutic drugs administered in conjunction with each IDO inhibitor drug are: 1] Paclitaxel: 20 mg/kg/day i.p, every 4 days, 4 times (q4d×4) (in Cremophor); 2] Doxorubicin: 5 mg/kg, once a week for 3 weeks (q7d×3); 3] Cyclophosphamide: 100 mg/kg, I.P., every 4 days, 4 times (q4d×4); 4] Gemcitabine: 80 mg/kg every 4 days, 4 times, i.p. (q4d×4).

All animals receive a subcutaneous injection of a tumor forming dose of live tumor cells (~50000-1000000 cells) suspended in 0.1 mL of PBS or saline on day 1. Subcutaneous injection forms a localized tumor that allows monitoring tumor growth over time.

To mimic the effect of IDO inhibitor drugs as therapeutic compositions, administration of IDO inhibitor drugs begins at day 5-8 after tumor inoculation. Dosing, route of administration, dosing frequency varies depending on the toxicity and pharmacokinetics profile of each drug. Duration of the treatment is 2 weeks. Most preferably, drug is administered continuously via oral gavage or dissolution in the drinking water. Alternatively, subcutaneous slow release pellets containing 100 mg of each drug are implanted under the skin by surgical procedure. IDO inhibitor drug are administered at the maximum tolerated dose or at a concentration corresponding to the $LD_{50}$.

Biological Example 6

Pharmacological Values

Pharmacological values for compounds tested according to one or more of the preceding examples are reported in the following table, including, Human IDO $IC_{50}$: this is the concentration of the compound at which we observe 50% of enzymatic activity using recombinant human IDO under the assay conditions described in one of the examples;

Human IDO $LD_{50}$: this is the concentration of the compound at which we observe 50% of cell death under the assay conditions described in one of the examples;

$IC_{50}$ and $LD_{50}$ values are reported in ranges: A: <1 µM; B: 1 µM-10 µM, C: 10-100 µM; D:>100 µM.

| No. | Structure | Name | hIDO IC$_{50}$ |
|---|---|---|---|
| 926 | 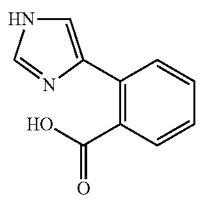 [SMILES: O=C(O)c1ccccc1-c1c[nH]cn1] | 2-(1H-imidazol-4-yl)benzoic acid | D |
| 934 | 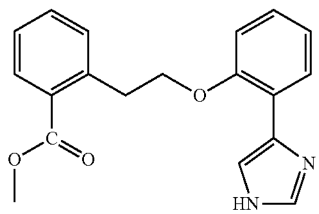 [SMILES: COC(=O)c1ccccc1CCOc1ccccc1-c1c[nH]cn1] | methyl 2-(2-(2-(1H-imidazol-4-yl)phenoxy)ethyl)benzoate | D |
| 945 | 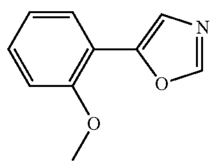 | 5-(2-methoxyphenyl)oxazole | D |
| 947 | 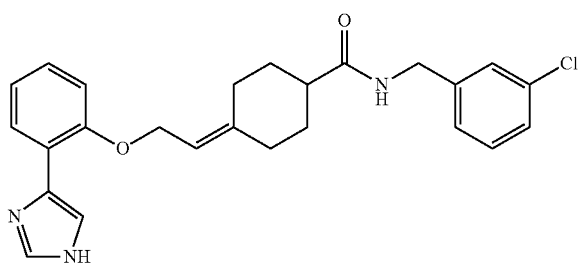 [SMILES: O=C(NCc1cccc(Cl)c1)C1CCC(=CCOc2ccccc2-c2c[nH]cn2)CC1] | 4-(2-(2-(1H-imidazol-4-yl)phenoxy)ethylidene)-N-(3-chlorobenzyl)cyclohexanecarboxamide | C |
| 948 | 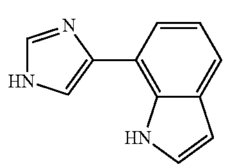 [SMILES: c1cc(-c2c[nH]cn2)c2[nH]ccc2c1] | 7-(1H-imidazol-4-yl)-1H-indole | C |
| 949 | 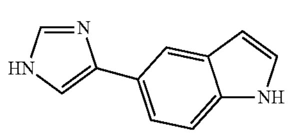 [SMILES: c1nc(-c2ccc3[nH]ccc3c2)c[nH]1] | 5-(1H-imidazol-4-yl)-1H-indole | D |
| 952 | 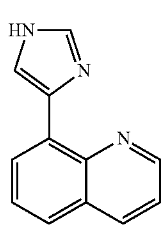 [SMILES: c1cnc2c(-c3c[nH]cn3)cccc2c1] | 8-(1H-imidazol-4-yl)quinoline | D |

-continued
| No. | Structure | Name | hIDO IC$_{50}$ |
|---|---|---|---|
| 953 | 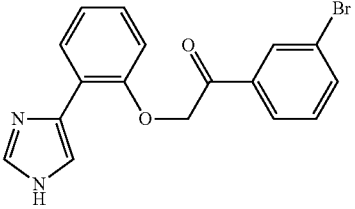 [SMILES: O=C(COc1ccccc1-c1c[nH]cn1)c1cccc(Br)c1] | 2-(2-(1H-imidazol-4-yl)phenoxy)-1-(3-bromo-phenyl)ethanone | C |
| 954 | 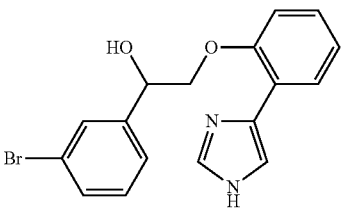 [SMILES: OC(COc1ccccc1-c1c[nH]cn1)c1cccc(Br)c1] | 2-(2-(1H-imidazol-4-yl)phenoxy)-1-(3-bromo-phenyl)ethanol | C |
| 955 | 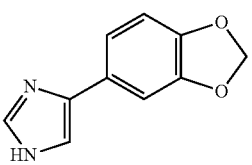 [SMILES: c1nc(-c2ccc3c(c2)OCO3)c[nH]1] | 4-(benzo[d][1,3]dioxol-5-yl)-1H-imidazole | D |
| 956 | 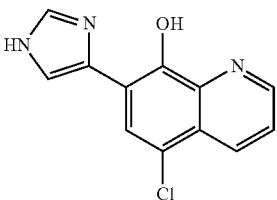 [SMILES: Oc1c(-c2c[nH]cn2)cc(Cl)c2cccnc12] | 5-chloro-7-(1H-imidazol-4-yl)quinolin-8-ol | D |
| 957 | 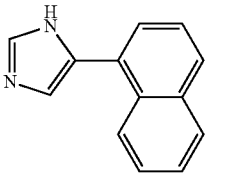 [SMILES: c1ccc2c(-c3cnc[nH]3)cccc2c1] | 5-(naphthalen-1-yl)-1H-imidazole | C |
| 958 | 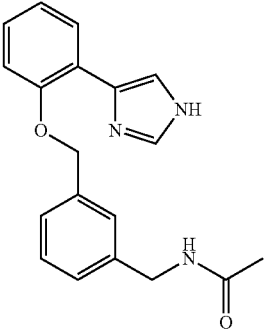 [SMILES: CC(=O)NCc1cccc(COc2ccccc2-c2c[nH]cn2)c1] | N-(3-((2-(1H-imidazol-4-yl)phenoxy)methyl)benzyl)acetamide | C |

| No. | Structure | Name | hIDO IC$_{50}$ |
|---|---|---|---|
| 959 | 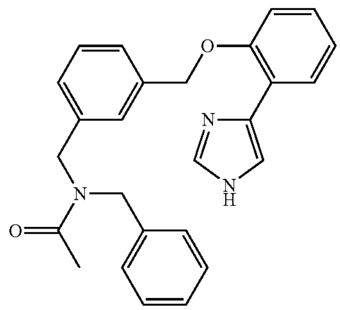 [SMILES: CC(=O)N(Cc1ccccc1)Cc1cccc(COc2ccccc2-c2c[nH]cn2)c1] | N-(3-((2-(1H-imidazol-4-yl)phenoxy)methyl)benzyl)-N-benzylacetamide | C |
| 961 | 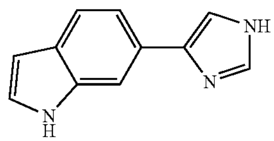 [SMILES: c1nc(-c2ccc3cc[nH]c3c2)c[nH]1] | 6-(1H-imidazol-4-yl)-1H-indole | C |
| 962 | 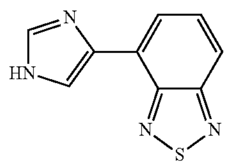 [SMILES: c1cc(-c2c[nH]cn2)c2nsnc2c1] | 4-(1H-imidazol-4-yl)benzo[c][1,2,5]thiadiazole | C |
| 964 | 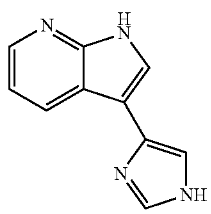 [SMILES: c1cnc2[nH]cc(-c3c[nH]cn3)c2c1] | 3-(1H-imidazol-4-yl)-1H-pyrrolo[2,3-b]pyridine | D |
| 967 | 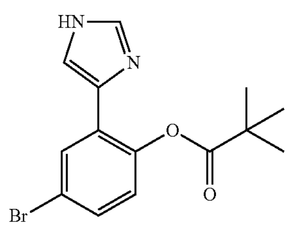 [SMILES: CC(C)(C)C(=O)Oc1ccc(Br)cc1-c1c[nH]cn1] | 4-bromo-2-(1H-imidazol-4-yl)phenyl pivalate | B |
| 969 | 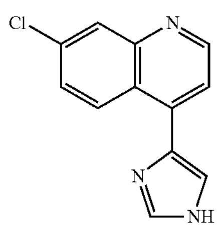 [SMILES: Clc1ccc2c(-c3c[nH]cn3)ccnc2c1] | 7-chloro-4-(1H-imidazol-4-yl)quinoline | D |
| 971 | 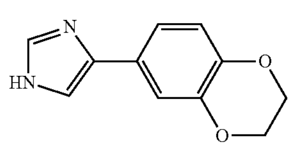 [SMILES: c1nc(-c2ccc3c(c2)OCCO3)c[nH]1] | 4-(2,3-dihydrobenzo[b][1,4]dioxin-6-yl)-1H-imidazole | D |
| 972 | 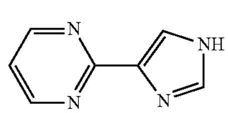 [SMILES: c1cnc(-c2c[nH]cn2)nc1] | 2-(1H-imidazol-4-yl)pyrimidine | D |

-continued

| No. | Structure | Name | hIDO IC$_{50}$ |
|---|---|---|---|
| 975 | 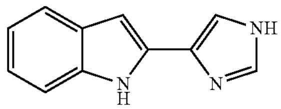 [SMILES: c1ccc2[nH]c(-c3c[nH]cn3)cc2c1] | 2-(1H-imidazol-4-yl)-1H-indole | C |
| 976 | 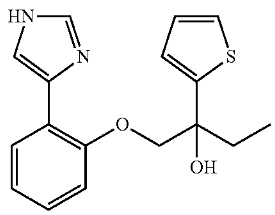 [SMILES: CCC(O)(COc1ccccc1-c1c[nH]cn1)c1cccs1] | 1-(2-(1H-imidazol-4-yl)phenoxy)-2-(thiophen-2-yl)butan-2-ol | C |
| 977 | 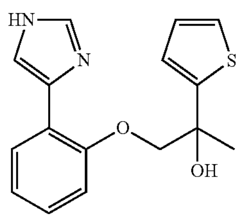 [SMILES: CC(O)(COc1ccccc1-c1c[nH]cn1)c1cccs1] | 1-(2-(1H-imidazol-4-yl)phenoxy)-2-(thiophen-2-yl)propan-2-ol | C |
| 978 | 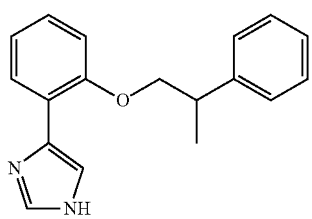 [SMILES: CC(COc1ccccc1-c1c[nH]cn1)c1ccccc1] | 4-(2-(2-phenylpropoxy)phenyl)-1H-imidazole | C |
| 979 | 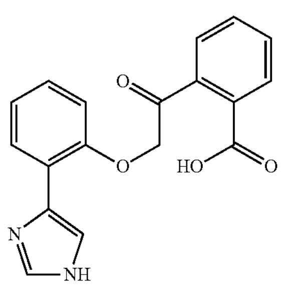 [SMILES: O=C(O)c1ccccc1C(=O)COc1ccccc1-c1c[nH]cn1] | 2-(2-(2-(1H-imidazol-4-yl)phenoxy)acetyl)benzoic acid | D |
| 982 | 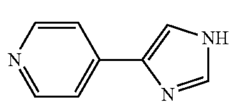 | 4-(1H-imidazol-4-yl)pyridine | D |
| 996 | 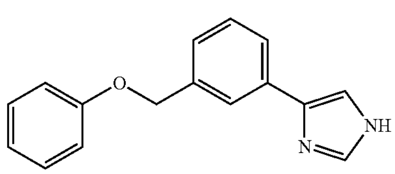 [SMILES: c1ccc(OCc2cccc(-c3c[nH]cn3)c2)cc1] | 4-(3-(phenoxymethyl)phenyl)-1H-imidazole | C |

-continued

| No. | Structure | Name | hIDO IC$_{50}$ |
|---|---|---|---|
| 1003 | 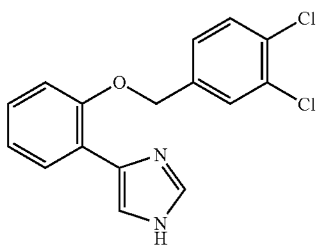 [SMILES: Clc1ccc(COc2ccccc2-c2c[nH]cn2)cc1Cl] | 4-(2-(3,4-dichlorobenzyloxy)phenyl)-1H-imidazole | B |
| 1004 | 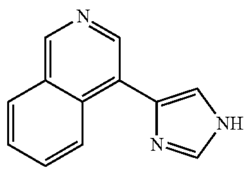 [SMILES: c1ccc2c(-c3c[nH]cn3)cncc2c1] | 4-(1H-imidazol-4-yl)isoquinoline | D |
| 1005 | 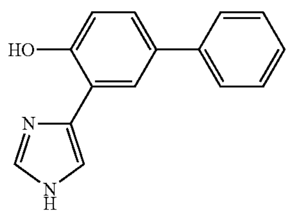 [SMILES: Oc1ccc(-c2ccccc2)cc1-c1c[nH]cn1] | 3-(1H-imidazol-4-yl)biphenyl-4-ol | C |
| 1006 | 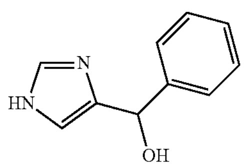 [SMILES: OC(c1ccccc1)c1c[nH]cn1] | (1H-imidazol-4-yl)(phenyl)methanol | D |
| 1007 | 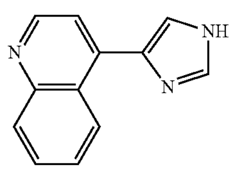 [SMILES: c1ccc2c(-c3c[nH]cn3)ccnc2c1] | 4-(1H-imidazol-4-yl)quinoline | D |
| 1009 | 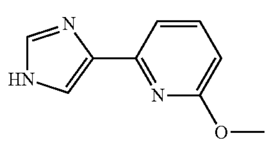 | 2-(1H-imidazol-4-yl)-6-methoxypyridine | D |
| 1010 | 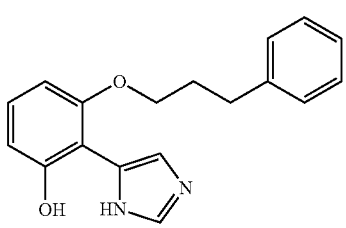 [SMILES: Oc1cccc(OCCCc2ccccc2)c1-c1cnc[nH]1] | 2-(1H-imidazol-5-yl)-3-(3-phenylpropoxy)phenol | C |
| 1011 | 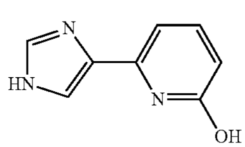 [SMILES: Oc1cccc(-c2c[nH]cn2)n1] | 6-(1H-imidazol-4-yl)pyridin-2-ol | D |

-continued

| No. | Structure | Name | hIDO IC$_{50}$ |
|---|---|---|---|
| 1012 | 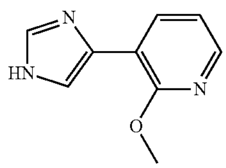 | 3-(1H-imidazol-4-yl)-2-methoxypyridine | D |
| 1013 | 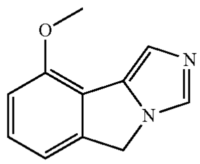 | 9-methoxy-5H-imidazo[5,1-a]isoindole | C |
| 1014 | 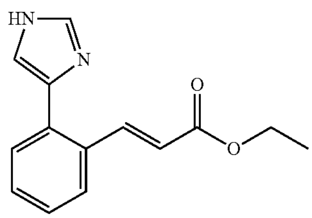 [SMILES: CCOC(=O)/C=C/c1ccccc1-c1c[nH]cn1] | (E)-ethyl 3-(2-(1H-imidazol-4-yl)phenyl)acrylate | C |
| 1015 | 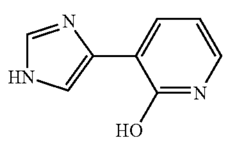 [SMILES: Oc1ncccc1-c1c[nH]cn1] | 3-(1H-imidazol-4-yl)pyridin-2-ol | D |
| 1016 | 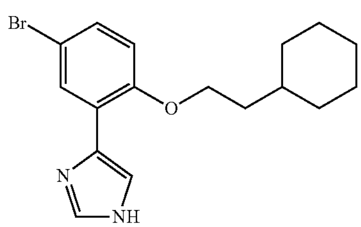 [SMILES: Brc1ccc(OCCC2CCCCC2)c(-c2c[nH]cn2)c1] | 4-(5-bromo-2-(2-cyclohexylethoxy)phenyl)-1H-imidazole | C |
| 1017 | 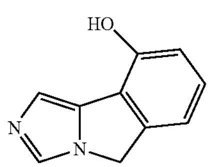 [SMILES: Oc1cccc2c1-c1cncn1C2] | 5H-imidazo[5,1-a]isoindol-9-ol | B |
| 1018 | 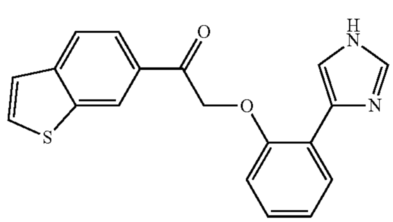 [SMILES: O=C(COc1ccccc1-c1c[nH]cn1)c1ccc2ccsc2c1] | 2-(2-(1H-imidazol-4-yl)phenoxy)-1-(benzo[b]thiophen-6-yl)ethanone | B |
| 1021 | 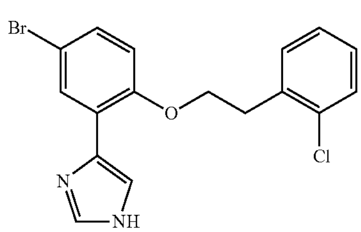 [SMILES: Clc1ccccc1CCOc1ccc(Br)cc1-c1c[nH]cn1] | 4-(5-bromo-2-(2-chlorophenethoxy)phenyl)-1H-imidazole | C |

| No. | Structure | Name | hIDO IC$_{50}$ |
|---|---|---|---|
| 1022 | 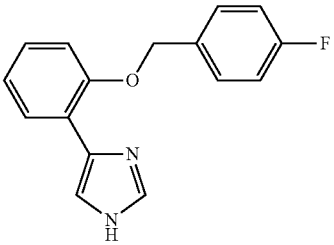 [SMILES: Fc1ccc(COc2ccccc2-c2c[nH]cn2)cc1] | 4-(2-(4-fluorobenzyloxy)phenyl)-1H-imidazole | C |
| 1023 | 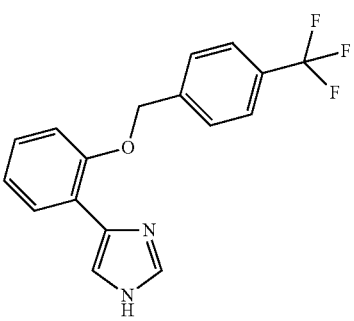 [SMILES: FC(F)(F)c1ccc(COc2ccccc2-c2c[nH]cn2)cc1] | 4-(2-(4-(trifluoromethyl)benzyloxy)phenyl)-1H-imidazole | D |
| 1024 | 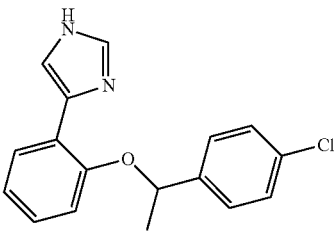 [SMILES: CC(Oc1ccccc1-c1c[nH]cn1)c1ccc(Cl)cc1] | 4-(2-(1-(4-chlorophenyl)ethoxy)phenyl)-1H-imidazole | C |
| 1026 | 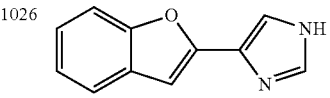 | 4-(benzofuran-2-yl)-1H-imidazole | D |
| 1027 | 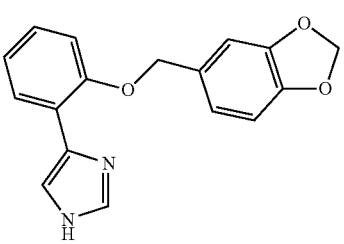 [SMILES: c1ccc(-c2c[nH]cn2)c(OCc2ccc3c(c2)OCO3)c1] | 4-(2-(benzo[d][1,3]dioxol-5-ylmethoxy)phenyl)-1H-imidazole | C |
| 1028 | 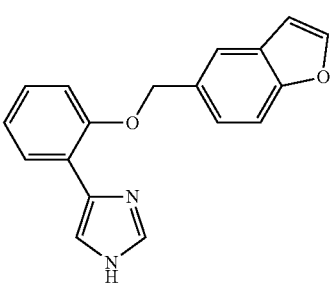 [SMILES: c1ccc(-c2c[nH]cn2)c(OCc2ccc3occc3c2)c1] | 4-(2-(benzofuran-5-ylmethoxy)phenyl)-1H-imidazole | C |

| No. | Structure | Name | hIDO IC$_{50}$ |
|---|---|---|---|
| 1029 | 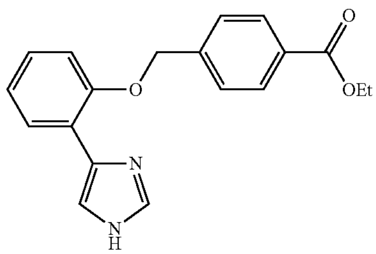 | ethyl 4-((2-(1H-imidazol-4-yl)phenoxy)methyl)benzoate | C |
| 1030 | 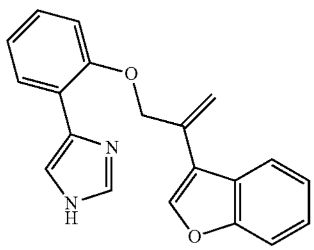 [SMILES: C=C(COc1ccccc1-c1c[nH]cn1)c1coc2ccccc12] | 4-(2-(2-(benzofuran-3-yl)allyloxy)phenyl)-1H-imidazole | B |
| 1031 | 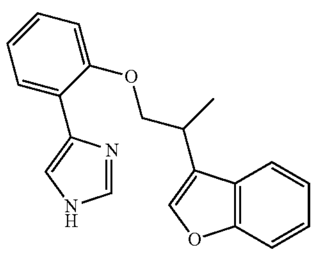 [SMILES: CC(COc1ccccc1-c1c[nH]cn1)c1coc2ccccc12] | 4-(2-(2-(benzofuran-3-yl)propoxy)phenyl)-1H-imidazole | B |
| 1032 | 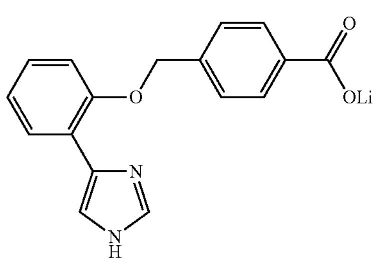 | lithium 4-((2-(1H-imidazol-4-yl)phenoxy)methyl)benzoate | C |
| 1035 | 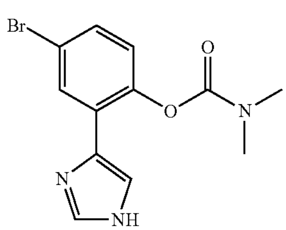 | 4-bromo-2-(1H-imidazol-4-yl)phenyl dimethylcarbamate | D |
| 1036 | 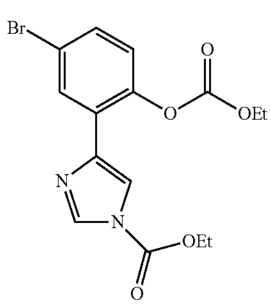 [SMILES: CCOC(=O)Oc1ccc(Br)cc1-c1cn(C(=O)OCC)cn1] | ethyl 4-(5-bromo-2-(ethoxycarbonyloxy)phenyl)-1H-imidazole-1-carboxylate | C |

-continued

| No. | Structure | Name | hIDO IC$_{50}$ |
|---|---|---|---|
| 1037 | 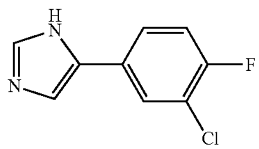 [SMILES: Fc1ccc(-c2cnc[nH]2)cc1Cl] | 5-(3-chloro-4-fluorophenyl)-1H-imidazole | C |
| 1038 | 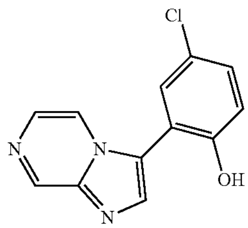 [SMILES: Oc1ccc(Cl)cc1-c1cnc2cnccn12] | 4-chloro-2-(imidazo[1,2-a]pyrazin-3-yl)phenol | D |
| 1039 | 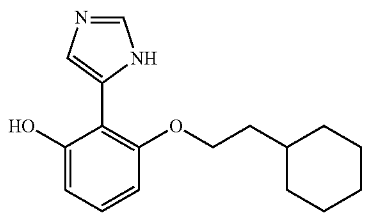 [SMILES: Oc1cccc(OCCC2CCCCC2)c1-c1cnc[nH]1] | 3-(2-cyclohexylethoxy)-2-(1H-imidazol-5-yl)phenol | B |
| 1040 | 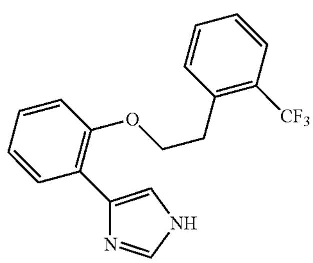 [SMILES: FC(F)(F)c1ccccc1CCOc1ccccc1-c1c[nH]cn1] | 4-(2-(2-(trifluoromethyl)phenethoxy)phenyl)-1H-imidazole | B |
| 1043 | 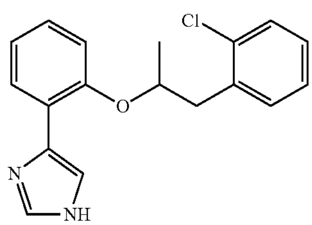 [SMILES: CC(Cc1ccccc1Cl)Oc1ccccc1-c1c[nH]cn1] | 4-(2-(1-(2-chlorophenyl)propan-2-yloxy)phenyl)-1H-imidazole | B |
| 1044 | 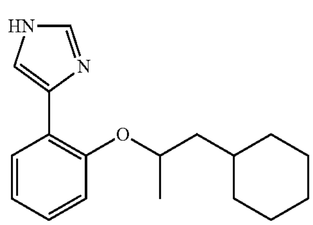 [SMILES: CC(CC1CCCCC1)Oc1ccccc1-c1c[nH]cn1] | 4-(2-(1-cyclohexylpropan-2-yloxy)phenyl)-1H-imidazole | C |
| 1045 | 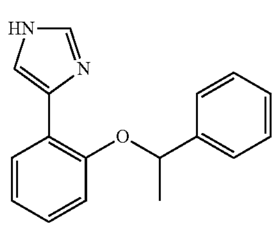 [SMILES: CC(Oc1ccccc1-c1c[nH]cn1)c1ccccc1] | 4-(2-(1-phenylethoxy)phenyl)-1H-imidazole | C |

| No. | Structure | Name | hIDO IC$_{50}$ |
|---|---|---|---|
| 1046 | 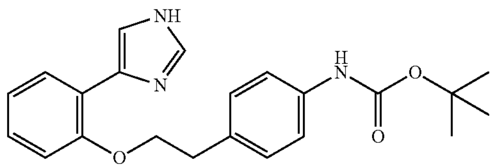 [SMILES: CC(C)(C)OC(=O)Nc1ccc(CCOc2ccccc2-c2c[nH]cn2)cc1] | tert-butyl 4-(2-(2-(1H-imidazol-4-yl)phenoxy)ethyl) phenylcarbamate | B |
| 1047 | 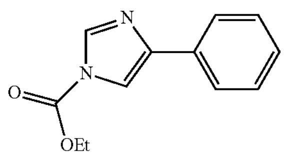 [SMILES: CCOC(=O)n1cnc(-c2ccccc2)c1] | ethyl 4-phenyl-1H-imidazole-1-carboxylate | D |
| 1048 | 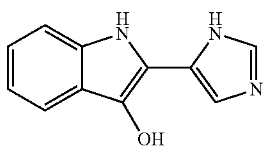 [SMILES: Oc1c(-c2cnc[nH]2)[nH]c2ccccc12] | 2-(1H-imidazol-5-yl)-1H-indol-3-ol | D |
| 1050 | 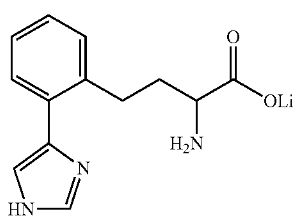 | lithium 4-(2-(1H-imidazol-4-yl)phenyl)-2-aminobutanoate | D |
| 1051 | 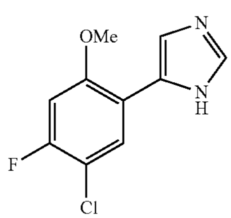 [SMILES: COc1cc(F)c(Cl)cc1-c1cnc[nH]1] | 5-(5-chloro-4-fluoro-2-methoxyphenyl)-1H-imidazole | D |
| 1052 | 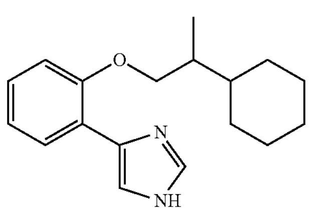 | 4-(2-(2-cyclohexylpropoxy)phenyl)-1H-imidazole hydrochloride | B |
| 1060 | 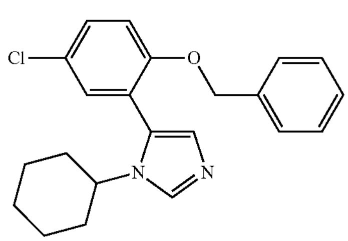 [SMILES: Clc1ccc(OCc2ccccc2)c(-c2cncn2C2CCCCC2)c1] | 5-(2-(benzyloxy)-5-chlorophenyl)-1-cyclohexyl-1H-imidazole | D |

-continued

| No. | Structure | Name | hIDO IC$_{50}$ |
|---|---|---|---|
| 1076 | 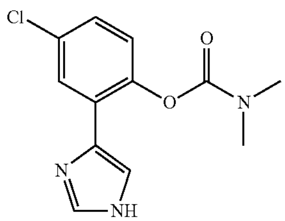 [SMILES: CN(C)C(=O)Oc1ccc(Cl)cc1-c1c[nH]cn1] | 4-chloro-2-(1H-imidazol-4-yl)phenyl dimethylcarbamate | D |
| 1077 | 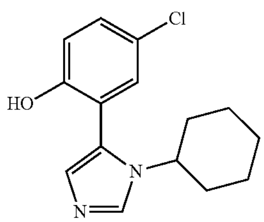 [SMILES: Oc1ccc(Cl)cc1-c1cncn1C1CCCCC1] | 4-chloro-2-(1-cyclohexyl-1H-imidazol-5-yl)phenol | B |
| 1078 | 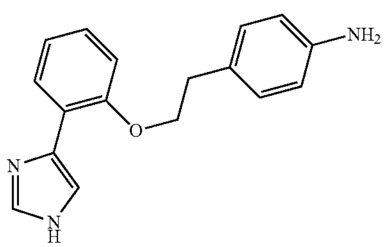 [SMILES: Nc1ccc(CCOc2ccccc2-c2c[nH]cn2)cc1] | 4-(2-(2-(1H-imidazol-4-yl)phenoxy)ethyl)aniline | B |
| 1079 | 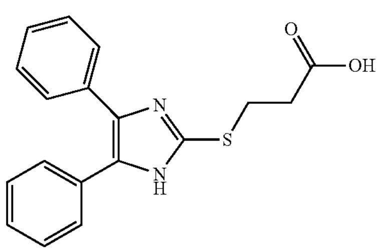 [SMILES: O=C(O)CCSc1nc(-c2ccccc2)c(-c2ccccc2)[nH]1] | 3-(4,5-diphenyl-1H-imidazol-2-ylthio)propanoic acid | D |
| 1085 | 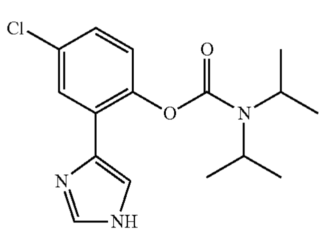 [SMILES: CC(C)N(C(=O)Oc1ccc(Cl)cc1-c1c[nH]cn1)C(C)C] | 4-chloro-2-(1H-imidazol-4-yl)phenyl diisopropylcarbamate | D |
| 1086 | 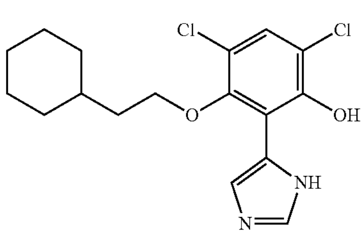 [SMILES: Oc1c(Cl)cc(Cl)c(OCCC2CCCCC2)c1-c1cnc[nH]1] | 4,6-dichloro-3-(2-cyclohexylethoxy)-2-(1H-imidazol-5-yl)phenol | D |

-continued

| No. | Structure | Name | hIDO IC$_{50}$ |
|---|---|---|---|
| 1087 | 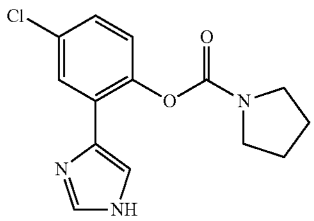 [SMILES: O=C(Oc1ccc(Cl)cc1-c1c[nH]cn1)N1CCCC1] | 4-chloro-2-(1H-imidazol-4-yl)phenyl pyrrolidine-1-carboxylate | D |
| 1088 | 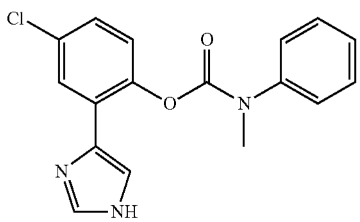 [SMILES: CN(C(=O)Oc1ccc(Cl)cc1-c1c[nH]cn1)c1ccccc1] | 4-chloro-2-(1H-imidazol-4-yl)phenyl methyl(phenyl)carbamate | D |
| 1101 | 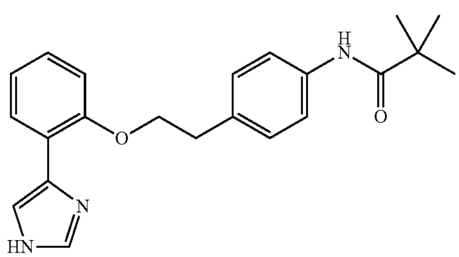 [SMILES: CC(C)(C)C(=O)Nc1ccc(CCOc2ccccc2-c2c[nH]cn2)cc1] | N-(4-(2-(2-(1H-imidazol-4-yl)phenoxy)ethyl) phenyl)pivalamide | B |
| 1102 | 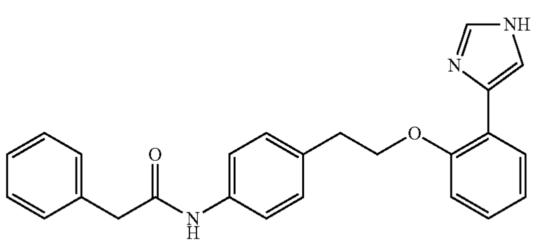 [SMILES: O=C(Cc1ccccc1)Nc1ccc(CCOc2ccccc2-c2c[nH]cn2)cc1] | N-(4-(2-(2-(1H-imidazol-4-yl)phenoxy)ethyl) phenyl)-2-phenylacetamide | A |
| 1103 | 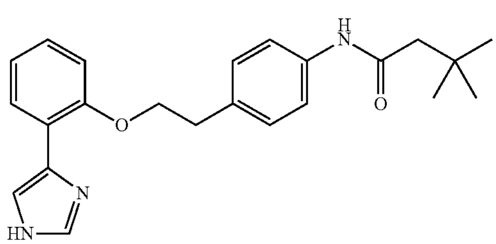 [SMILES: CC(C)(C)CC(=O)Nc1ccc(CCOc2ccccc2-c2c[nH]cn2)cc1] | N-(4-(2-(2-(1H-imidazol-4-yl)phenoxy)ethyl) phenyl)-3,3-dimethylbutanamide | B |
| 1104 | 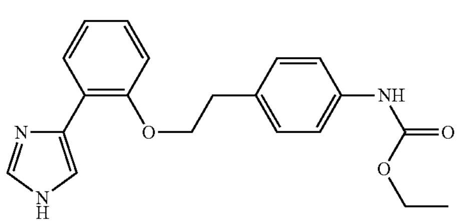 [SMILES: CCOC(=O)Nc1ccc(CCOc2ccccc2-c2c[nH]cn2)cc1] | ethyl 4-(2-(2-(1H-imidazol-4-yl)phenoxy)ethyl) phenylcarbamate | B |

-continued

| No. | Structure | Name | hIDO IC$_{50}$ |
|---|---|---|---|
| 1105 | 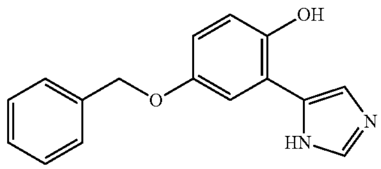 [SMILES: Oc1ccc(OCc2ccccc2)cc1-c1cnc[nH]1] | 4-(benzyloxy)-2-(1H-imidazol-5-yl)phenol | C |
| 1106 | 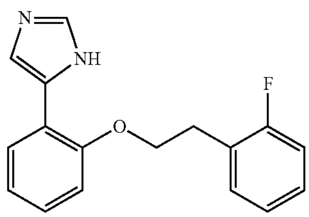 [SMILES: Fc1ccccc1CCOc1ccccc1-c1cnc[nH]1] | 5-(2-(2-fluorophenethoxy)phenyl)-1H-imidazole | B |
| 1107 | 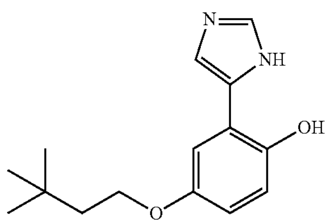 [SMILES: CC(C)(C)CCOc1ccc(O)c(-c2cnc[nH]2)c1] | 4-(3,3-dimethylbutoxy)-2-(1H-imidazol-5-yl)phenol | C |
| 1108 | 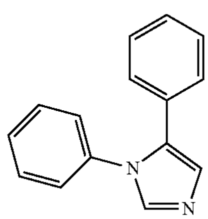 [SMILES: c1ccc(-c2cncn2-c2ccccc2)cc1] | 1,5-diphenyl-1H-imidazole | C |
| 1109 | 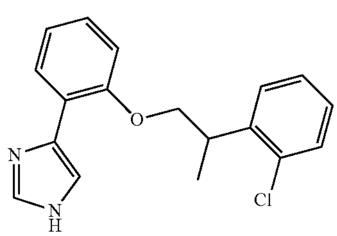 [SMILES: CC(COc1ccccc1-c1c[nH]cn1)c1ccccc1Cl] | 4-(2-(2-(2-chlorophenyl)propoxy)phenyl)-1H-imidazole | C |
| 1110 | 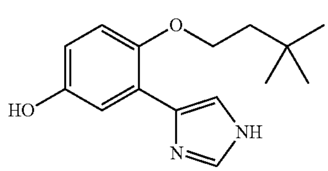 [SMILES: CC(C)(C)CCOc1ccc(O)cc1-c1c[nH]cn1] | 4-(3,3-dimethylbutoxy)-3-(1H-imidazol-4-yl)phenol | C |
| 1111 | 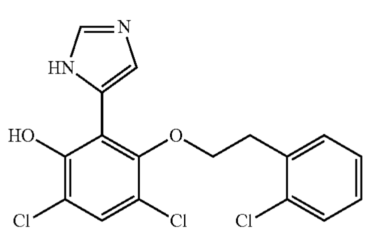 [SMILES: Oc1c(Cl)cc(Cl)c(OCCc2ccccc2Cl)c1-c1cnc[nH]1] | 4,6-dichloro-3-(2-chlorophenethoxy)-2-(1H-imidazol-5-yl)phenol | C |

-continued

| No. | Structure | Name | hIDO IC$_{50}$ |
|---|---|---|---|
| 1112 | 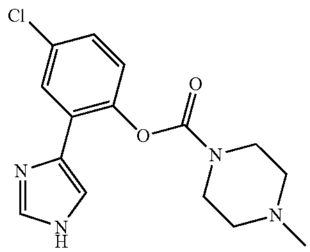 [SMILES: CN1CCN(C(=O)Oc2ccc(Cl)cc2-c2c[nH]cn2)CC1] | 4-chloro-2-(1H-imidazol-4-yl)phenyl 4-methylpiperazine-1-carboxylate | C |
| 1113 | 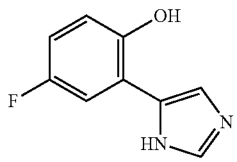 [SMILES: Oc1ccc(F)cc1-c1cnc[nH]1] | 4-fluoro-2-(1H-imidazol-5-yl)phenol | B |
| 1114 | 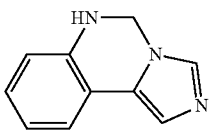 [SMILES: c1ccc2c(c1)NCn1cncc1-2] | 5,6-dihydroimidazo[1,5-c]quinazoline | D |
| 1115 | 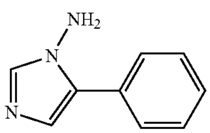 [SMILES: Nn1cncc1-c1ccccc1] | 5-phenyl-1H-imidazol-1-amine | D |
| 1119 | 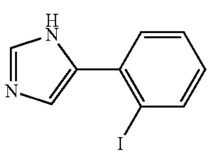 [SMILES: Ic1ccccc1-c1cnc[nH]1] | 5-(2-iodophenyl)-1H-imidazole | C |
| 1120 | 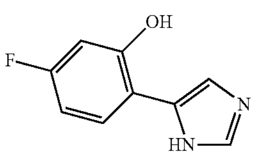 [SMILES: Oc1cc(F)ccc1-c1cnc[nH]1] | 5-fluoro-2-(1H-imidazol-5-yl)phenol | C |
| 1121 | 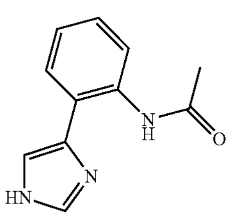 | N-(2-(1H-imidazol-4-yl)phenyl)acetamide | D |
| 1122 | 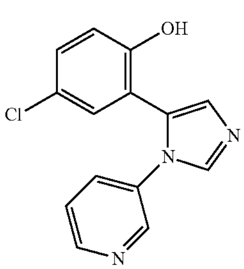 [SMILES: Oc1ccc(Cl)cc1-c1cncn1-c1cccnc1] | 4-chloro-2-(1-(pyridin-3-yl)-1H-imidazol-5-yl)phenol | C |

| No. | Structure | Name | hIDO IC$_{50}$ |
|---|---|---|---|
| 1129 | 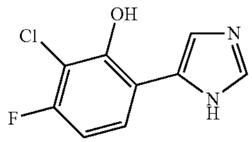 [SMILES: Oc1c(-c2cnc[nH]2)ccc(F)c1Cl] | 2-chloro-3-fluoro-6-(1H-imidazol-5-yl)phenol | C |
| 1130 | 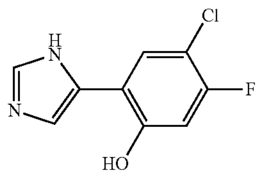 [SMILES: Oc1cc(F)c(Cl)cc1-c1cnc[nH]1] | 4-chloro-5-fluoro-2-(1H-imidazol-5-yl)phenol | B |
| 1131 | 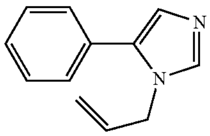 | 1-allyl-5-phenyl-1H-imidazole | D |
| 1136 | 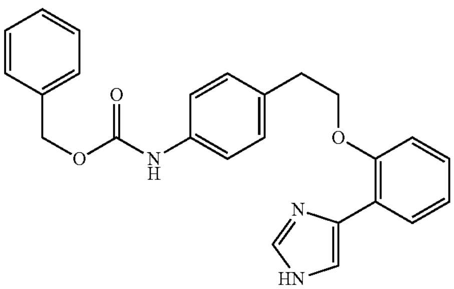 [SMILES: O=C(Nc1ccc(CCOc2ccccc2-c2c[nH]cn2)cc1)OCc1ccccc1] | benzyl 4-(2-(2-(1H-imidazol-4-yl)phenoxy)ethyl)phenylcarbamate | B |
| 1137 | 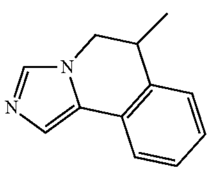 | 6-methyl-5,6-dihydroimidazo[5,1-a]isoquinoline | D |
| 1139 | 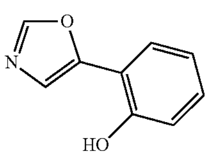 [SMILES: Oc1ccccc1-c1cnco1] | 2-(oxazol-5-yl)phenol | C |
| 1141 | 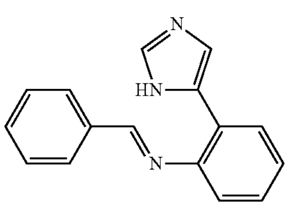 [SMILES: C(=N\c1ccccc1-c1cnc[nH]1)/c1ccccc1] | (E)-N-benzylidene-2-(1H-imidazol-5-yl)aniline | D |
| 1143 | 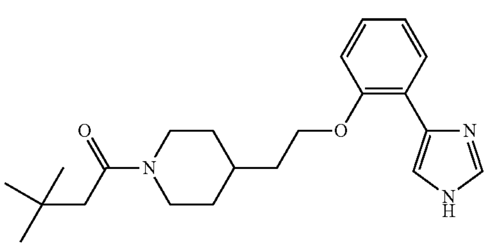 [SMILES: CC(C)(C)CC(=O)N1CCC(CCOc2ccccc2-c2c[nH]cn2)CC1] | 1-(4-(2-(2-(1H-imidazol-4-yl)phenoxy)ethyl)piperidin-1-yl)-3,3-dimethylbutan-1-one | C |

| No. | Structure | Name | hIDO IC$_{50}$ |
|---|---|---|---|
| 1147 | 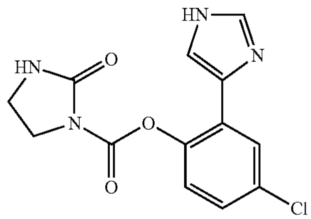 [SMILES: O=C1NCCN1C(=O)Oc1ccc(Cl)cc1-c1c[nH]cn1] | 4-chloro-2-(1H-imidazol-4-yl)phenyl 2-oxoimidazolidine-1-carboxylate | B |
| 1148 | 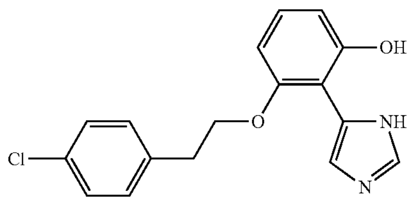 [SMILES: Oc1cccc(OCCc2ccc(Cl)cc2)c1-c1cnc[nH]1] | 3-(4-chlorophenethoxy)-2-(1H-imidazol-5-yl)phenol | B |
| 1149 | 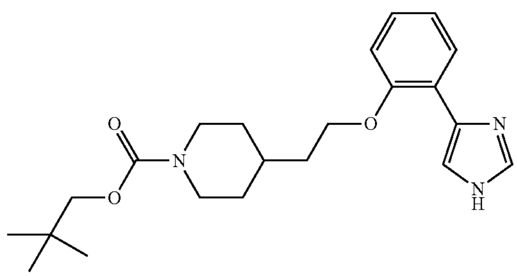 [SMILES: CC(C)(C)COC(=O)N1CCC(CCOc2ccccc2-c2c[nH]cn2)CC1] | neopentyl 4-(2-(2-(1H-imidazol-4-yl)phenoxy)ethyl)piperidine-1-carboxylate | C |
| 1150 | 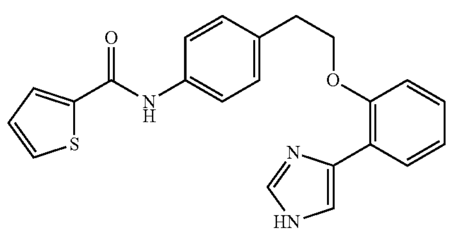 [SMILES: O=C(Nc1ccc(CCOc2ccccc2-c2c[nH]cn2)cc1)c1cccs1] | N-(4-(2-(2-(1H-imidazol-4-yl)phenoxy)ethyl)phenyl)thiophene-2-carboxamide | B |
| 1151 | 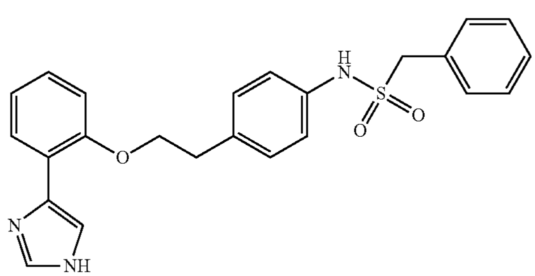 [SMILES: O=S(=O)(Cc1ccccc1)Nc1ccc(CCOc2ccccc2-c2c[nH]cn2)cc1] | N-(4-(2-(2-(1H-imidazol-4-yl)phenoxy)ethyl)phenyl)-1-phenylmethanesulfonamide | B |
| 1152 | 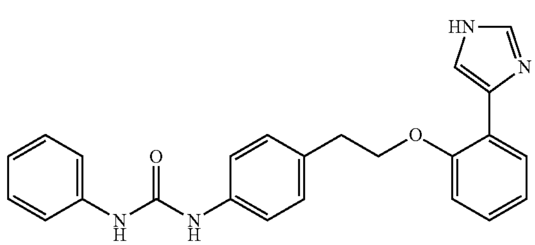 [SMILES: O=C(Nc1ccccc1)Nc1ccc(CCOc2ccccc2-c2c[nH]cn2)cc1] | 1-(4-(2-(2-(1H-imidazol-4-yl)phenoxy)ethyl)phenyl)-3-phenylurea | A |

-continued

| No. | Structure | Name | hIDO IC$_{50}$ |
|---|---|---|---|
| 1153 | 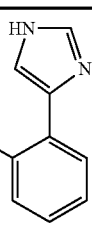 | N-(4-(2-(2-(1H-imidazol-4-yl)phenoxy)ethyl)phenyl)-2-(pyrazin-2-yl)acetamide | C |
| 1154 | 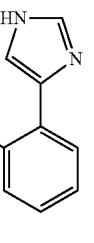 | N-(4-(2-(2-(1H-imidazol-4-yl)phenoxy)ethyl)phenyl)-2-(thiophen-2-yl)acetamide | B |
| 1156 | 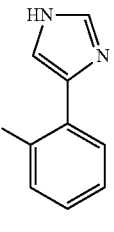 | N-(4-(2-(2-(1H-imidazol-4-yl)phenoxy)ethyl)phenyl)-2-(pyrazin-2-yl)acetamide | B |
| 1157 | 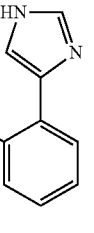 | N-(4-(2-(2-(1H-imidazol-4-yl)phenoxy)ethyl)phenyl)-2-(thiophen-2-yl)acetamide | B |
| 1159 | 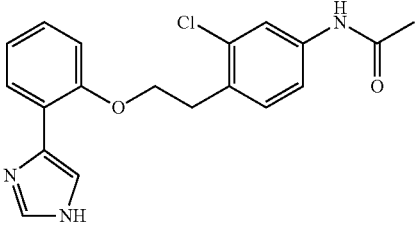 [SMILES: CC(=O)Nc1ccc(CCOc2ccccc2-c2c[nH]cn2)c(Cl)c1] | N-(4-(2-(2-(1H-imidazol-4-yl)phenoxy)ethyl)-3-chlorophenyl)acetamide | B |
| 1160 | 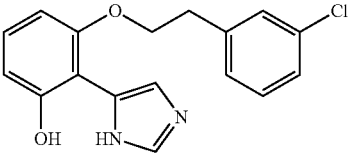 [SMILES: Oc1cccc(OCCc2cccc(Cl)c2)c1-c1cnc[nH]1] | 3-(3-chlorophenethoxy)-2-(1H-imidazol-5-yl)phenol | B |
| 1163 | 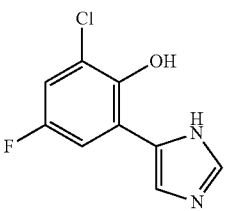 [SMILES: Oc1c(Cl)cc(F)cc1-c1cnc[nH]1] | 2-chloro-4-fluoro-6-(1H-imidazol-5-yl)phenol | C |

-continued

| No. | Structure | Name | hIDO IC$_{50}$ |
|---|---|---|---|
| 1165 | 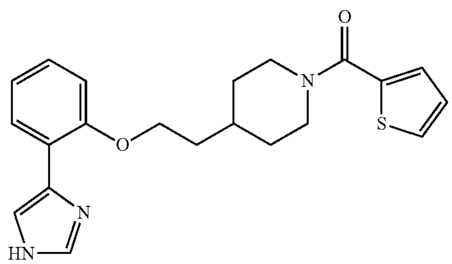 [SMILES: O=C(c1cccs1)N1CCC(CCOc2ccccc2-c2c[nH]cn2)CC1] | (4-(2-(2-(1H-imidazol-4-yl)phenoxy)ethyl) piperidin-1-yl)(thiophen-2-yl)methanone | B |
| 1170 | 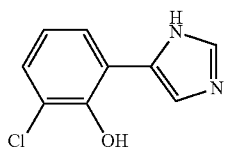 [SMILES: Oc1c(Cl)cccc1-c1cnc[nH]1] | 2-chloro-6-(1H-imidazol-5-yl)phenol | C |
| 1172 | 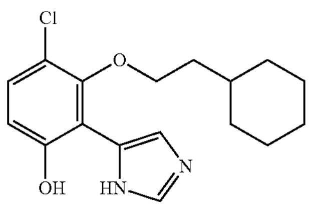 [SMILES: Oc1ccc(Cl)c(OCCC2CCCCC2)c1-c1cnc[nH]1] | 4-chloro-3-(2-cyclohexylethoxy)-2-(1H-imidazol-5-yl)phenol | B |
| 1176 | 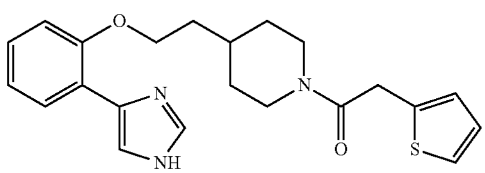 [SMILES: O=C(Cc1cccs1)N1CCC(CCOc2ccccc2-c2c[nH]cn2)CC1] | 1-(4-(2-(2-(1H-imidazol-4-yl)phenoxy)ethyl) piperidin-1-yl)-2-(thiophen-2-yl)ethanone | B |
| 1177 | 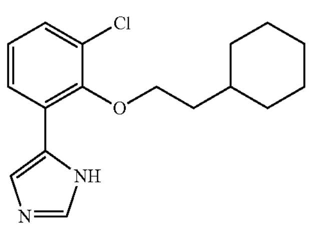 [SMILES: Clc1cccc(-c2cnc[nH]2)c1OCCC1CCCCC1] | 5-(3-chloro-2-(2-cyclohexylethoxy)phenyl)-1H-imidazole | B |
| 1181 | 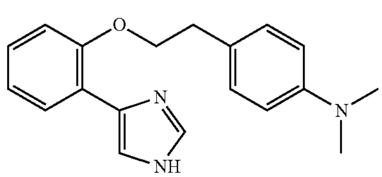 [SMILES: CN(C)c1ccc(CCOc2ccccc2-c2c[nH]cn2)cc1] | 4-(2-(2-(1H-imidazol-4-yl)phenoxy)ethyl)-N,N-dimethylaniline | C |
| 1182 | 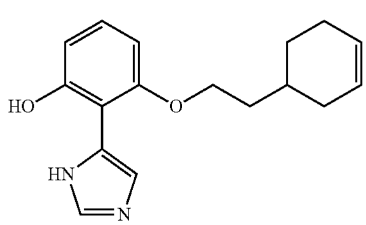 [SMILES: Oc1cccc(OCCC2CC=CCC2)c1-c1cnc[nH]1] | 3-(2-(cyclohex-3-en-1-yl)ethoxy)-2-(1H-imidazol-5-yl)phenol | B |

-continued

| No. | Structure | Name | hIDO IC$_{50}$ |
|---|---|---|---|
| 1186 | 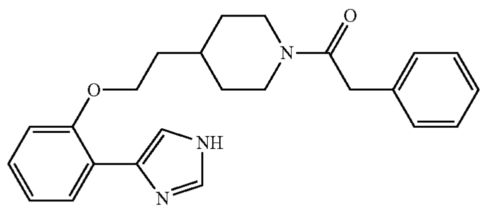 [SMILES: O=C(Cc1ccccc1)N1CCC(CCOc2ccccc2-c2c[nH]cn2)CC1] | 1-(4-(2-(2-(1H-imidazol-4-yl)phenoxy)ethyl)piperidin-1-yl)-2-phenylethanone | B |
| 1191 | 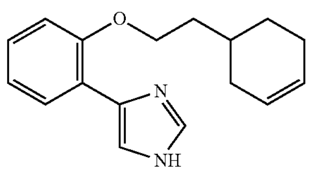 [SMILES: C1=CCC(CCOc2ccccc2-c2c[nH]cn2)CC1] | 4-(2-(2-(cyclohex-3-en-1-yl)ethoxy)phenyl)-1H-imidazole | B |
| 1192 | 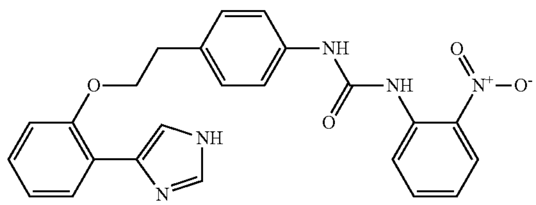 [SMILES: O=C(Nc1ccc(CCOc2ccccc2-c2c[nH]cn2)cc1)Nc1ccccc1[N+](=O)[O-]] | 1-(4-(2-(2-(1H-imidazol-4-yl)phenoxy)ethyl)phenyl)-3-(2-nitrophenyl)urea | A |
| 1193 | 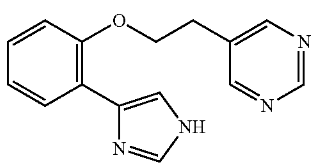 [SMILES: c1ccc(-c2c[nH]cn2)c(OCCc2cncnc2)c1] | 5-(2-(2-(1H-imidazol-4-yl)phenoxy)ethyl)pyrimidine | D |
| 1198 | 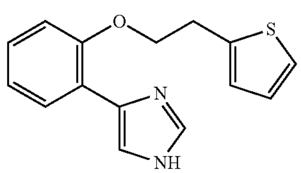 [SMILES: c1csc(CCOc2ccccc2-c2c[nH]cn2)c1] | 4-(2-(2-(thiophen-2-yl)ethoxy)phenyl)-1H-imidazole | C |
| 1199 | 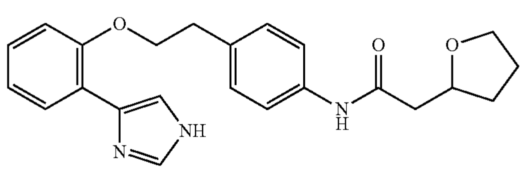 [SMILES: O=C(CC1CCCO1)Nc1ccc(CCOc2ccccc2-c2c[nH]cn2)cc1] | N-(4-(2-(2-(1H-imidazol-4-yl)phenoxy)ethyl)phenyl)-2-(tetrahydrofuran-2-yl)acetamide | B |
| 1200 | 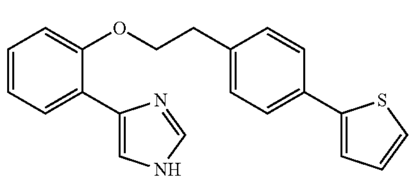 [SMILES: c1csc(-c2ccc(CCOc3ccccc3-c3c[nH]cn3)cc2)c1] | 4-(2-(4-(thiophen-2-yl)phenethoxy)phenyl)-1H-imidazole | C |
| 1201 | 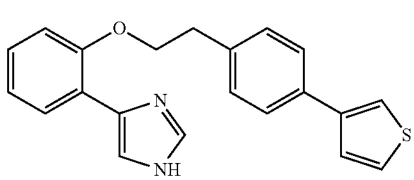 [SMILES: c1ccc(-c2c[nH]cn2)c(OCCc2ccc(-c3ccsc3)cc2)c1] | 4-(2-(4-(thiophen-3-yl)phenethoxy)phenyl)-1H-imidazole | C |

| No. | Structure | Name | hIDO IC$_{50}$ |
|---|---|---|---|
| 1202 | 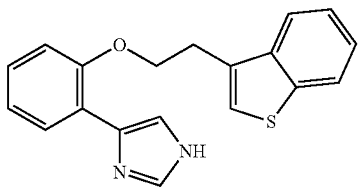 [SMILES: c1ccc(-c2c[nH]cn2)c(OCCc2csc3ccccc23)c1] | 4-(2-(2-(benzo[b]thiophen-3-yl)ethoxy)phenyl)-1H-imidazole | C |
| 1203 | 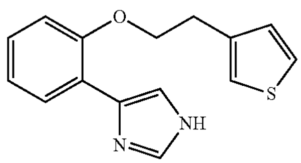 [SMILES: c1ccc(-c2c[nH]cn2)c(OCCc2ccsc2)c1] | 4-(2-(2-(thiophen-3-yl)ethoxy)phenyl)-1H-imidazole | C |
| 1204 | 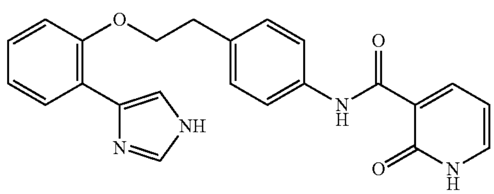 [SMILES: O=C(Nc1ccc(CCOc2ccccc2-c2c[nH]cn2)cc1)c1ccc[nH]c1=O] | N-(4-(2-(2-(1H-imidazol-4-yl)phenoxy)ethyl)phenyl)-2-oxo-1,2-dihydropyridine-3-carboxamide | B |
| 1207 | 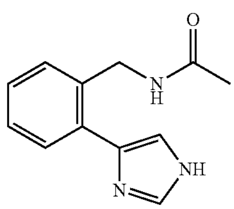 [SMILES: CC(=O)NCc1ccccc1-c1c[nH]cn1] | N-(2-(1H-imidazol-4-yl)benzyl)acetamide | D |
| 1211 | 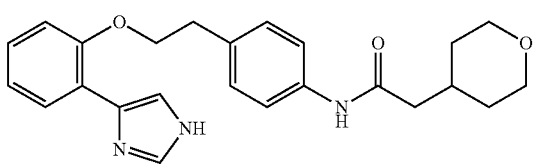 [SMILES: O=C(CC1CCOCC1)Nc1ccc(CCOc2ccccc2-c2c[nH]cn2)cc1] | N-(4-(2-(2-(1H-imidazol-4-yl)phenoxy)ethyl)phenyl)-2-(tetrahydro-2H-pyran-4-yl)acetamide | B |
| 1212 | 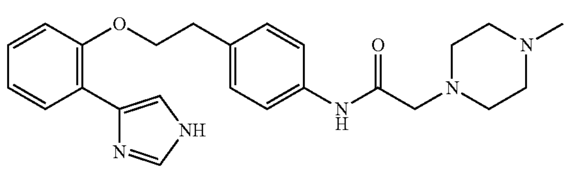 [SMILES: CN1CCN(CC(=O)Nc2ccc(CCOc3ccccc3-c3c[nH]cn3)cc2)CC1] | N-(4-(2-(2-(1H-imidazol-4-yl)phenoxy)ethyl)phenyl)-2-(4-methylpiperazin-1-yl)acetamide | C |
| 1213 | 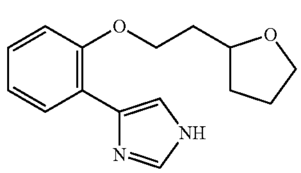 [SMILES: c1ccc(-c2c[nH]cn2)c(OCCC2CCCO2)c1] | 4-(2-(2-(tetrahydrofuran-2-yl)ethoxy)phenyl)-1H-imidazole | C |
| 1214 | 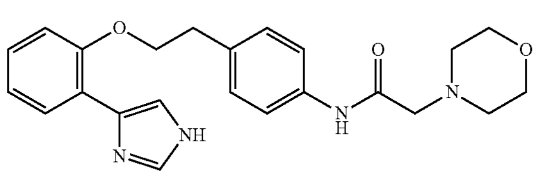 [SMILES: O=C(CN1CCOCC1)Nc1ccc(CCOc2ccccc2-c2c[nH]cn2)cc1] | N-(4-(2-(2-(1H-imidazol-4-yl)phenoxy)ethyl)phenyl)-2-morpholinoacetamide | B |

| No. | Structure | Name | hIDO IC$_{50}$ |
|---|---|---|---|
| 1216 | 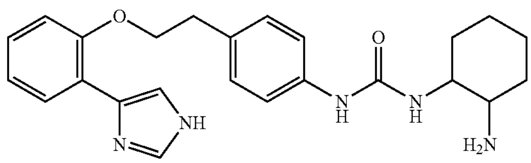 [SMILES: NC1CCCCC1NC(=O)Nc1ccc(CCOc2ccccc2-c2c[nH]cn2)cc1] | 1-(4-(2-(2-(1H-imidazol-4-yl)phenoxy)ethyl) phenyl)-3-(2-aminocyclohexyl)urea | B |
| 1217 | 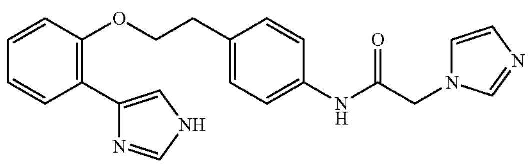 [SMILES: O=C(Cn1ccnc1)Nc1ccc(CCOc2ccccc2-c2c[nH]cn2)cc1] | N-(4-(2-(2-(1H-imidazol-4-yl)phenoxy)ethyl) phenyl)-2-(1H-imidazol-1-yl)acetamide | B |
| 1218 | 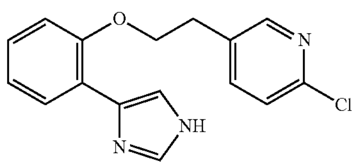 [SMILES: Clc1ccc(CCOc2ccccc2-c2c[nH]cn2)cn1] | 5-(2-(2-(1H-imidazol-4-yl)phenoxy)ethyl)-2-chloropyridine | C |
| 1219 | 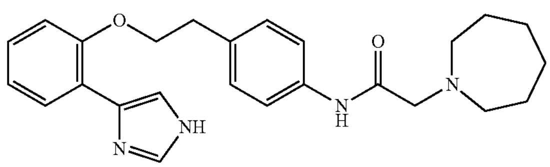 [SMILES: O=C(CN1CCCCCC1)Nc1ccc(CCOc2ccccc2-c2c[nH]cn2)cc1] | N-(4-(2-(2-(1H-imidazol-4-yl)phenoxy)ethyl) phenyl)-2-(azepan-1-yl)acetamide | C |
| 1221 | 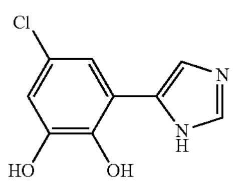 [SMILES: Oc1cc(Cl)cc(-c2cnc[nH]2)c1O] | 5-chloro-3-(1H-imidazol-5-yl)benzene-1,2-diol | B |
| 1222 | 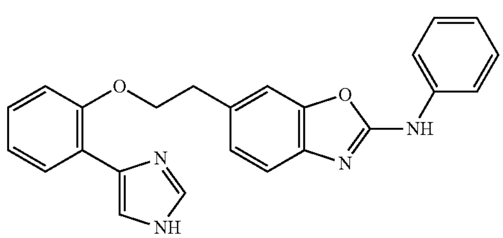 [SMILES: c1ccc(Nc2nc3ccc(CCOc4ccccc4-c4c[nH]cn4)cc3o2)cc1] | 6-(2-(2-(1H-imidazol-4-yl)phenoxy)ethyl)-N-phenylbenzo[d]oxazol-2-amine | B |
| 1223 | 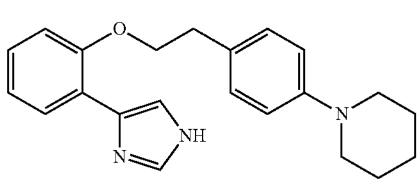 [SMILES: c1ccc(-c2c[nH]cn2)c(OCCc2ccc(N3CCCCC3)cc2)c1] | 1-(4-(2-(2-(1H-imidazol-4-yl)phenoxy)ethyl) phenyl)piperidine | C |
| 1224 | 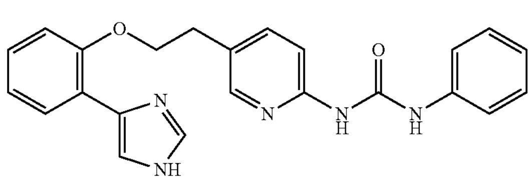 [SMILES: O=C(Nc1ccccc1)Nc1ccc(CCOc2ccccc2-c2c[nH]cn2)cn1] | 1-(5-(2-(2-(1H-imidazol-4-yl)phenoxy)ethyl) pyridin-2-yl)-3-phenylurea | B |

-continued

| No. | Structure | Name | hIDO IC$_{50}$ |
|---|---|---|---|
| 1225 | 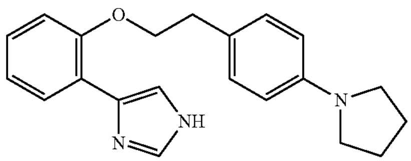 [SMILES: c1ccc(-c2c[nH]cn2)c(OCCc2ccc(N3CCCC3)cc2)c1] | 4-(2-(4-(pyrrolidin-1-yl)phenethoxy)phenyl)-1H-imidazole | C |
| 1226 | 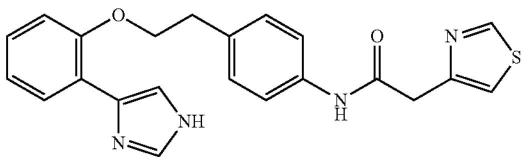 [SMILES: O=C(Cc1cscn1)Nc1ccc(CCOc2ccccc2-c2c[nH]cn2)cc1] | N-(4-(2-(2-(1H-imidazol-4-yl)phenoxy)ethyl)phenyl)-2-(thiazol-4-yl)acetamide | B |
| 1227 | 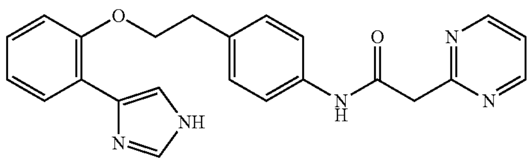 [SMILES: O=C(Cc1ncccn1)Nc1ccc(CCOc2ccccc2-c2c[nH]cn2)cc1] | N-(4-(2-(2-(1H-imidazol-4-yl)phenoxy)ethyl)phenyl)-2-(pyrimidin-2-yl)acetamide | B |
| 1228 | 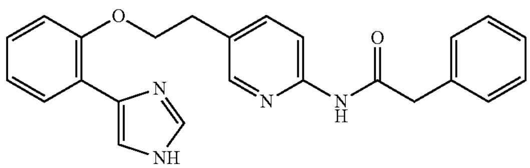 [SMILES: O=C(Cc1ccccc1)Nc1ccc(CCOc2ccccc2-c2c[nH]cn2)cn1] | N-(5-(2-(2-(1H-imidazol-4-yl)phenoxy)ethyl)pyridin-2-yl)-2-phenylacetamide | B |
| 1229 | 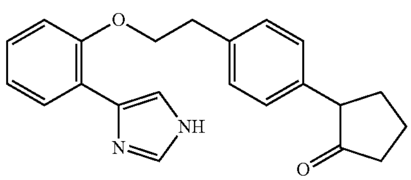 [SMILES: O=C1CCCC1c1ccc(CCOc2ccccc2-c2c[nH]cn2)cc1] | 2-(4-(2-(2-(1H-imidazol-4-yl)phenoxy)ethyl)phenyl)cyclopentanone | C |
| 1230 | 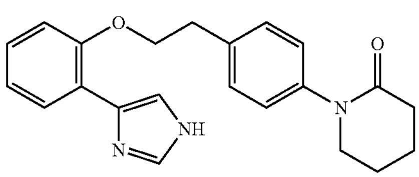 [SMILES: O=C1CCCCN1c1ccc(CCOc2ccccc2-c2c[nH]cn2)cc1] | 1-(4-(2-(2-(1H-imidazol-4-yl)phenoxy)ethyl)phenyl)piperidin-2-one | C |
| 1231 | 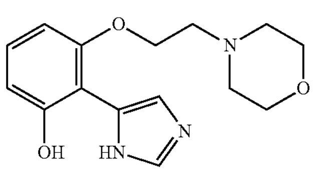 [SMILES: Oc1cccc(OCCN2CCOCC2)c1-c1cnc[nH]1] | 2-(1H-imidazol-5-yl)-3-(2-morpholinoethoxy)phenol | C |
| 1232 | 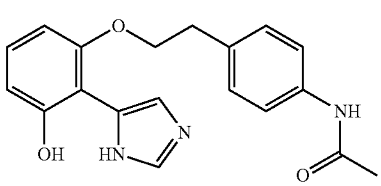 [SMILES: CC(=O)Nc1ccc(CCOc2cccc(O)c2-c2cnc[nH]2)cc1] | N-(4-(2-(3-hydroxy-2-(1H-imidazol-5-yl)phenoxy)ethyl)phenyl)acetamide | C |
| 1234 | 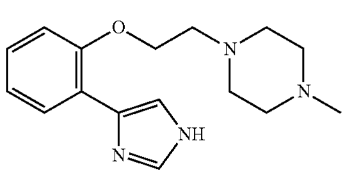 [SMILES: CN1CCN(CCOc2ccccc2-c2c[nH]cn2)CC1] | 1-(2-(2-(1H-imidazol-4-yl)phenoxy)ethyl)-4-methylpiperazine | D |

| No. | Structure | Name | hIDO IC$_{50}$ |
|---|---|---|---|
| 1235 | 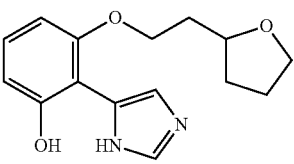 [SMILES: Oc1cccc(OCCC2CCCO2)c1-c1cnc[nH]1] | 2-(1H-imidazol-5-yl)-3-(2-(tetrahydrofuran-2-yl)ethoxy)phenol | C |
| 1236 | 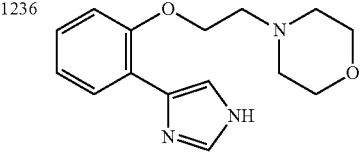 | 4-(2-(2-(1H-imidazol-4-yl)phenoxy)ethyl)morpholine | D |
| 1238 | 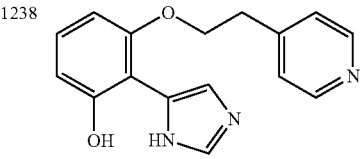 | 2-(1H-imidazol-5-yl)-3-(2-(pyridin-4-yl)ethoxy)phenol | C |
| 1239 | 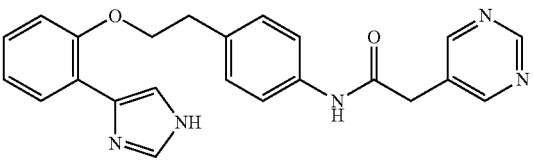 [SMILES: O=C(Cc1cncnc1)Nc1ccc(CCOc2ccccc2-c2c[nH]cn2)cc1] | N-(4-(2-(2-(1H-imidazol-4-yl)phenoxy)ethyl)phenyl)-2-(pyrimidin-5-yl)acetamide | B |
| 1240 | 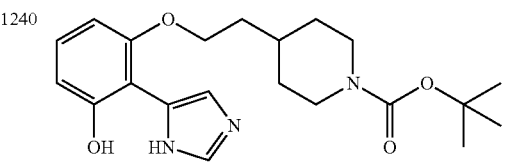 | tert-butyl 4-(2-(3-hydroxy-2-(1H-imidazol-5-yl)phenoxy)ethyl)piperidine-1-carboxylate | C |
| 1241 | 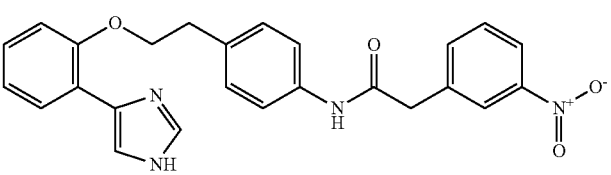 [SMILES: O=C(Cc1cccc([N+](=O)[O-])c1)Nc1ccc(CCOc2ccccc2-c2c[nH]cn2)cc1] | N-(4-(2-(2-(1H-imidazol-4-yl)phenoxy)ethyl)phenyl)-2-(3-nitrophenyl)acetamide | B |
| 1242 | 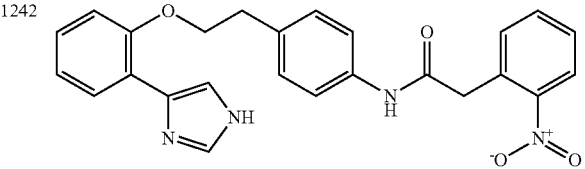 | N-(4-(2-(2-(1H-imidazol-4-yl)phenoxy)ethyl)phenyl)-2-(2-nitrophenyl)acetamide | A |
| 1243 | 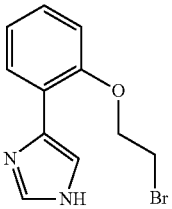 | 4-(2-(2-bromoethoxy)phenyl)-1H-imidazole | C |

-continued

| No. | Structure | Name | hIDO IC$_{50}$ |
|---|---|---|---|
| 1244 | 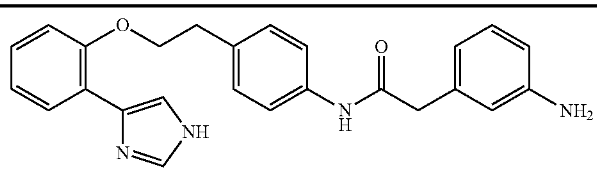 | N-(4-(2-(2-(1H-imidazol-4-yl)phenoxy)ethyl)phenyl)-2-(3-aminophenyl)acetamide | B |
| 1247 | 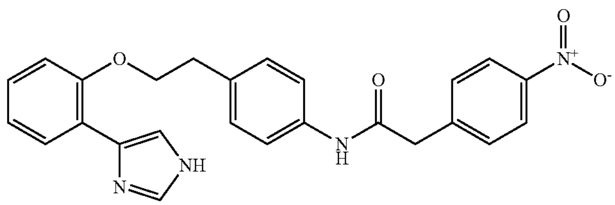 [SMILES: O=C(Cc1ccc([N+](=O)[O-])cc1)Nc1ccc(CCOc2ccccc2-c2c[nH]cn2)cc1] | N-(4-(2-(2-(1H-imidazol-4-yl)phenoxy)ethyl)phenyl)-2-(4-nitrophenyl)acetamide | A |
| 1248 | 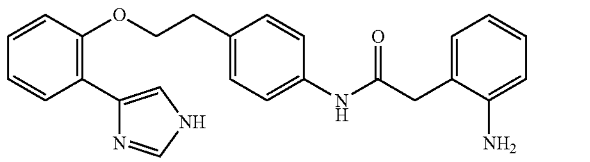 [SMILES: Nc1ccccc1CC(=O)Nc1ccc(CCOc2ccccc2-c2c[nH]cn2)cc1] | N-(4-(2-(2-(1H-imidazol-4-yl)phenoxy)ethyl)phenyl)-2-(2-aminophenyl)acetamide | A |
| 1250 | 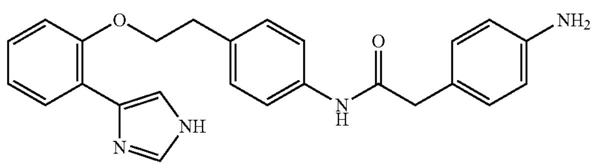 [SMILES: Nc1ccc(CC(=O)Nc2ccc(CCOc3ccccc3-c3c[nH]cn3)cc2)cc1] | N-(4-(2-(2-(1H-imidazol-4-yl)phenoxy)ethyl)phenyl)-2-(4-aminophenyl)acetamide | B |
| 1253 | 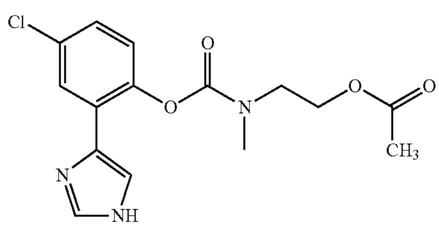 [SMILES: CC(=O)OCCN(C)C(=O)Oc1ccc(Cl)cc1-c1c[nH]cn1] | 2-(((4-chloro-2-(1H-imidazol-4-yl)phenoxy)carbonyl)(methyl)amino)ethyl acetate | D |
| 1257 | 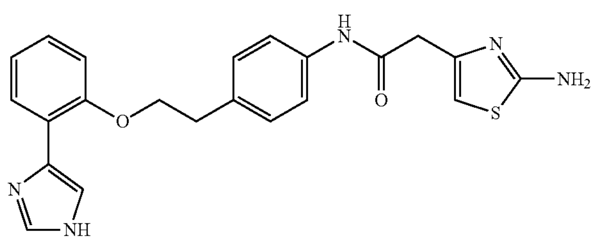 [SMILES: Nc1nc(CC(=O)Nc2ccc(CCOc3ccccc3-c3c[nH]cn3)cc2)cs1] | N-(4-(2-(2-(1H-imidazol-4-yl)phenoxy)ethyl)phenyl)-2-(2-aminothiazol-4-yl)acetamide | B |
| 1260 | 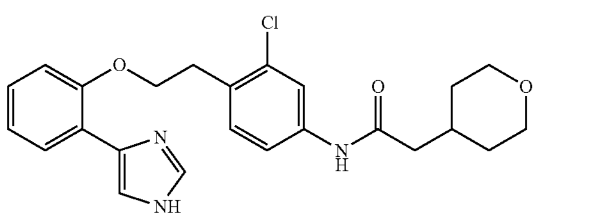 [SMILES: O=C(CC1CCOCC1)Nc1ccc(CCOc2ccccc2-c2c[nH]cn2)c(Cl)c1] | N-(4-(2-(2-(1H-imidazol-4-yl)phenoxy)ethyl)-3-chlorophenyl)-2-(tetrahydro-2H-pyran-4-yl)acetamide | A |
| 1261 | 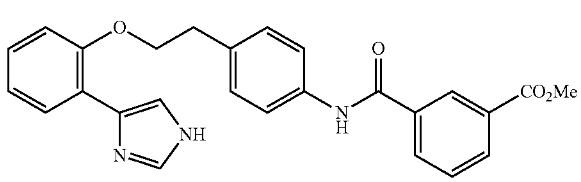 [SMILES: COC(=O)c1cccc(C(=O)Nc2ccc(CCOc3ccccc3-c3c[nH]cn3)cc2)c1] | methyl 3-((4-(2-(2-(1H-imidazol-4-yl)phenoxy)ethyl)phenyl)carbamoyl)benzoate | A |

| No. | Structure | Name | hIDO IC$_{50}$ |
|---|---|---|---|
| 1263 | 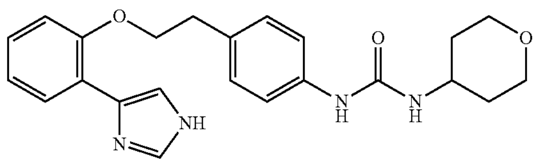 [SMILES: O=C(Nc1ccc(CCOc2ccccc2-c2c[nH]cn2)cc1)NC1CCOCC1] | 1-(4-(2-(2-(1H-imidazol-4-yl)phenoxy)ethyl)phenyl)-3-(tetrahydro-2H-pyran-4-yl)urea | C |
| 1264 | 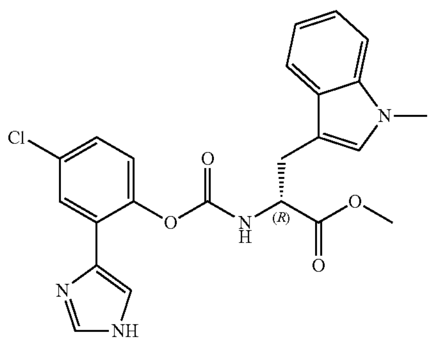 | (R)-methyl 2-(((4-chloro-2-(1H-imidazol-4-yl)phenoxy)carbonyl)amino)-3-(1-methyl-1H-indol-3-yl)propanoate | B |
| 1265 | 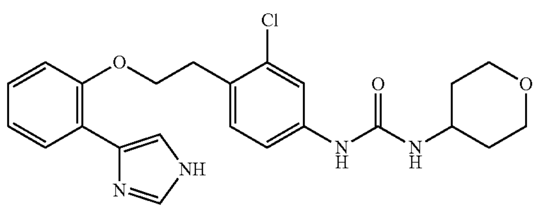 [SMILES: O=C(Nc1ccc(CCOc2ccccc2-c2c[nH]cn2)c(Cl)c1)NC1CCOCC1] | 1-(4-(2-(2-(1H-imidazol-4-yl)phenoxy)ethyl)-3-chlorophenyl)-3-(tetrahydro-2H-pyran-4-yl)urea | A |
| 1270 | 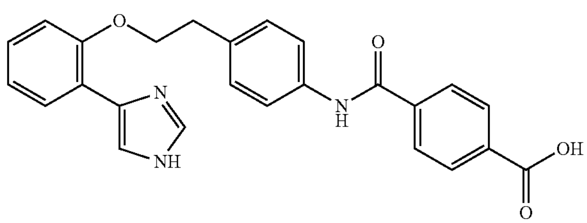 [SMILES: O=C(O)c1ccc(C(=O)Nc2ccc(CCOc3ccccc3-c3c[nH]cn3)cc2)cc1] | 4-((4-(2-(2-(1H-imidazol-4-yl)phenoxy)ethyl)phenyl)carbamoyl)benzoic acid | B |
| 1271 | 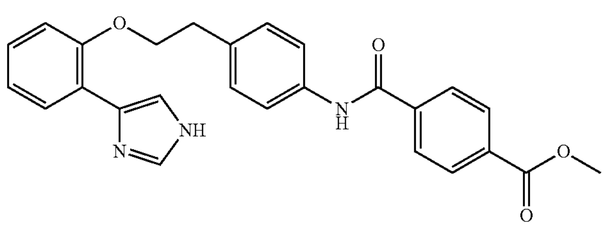 [SMILES: COC(=O)c1ccc(C(=O)Nc2ccc(CCOc3ccccc3-c3c[nH]cn3)cc2)cc1] | methyl 4-((4-(2-(2-(1H-imidazol-4-yl)phenoxy)ethyl)phenyl)carbamoyl)benzoate | B |
| 1272 | 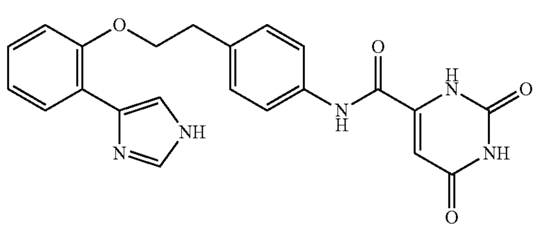 [SMILES: O=C(Nc1ccc(CCOc2ccccc2-c2c[nH]cn2)cc1)c1cc(=O)[nH]c(=O)[nH]1] | N-(4-(2-(2-(1H-imidazol-4-yl)phenoxy)ethyl)phenyl)-2,6-dioxo-1,2,3,6-tetrahydropyrimidine-4-carboxamide | B |
| 1276 | 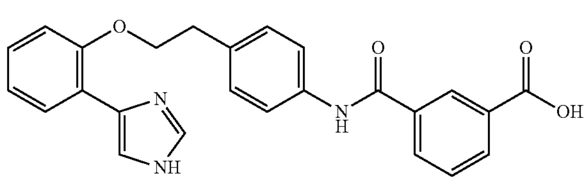 [SMILES: O=C(O)c1cccc(C(=O)Nc2ccc(CCOc3ccccc3-c3c[nH]cn3)cc2)c1] | 3-((4-(2-(2-(1H-imidazol-4-yl)phenoxy)ethyl)phenyl)carbamoyl)benzoic acid | B |

| No. | Structure | Name | hIDO IC$_{50}$ |
|---|---|---|---|
| 1285 | 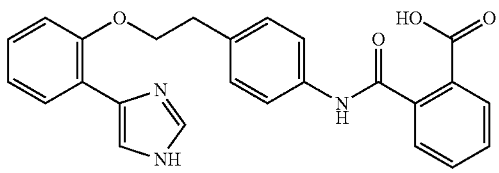 [SMILES: O=C(O)c1ccccc1C(=O)Nc1ccc(CCOc2ccccc2-c2c[nH]cn2)cc1] | 2-((4-(2-(2-(1H-imidazol-4-yl)phenoxy)ethyl)phenyl)carbamoyl)benzoic acid | B |
| 1289 | 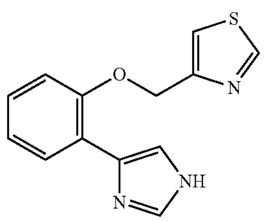 [SMILES: c1ccc(-c2c[nH]cn2)c(OCc2cscn2)c1] | 4-((2-(1H-imidazol-4-yl)phenoxy)methyl)thiazole | C |
| 1292 | 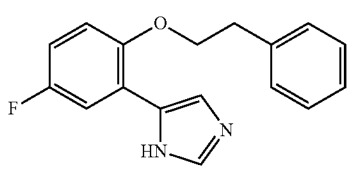 [SMILES: Fc1ccc(OCCc2ccccc2)c(-c2cnc[nH]2)c1] | 5-(5-fluoro-2-phenethoxyphenyl)-1H-imidazole | C |
| 1295 | 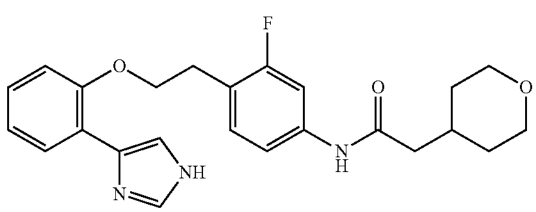 [SMILES: O=C(CC1CCOCC1)Nc1ccc(CCOc2ccccc2-c2c[nH]cn2)c(F)c1] | N-(4-(2-(2-(1H-imidazol-4-yl)phenoxy)ethyl)-3-fluorophenyl)-2-(tetrahydro-2H-pyran-4-yl)acetamide | A |
| 1296 | 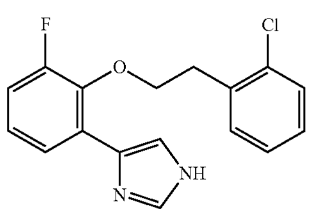 [SMILES: Fc1cccc(-c2c[nH]cn2)c1OCCc1ccccc1Cl] | 4-(2-(2-chlorophenethoxy)-3-fluorophenyl)-1H-imidazole | C |
| 1297 | 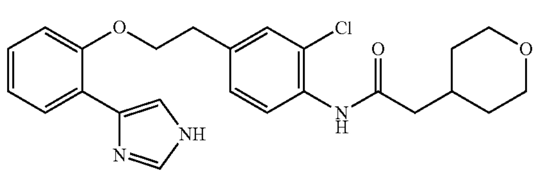 [SMILES: O=C(CC1CCOCC1)Nc1ccc(CCOc2ccccc2-c2c[nH]cn2)cc1Cl] | N-(4-(2-(2-(1H-imidazol-4-yl)phenoxy)ethyl)-2-chlorophenyl)-2-(tetrahydro-2H-pyran-4-yl)acetamide | C |
| 1298 | 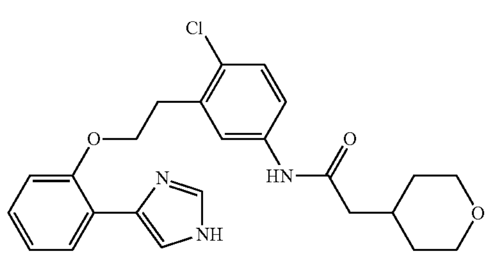 [SMILES: O=C(CC1CCOCC1)Nc1ccc(Cl)c(CCOc2ccccc2-c2c[nH]cn2)c1] | N-(3-(2-(2-(1H-imidazol-4-yl)phenoxy)ethyl)-4-chlorophenyl)-2-(tetrahydro-2H-pyran-4-yl)acetamide | C |

| No. | Structure | Name | hIDO IC$_{50}$ |
|---|---|---|---|
| 1305 | 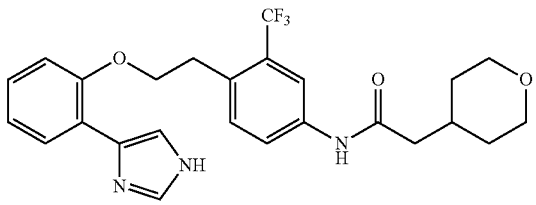 [SMILES: O=C(CC1CCOCC1)Nc1ccc(CCOc2ccccc2-c2c[nH]cn2)c(C(F)(F)F)c1] | N-(4-(2-(2-(1H-imidazol-4-yl)phenoxy)ethyl)-3-(trifluoromethyl)phenyl)-2-(tetrahydro-2H-pyran-4-yl)acetamide | A |
| 1325 | 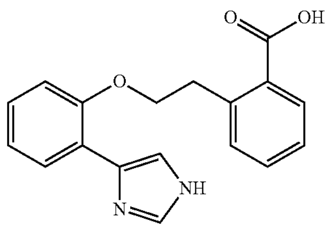 [SMILES: O=C(O)c1ccccc1CCOc1ccccc1-c1c[nH]cn1] | 2-(2-(2-(1H-imidazol-4-yl)phenoxy)ethyl)benzoic acid | D |
| 1332 | 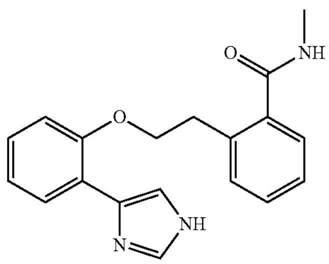 [SMILES: CNC(=O)c1ccccc1CCOc1ccccc1-c1c[nH]cn1] | 2-(2-(2-(1H-imidazol-4-yl)phenoxy)ethyl)-N-methylbenzamide | D |
| 1333 | 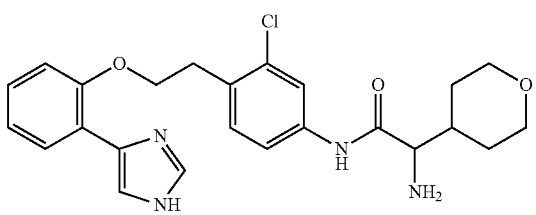 [SMILES: NC(C(=O)Nc1ccc(CCOc2ccccc2-c2c[nH]cn2)c(Cl)c1)C1CCOCC1] | N-(4-(2-(2-(1H-imidazol-4-yl)phenoxy)ethyl)-3-chlorophenyl)-2-amino-2-(tetrahydro-2H-pyran-4-yl)acetamide | A |
| 1337 | 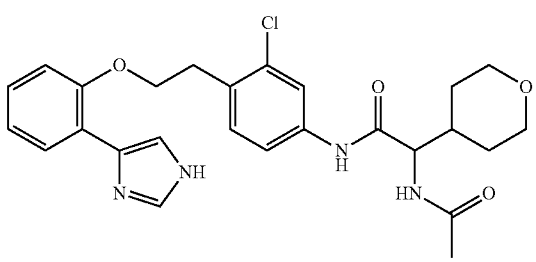 [SMILES: CC(=O)NC(C(=O)Nc1ccc(CCOc2ccccc2-c2c[nH]cn2)c(Cl)c1)C1CCOCC1] | N-(4-(2-(2-(1H-imidazol-4-yl)phenoxy)ethyl)-3-chlorophenyl)-2-acetamido-2-(tetrahydro-2H-pyran-4-yl)acetamide | A |
| 1344 | 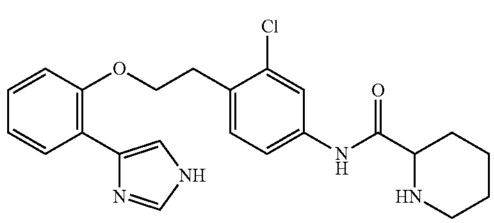 [SMILES: O=C(Nc1ccc(CCOc2ccccc2-c2c[nH]cn2)c(Cl)c1)C1CCCCN1] | N-(4-(2-(2-(1H-imidazol-4-yl)phenoxy)ethyl)-3-chlorophenyl)piperidine-2-carboxamide | B |

-continued

| No. | Structure | Name | hIDO IC$_{50}$ |
|---|---|---|---|
| 1345 | 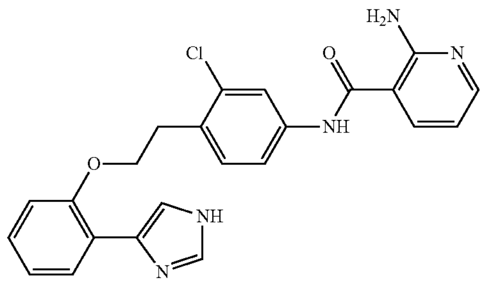 [SMILES: Nc1ncccc1C(=O)Nc1ccc(CCOc2ccccc2-c2c[nH]cn2)c(Cl)c1] | N-(4-(2-(2-(1H-imidazol-4-yl)phenoxy)ethyl)-3-chlorophenyl)-2-aminonicotinamide | A |
| 1346 | 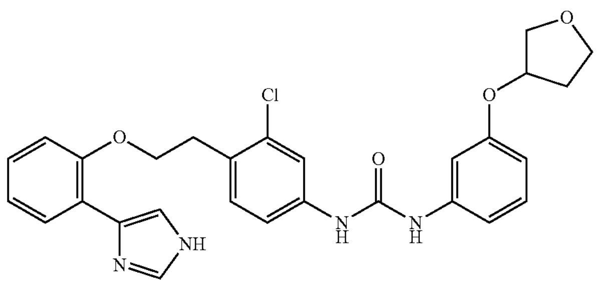 [SMILES: O=C(Nc1cccc(OC2CCOC2)c1)Nc1ccc(CCOc2ccccc2-c2c[nH]cn2)c(Cl)c1] | 1-(4-(2-(2-(1H-imidazol-4-yl)phenoxy)ethyl)-3-chlorophenyl)-3-(3-((tetrahydrofuran-3-yl)oxy)phenyl)urea | B |
| 1347 | 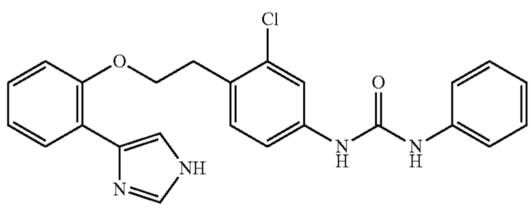 [SMILES: O=C(Nc1ccccc1)Nc1ccc(CCOc2ccccc2-c2c[nH]cn2)c(Cl)c1] | 1-(4-(2-(2-(1H-imidazol-4-yl)phenoxy)ethyl)-3-chlorophenyl)-3-phenylurea | A |
| 1354 | 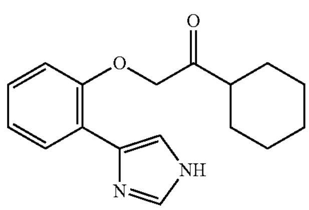 [SMILES: O=C(COc1ccccc1-c1c[nH]cn1)C1CCCCC1] | 2-(2-(1H-imidazol-4-yl)phenoxy)-1-cyclohexylethanone | B |
| 1361 | 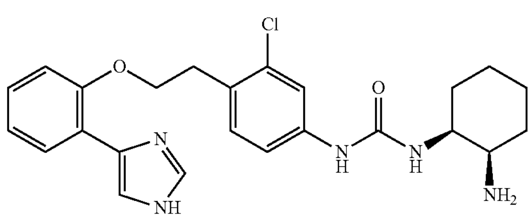 [SMILES: N[C@@H]1CCCC[C@@H]1NC(=O)Nc1ccc(CCOc2ccccc2-c2c[nH]cn2)c(Cl)c1] | 1-(4-(2-(2-(1H-imidazol-4-yl)phenoxy)ethyl)-3-chlorophenyl)-3-((1R,2R)-2-aminocyclohexyl)urea | A |
| 1366 | 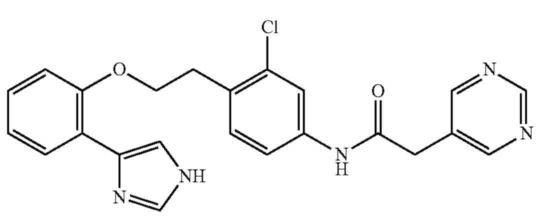 [SMILES: O=C(Cc1cncnc1)Nc1ccc(CCOc2ccccc2-c2c[nH]cn2)c(Cl)c1] | N-(4-(2-(2-(1H-imidazol-4-yl)phenoxy)ethyl)-3-chlorophenyl)-2-(pyrimidin-5-yl)acetamide | A |

| No. | Structure | Name | hIDO IC$_{50}$ |
|---|---|---|---|
| 1368 | 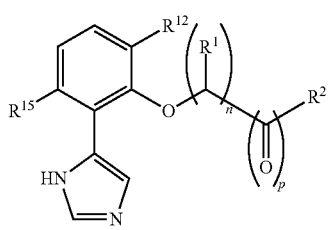 | 1-(4-(2-(2-(1H-imidazol-4-yl)phenoxy)ethyl)-3-chlorophenyl)-3-((1R,2S)-2-aminocyclohexyl)urea | A |

We claim:

1. A compound according to the formula, (VII)

a tautomer thereof, or a pharmaceutically acceptable salt thereof, wherein
n is 1, 2, or 3;
p is 0 or 1;
each $R^1$ is independently hydrogen or methyl;
$R^{12}$ is hydrogen or halogen;
$R^{15}$ is hydrogen or hydroxy; and
$R^2$ is $C_3$-$C_8$cycloalkyl, $C_3$-$C_8$cycloalkenyl, heterocyclyl, aryl, or heteroaryl, each optionally substituted with one $R^{20}$ group and optionally substituted with one $R^{21}$ group, wherein $C_3$-$C_8$cycloalkyl is cyclopentyl, cyclopentenyl, cyclohexyl, cyclohexenyl, cycloheptyl, cyclooctyl, bicyclo[3.1.1]heptane, bicyclo[2.2.1]heptane, bicyclo[2.2.2]octane, bicyclo[3.2.2]nonane, bicyclo[3.3.1]nonane or bicyclo[4.2.1]nonane;
$R^{20}$ is halogen, —C(O)R, —C(O)OR, —N(H)R, —N(H)C(O)C(H)($R^{22}$)R, —N(H)S(O)$_2$R, —N(H)C(O)R, —N(H)C(O)OR, —N(H)C(O)N(H)R, heteroaryl, heterocyclyl, wherein $R^{22}$ is N($R^{23}$)$_2$ or —N(H)C(O)$R^{23}$, wherein $R^{23}$ is hydrogen or $C_1$-$C_6$ alkyl;
$R^{21}$ is halogen or trifluoromethyl; and
R is hydrogen, $C_1$-$C_6$ alkyl, aryl, heteroaryl, $C_3$-$C_8$cycloalkyl, heterocyclyl, aryl($C_1$-$C_6$)alkyl, heteroaryl($C_1$-$C_6$)alkyl, heterocyclyl($C_1$-$C_6$)alkyl, wherein the heterocyclyl, aryl, heteroaryl, cycloalkyl, heterocyclyl, heterocyclylalkyl, arylalkyl, and heteroarylalkyl are each optionally substituted with one group that is halogen, cyano, nitro, —OR$^{10}$, —N(R$^{10}$)$_2$, —C(O)OR$^{10}$, —C(O)N(R$^{10}$)$_2$, —C(O)R$^{10}$, or $C_1$-$C_6$ alkyl, wherein each $R^{10}$ is independently hydrogen, $C_1$-$C_6$ alkyl, $C_3$-$C_8$cycloalkyl, heterocyclyl, aryl, or heteroaryl, provided that the compound is not
4-(2-(2-bromophenethoxy)phenyl)-1H-imidazole;
3-(2-chlorophenethoxy)-2-(1H-imidazol-5-yl)phenol;
5-(2-(4-chlorobenzyloxy)phenyl)-1H-imidazole;
4-(2-(2-chlorophenethoxy)phenyl)-1H-imidazole;
4-(2-(2-cyclohexylethoxy)phenyl)-1H-imidazole;
4-(2-(2-cyclopropylethoxy)phenyl)-1H-imidazole;
5-(2-(2-cyclopentylethoxy)phenyl)-1H-imidazole;
4-(2-phenethoxyphenyl)-1H-imidazole;
5-(2-(3-chlorobenzyloxy)phenyl)-1H-imidazole;
4-(2-(3-chlorophenethoxy)phenyl)-1H-imidazole;
N-(4-(2-(2-(1H-imidazol-4-yl)phenoxy)ethyl)phenyl)acetamide;
N-(3-(2-(2-(1H-imidazol-4-yl)phenoxy)ethyl)phenyl)acetamide;
5-(2-(3-phenylpropoxy)phenyl)-1H-imidazole;
4-(2-(benzyloxy)phenyl)-1H-imidazole;
4-(3-bromo-2-(4-chlorobenzyloxy)phenyl)-1H-imidazole;
4-(2-(4-chlorophenethoxy)phenyl)-1H-imidazole;
3-(4-chlorobenzyloxy)-2-(1H-imidazol-5-yl)phenol;
4-(2-(2-chlorobenzyloxy)phenyl)-1H-imidazole;
3-((2-(1H-imidazol-4-yl)phenoxy)methyl)piperidine;
1-(4-((2-(1H-imidazol-4-yl)phenoxy)methyl)piperidin-1-yl)ethanone;
1-(3-((2-(1H-imidazol-4-yl)phenoxy)methyl)piperidin-1-yl)ethanone;
4-(2-(2-bromophenethoxy)phenyl)-1H-imidazole;
tert-butyl 4-(2-(2-(1H-imidazol-4-yl)phenoxy)ethyl)piperidine-1-carboxylate;
1-(4-(2-(2-(1H-imidazol-4-yl)phenoxy)ethyl)piperidin-1-yl)ethanone;
4-((2-(1H-imidazol-4-yl)phenoxy)methyl)piperidine;
N-(2-(2-(2-(1H-imidazol-4-yl)phenoxy)ethyl)phenyl)acetamide;
4-((2-(1H-imidazol-5-yl)phenoxy)methyl)-7-methoxy-2H-chromen-2-one;
3-(2-(2-(1H-imidazol-5-yl)phenoxy)ethyl)-1H-indole;
2-(2-(1H-imidazol-5-yl)phenoxy)-1-(4-(pyrrolidin-1-yl)phenyl)ethanone;
2-(2-(1H-imidazol-5-yl)phenoxy)-1-(benzofuran-2-yl)ethanone;
2-(2-(1H-imidazol-5-yl)phenoxy)-1-(thiazol-2-yl)ethanone;
2-(2-(1H-imidazol-5-yl)phenoxy)-1-(benzofuran-5-yl)ethanone;
2-(3-(2-(1H-imidazol-5-yl)phenoxy)propyl)isoindoline-1,3-dione;
2-(2-(1H-imidazol-5-yl)phenoxy)-1-(4-(diethylamino)phenyl)ethanone;
2-(2-(1H-imidazol-5-yl)phenoxy)-1-(thiophen-3-yl)ethanone;
2-(2-(1H-imidazol-5-yl)phenoxy)-1-(thiophen-2-yl)ethanone;
2-(2-(1H-imidazol-5-yl)phenoxy)-1-(benzofuran-3-yl)ethanone;
2-(2-(1H-imidazol-5-yl)phenoxy)-1-(pyridin-2-yl)ethanone;

2-(2-(1H-imidazol-5-yl)phenoxy)-1-(pyridin-4-yl)ethanone;
1-(2-(2-(1H-imidazol-5-yl)phenoxy)ethyl)-1H-pyrazole;
2-(2-(1H-imidazol-5-yl)phenoxy)-1-(benzo[b]thiophen-5-yl)ethanone;
2-(2-(2-(1H-imidazol-5-yl)phenoxy)ethyl)isoindoline-1,3-dione;
2-(2-(1H-imidazol-5-yl)phenoxy)-1-(3-phenylisoxazol-5-yl)ethanone;
5-(2-(2-(2,3-dihydrobenzofuran-5-yl)ethoxy)phenyl)-1H-imidazole;
5-(2-(1-phenylpropan-2-yloxy)phenyl)-1H-imidazole;
3-(2-(2-(1H-imidazol-5-yl)phenoxy)acetyl)-2H-chromen-2-one;
2-(2-(1H-imidazol-5-yl)phenoxy)-2,3-dihydro-1H-inden-1-one;
5-(2-((2,3-dihydrobenzo[b][1,4]dioxin-2-yl)methoxy)phenyl)-1H-imidazole;
5-(2-(2-(1H-pyrrol-1-yl)ethoxy)phenyl)-1H-imidazole;
2-((2-(1H-imidazol-5-yl)phenoxy)methyl)-1H-benzo[d]imidazole;
6-(2-(2-(1H-imidazol-5-yl)phenoxy)acetyl)-2H-benzo[b][1,4]oxazin-3(4H)-one;
6-(2-(2-(1H-imidazol-5-yl)phenoxy)acetyl)benzo[d]oxazol-2(3H)-one;
2-((2-(1H-imidazol-5-yl)phenoxy)methyl)pyridine;
5-((2-(1H-imidazol-5-yl)phenoxy)methyl)-2-chloropyridine;
4-((2-(1H-imidazol-5-yl)phenoxy)methyl)pyridine;
2-((2-(1H-imidazol-5-yl)phenoxy)methyl)quinazolin-4(3H)-one;
2-((2-(1H-imidazol-5-yl)phenoxy)methyl)quinoline;
3-((2-(1H-imidazol-5-yl)phenoxy)methyl)quinoxalin-2(1H)-one;
3-((2-(1H-imidazol-5-yl)phenoxy)methyl)benzo[d]thiazol-2(3H)-one;
5-(2-(naphthalen-2-ylmethoxy)phenyl)-1H-imidazole; and
5-(2-(naphthalen-1-yl)ethoxy)phenyl)-1H-imidazole.

2. The compound of claim 1 according to the formula,

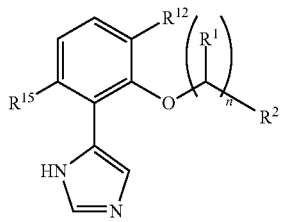

or a pharmaceutically acceptable salt thereof.

3. The compound of claim 1 according to the formula,

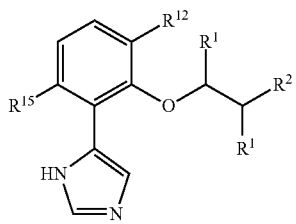

or a pharmaceutically acceptable salt thereof.

4. The compound of claim 1 according to the formula,

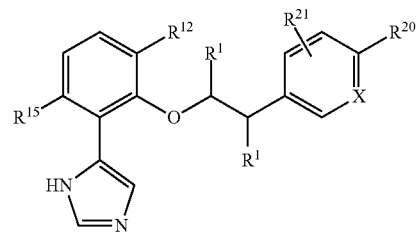

or a pharmaceutically acceptable salt thereof, wherein $R^{21}$ is hydrogen, halogen, or trifluoromethyl; and X is —C(H)= or —N=.

5. The compound of claim 1 according to the formula,

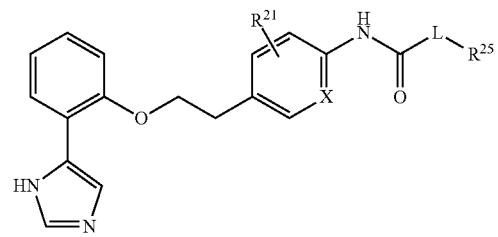

a tautomer thereof, or a pharmaceutically acceptable salt thereof, wherein
X is —C(H)= or —N=;
L is a bond, —CH$_2$—, —O—, or —N(H)—;
$R^{25}$ is hydrogen, $C_1$-$C_6$ alkyl, aryl, heteroaryl, $C_3$-$C_8$cycloalkyl, or heterocyclyl, wherein the aryl, heteroaryl, cycloalkyl, and heterocyclyl, groups are each optionally substituted with one group that is halogen, cyano, nitro, —OR$^{11}$, —N(R$^{11}$)$_2$, —C(O)OR$^{11}$, —C(O)N(R$^{11}$)$_2$, —C(O)R$^{11}$, or $C_1$-$C_6$ alkyl, wherein each $R^{11}$ is independently hydrogen, $C_1$-$C_6$ alkyl, $C_3$-$C_8$cycloalkyl, heterocyclyl, aryl, or heteroaryl; and
$R^{21}$ is hydrogen, halogen, or trifluoromethyl;
provided that $R^{25}$ can be hydrogen only when L is —CH$_2$—; and the compound is not
N-(4-(2-(2-(1H-imidazol-4-yl)phenoxy)ethyl)phenyl)acetamide.

6. The compound according to claim 1 that is
4-(2-(3,4-dichlorobenzyloxy)phenyl)-1H-imidazole;
2-(2-(1H-imidazol-4-yl)phenoxy)-1-(benzo[b]thiophen-6-yl)ethanone;
4-(2-(4-fluorobenzyloxy)phenyl)-1H-imidazole;
4-(2-(benzo[d][1,3]dioxol-5-ylmethoxy)phenyl)-1H-imidazole;
4-(2-(benzofuran-5-ylmethoxy)phenyl)-1H-imidazole;
4-(2-(2-(benzofuran-3-yl)propoxy)phenyl)-1H-imidazole;
3-(2-cyclohexylethoxy)-2-(1H-imidazol-5-yl)phenol;
4-(2-(2-(trifluoromethyl)phenethoxy)phenyl)-1H-imidazole;
4-(2-(1-(2-chlorophenyl)propan-2-yloxy)phenyl)-1H-imidazole;
4-(2-(1-cyclohexylpropan-2-yloxy)phenyl)-1H-imidazole;
tert-butyl 4-(2-(2-(1H-imidazol-4-yl)phenoxy)ethyl)phenylcarbamate;

4-(2-(2-cyclohexylpropoxy)phenyl)-1H-imidazole hydrochloride;
4-(2-(2-(1H-imidazol-4-yl)phenoxy)ethyl)aniline;
N-(4-(2-(2-(1H-imidazol-4-yl)phenoxy)ethyl)phenyl)pivalamide;
N-(4-(2-(2-(1H-imidazol-4-yl)phenoxy)ethyl)phenyl)-2-phenylacetamide;
N-(4-(2-(2-(1H-imidazol-4-yl)phenoxy)ethyl)phenyl)-3,3-dimethylbutanamide;
ethyl 4-(2-(2-(1H-imidazol-4-yl)phenoxy)ethyl)phenylcarbamate;
5-(2-(2-fluorophenethoxy)phenyl)-1H-imidazole;
benzyl 4-(2-(2-(1H-imidazol-4-yl)phenoxy)ethyl)phenylcarbamate;
3-(4-chlorophenethoxy)-2-(1H-imidazol-5-yl)phenol;
neopentyl 4-(2-(2-(1H-imidazol-4-yl)phenoxy)ethyl)piperidine-1-carboxylate;
N-(4-(2-(2-(1H-imidazol-4-yl)phenoxy)ethyl)phenyl) thiophene-2-carboxamide;
N-(4-(2-(2-(1H-imidazol-4-yl)phenoxy)ethyl)phenyl)-1-phenylmethanesulfonamide;
1-(4-(2-(2-(1H-imidazol-4-yl)phenoxy)ethyl)phenyl)-3-phenylurea;
N-(4-(2-(2-(1H-imidazol-4-yl)phenoxy)ethyl)phenyl)-2-(pyrazin-2-yl)acetamide;
N-(4-(2-(2-(1H-imidazol-4-yl)phenoxy)ethyl)phenyl)-2-(thiophen-2-yl)acetamide;
or a pharmaceutically acceptable salt thereof.

7. The compound according to claim 1 that is
N-(4-(2-(2-(1H-imidazol-4-yl)phenoxy)ethyl)-3-chlorophenyl)acetamide;
3-(3-chlorophenethoxy)-2-(1H-imidazol-5-yl)phenol;
(4-(2-(2-(1H-imidazol-4-yl)phenoxy)ethyl)piperidin-1-yl)(thiophen-2-yl)methanone;
4-chloro-3-(2-cyclohexylethoxy)-2-(1H-imidazol-5-yl) phenol;
1-(4-(2-(2-(1H-imidazol-4-yl)phenoxy)ethyl)piperidin-1-yl)-2-(thiophen-2-yl)ethanone;
5-(3-chloro-2-(2-cyclohexylethoxy)phenyl)-1H-imidazole;
3-(2-(cyclohex-3-en-1-yl)ethoxy)-2-(1H-imidazol-5-yl) phenol;
1-(4-(2-(2-(1H-imidazol-4-yl)phenoxy)ethyl)piperidin-1-yl)-2-phenylethanone;
4-(2-(2-(cyclohex-3-en-1-yl)ethoxy)phenyl)-1H-imidazole;
1-(4-(2-(2-(1H-imidazol-4-yl)phenoxy)ethyl)phenyl)-3-(2-nitrophenyl)urea;
4-(2-(2-(thiophen-2-yl)ethoxy)phenyl)-1H-imidazole;
N-(4-(2-(2-(1H-imidazol-4-yl)phenoxy)ethyl)phenyl)-2-(tetrahydrofuran-2-yl)acetamide;
4-(2-(4-(thiophen-3-yl)phenethoxy)phenyl)-1H-imidazole;
4-(2-(2-(thiophen-3-yl)ethoxy)phenyl)-1H-imidazole;
N-(4-(2-(2-(1H-imidazol-4-yl)phenoxy)ethyl)phenyl)-2-oxo-1,2-dihydropyridine-3-carboxamide;
N-(4-(2-(2-(1H-imidazol-4-yl)phenoxy)ethyl)phenyl)-2-(tetrahydro-2H-pyran-4-yl)acetamide;
N-(4-(2-(2-(1H-imidazol-4-yl)phenoxy)ethyl)phenyl)-2-morpholinoacetamide;
1-(4-(2-(2-(1H-imidazol-4-yl)phenoxy)ethyl)phenyl)-3-(2-aminocyclohexyl)urea;
N-(4-(2-(2-(1H-imidazol-4-yl)phenoxy)ethyl)phenyl)-2-(1H-imidazol-1-yl)acetamide;
6-(2-(2-(1H-imidazol-4-yl)phenoxy)ethyl)-N-phenylbenzo[d]oxazol-2-amine;
1-(5-(2-(2-(1H-imidazol-4-yl)phenoxy)ethyl)pyridin-2-yl)-3-phenylurea;
4-(2-(4-(pyrrolidin-1-yl)phenethoxy)phenyl)-1H-imidazole;
N-(4-(2-(2-(1H-imidazol-4-yl)phenoxy)ethyl)phenyl)-2-(thiazol-4-yl)acetamide;
N-(4-(2-(2-(1H-imidazol-4-yl)phenoxy)ethyl)phenyl)-2-(pyrimidin-2-yl)acetamide;
N-(5-(2-(2-(1H-imidazol-4-yl)phenoxy)ethyl)pyridin-2-yl)-2-phenylacetamide;
N-(4-(2-(2-(1H-imidazol-4-yl)phenoxy)ethyl)phenyl)-2-(pyrimidin-5-yl)acetamide;
N-(4-(2-(2-(1H-imidazol-4-yl)phenoxy)ethyl)phenyl)-2-(3-nitrophenyl)acetamide;
N-(4-(2-(2-(1H-imidazol-4-yl)phenoxy)ethyl)phenyl)-2-(2-nitrophenyl)acetamide;
N-(4-(2-(2-(1H-imidazol-4-yl)phenoxy)ethyl)phenyl)-2-(3-aminophenyl)acetamide;
N-(4-(2-(2-(1H-imidazol-4-yl)phenoxy)ethyl)phenyl)-2-(4-nitrophenyl)acetamide;
N-(4-(2-(2-(1H-imidazol-4-yl)phenoxy)ethyl)phenyl)-2-(2-aminophenyl)acetamide;
N-(4-(2-(2-(1H-imidazol-4-yl)phenoxy)ethyl)phenyl)-2-(4-aminophenyl)acetamide;
N-(4-(2-(2-(1H-imidazol-4-yl)phenoxy)ethyl)phenyl)-2-(2-aminothiazol-4-yl)acetamide;
N-(4-(2-(2-(1H-imidazol-4-yl)phenoxy)ethyl)-3-chlorophenyl)-2-(tetrahydro-2H-pyran-4-yl)acetamide;
methyl 3-((4-(2-(2-(1H-imidazol-4-yl)phenoxy)ethyl) phenyl)carbamoyl)benzoate;
1-(4-(2-(2-(1H-imidazol-4-yl)phenoxy)ethyl)-3-chlorophenyl)-3-(tetrahydro-2H-pyran-4-yl)urea;
4-((4-(2-(2-(1H-imidazol-4-yl)phenoxy)ethyl)phenyl)carbamoyl)benzoic acid;
methyl 4-((4-(2-(2-(1H-imidazol-4-yl)phenoxy)ethyl) phenyl)carbamoyl)benzoate;
N-(4-(2-(2-(1H-imidazol-4-yl)phenoxy)ethyl)phenyl)-2,6-dioxo-1,2,3,6-tetrahydropyrimidine-4-carboxamide;
3-((4-(2-(2-(1H-imidazol-4-yl)phenoxy)ethyl)phenyl)carbamoyl)benzoic acid;
2-((4-(2-(2-(1H-imidazol-4-yl)phenoxy)ethyl)phenyl)carbamoyl)benzoic acid;
N-(4-(2-(2-(1H-imidazol-4-yl)phenoxy)ethyl)-3-fluorophenyl)-2-(tetrahydro-2H-pyran-4-yl)acetamide;
4-(2-(2-chlorophenethoxy)-3-fluorophenyl)-1H-imidazole;
N-(4-(2-(2-(1H-imidazol-4-yl)phenoxy)ethyl)-2-chlorophenyl)-2-(tetrahydro-2H-pyran-4-yl)acetamide;
N-(3-(2-(2-(1H-imidazol-4-yl)phenoxy)ethyl)-4-chlorophenyl)-2-(tetrahydro-2H-pyran-4-yl)acetamide;
N-(4-(2-(2-(1H-imidazol-4-yl)phenoxy)ethyl)-3-(trifluoromethyl)phenyl)-2-(tetrahydro-2H-pyran-4-yl)acetamide;
N-(4-(2-(2-(1H-imidazol-4-yl)phenoxy)ethyl)-3-chlorophenyl)-2-amino-2-(tetrahydro-2H-pyran-4-yl)acetamide;
N-(4-(2-(2-(1H-imidazol-4-yl)phenoxy)ethyl)-3-chlorophenyl)-2-acetamido-2-(tetrahydro-2H-pyran-4-yl) acetamide;
N-(4-(2-(2-(1H-imidazol-4-yl)phenoxy)ethyl)-3-chlorophenyl)piperidine-2-carboxamide;
N-(4-(2-(2-(1H-imidazol-4-yl)phenoxy)ethyl)-3-chlorophenyl)-2-aminonicotinamide;
1-(4-(2-(2-(1H-imidazol-4-yl)phenoxy)ethyl)-3-chlorophenyl)-3-(3-((tetrahydrofuran-3-yl)oxy)phenyl) urea;

1-(4-(2-(2-(1H-imidazol-4-yl)phenoxy)ethyl)-3-chlorophenyl)-3-phenylurea;
2-(2-(1H-imidazol-4-yl)phenoxy)-1-cyclohexylethanone;
1-(4-(2-(2-(1H-imidazol-4-yl)phenoxy)ethyl)-3-chlorophenyl)-3-((1R,2R)-2-aminocyclohexyl)urea;
N-(4-(2-(2-(1H-imidazol-4-yl)phenoxy)ethyl)-3-chlorophenyl)-2-(pyrimidin-5-yl)acetamide;
1-(4-(2-(2-(1H-imidazol-4-yl)phenoxy)ethyl)-3-chlorophenyl)-3-((1R,2S)-2-aminocyclohexyl)urea;
or a pharmaceutically acceptable salt thereof.

8. A compound according to the formula,

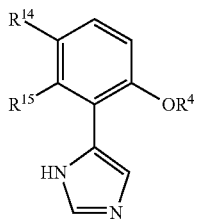

a tautomer thereof, or a pharmaceutically acceptable salt thereof, wherein
$R^{14}$ is halogen;
$R^{15}$ is hydrogen or hydroxy, and
$R^4$ is hydrogen or —C(O)$R^5$, wherein
$R^5$ is (i) $C_1$-$C_6$ alkyl; or
(ii) —N($R^2$)($R^3$), wherein
$R^2$ is $C_1$-$C_6$ alkyl, aryl, —$C_1$-$C_6$ alkyl-OC(O)$R^6$, or —C(H)($R^{22}$)C(O)O$R^7$, wherein
$R^{22}$ is hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with one group that is halo, cyano, —O$R^{23}$, —S$R^{23}$, —N($R^{23}$)$_2$, —C(O)O$R^{23}$, —C(O)N($R^{23}$)$_2$, —N($R^{23}$)C(=N$R^{23}$)N($R^{23}$)$_2$, or $C_1$-$C_6$alkyl, wherein each $R^{23}$ is hydrogen or $C_1$-$C_6$alkyl; and
$R^6$ is $C_1$-$C_6$ alkyl;
$R^7$ is hydrogen or $C_1$-$C_6$ alkyl;
$R^3$ is hydrogen or $C_1$-$C_6$ alkyl;
or $R^2$ and $R^3$ taken together with the nitrogen to which they are attached form a heterocyclyl group, wherein the heterocyclyl group is optionally substituted with one or two groups that are each independently oxo or $C_1$-$C_6$ alkyl;
provided that the compound is not
4-chloro-2-(1H-imidazol-5-yl)phenol; and
4-bromo-2-(1H-imidazol-5-yl)phenol.

9. The compound of claim 8, wherein $R^4$ is hydrogen.

10. The compound of claim 8, according to the formula,

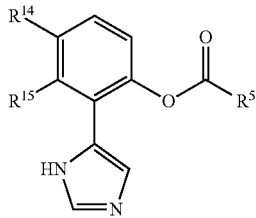

a tautomer thereof, or a pharmaceutically acceptable salt thereof, wherein
$R^{14}$ is halogen;
$R^{15}$ is hydrogen or hydroxy, and
$R^5$ is (i) $C_1$-$C_6$ alkyl; or
(ii) —N($R^2$)($R^3$), wherein
$R^2$ is $C_1$-$C_6$ alkyl, aryl, —$C_1$-$C_6$ alkyl-OC(O)$R^6$, or —C(H)($R^{22}$)C(O)O$R^7$, wherein
$R^{22}$ is hydrogen, $C_1$-$C_6$alkyl, aryl, heteroaryl, aryl$C_1$-$C_6$alkyl, or heteroaryl$C_1$-$C_6$alkyl, wherein the alkyl, arylalkyl, and heteroarylalkyl groups are optionally substituted with one group that is halo, cyano, —O$R^{23}$, —S$R^{23}$, —N($R^{23}$)$_2$, —C(O)O$R^{23}$, —C(O)N($R^{23}$)$_2$, —N($R^{23}$)C(=N$R^{23}$)N($R^{23}$)$_2$, or $C_1$-$C_6$alkyl, wherein each $R^{23}$ is hydrogen or $C_1$-$C_6$alkyl; and
$R^6$ is $C_1$-$C_6$ alkyl;
$R^7$ is hydrogen or $C_1$-$C_6$ alkyl; and
$R^3$ is hydrogen or $C_1$-$C_6$ alkyl;
or $R^2$ and $R^3$ taken together with the nitrogen to which they are attached form a heterocyclyl group, wherein the heterocyclyl group is optionally substituted with one or two groups that are each independently oxo or $C_1$-$C_6$ alkyl.

11. The compound of claim 8 that is
4-bromo-2-(1H-imidazol-4-yl)phenyl pivalate;
4-chloro-2-(1H-imidazol-4-yl)phenyl dimethylcarbamate;
4-chloro-2-(1H-imidazol-4-yl)phenyl diisopropylcarbamate;
4-chloro-2-(1H-imidazol-4-yl)phenyl pyrrolidine-1-carboxylate;
4-chloro-2-(1H-imidazol-4-yl)phenyl methyl(phenyl)carbamate;
4-chloro-2-(1H-imidazol-4-yl)phenyl 4-methylpiperazine-1-carboxylate;
4-chloro-2-(1H-imidazol-4-yl)phenyl 2-oxoimidazolidine-1-carboxylate;
or a pharmaceutically acceptable salt thereof.

12. The compound of claim 8 that is
2-(((4-chloro-2-(1H-imidazol-4-yl)phenoxy)carbonyl)(methyl)amino)ethyl acetate;
(R)-methyl 2-(((4-chloro-2-(1H-imidazol-4-yl)phenoxy)carbonyl)amino)-3-(1-methyl-1H-indol-3-yl)propanoate;
or a pharmaceutically acceptable salt thereof.

13. A compound according to the formula,

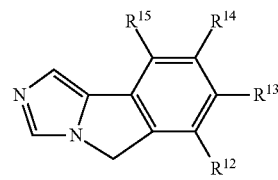

a tautomer thereof, or a pharmaceutically acceptable salt thereof, wherein
$R^{13}$ is hydrogen, halogen, or —SH; and
$R^{12}$ is $R^{20}$;
$R^{14}$ and $R^{15}$ are each independently hydrogen or $R^{20}$, wherein
each $R^{20}$ is independently halogen, cyano, —OR, —SR, —NR$_2$, —C(O)OR, —C(O)NR$_2$, —N(R)S(O)$_2$R, —C(O)$R^2$, —S(O)R, —S(O)$_2$R, —S(O)OR, —S(O)$_2$OR, —S(O)NR$_2$, —S(O)$_2$NR$_2$, —OC(O)R, —OC(O)OR, —OC(O)NR$_2$, —N(R)C(O)R, —N(R)C(O)OR, —N(R)C(O)NR$_2$, —N(R)S(O)R, $C_1$-$C_6$alkyl, $C_2$-$C_6$alkenyl, $C_2$-$C_6$alkynyl, $C_1$-$C_6$haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl;

each R is independently hydrogen or $R^2$, wherein $R^2$ is $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl, wherein the alkyl, cycloalkyl, heterocyclyl, aryl, heteroaryl, cycloalkylalkyl, heterocyclylalkyl, arylalkyl, and heteroarylalkyl are each optionally substituted with 1, 2, 3, or 4 groups which are each independently halogen, cyano, nitro, —$OR^{10}$, —$SR^{10}$, —$N(R^{10})_2$, —$C(O)OR^{10}$, —$C(O)N(R^{10})_2$, —$C(O)R^{10}$, —$S(O)R^{10}$, —$S(O)_2R^{10}$, —$S(O)OR^{10}$, —$S(O)_2OR^{10}$, —$S(O)N(R^{10})_2$, —$S(O)_2N(R^{10})_2$, —$OC(O)R^{10}$, —$OC(O)OR^{10}$, —$OC(O)N(R^{10})_2$, —$N(R^{10})C(O)R^{10}$, —$N(R^{10})C(O)OR^{10}$, —$N(R^{10})C(O)N(R^{10})_2$, —$N(R^{10})S(O)R^{10}$, —$N(R^{10})S(O)_2R^{10}$, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, or heteroaryl, wherein each $R^{10}$ is independently hydrogen, $C_1$-$C_6$ alkyl, $C_2$-$C_6$ alkenyl, $C_2$-$C_6$ alkynyl, $C_1$-$C_6$ haloalkyl, $C_3$-$C_8$cycloalkyl, heterocyclyl, aryl, heteroaryl, $C_3$-$C_8$cycloalkyl($C_1$-$C_6$)alkyl, heterocyclyl($C_1$-$C_6$)alkyl, aryl($C_1$-$C_6$)alkyl, or heteroaryl($C_1$-$C_6$)alkyl.

14. A pharmaceutical composition comprising a pharmaceutically acceptable excipient, diluent, or carrier, and a compound according to any one of claims 1, 2, 3, 4, 5, 6, 7, 8, 9, 10, 11, 12, and 13.

15. A method for treating indoleamine 2,3-dioxygenase (IDO) mediated immunosuppression in a subject in need thereof, comprising administering an effective indoleamine 2,3-dioxygenase inhibiting amount of (i) a compound or (ii) a pharmaceutical composition comprising a pharmaceutically acceptable excipient, diluent, or carrier, and the compound, wherein the compound is according to any one of claims 1, 2, 3, 4, 5, 6, 7, 8, 9, 10, 11, 12, and 13.

* * * * *